US012485108B2

(12) United States Patent
Jiang et al.

(10) Patent No.: US 12,485,108 B2
(45) Date of Patent: Dec. 2, 2025

(54) METHOD FOR TREATING FATTY LIVER DISEASE AND/OR STEATOHEPATITIS

(71) Applicant: BEIJING TIDE PHARMACEUTICAL CO., LTD., Beijing (CN)

(72) Inventors: Yuanyuan Jiang, Beijing (CN); Weiting Zhong, Beijing (CN); Yanping Zhao, Beijing (CN); Hongjun Wang, Beijing (CN); Jing Zhao, Beijing (CN); Jing Li, Beijing (CN); Weina Liu, Beijing (CN); Liying Zhou, Beijing (CN); Yanan Liu, Beijing (CN)

(73) Assignee: BEIJING TIDE PHARMACEUTICAL CO., LTD., Beijing (CN)

( * ) Notice: Subject to any disclaimer, the term of this patent is extended or adjusted under 35 U.S.C. 154(b) by 1128 days.

(21) Appl. No.: 17/435,061

(22) PCT Filed: Feb. 26, 2020

(86) PCT No.: PCT/CN2020/076723
§ 371 (c)(1),
(2) Date: Mar. 24, 2022

(87) PCT Pub. No.: WO2020/177587
PCT Pub. Date: Sep. 10, 2020

(65) Prior Publication Data

US 2022/0378743 A1 Dec. 1, 2022

(30) Foreign Application Priority Data

Mar. 1, 2019 (WO) ................ PCT/CN2019/076688

(51) Int. Cl.
*A61K 31/416* (2006.01)
*A61P 3/04* (2006.01)

(52) U.S. Cl.
CPC .............. *A61K 31/416* (2013.01); *A61P 3/04* (2018.01)

(58) Field of Classification Search
CPC ................................ A61K 31/416; A61P 3/04
See application file for complete search history.

(56) References Cited

U.S. PATENT DOCUMENTS 10,323,023 B2 * 6/2019 Zhao ...................... A61K 31/53
10,329,282 B2 * 6/2019 Zhao .................. A61K 31/4155
11,390,609 B2 * 7/2022 Zhao .................... A61K 31/506
2017/0137385 A1 5/2017 Chimenti et al.
2019/0010143 A1 1/2019 Zhao et al.

FOREIGN PATENT DOCUMENTS

CN 105980361 9/2016
WO 2012040499 9/2011
WO 2016004254 7/2016
WO 2018039539 3/2018
WO 2019000682 1/2019
WO 2019001572 1/2019
WO 2019145729 8/2019

OTHER PUBLICATIONS

Klein et al. "Rho-kinase inhibitor coupled to peptide-modified albumin carrier reduces portal pressure and increases renal perfusion in cirrhotic rats." Scientific reports. Feb. 19, 2019;9(1):1-1.
Xie et al. "Fasudil alleviates hepatic fibrosis in type 1 diabetic rats: involvement of the inflammation and RhoA/ROCK pathway." Eur. Rev. Med. Pharmacol. Sci. Sep. 1, 2018;22:5665-77.
Tada et al. "A selective ROCK inhibitor, Y27632, prevents dimethylnitrosamine-induced hepatic fibrosis in rats." Journal of hepatology. Apr. 1, 2001;34(4):529-36.
Fernández-Simón et al. "RhoA/ROCK2 signalling is enhanced by PDGF-AA in fibro-adipogenic progenitor cells in DMD." bioRxiv. Apr. 14, 2021.
Zhu X, Xiong T, Liu P, Guo X, Xiao L, Zhou F, Tang Y, Yao P. Quercetin ameliorates HFD-induced NAFLD by promoting hepatic VLDL assembly and lipophagy via the IRE1a/XBP1s pathway. Food and chemical toxicology. Apr. 1, 2018;114:52-60.
Huang et al. "Rho-kinase/AMPK axis regulates hepatic lipogenesis during overnutrition." The Journal of clinical 1 investigation. Dec. 3, 2018;128(12):5335-50.
Sunamura et al. "Different roles of myocardial ROCK1 and ROCK2 in cardiac dysfunction and postcapillary pulmonary hypertension in mice." Proceedings of the National Academy of Sciences. Jul. 24, 2018;115(30):E7129-38.
Lock et al. "Distinct roles for ROCK1 and ROCK2 in the regulation of keratinocyte differentiation." PloS one. Dec. 4, 2009;4(12):e8190.
Chen et al. "ROCK2, but not ROCK1 interacts with phosphorylated STAT3 and co-occupies TH17/TFH gene promoters in TH17-activated human T cells." Scientific reports. Nov. 9, 2018;8(1):1-0.

* cited by examiner

*Primary Examiner* — Kevin E Weddington
(74) *Attorney, Agent, or Firm* — Robin L. Teskin; Baker, Donelson, Bearman, Caldwell & Berkowitz PC

(57) ABSTRACT

The present invention falls within the field of biological medicine, and specifically relates to a method for preventing, alleviating and/or treating fatty liver disease and/or steatohepatitis. The method comprises administering, to an individual in need thereof, an effective amount of a compound of formula (I) or a pharmaceutically acceptable salt, an ester, a stereoisomer, a polymorph, a solvate, an N-oxide, an isotopically labeled compound, a metabolite or a prodrug thereof.

(I)

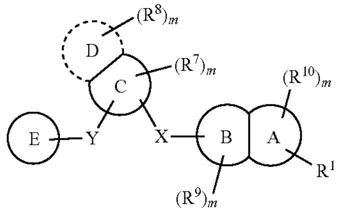

17 Claims, 8 Drawing Sheets #### represents P<0.0001. compared to the normal group #### represents P<0.0001, compared to the normal group p<0.01, **p<0.0001, compared to the model group
A-Normal group, B-Model group, C-Compound C (100 mg/kg) administration group,D-Telmisartan administration group.

*p<0.05, **p<0.01, compared to the model group
A-Normal group, B-Model group, C-Compound C (100 mg/kg) administration group, D-Telmisartan administration group.

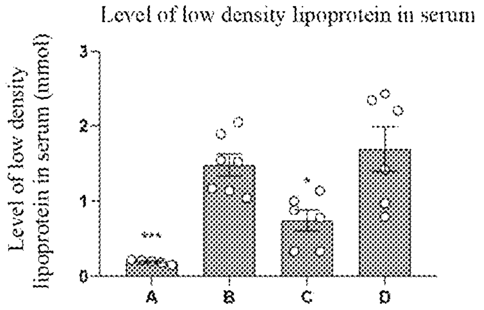

*p<0.05, ***p<0.001, compared to the model group
A-Normal group, B-Model group, C-Compound C (100 mg/kg) administration group, D-Telmisartan administration group.

Fig.5B

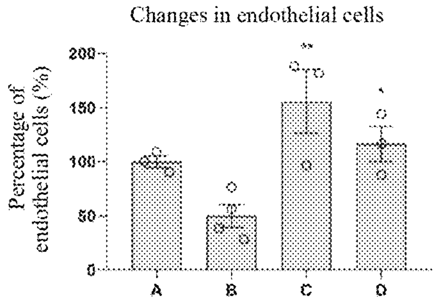

*p<0.05, **p<0.01, compared to the model group
A-Normal group, B-Model group, C-Compound C (100 mg/kg) administration group, D-Telmisartan administration group.

Fig.6A

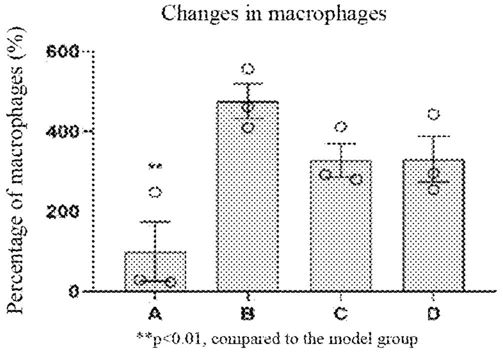

**p<0.01, compared to the model group
A-Normal group, B-Model group, C-Compound C (100 mg/kg) administration group, D-Telmisartan administration group.

Fig.6B p<0.01, *p<0.001, compared to the model group
A-Normal group, B-Model group, C-Compound C (100 mg/kg) administration group, D-Telmisartan administration group.

p<0.01, *p<0.001, compared to the model group
A-Normal group, B-Model group, C-Compound C (100 mg/kg) administration group, D-Telmisartan administration group.

***p<0.001, compared to the model group
A-Normal group, B-Model group, C-Compound C (300 mg/kg) administration group, D-Compound C (100 mg/kg) administration group, E-Telmisartan administration group.

*p<0.001, **p<0.0001, compared to the model group
A-Normal group, B-Model group, C-OCA (30 mg/kg) administration group, D-Compound C (50 mg/kg) administration group, E-Compound C (100 mg/kg) administration group

METHOD FOR TREATING FATTY LIVER DISEASE AND/OR STEATOHEPATITIS

CROSS-REFERENCE TO RELATED APPLICATIONS

This application is a U.S. National Phase application of Int'l Appl. No. PCT/CN2020/076723, filed Feb. 26, 2020, which claims priority to Int'l Appl. No. PCT/CN2019/076688, filed Mar. 1, 2019, each of which are incorporated herein by reference in their entireties.

FIELD OF THE INVENTION

The present disclosure falls within the field of biological medicine, and specifically relates to a method for preventing, alleviating and/or treating a fatty liver disease and/or steatohepatitis, comprising administering to a subject in need thereof an effective amount of a compound of Formula (I) or a pharmaceutically acceptable salt, ester, stereoisomer, polymorph, solvate, N-oxide, isotopically labeled compound, metabolite or prodrug thereof.

BACKGROUND OF THE INVENTION

The fatty liver disease is a general term for a class of diseases in which fat accumulates in liver cells and causes liver diseases. It comprises an alcoholic fatty liver disease and non-alcoholic fatty liver disease (NAFLD).

The alcoholic fatty liver disease is a liver disease caused by long-term heavy drinking. The clinical symptoms are non-specific. It may be asymptomatic, or may be right upper abdominal distending pain, loss of appetite, fatigue, weight loss, etc.

The non-alcoholic fatty liver disease and non-alcoholic steatohepatitis (NASH) are common liver disorders. Histopathoiogically, these disorders resemble alcoholic liver diseases, but they occur in people who drink little or no alcohol. The pathological changes in the liver include, but are not limited to, fat accumulation in hepatocytes, evidence of hepatocellular degeneration, infiltration of inflammatory cells, hepatocellular nodule formation, cirrhosis, and hepatocellular carcinoma. To date, no specific therapies for these disorders are available. Therefore, there is a need to provide methods for treating these disorders.

SUMMARY OF THE INVENTION

In one aspect, the present disclosure provides a method for preventing, alleviating and/or treating a fatty liver disease and/or steatohepatitis, comprising administering to a subject in need thereof an effective amount of a compound of Formula (I) or a pharmaceutically acceptable salt, ester, stereoisomer, polymorph, solvate, N-oxide, isotopically labeled compound, metabolite or prodrug thereof:

Formula (I)

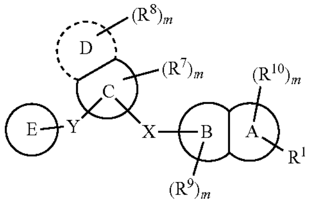

wherein:

X and Y are each independently selected from the group consisting of a direct bond, C(═O), O, $S(═O)_1$ and NR;

R is selected from the group consisting of H, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl and $C_{6-12}$ aralkyl, and at most 2 ring members in the cyclic hydrocarbyl and heterocyclyl are C(═O);

ring A and ring B are each independently selected from the group consisting of saturated or partially unsaturated $C_{3-10}$ hydrocarbon ring, saturated or partially unsaturated 3- to 10-membered heterocycle, $C_{6-10}$ aromatic ring and 5- to 14-membered heteroaromatic ring, and at most 2 ring members in the hydrocarbon ring and heterocycle are C(═O); provided that when ring B is a heterocycle containing a nitrogen atom, ring B is not attached to X via the nitrogen atom;

ring C is selected from the group consisting of saturated or partially unsaturated $C_{3-10}$ hydrocarbon ring, saturated or partially unsaturated 3- to 10-membered heterocycle, $C_{6-10}$ aromatic ring and 5- to 14-membered heteroaromatic ring, and at most 2 ring members in the hydrocarbon ring and heterocycle are C(═O);

ring D is absent, or is selected from the group consisting of saturated or partially unsaturated $C_{3-10}$ hydrocarbon ring, saturated or partially unsaturated 3- to 10-membered heterocycle, $C_{6-10}$ aromatic ring and 5- to 14-membered heteroaromatic ring, and at most 2 ring members in the hydrocarbon ring and heterocycle are C(═O);

ring E is selected from the group consisting of

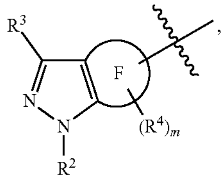

,

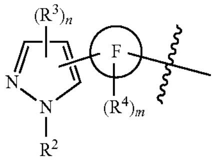

and

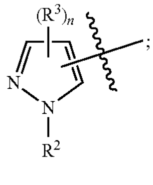

;

ring F is selected from the group consisting of saturated or partially unsaturated $C_{3-10}$ hydrocarbon ring, saturated or partially unsaturated 3- to 10-membered heterocycle, $C_{6-10}$ aromatic ring and 5- to 14-membered heteroaromatic ring, and at most 2 ring members in the hydrocarbon ring and heterocycle are C(═O);

$R^1$ is selected from the group consisting of H, $—NH_2$, $C_{1-6}$ alkyl, $C_{6-10}$ aryl, 5- to 14-membered heteroaryl, N-methylpyrrolidinyl, N-methylpiperidinyl,

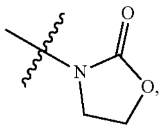 [SMILES: *N1CCOC1=O]

acetyl,

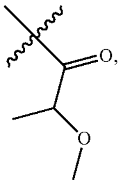

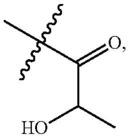

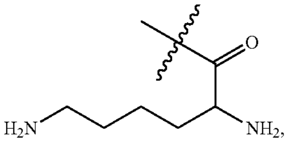

—C(═O)—($C_{1-6}$ alkylene)$_n$-$CF_3$, —C(═O)—($C_{1-6}$ alkylene)$_n$-CN, —C(═O)-(saturated or partially unsaturated $C_{3-10}$ cyclic hydrocarbyl), —NHC(═O)-(saturated or partially unsaturated $C_{3-10}$ cyclic hydrocarbyl), —C(═O)-(saturated or partially unsaturated 3- to 10-membered heterocyclyl), —C(═O)—$C_{1-6}$ alkylene-(saturated or partially unsaturated 3- to 10-membered heterocyclyl), —C(═O)-(5- to 14-membered heteroaryl), —C(═O)—$C_{1-6}$ alkylene-NH ($C_{1-6}$ alkyl), —C(═O)—$C_{1-6}$ alkylene-N($C_{1-6}$ alkyl)$_2$, N-methylpiperazine substituted acetyl, —S(═O)$_2R^{1a}$, —P(═O)$R^{1a}R^{1b}$,

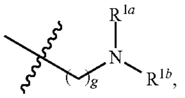

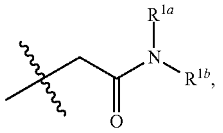

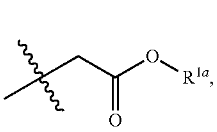

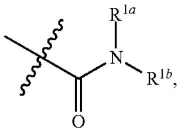

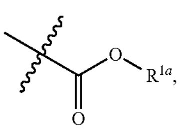

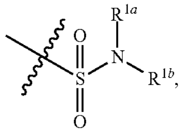

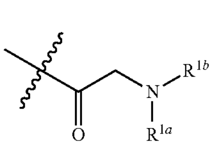

and

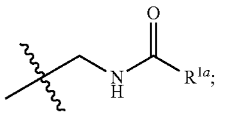

provided that when one of $R^1$ and $R^{10}$ is $C_{1-6}$ alkyl, and the other is H or $C_{3-10}$ cyclic hydrocarbyl, then at least one of X and Y is a direct bond, and ring C is not a 5-membered heteroaromatic ring; when one of $R^1$ and $R^{10}$ is H, and the other is

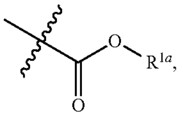

then ring C is not a 5-membered heteroaromatic ring; when both $R^1$ and $R^{10}$ are H, then ring A contains at least one nitrogen atom, and is not a 5- or 6-membered ring; when one of $R^1$ and $R^{10}$ is H, and the other is

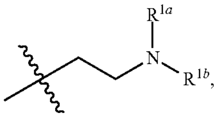

then ring C is not a 5-membered heteroaromatic ring; and when one of $R^1$ and $R^{10}$ is H, and the other is H or acetyl, then ring D is absent;

$R^{1a}$ and $R^{1b}$ are each independently selected from the group consisting of H, halogen, amino, cyano, nitro, $C_{1-6}$ alkyl, $C_{2-6}$ alkenyl, $C_{2-6}$ alkynyl, $C_{3-10}$ cyclic hydrocarbyl, 3- to 10-membered heterocyclyl, $C_{6-10}$ aryl, 5- to 14-membered heteroaryl, $C_{6-12}$ aralkyl, —C(═O)$R^5$, —OC(═O)$R^5$, —C(═O)O$R^5$, —O$R^5$, —S$R^5$, —S(═O)$R^5$, —S(═O)$_2R^5$, —S(═O)$_2NR^5R^6$, —$NR^5R^6$, —C(═O)$NR^5R^6$, —$NR^5$—C(═O)$R^6$, —$NR^5$—C(═O)O$R^6$, —$NR^5$—S(═O)$_2$—$R^6$, —$NR^5$—C(═O)—$NR^5R^6$, —$C_{1-6}$ alkylene-$NR^5R^6$, —$C_{1-6}$ alkylene-O$R^5$ and —O—$C_{1-6}$ alkylene-$NR^5R^6$, provided that when one of $R^{1a}$ and $R^{1b}$ is n-propyl, then the other is not H; or $R^{1a}$ and $R^{1b}$ together with the atom to which they are attached form a 3- to 12-membered heterocycle or heteroaromatic ring;

$R^2$, $R^3$, $R^4$, $R^7$, $R^8$, $R^9$ and $R^{10}$, at each occurrence, are each independently selected from the group consisting of H, halogen, amino, cyano, nitro, $C_{1-6}$ alkyl, $C_{2-6}$ alkenyl, $C_{2-6}$ alkynyl, $C_{3-10}$ cyclic hydrocarbyl, 3- to 10-membered heterocyclyl, $C_{6-10}$ aryl, 5- to 14-membered heteroaryl, $C_{6-12}$ aralkyl, —C(═O)$R^5$, —OC(═O)$R^5$, —C(═O)O$R^5$, —O$R^5$, —S$R^5$, —S(═O)$R^5$, —S(═O)$_2R^5$, —S(═O)$_2NR^5R^6$, —$NR^5R^6$, —C(═O)$NR^5R^6$, —$NR^5$—C(═O)$R^6$, —$NR^5$—C(═O)O$R^6$, —$NR^5$—S(═O)$_2$—$R^6$, —$NR^5$—C(═O)—$NR^5R^6$, —$C_{1-6}$ alkylene-$NR^5R^6$, —$C_{1-6}$ alkylene-O(P═O)(OH)$_2$ and —O—$C_{1-6}$ alkylene-$NR^5R^6$;

the above alkyl, alkylene, alkenyl, alkynyl, cyclic hydrocarbyl, hydrocarbon ring, heterocyclyl, heterocycle, aryl, aromatic ring, heteroaryl, heteroaromatic ring and aralkyl, at each occurrence, are each optionally substituted with one or more substituents independently selected from the group consisting of halogen, hydroxyl, oxo, amino, cyano, nitro, $C_{1-6}$ alkyl, $C_{2-6}$ alkenyl, $C_{2-6}$ alkynyl, $C_{3-6}$ cyclic hydrocarbyl, 3- to 10-membered heterocyclyl, $C_{6-10}$ aryl, 5- to 14-membered heteroaryl, $C_{6-12}$ aralkyl, ═N—O$R^5$, —C(═NH)$NH_2$, —C(═O)$R^5$, —OC(═O)$R^5$, —C(═O)O$R^5$, —O$R^5$, —S$R^5$, —S(═O)$R^5$, —S(═O)$_2$ $R^5$, —S(═O)$_2NR^5R^6$, —$NR^5R^6$, —C(═O)$NR^5R^6$, —$NR^5$—C(═O)$R^6$, —$NR^5$—C(═O)O$R^6$, —$NR^5$—S(═O)$_2$—$R^6$, —$NR^5$—C(═O)—$NR^5R^6$, —$C_{1-6}$ alkylene-$NR^5R^6$ and —O—$C_{1-6}$ alkylene-$NR^5R^6$, and the alkyl, cyclic hydrocarbyl, heterocyclyl, aryl, heteroaryl and aralkyl are further optionally substituted with one or more substituents independently selected from the group consisting of halogen, hydroxyl, oxo, amino, cyano, nitro, $C_{1-6}$ alkyl, $C_{3-6}$ cyclic hydrocarbyl, 3- to 10-membered heterocyclyl, $C_{6-10}$ aryl, 5- to 14-membered heteroaryl and $C_{6-12}$ aralkyl;

$R^5$ and $R^6$, at each occurrence, are each independently selected from the group consisting of H, $C_{1-6}$ alkyl, $C_{3-10}$ cyclic hydrocarbyl, 3- to 10-membered heterocyclyl, $C_{6-10}$ aryl, 5- to 14-membered heteroaryl and $C_{6-12}$ aralkyl;

m, at each occurrence, is each independently an integer of 0, 1, 2 or 3;

n is an integer of 0, 1 or 2;

i is an integer of 0, 1 or 2; and g is an integer of 0, 1, 2, 3 or 4;

wherein the fatty liver disease is preferably an alcoholic fatty liver disease (AFLD) or a non-alcoholic fatty liver disease (NAFLD), and the steatohepatitis is preferably an alcoholic steatohepatitis (ASH) or a non-alcoholic steatohepatitis (NASH).

In another aspect, the present disclosure provides use of the compound of Formula (I) or a pharmaceutically acceptable salt, ester, stereoisomer, polymorph, solvate, N-oxide, isotopically labeled compound, metabolite or prodrug thereof in the manufacture of a medicament for preventing, alleviating and/or treating a fatty liver disease and/or steatohepatitis, wherein the fatty liver disease is preferably an alcoholic fatty liver disease (AFLD) or a non-alcoholic fatty liver disease (NAFLD), and the steatohepatitis is preferably an alcoholic steatohepatitis (ASH) or a non-alcoholic steatohepatitis (NASH).

In yet another aspect, the present disclosure provides the compound of Formula (I) or a pharmaceutically acceptable salt, ester, stereoisomer, polymorph, solvate, N-oxide, isotopically labeled compound, metabolite or prodrug thereof for use of preventing, alleviating and/or treating a fatty liver disease and/or steatohepatitis, wherein the fatty liver disease is preferably an alcoholic fatty liver disease (AFLD) or a non-alcoholic fatty liver disease (NAFLD), and the steatohepatitis is preferably an alcoholic steatohepatitis (ASH) or a non-alcoholic steatohepatitis (NASH).

BRIEF DESCRIPTION OF THE DRAWINGS

FIG. 5B shows the serum low density lipoprotein level in the mouse model of Example 2.

FIG. 6A shows the percentage of endothelial cells in the liver tissue of Example 2.

FIG. 6B shows the percentage of macrophages in the liver tissue of Example 2.

DETAILED DESCRIPTION OF THE INVENTION

Definition

Figure 1A:
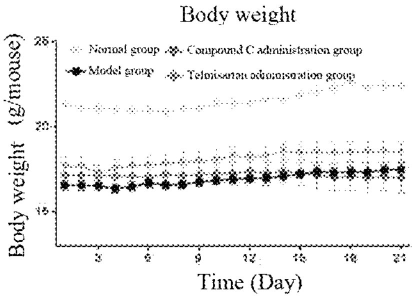
FIG. 1 shows the body weights (FIG. 1A) and body weight changes (FIG. 1B) of the animals during the test.

Unless otherwise defined in the context, all technical and scientific terms used herein are intended to have the same meaning as commonly understood by a person skilled in the art. References to techniques employed herein are intended to refer to the techniques as commonly understood in the art, including variations on those techniques or substitutions of equivalent techniques which would be apparent to a person skilled in the art. While it is believed that the following terms will be readily understood by a person skilled in the art, the following definitions are nevertheless put forth to better illustrate the present invention.

The terms "contain", "include", "comprise", "have", or "relate to", as well as other variations used herein are inclusive or open-ended, and do not exclude additional, unrecited elements or method steps.

As used herein, the term "alkylene" refers to a saturated divalent hydrocarbyl, preferably refers to a saturated divalent hydrocarbyl having 1, 2, 3, 4, 5 or 6 carbon atoms, e.g., methylene, ethylene, propylene or butylene.

As used herein, the term "alkyl" is defined as a linear or branched saturated aliphatic hydrocarbon. In some embodiments, alkyl has 1-12, e.g., 1-6, carbon atoms. For example, as used herein, the term "$C_{1-6}$ alkyl" refers to a linear or branched group having 1-6 carbon atoms (such as methyl, ethyl, n-propyl, isopropyl, n-butyl, isobutyl, sec-butyl, tert-butyl, n-pentyl, isopentyl, neopentyl, or n-hexyl), which is optionally substituted with one or more (e.g., 1 to 3) suitable substituents such as halogen (in which case the group may be referred to as "haloalkyl") (e.g., $CH_2F$, $CHF_2$, $CF_3$, $CCl_3$, $C_2F_5$, $C_2Cl_5$, $CH_2CF_3$, $CH_2Cl$ or $—CH_2CH_2CF_3$ etc.). The term "$C_{1-4}$ alkyl" refers to a linear or branched aliphatic hydrocarbon chain having 1-4 carbon atoms (i.e., methyl, ethyl, n-propyl, isopropyl, n-butyl, isobutyl, sec-butyl or tert-butyl).

As used herein, the term "alkenyl" refers to a linear or branched monovalent hydrocarbyl having a double bond and 2-6 carbon atoms ("$C_{2-6}$ alkenyl"). The alkenyl is e.g., vinyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl and 4-methyl-3-pentenyl. When the compound of the present invention contains an alkenylene group, the compound may exist as the pure E (entgegen) form, the pure Z (zusammen) form, or any mixture thereof.

As used herein, the term "alkynyl" refers to a monovalent hydrocarbyl containing one or more triple bond, and preferably having 2, 3, 4, 5 or 6 carbon atoms, e.g., ethynyl or propynyl.

As used herein, the term "cycloalkyl" refers to a saturated monocyclic or polycyclic (e.g., bicyclic) hydrocarbon ring (e.g., monocyclic, such as cyclopropyl, cyclobutyl, cyclopentyl, cyclohexyl, cycloheptyl, cyclooctyl, or cyclononyl, or bicyclic, including spiro, fused or bridged cyclic system (such as bicyclo[1.1.1]pentyl, bicyclo[2.2.1]heptyl, bicyclo[3.2.1]octyl or bicyclo[5.2.0]nonyl, or decahydronaphthalene etc.)), which is optionally substituted with one or more (e.g., 1 to 3) suitable substituents. The cycloalkyl has 3 to 15 carbon atoms. For example, the term "$C_{3-6}$ cycloalkyl" refers to a saturated monocyclic or polycyclic (e.g., bicyclic) hydrocarbon ring having 3 to 6 ring forming carbon atoms (e.g., cyclopropyl, cyclobutyl, cyclopentyl, or cyclohexyl), which is optionally substituted with one or more (e.g., 1 to 3) suitable substituents, e.g., methyl substituted cyclopropyl.

As used herein, the terms "cyclic hydrocarbylene", "cyclic hydrocarbyl" and "hydrocarbon ring" refer to a saturated (i.e., "cycloalkylene" and "cycloalkyl") or unsaturated (i.e., having one or more double and/or triple bonds in the ring) monocyclic or polycyclic hydrocarbon ring having e.g., 3-10 (suitably having 3-8, and more suitably having 3-6) ring carbon atoms, including but not limited to cyclopropyl(ene) (ring), cyclobutyl(ene) (ring), cyclopentyl(ene) (ring), cyclohexyl(ene) (ring), cycloheptyl(ene) (ring), cyclooctyl(ene) (ring), cyclononyl(ene) (ring), cyclohexenyl(ene) (ring), and the like.

As used herein, the terms "heterocyclyl", "heterocyclylene" and "heterocycle" refer to a saturated (i.e., heterocycloalkyl) or partially unsaturated (i.e., having one or more double and/or triple bonds in the ring) cyclic group having e.g., 3-10 (suitably having 3-8, and more suitably having 3-6) ring atoms, wherein at least one ring atom is a heteroatom selected from the group consisting of N, O and S, and the remaining ring atoms are C. For example, "3- to 10-membered heterocyclyl(ene)" of "3- to 10-membered heterocycle" refers to saturated or partially unsaturated heterocyclyl(ene) or heterocycle having 2-9 (e.g., 2, 3, 4, 5, 6, 7, 8 or 9) ring carbon atoms and one or more (e.g., 1, 2, 3, or 4) heteroatoms independently selected from the group consisting of N, O and S. Examples of heterocyclylene, heterocyclyl and heterocycle include, but are not limited to oxiranyl(ene), aziridinyl(ene), azetidinyl(ene), oxetanyl(ene), tetrahydrofuranyl(ene), dioxolinyl(ene), pyrrolidinyl(ene), pyrrolidonyl(ene), imidazolidinyl(ene), pyrazolidinyl(ene), pyrrolinyl(ene), tetrahydropyranyl(ene), piperidinyl(ene), morpholinyl(ene), dithianyl(ene), thiomorpholinyl(ene), piperazinyl(ene) or trithianyl(ene). Said group also encompasses a bicyclic system, including a spiro, fused, or bridged system (e.g., 8-azaspiro[4.5]decane, 3,9-diazaspiro[5.5]undecane, 2-azabicyclo[2.2.2]octane, etc.). Heterocyclylene, heterocyclyl and heterocycle may optionally be substituted with one or more (e.g., 1, 2, 3 or 4) suitable substituents.

As used herein, the terms "aryl(ene)" and "aromatic ring" refer to an all-carbon monocyclic or fused-ring polycyclic aromatic group having a conjugated n electron system. For example, as used herein, the terms "$C_{6-10}$ aryl(ene)" and "$C_{6-10}$ aromatic ring" refer to an aromatic group containing 6 to 10 carbon atoms, such as phenyl(ene) (benzene ring) or naphthyl(ene) (naphthalene ring). Aryl(ene) or aromatic ring is optionally substituted with one or more (such as 1 to 3) suitable substituents (e.g., halogen, —OH, —CN, $—NO_2$, and $C_{1-6}$ alkyl, etc.).

As used herein, the terms "heteroaryl(ene)" and "heteroaromatic ring" refer to a monocyclic, bicyclic or tricyclic aromatic ring system having 5, 6, 8, 9, 10, 11, 12, 13 or 14 ring atoms, particularly 1 or 2 or 3 or 4 or 5 or 6 or 9 or 10 carbon atoms, and containing at least one heteroatom (such as O, N, or S), which can be same to different. Moreover, in each case, it can be benzo-fused. In particular, "heteroaryl(ene)" or "heteroaromatic ring" is selected from the group consisting of thienyl(ene), furyl(ene), pyrrolyl(ene), oxazolyl(ene), thiazolyl(ene), imidazolyl(ene), pyrazolyl(ene), isoxazolyl(ene), isothiazolyl(ene), oxadiazolyl(ene), triazolyl(ene), thiadiazolyl(ene) etc., and benzo derivatives thereof; or pyridinyl(ene), pyridazinyl(ene), pyrimidinyl(ene), pyrazinyl(ene), triazinyl(ene), etc., and benzo derivatives thereof.

As used herein, the term "aralkyl" preferably means aryl or heteroaryl substituted alkyl, wherein aryl, heteroaryl and alkyl are as defined herein. Normally, the aryl group may have 6-14 carbon atoms, the heteroaryl group may have 5-14 ring atoms, and the alkyl group may have 1-6 carbon atoms. Exemplary aralkyl group includes, but is not limited to, benzyl, phenylethyl, phenylpropyl, phenylbutyl.

As used herein, the term "halo" or "halogen" are defined to include F, Cl, Br, or I.

As used herein, the term "nitrogen containing heterocycle" refers to a saturated or unsaturated monocyclic or bicyclic group having 2, 3, 4, 5, 6, 7, 8, 9, 10, 11, 12 or 13 carbon atoms and at least one nitrogen atom in the ring, which may further optionally comprise one or more (e.g., one, two, three or four) ring members selected from the group consisting of N, O, C═O, S, S═O and $S(═O)_2$. The nitrogen containing heterocycle is attached to the rest of the molecule through the nitrogen atom and any other ring atom in said nitrogen containing heterocycle. The nitrogen containing heterocycle is optionally benzo-fused, and is preferably attached to the rest of the molecule through the nitrogen atom in said nitrogen containing heterocycle and any carbon atom in the fused benzene ring.

The term "substituted" means that one or more (e.g., one, two, three, or four) hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

If a substituent is described as being "optionally substituted," the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more of a list of substituents, one or more of the hydrogens on the nitrogen (to the extent there are any) may each be replaced with an independently selected optional substituent.

If substituents are described as being "independently selected" from a group, each substituent is selected independent of the other(s). Each substituent therefore may be identical to or different from the other substituent(s).

As used herein, the term "one or more" means one or more than one (e.g., 2, 3, 4, 5 or 10) as reasonable.

As used herein, unless specified, the point of attachment of a substituent can be from any suitable position of the substituent.

When a bond to a substituent is shown to cross a bond connecting two atoms in a ring, then such substituent may be bonded to any of the ring-forming atoms in that ring that are substitutable.

The present invention also includes all pharmaceutically acceptable isotopically labeled compounds, which are identical to those of the present invention except that one or more atoms are replaced by an atom having the same atomic number, but an atomic mass or mass number different from the atomic mass or mass number which predominates in nature. Examples of isotopes suitable for inclusion in the compound of the present invention include, but are not limited to, isotopes of hydrogen, such as $^{2}H$, $^{3}H$; carbon, such as $^{11}C$, $^{13}C$, and $^{14}C$; chlorine, such as $^{36}Cl$; fluorine, such as $^{18}F$; iodine, such as $^{123}I$ and $^{125}I$; nitrogen, such as $^{13}N$ and $^{15}N$; oxygen, such as $^{15}O$, $^{17}O$, and $^{18}O$; phosphorus, such as $^{32}P$; and sulfur, such as $^{35}S$. Certain isotopically labeled compounds of the present invention, for example those incorporating a radioactive isotope, are useful in drug and/or substrate tissue distribution studies (e.g., assays). The radioactive isotopes tritium, i.e., $^{3}H$, and carbon-14, i.e., $^{14}C$, are particularly useful for this purpose in view of their ease of incorporation and ready means of detection. Substitution with positron-emitting isotopes, such as $^{11}C$, $^{18}F$, $^{15}O$ and $^{13}N$, can be useful in positron emission tomography (PET) studies for examining substrate receptor occupancy. Isotopically labeled compounds of the present invention can generally be prepared by processes analogous to those described in the accompanying Schemes and/or in the Examples and Preparations, by using an appropriate isotopically labeled reagent in place of the non-labeled reagent previously employed. Pharmaceutically acceptable solvates in accordance with the invention include those wherein the solvent of crystallization may be isotopically substituted, e.g., $D_2O$, acetone-$d_6$, or DMSO-$d_6$.

The term "stereoisomer" refers to isomers with at least one asymmetric center. A compound having one or more (e.g., one, two, three or four) asymmetric centers can give rise to a racemic mixture, single enantiomer, diastereomer mixture and individual diastereomer. Certain individual molecules may exist as geometric isomers (cis/trans). Similarly, the compound of the present invention may exist as a mixture of two or more structurally different forms in rapid equilibrium (generally referred to as tautomer). Typical examples of a tautomer include a keto-enol tautomer, phenol-keto tautomer, nitroso-oxime tautomer, imine-enamine tautomer and the like. It is to be understood that all such isomers and mixtures thereof in any proportion (such as 60%, 65%, 70%, 75%, 80%, 85%, 90%, 95%, 96%, 97%, 98%, and 99%) are encompassed within the scope of the present invention.

The chemical bonds of the compound of the present invention may be depicted herein using a solid line ( ), a solid wedge ( ), or a dotted wedge ( ). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that the stereoisomer shown is present. When present in racemic compounds, solid and dotted wedges are used to define relative stereochemistry, rather than absolute stereochemistry. Unless stated otherwise, it is intended that the compound of the present invention can exist as stereoisomers, which include cis and trans isomers, optical isomers such as R and S enantiomers, diastereomers, geometric isomers, rotational isomers, conformational isomers, atropisomers, and mixtures thereof. The compound of the present invention may exhibit more than one type of isomerism, and consist of mixtures thereof (such as racemates and diastereomeric pairs).

The present invention includes all possible crystalline forms or polymorphs of the compound of the present invention, either as a single polymorph, or as a mixture of more than one polymorphs, in any ratio.

It also should be understood that, certain compounds of the present invention can be used for the treatment in a free form, or where appropriate, in a form of a pharmaceutically acceptable derivative. In the present invention, the pharmaceutically acceptable derivative includes, but is not limited to a pharmaceutically acceptable salt, ester, solvate, N-oxide, metabolite or prodrug, which can directly or indirectly provide the compound of the present invention or a metabolite or residue thereof after being administered to a patient in need thereof. Therefore, "the compound of the present invention" mentioned herein also means to encompass various derivative forms of the compound as mentioned above.

A pharmaceutically acceptable salt of the compound of the present invention includes an acid addition salt and a base addition salt thereof.

A suitable acid addition salt is formed from an acid which forms a pharmaceutically acceptable salt. Specific examples include acetate, adipate, aspartate, benzoate, besylate, bicarbonate/carbonate, bisulfate/sulfate, borate, camphorsulfonate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

A suitable base addition salt is formed from a base which forms a pharmaceutically acceptable salt. Specific examples include aluminum, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, 2002). The method for preparing a pharmaceutically acceptable salt of the compound of the present invention is known to a person skilled in the art.

As used herein, the term "ester" refers to those derived from the compounds of the various formulae in the present application, which include physiologically-hydrolyzable esters (which may be hydrolyzed under physiological conditions to release the compounds of the present invention in the form of free acids or alcohols). The compound of the present invention itself may be an ester as well.

The compound of the present invention can exist as a solvate (preferably a hydrate), wherein the compound of the present invention contains a polar solvent, in particular water, methanol or ethanol for example, as a structural element of the crystal lattice of the compound. The amount of the polar solvent, in particular water, may exist in a stoichiometric or non-stoichiometric ratio.

As can be appreciated by a person skilled in the art, not all nitrogen containing heterocycles can form N-oxides since the nitrogen requires an available lone-pair electron for oxidation to the oxide; a person skilled in the art will recognize those nitrogen containing heterocycles which can form N-oxides. A person skilled in the art will also recognize that tertiary amines can form N-oxides. Synthetic methods for the preparation of N-oxides of heterocycles and tertiary amines are well known to a person skilled in the art, and they include the oxidation of heterocycles and tertiary amines with peroxy acids such as peracetic acid and m-chloroperbenzoic acid (MCPBA), hydrogen peroxide, alkyl hydroperoxides such as tert-butyl hydroperoxide, sodium perborate, and dioxiranes such as dimethyldioxirane. These methods for the preparation of N-oxides have been extensively described and reviewed in literatures, see e.g., T. L. Gilchrist, *Comprehensive Organic Synthesis*, vol. 7, pp 748-750; A. R. Katritzky and A. J. Boulton, Eds., Academic Press; and G. W. H. Cheeseman and E. S. G. Werstiuk, *Advances in Heterocyclic Chemistry*, vol. 22, pp 390-392, A. R. Katritzky and A. J. Boulton, Eds., Academic Press.

The metabolite of the compound of the present invention, namely a substance formed in vivo upon administration of the compound of the present invention, is also included within the scope of the present invention. Such a product may result e.g., from the oxidation, reduction, hydrolysis, amidation, de-amidation, esterification, enzymolysis, and the like, of the administered compound. Accordingly, the present invention encompasses the metabolite of the compound of the present invention, including a compound produced by a method comprising contacting the compound of the present invention with a mammal for a period of time sufficient to result in a metabolic product thereof.

Also within the scope of the present invention is a prodrug of the compound of the invention, which is certain derivative of the compound of the invention that may have little or no pharmacological activity itself, but can, when administered into or onto the body, be converted into the compound of the invention having the desired activity, for example, by hydrolytic cleavage. In general, such prodrug will be a functional derivative of the compound which is readily converted in vivo into the compound with desired therapeutic activity. Further information on the use of the prodrug may be found in "Pro-drugs as Novel Delivery Systems", Vol. 14, ACS Symposium Series (T. Higuchi and V. Stella). The prodrug in accordance with the invention can, for example, be produced by replacing appropriate functionalities present in the compound of the present invention with certain moieties known to those skilled in the art as "pro-moieties" as described, for example, in "Design of Prodrugs" by H. Bundgaard (Elsevier, 1985).

The present invention further encompasses the compound of the present invention having a protecting group. During any of the processes for preparation of the compound of the present invention, it may be necessary and/or desirable to protect sensitive or reactive groups on any of the molecules concerned, thereby resulting in the chemically protected form of the compound of the present invention. This may be achieved by means of conventional protecting groups, e.g., those described in T. W. Greene & P. G. M. Wuts, Protective Groups in Organic Synthesis, John Wiley & Sons, 1991, which is incorporated herein by reference. The protecting groups may be removed at a convenient subsequent stage using methods known from the art.

The term "about" refers to a range within ±10%, preferably within ±5%, and more preferably within ±2% of the specified value.

"Non-alcoholic steatohepatitis (NASH)" is a liver disease, not associated with alcohol consumption, characterized by fatty change of hepatocytes, accompanied by intralobular inflammation and fibrosis.

NASH resembles the alcoholic liver disease, but occurs in people who drink little or no alcohol. The major feature in NASH is fat in the liver, along with inflammation and damage. Most people with NASH feel well and are not aware that they have a liver problem. Nevertheless, NASH can be severe and can lead to cirrhosis in which the liver is permanently damaged and scarred and no longer able to function properly.

Non-alcoholic fatty liver disease (NAFLD) is a fatty liver disease common in chronic liver disease subjects. Excess liver fat can lead to liver complications. While not alcohol-related, these conditions can be related to obesity, diet, and other health-related issues.

Individuals with elevated liver enzymes and/or one having a fatty liver (e.g., determined by ultrasound or fatty liver index) are considered to have NASH or NAFLD. A reduction in enzymes, fat, or fatty liver index is an indicator of an improving or corrected condition.

The term "effective amount" refers to an amount sufficient to achieve the desired therapeutic effect, under the conditions of administration, such as an amount sufficient to lower fasting plasma glucose (FPG), reduce weight, reduce blood lipids such as cholesterol and triglycerides (TGs), reduce liver enzymes, raise high density lipoprotein cholesterol (HDL-C) levels, and lower blood pressure. For example, an "effective amount" of a compound of Formula (I) administered to a patient exhibiting, suffering, or prone to suffer from a fatty liver disease and/or steatohepatitis (e.g., NASH or NAFLD) is such an amount which causes an improvement in the pathological symptoms, disease progression, physiological conditions associated with or induces resistance to succumbing to the afore mentioned disorders.

The term "prevent", "preventing" or "prevention" as used herein refers to administering a medicament beforehand to avert or forestall the appearance of one or more symptoms of a disease or disorder. The person of ordinary skill in the medical art recognizes that the term "prevent", "preventing" or "prevention" is not an absolute term. In the medical art, it is understood to refer to the prophylactic administration of a drug to substantially diminish the likelihood or seriousness of a condition, or symptom of the condition, and this is the sense intended in this disclosure. Prophylactic measures are divided between primary prophylaxis (to prevent the development of a disease) and secondary prophylaxis (whereby the disease has already developed, and the patient is protected against worsening of this process).

Unless otherwise indicated, the term "treat", "treating" or "treatment", as used herein, means reversing, alleviating, inhibiting the progress of, or preventing the disorder or condition to which such term applies, or one or more symptoms of such disorder or condition.

In some embodiments, treatment results in the amelioration of at least one measurable physical symptom of a fatty liver disease and/or steatohepatitis (e.g., NAFLD and/or NASH), such as, for example, weight loss, weakness or fatigue. In other embodiments, treatment results in amelioration of at least one clinical parameter or finding of a fatty liver disease and/or steatohepatitis (e.g., NAFLD and/or NASH), such as, for example, abnormal liver fat accumulation, abnormal levels of liver enzymes, fatty degeneration (e.g., assessed by the percentage of hepatocytes containing fat, or grading by image analysis), collagen accumulation (e.g., assessed by the staining positive percentage of liver tissue by Picrosirius red which indicates the presence of collagen) or ballooning degeneration (e.g., assessed by the percentage of swollen hepatocytes).

In other embodiments, treatment results in the reduction, inhibition or slowing down of the progression of a fatty liver disease and/or steatohepatitis (e.g., NAFLD and/or NASH), either physically by, e.g., stabilization of a measurable symptom or a set of symptoms (such as fatigue, weight loss or weakness), or clinically/physiologically by, e.g., stabilization of a measurable parameter, such as abnormal fat accumulation in liver, abnormal levels of liver enzymes, abnormal findings in a liver biopsy, fatty degeneration, collagen accumulation or ballooning degeneration, or both. In another embodiment, treatment may also result in averting the cause and/or effects or clinical manifestation of a fatty liver disease and/or steatohepatitis (e.g., NAFLD and/or NASH), or one of the symptoms developed as a result of a fatty liver disease and/or steatohepatitis (e.g., NAFLD and/or NASH), prior to the disease or disorder fully manifesting itself.

In some embodiments, treatment results in an increase in survival rate or survival time in a patient with a fatty liver disease and/or steatohepatitis (e.g., NAFLD and/or NASH). In some embodiments, treatment results in the reduction of the potential for a patient with a fatty liver disease and/or steatohepatitis (e.g., NAFLD and/or NASH) needing a liver transplant. In other embodiments, treatment results in the elimination of the need for a patient with a fatty liver disease and/or steatohepatitis (e.g., NAFLD and/or NASH) to undergo a liver transplant.

As used herein, the term "subject" includes a human or non-human animal. An exemplary human subject includes a human subject having a disease (such as one described herein) (referred to as a patient), or a normal subject. The term "non-human animal" as used herein includes all vertebrates, such as non-mammals (e.g., birds, amphibians, reptiles) and mammals, such as non-human primates, livestock and/or domesticated animals (such as sheep, dog, cat, cow, pig and the like).

Mode of Carrying Out the Invention

In some embodiments, the present disclosure provides a method for preventing, alleviating and/or treating a fatty liver disease and/or steatohepatitis, comprising administering to a subject in need thereof an effective amount of a compound of Formula (I) or a pharmaceutically acceptable salt, ester, stereoisomer, polymorph, solvate, N-oxide, isotopically labeled compound, metabolite or prodrug thereof:

Formula (I)

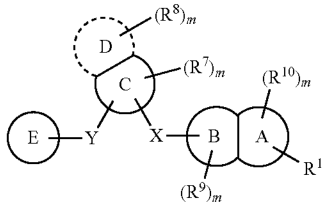

wherein:

X and Y are each independently selected from the group consisting of a direct bond, C(═O), O, S(═O), and NR;

R is selected from the group consisting of H, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl and $C_{6-12}$ aralkyl, and at most 2 ring members in the cyclic hydrocarbyl and heterocyclyl are C(═O);

ring A and ring B are each independently selected from the group consisting of saturated or partially unsaturated $C_{3-10}$ hydrocarbon ring, saturated or partially unsaturated 3- to 10-membered heterocycle, $C_{6-10}$ aromatic ring and 5- to 14-membered heteroaromatic ring, and at most 2 ring members in the hydrocarbon ring and heterocycle are C(═O); provided that when ring B is a heterocycle containing a nitrogen atom, ring B is not attached to X via the nitrogen atom;

ring C is selected from the group consisting of saturated or partially unsaturated $C_{3-10}$ hydrocarbon ring, saturated or partially unsaturated 3- to 10-membered heterocycle, $C_{6-10}$ aromatic ring and 5- to 14-membered heteroaromatic ring, and at most 2 ring members in the hydrocarbon ring and heterocycle are C(═O);

ring D is absent, or is selected from the group consisting of saturated or partially unsaturated $C_{3-10}$ hydrocarbon ring, saturated or partially unsaturated 3- to 10-membered heterocycle, $C_{6-10}$ aromatic ring and 5- to 14-membered heteroaromatic ring, and at most 2 ring members in the hydrocarbon ring and heterocycle are C(═O);

ring E is selected from the group consisting of

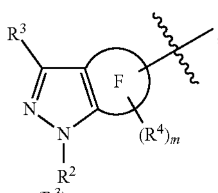

,

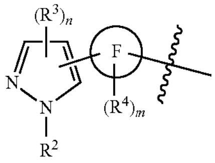

and

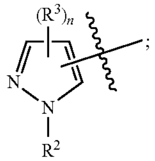

;

ring F is selected from the group consisting of saturated or partially unsaturated $C_{3-10}$ hydrocarbon ring, saturated or partially unsaturated 3- to 10-membered heterocycle, $C_{6-10}$ aromatic ring and 5- to 14-membered heteroaromatic ring, and at most 2 ring members in the hydrocarbon ring and heterocycle are C(═O);

$R^1$ is selected from the group consisting of H, —$NH_2$, $C_{1-6}$ alkyl, $C_{6-10}$ aryl, 5- to 14-membered heteroaryl, N-methylpyrrolidinyl, N-methylpiperidinyl,

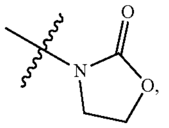 [SMILES: *N1CCOC1=O]

acetyl,

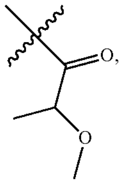 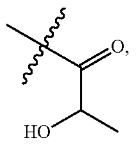

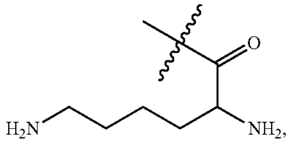

—C(═O)—($C_{1-6}$ alkylene)$_n$-$CF_3$, —C(═O)—($C_{1-6}$ alkylene)$_n$-CN, —C(═O)-(saturated or partially unsaturated $C_{3-10}$ cyclic hydrocarbyl), —NHC(═O)-(saturated or partially unsaturated $C_{3-10}$ cyclic hydrocarbyl), —C(═O)-(saturated or partially unsaturated 3- to 10-membered heterocyclyl), —C(═O)—$C_{1-6}$ alkylene-(saturated or partially unsaturated 3- to 10-membered heterocyclyl), —C(═O)-(5- to 14-membered heteroaryl), —C(═O)—$C_{1-6}$ alkylene-NH ($C_{1-6}$ alkyl), —C(═O)—$C_{1-6}$ alkylene-N($C_{1-6}$ alkyl)$_2$, N-methylpiperazine substituted acetyl, —S(═O)$_2R^{1a}$, —P(═O)$R^{1a}R^{1b}$,

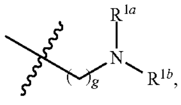 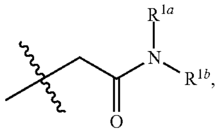

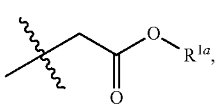 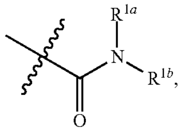

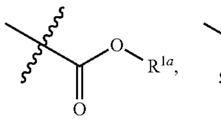 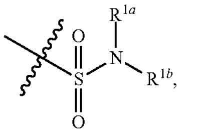

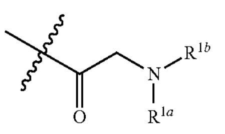 and 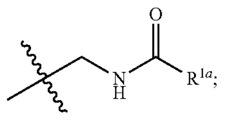

provided that when one of $R^1$ and $R^{10}$ is $C_{1-6}$ alkyl, and the other is H or $C_{3-10}$ cyclic hydrocarbyl, at least one of X and Y is a direct bond, and ring C is not a 5-membered heteroaromatic ring; when one of $R^1$ and $R^{10}$ is H, and the other is

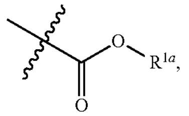

ring C is not a 5-membered heteroaromatic ring; when both $R^1$ and $R^{10}$ are H, ring A contains at least one nitrogen atom, and is not a 5- or 6-membered ring; when one of $R^1$ and $R^{10}$ is H, and the other is

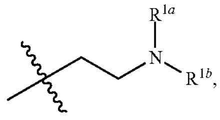

ring C is not a 5-membered heteroaromatic ring; and when one of $R^1$ and $R^{10}$ is H, and the other is H or acetyl, ring D is absent;

$R^{1a}$ and $R^{1b}$ are each independently selected from the group consisting of H, halogen, amino, cyano, nitro, $C_{1-6}$ alkyl, $C_{2-6}$ alkenyl, $C_{2-6}$ alkynyl, $C_{3-10}$ cyclic hydrocarbyl, 3- to 10-membered heterocyclyl, $C_{6-10}$ aryl, 5- to 14-membered heteroaryl, $C_{6-12}$ aralkyl, —C(═O)$R^5$, —OC(═O)$R^5$, —C(═O)O$R^5$, —O$R^5$, —S$R^5$, —S(═O)$R^5$, —S(═O)$_2R^5$, —S(═O)$_2NR^5R^6$, —$NR^5R^6$, —C(═O)$NR^5R^6$, —$NR^5$—C(═O)$R^6$, —$NR^5$—C(═O)O$R^6$, —$NR^5$—S(═O)$_2$—$R^6$, —$NR^5$—C(═O)—$NR^5R^6$, —$C_{1-6}$ alkylene-$NR^5R^6$, —$C_{1-6}$ alkylene-O$R^5$ and —O—$C_{1-6}$ alkylene-$NR^5R^6$, provided that when one of $R^{1a}$ and $R^{1b}$ is n-propyl, the other is not H; or $R^{1a}$ and $R^{1b}$ together with the atom to which they are attached form a 3- to 12-membered heterocycle or heteroaromatic ring;

$R^2$, $R^3$, $R^4$, $R^7$, $R^8$, $R^9$ and $R^{10}$, at each occurrence, are each independently selected from the group consisting of H, halogen, amino, cyano, nitro, $C_{1-6}$ alkyl, $C_{2-6}$ alkenyl, $C_{2-6}$ alkynyl, $C_{3-10}$ cyclic hydrocarbyl, 3- to 10-membered heterocyclyl, $C_{6-10}$ aryl, 5- to 14-membered heteroaryl, $C_{6-12}$ aralkyl, —C(═O)$R^5$, —OC(═O)$R^5$, —C(═O)O$R^5$, —O$R^5$, —S$R^5$, —S(═O)$R^5$, —S(═O)$_2R^5$, —S(═O)$_2NR^5R^6$, —$NR^5R^6$, —C(═O)$NR^5R^6$, —$NR^5$—C(═O)$R^6$, —$NR^5$—C(═O)O$R^6$, —$NR^5$—S(═O)$_2$—$R^6$, —$NR^5$—C(═O)—$NR^5R^6$, —$C_{1-6}$ alkylene-$NR^5R^6$, —$C_{1-6}$ alkylene-O(P═O)(OH)$_2$ and —O—$C_{1-6}$ alkylene-$NR^5R^6$;

the above alkyl, alkylene, alkenyl, alkynyl, cyclic hydrocarbyl, hydrocarbon ring, heterocyclyl, heterocycle, aryl, aromatic ring, heteroaryl, heteroaromatic ring and aralkyl, at each occurrence, are each optionally substituted with one or more substituents independently selected from the group consisting of halogen, hydroxyl, oxo, amino, cyano, nitro, $C_{1-6}$ alkyl, $C_{2-6}$ alkenyl, $C_{2-6}$ alkynyl, $C_{3-6}$ cyclic hydrocarbyl, 3- to 10-membered heterocyclyl, $C_{6-10}$ aryl, 5- to 14-membered heteroaryl, $C_{6-12}$ aralkyl, ═N—O$R^5$, —C(═NH)$NH_2$, —C(═O)$R^5$, —OC(═O)$R^5$, —C(═O)O$R^5$, —O$R^5$, —S$R^5$, —S(═O)$R^5$, —S(═O)$_2$ $R^5$, —S(═O)$_2NR^5R^6$, —$NR^5R^6$, —C(═O)$NR^5R^6$, —$NR^5$—C(═O)$R^6$, —$NR^5$—C(═O)O$R^6$, —$NR^5$—S(═O)$_2$—$R^6$, —$NR^5$—C(═O)—$NR^5R^6$, —$C_{1-6}$ alkylene-$NR^5R^6$ and —O—$C_{1-6}$ alkylene-$NR^5R^6$, and the alkyl, cyclic hydrocarbyl, heterocyclyl, aryl, heteroaryl and aralkyl are further optionally substituted with one or more substituents independently selected from the group consisting of halogen, hydroxyl, oxo, amino, cyano, nitro, $C_{1-6}$ alkyl, $C_{3-6}$ cyclic hydrocarbyl, 3- to 10-membered heterocyclyl, $C_{6-10}$ aryl, 5- to 14-membered heteroaryl and $C_{6-12}$ aralkyl;

$R^5$ and $R^6$, at each occurrence, are each independently selected from the group consisting of H, $C_{1-6}$ alkyl, $C_{3-10}$ cyclic hydrocarbyl, 3- to 10-membered heterocyclyl, $C_{6-10}$ aryl, 5- to 14-membered heteroaryl and $C_{6-12}$ aralkyl;

m, at each occurrence, is each independently an integer of 0, 1, 2 or 3;

n is an integer of 0, 1 or 2;

i is an integer of 0, 1 or 2; and g is an integer of 0, 1, 2, 3 or 4;

wherein the fatty liver disease is preferably an alcoholic fatty liver disease (AFLD) or a non-alcoholic fatty liver disease (NAFLD), and the steatohepatitis is preferably an alcoholic steatohepatitis (ASH) or a non-alcoholic steatohepatitis (NASH).

In preferred embodiments, X and Y are each independently selected from the group consisting of a direct bond, C(=O), O, S, S(=O), $S(=O)_2$, NH and $NCH_3$, and preferably, at least one of X and Y is a direct bond.

In preferred embodiments, at least one of ring A and ring B is selected from the group consisting of saturated or partially unsaturated 3- to 10-membered heterocycle and 5- to 14-membered heteroaromatic ring, and at most 2 ring members in the heterocycle are C(=O).

In some embodiments,

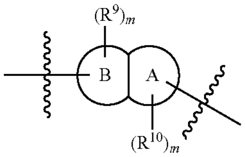

is

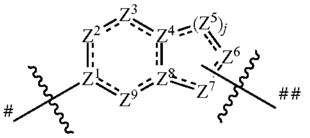

or

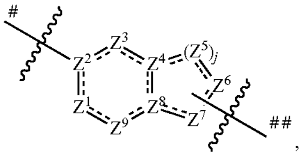

, preferably

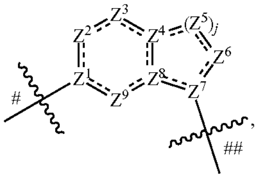

-continued

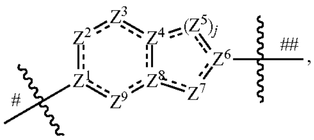

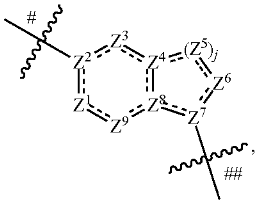

or

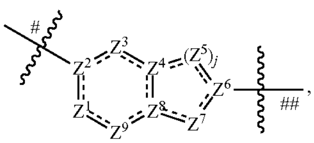

the above group is attached to X at either of the two positions labeled # or ##, and is attached to $R^1$ at the other position, wherein:

---- represents either a single or a double bond, and the adjacent bonds are not double bonds simultaneously;

$Z^1$, $Z^2$, $Z^3$, $Z^4$, $Z^5$, $Z^6$, $Z^7$, $Z^8$ and $Z^9$, at each occurrence, are each independently selected from the group consisting of C, $CR^9$, $C(R^9)_2$, $CR^{10}$, $C(R^{10})_2$, C(=O), N, $NR^9$, $NR^{10}$, O and S; preferably, $Z^1$, $Z^2$, $Z^3$, $Z^4$, $Z^5$, $Z^6$, $Z^7$, $Z^8$ and $Z^9$, at each occurrence, are each independently selected from the group consisting of C, CH, CF, CCl, $CCH_3$, $CH_2$, $C(CH_3)_2$, C—$OCH_3$, C(=O), N, NH, $NCH_3$, $NCH_2CH_3$, $NCH(CH_3)_2$, NCH=$CH_2$, $NCH_2F$, $NCHF_2$, $NCH_2CHF_2$, NC(=O)$CH_3$, $NCH_2OH$, $NCH_2OMe$, $NCH_2CH_2OMe$, $NCH_2$—O(P=O)$(OH)_2$,

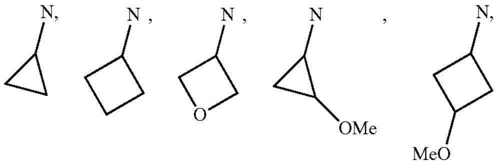

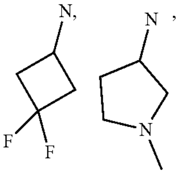

$NCH_2CH_2$—$N(CH_3)_2$, O and S; and j is 0, 1, 2, 3 or 4;

provided that at most two groups among $Z^1$-$Z^9$ are simultaneously C(=O), and the atom attached to X is not a nitrogen atom.

In more preferred embodiments,

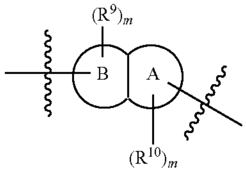

is

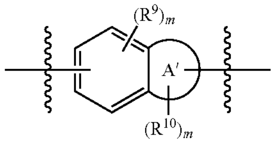

,

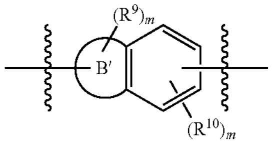

or

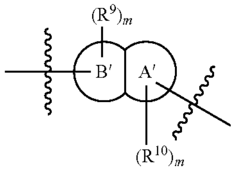

, wherein ring A' and ring B' are each independently selected from the group consisting of saturated or partially unsaturated 3- to 10-membered heterocycle and 5- to 14-membered heteroaromatic ring, and at most 2 ring members in the heterocycle are C(=O); provided that when ring B' is a heterocycle containing a nitrogen atom, ring B' is not attached to X via the nitrogen atom.

In some embodiments,

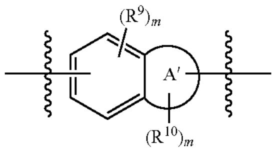

is preferably

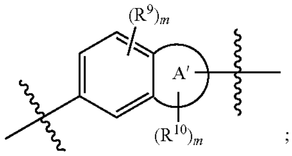

; and

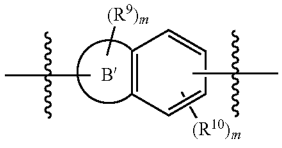

is preferably

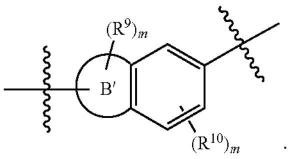

.

In preferred embodiments, $R^9$ and $R^{10}$, at each occurrence, are each independently selected from the group consisting of halogen (e.g., F, Cl, or Br), methyl, ethyl, propyl (e.g., n-propyl or isopropyl), vinyl, cyclopropyl, cyclobutyl, cyclopentyl, oxetanyl, monofluoromethyl, difluoromethyl, trifluoromethyl, $-CH_2CHF_2$, acetyl, $-OCH_3$, $-CH_2OH$, $-CH_2OCH_3$, $-CH_2CH_2OCH_3$, $-CH_2-O(P{=}O)(OH)_2$,

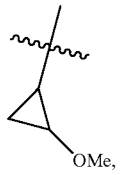

,

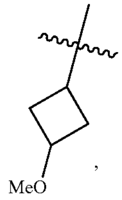

,

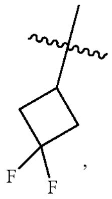

,

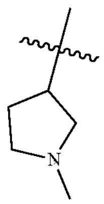

and $-CH_2CH_2-N(CH_3)_2$.

In the most preferred embodiments,

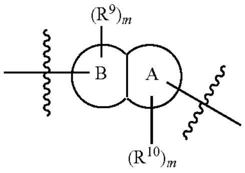

is selected from the group consisting of

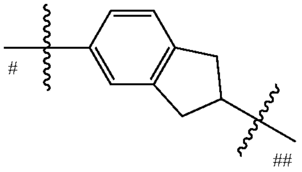

,

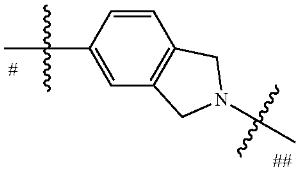

,

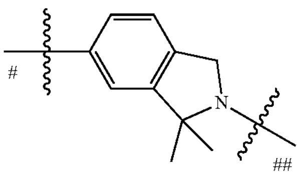

,

-continued
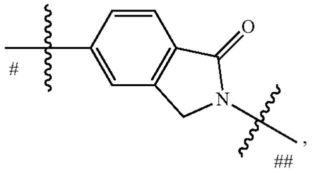
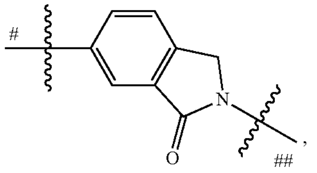
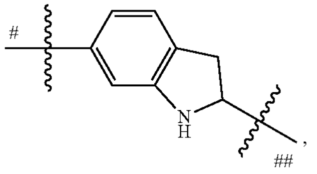
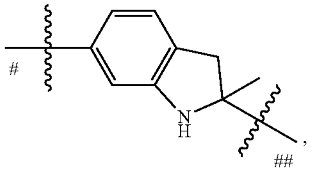
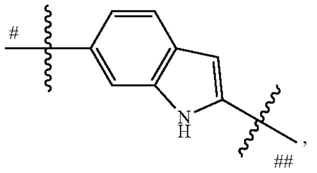
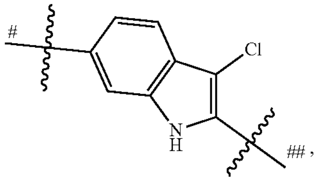
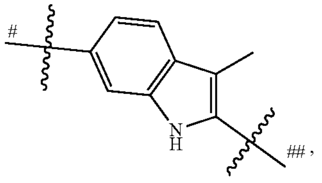
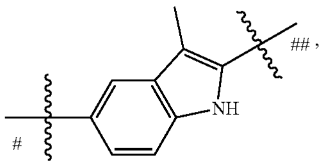
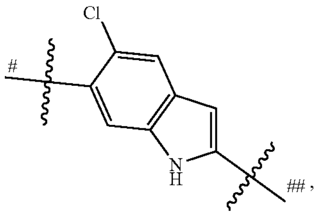
-continued
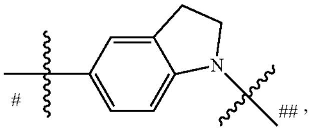
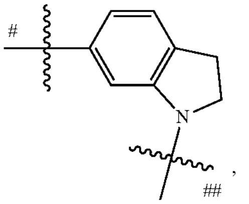
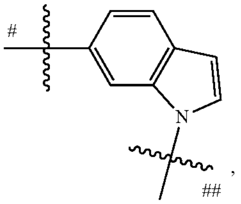
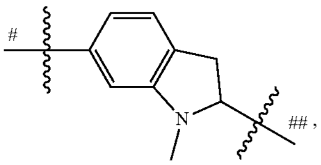
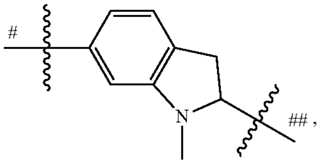
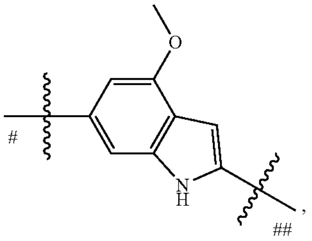
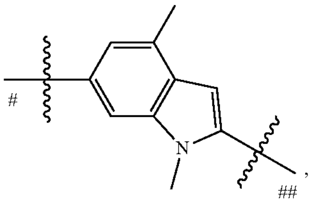
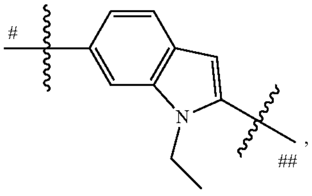
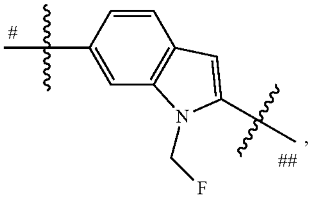
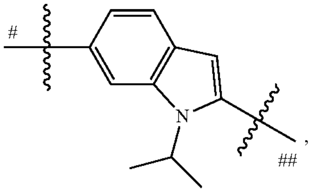

-continued
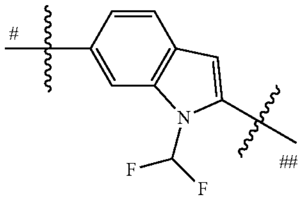
,
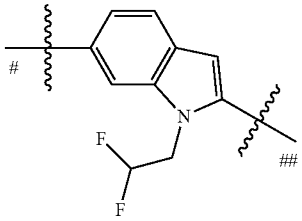
,
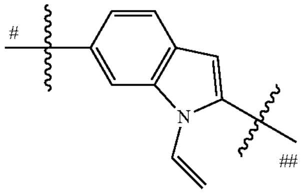
,
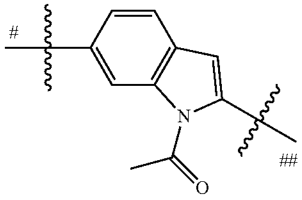
,
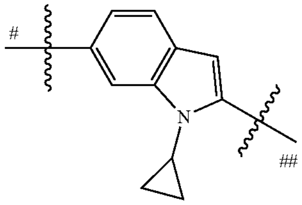
,
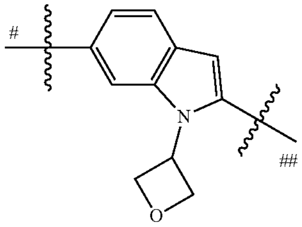
,
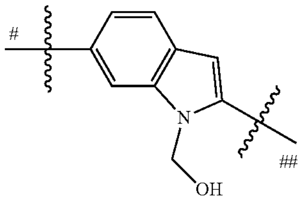
,
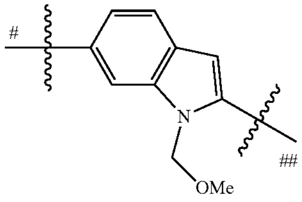
,
-continued
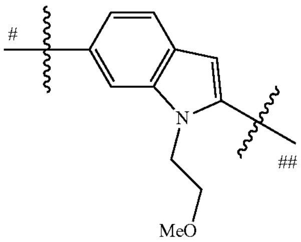
,
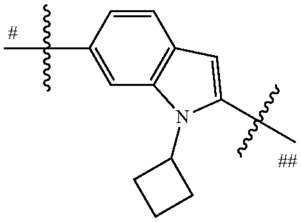
,
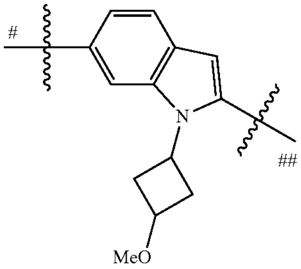
,
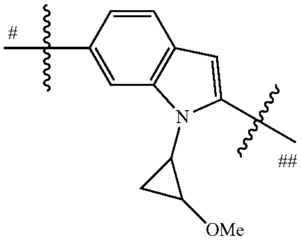
,
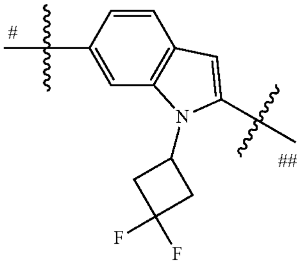
,
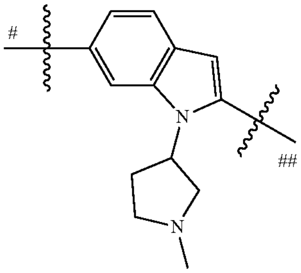
,
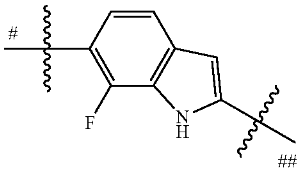
, -continued
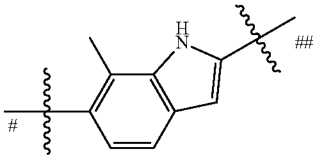
,
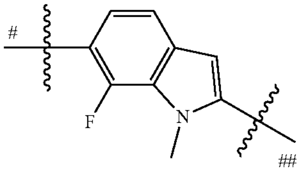
,
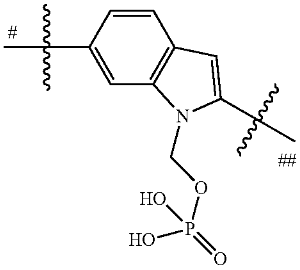
,
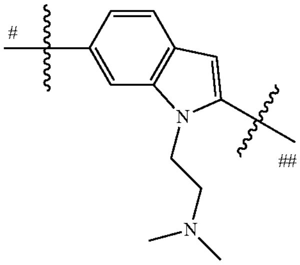
,
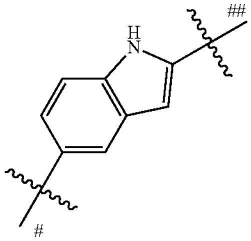
,
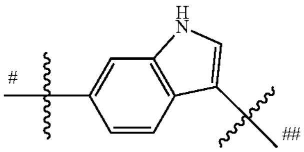
,
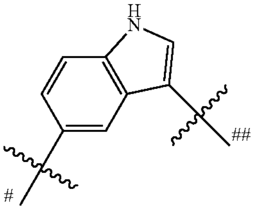
,
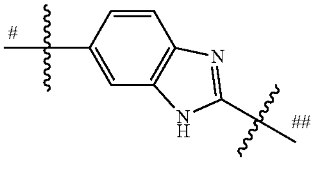
,
-continued
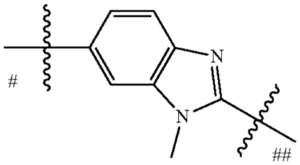
,
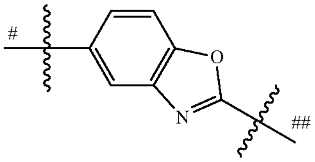
,
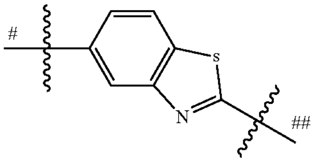
,
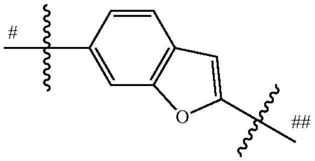
,
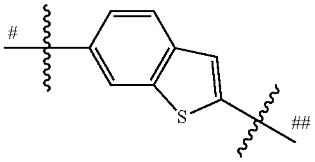
,
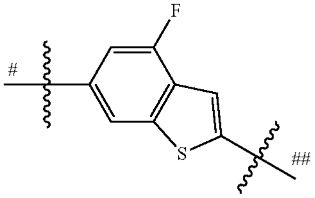
,
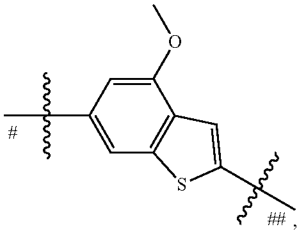
,
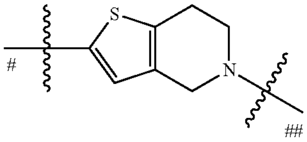
,
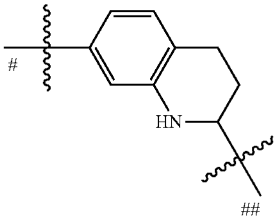
, -continued
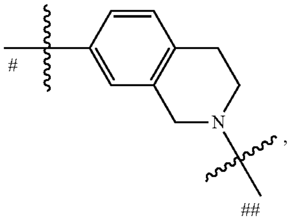
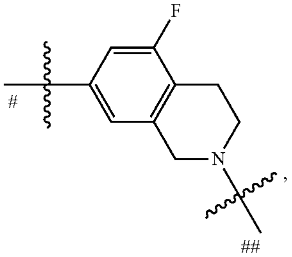
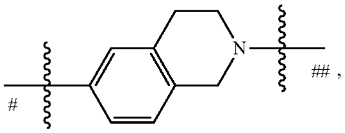
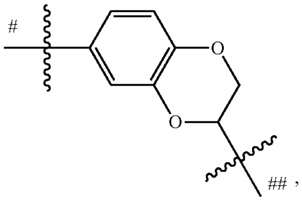
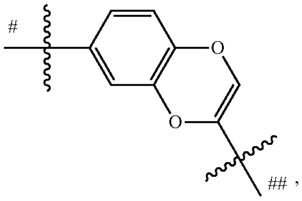
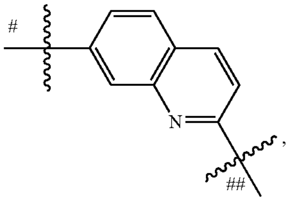
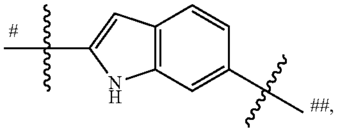
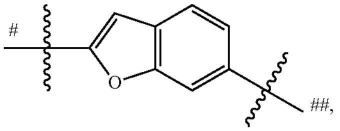
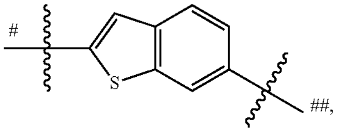
-continued
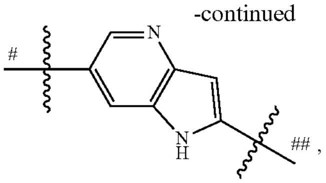
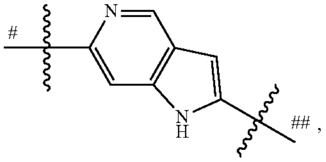
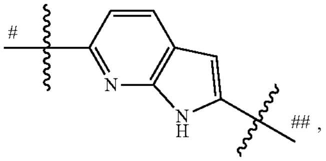
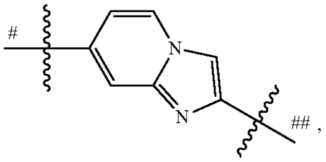
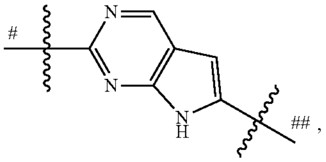
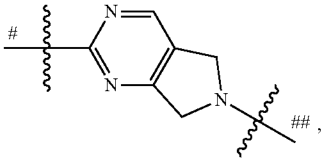
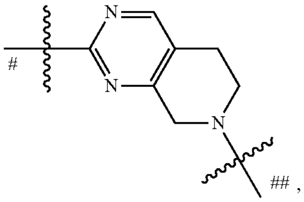
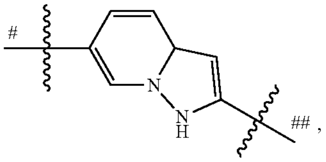
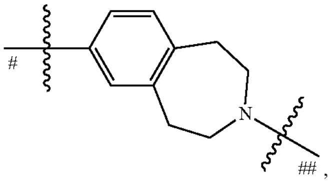
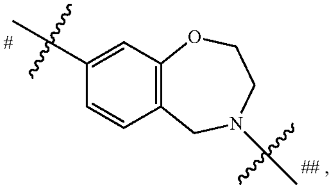

-continued

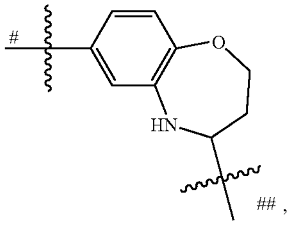

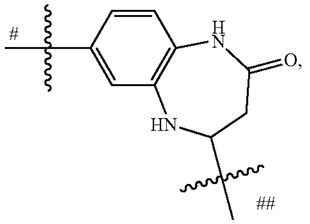

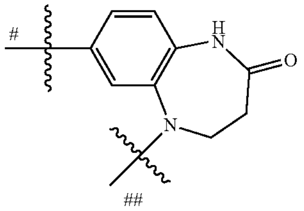

and

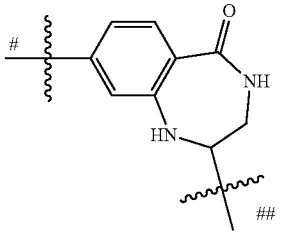

the above group is attached to X at either of the two positions labeled # or ##, and is attached to $R^1$ at the other position, provided that the atom attached to X is not a nitrogen atom.

In preferred embodiments,

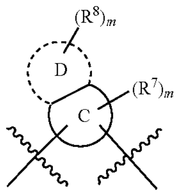

is

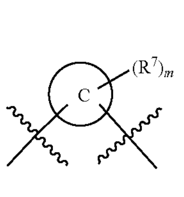

or

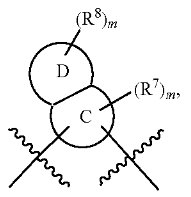

more preferably

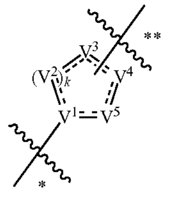

or

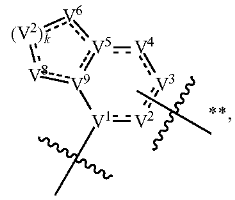

and more preferably

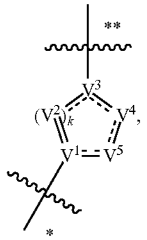

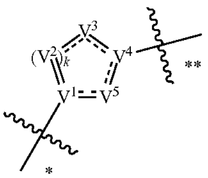

,

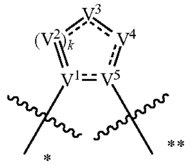

or

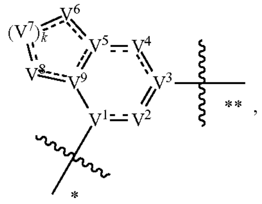

the above group is attached to Y at either of the two positions labeled * or **, and is attached to X at the other position, wherein:

---- represents either a single or a double bond, and the adjacent bonds are not double bonds simultaneously;

$V^1$, $V^2$, $V^3$, $V^4$, $V^5$, $V^6$, $V^7$, $V^8$ and $V^9$, at each occurrence, are each independently selected from the group consisting of C, $CR^7$, $C(R^7)_2$, $CR^8$, $C(R^8)_2$, C(=O), N, $NR^7$, $NR^8$, O and S; preferably, $V^1$, $V^2$, $V^3$, $V^4$, $V^5$, $V^6$, $V^7$, $V^8$ and $V^9$, at each occurrence, are each independently selected from the group consisting of C, CH, CF, CCl, CCN, $CCH_3$, C—$OCH_3$, $CCF_3$, C—$CH_2$-Ph, C—NH-Ph, C—O-Ph, C—$CH_2OCH_3$, C—$CH_2$—$NHCH_3$, C—$N(CH_3)_2$, C—$CH_2NH_2$, C—C(=O)OH, C—C(=O)$OCH_2CH_3$, C—C(=O)$NH_2$, —C—O—$CH_2CH_2$—$N(CH_3)_2$, $CH_2$, C(=O), N, NH, $NCH_3$, N—C(=O)$CH_3$, N-Ph, —N—$CH_2CH_2$—$N(CH_3)_2$, O and S;

k is 0, 1, 2, 3 or 4; and provided that at most two groups among $V^1$-$V^9$ are simultaneously C(=O).

In preferred embodiments,

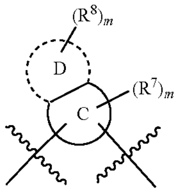

is

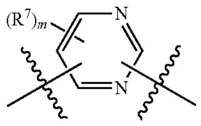

or

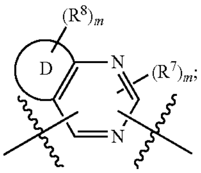

more preferably

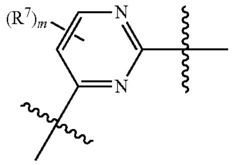

or

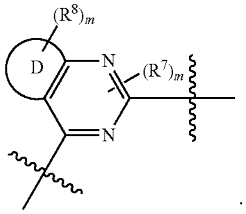

.

In preferred embodiments, $R^7$ and $R^8$, at each occurrence, are each independently selected from the group consisting of F, Cl, Br, I, cyano, —$N(CH_3)_2$, methyl, ethyl, propyl, methoxy, trifluoromethyl, phenyl, —$CH_2$-Ph, —NH-Ph, —O-Ph, —$CH_2OCH_3$, —$CH_2NH_2$, —$CH_2$—$NHCH_3$, —C(═O)$CH_3$, —C(═O)OH, —C(═O)$OCH_2CH_3$, —C(═O)$NH_2$, —O—$CH_2CH_2$—$N(CH_3)_2$ and —$CH_2CH_2$—$N(CH_3)_2$.

In the most preferred embodiments,

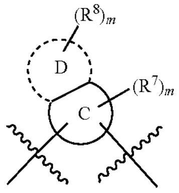

is

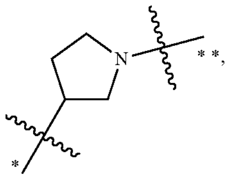

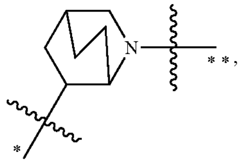

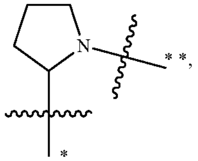

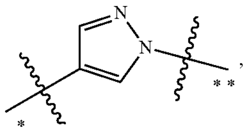

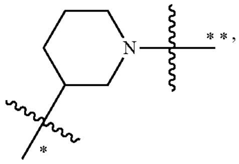

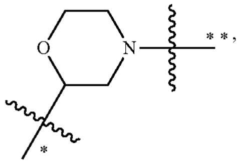

-continued

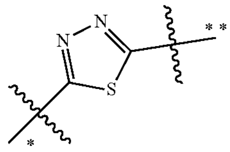

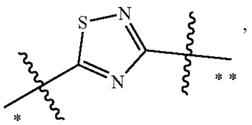

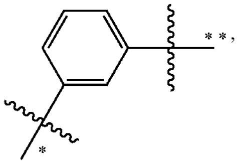

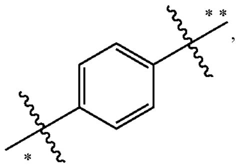

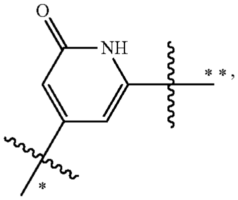

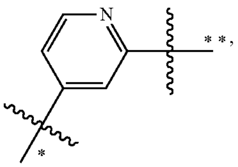

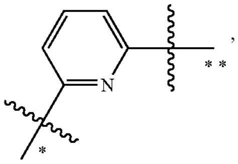

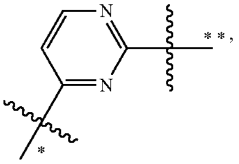

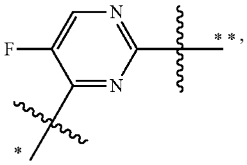

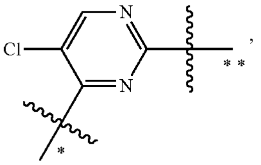

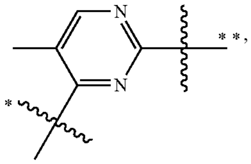

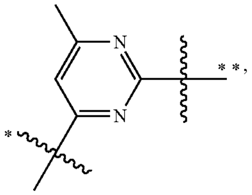

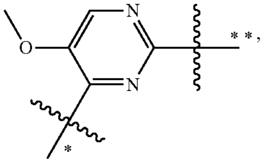

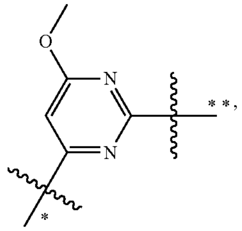

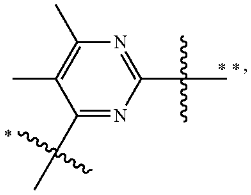

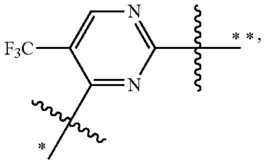

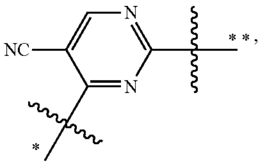

-continued
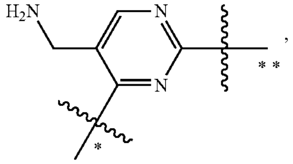
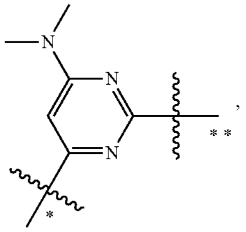
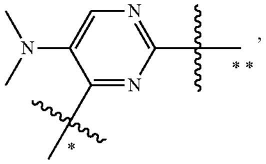
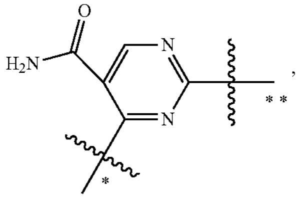
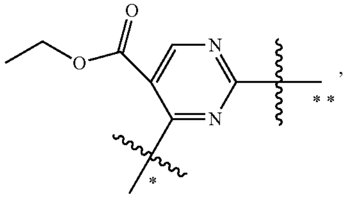
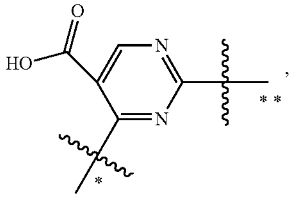
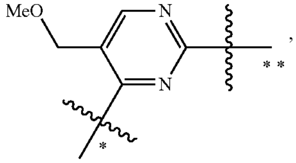
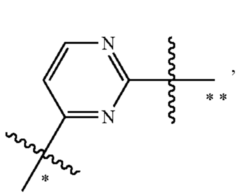
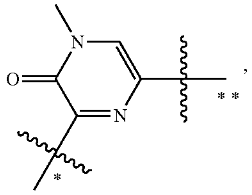
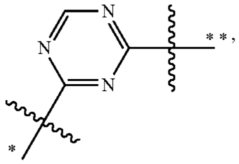
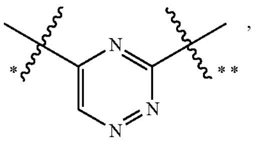
-continued
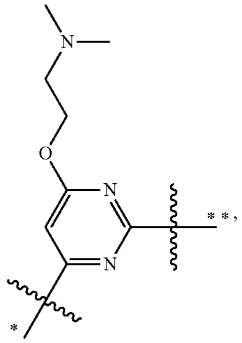
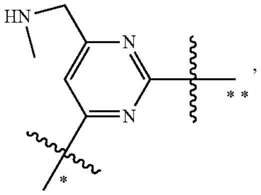
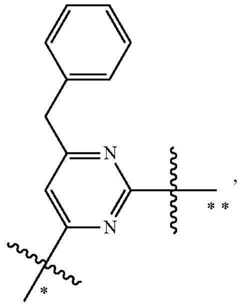
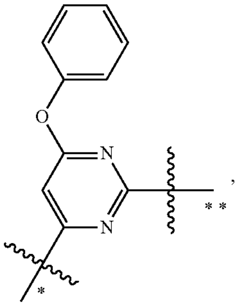
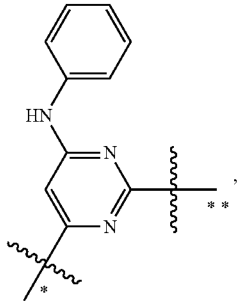
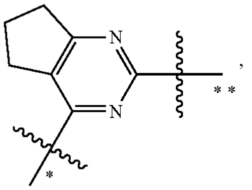
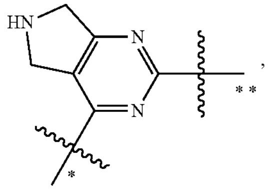
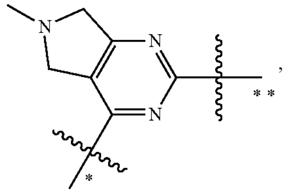
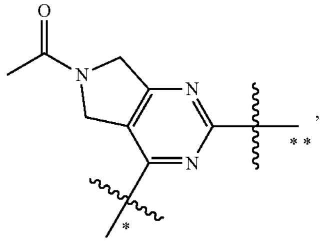

-continued
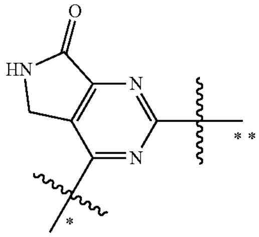
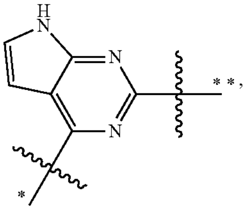
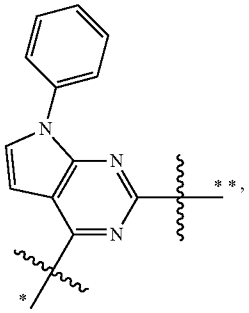
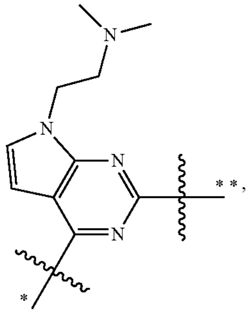
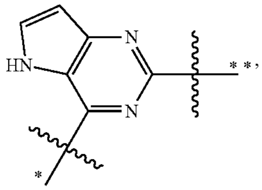
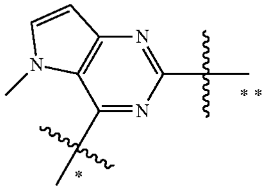
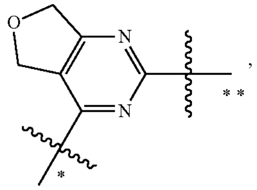
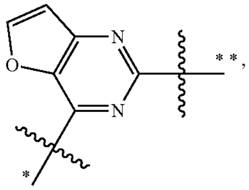
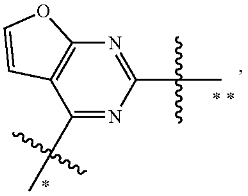
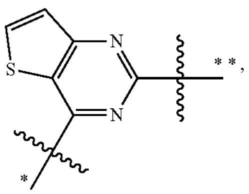
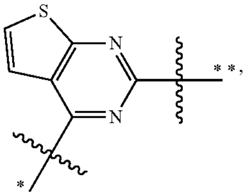
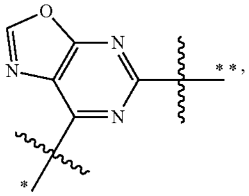
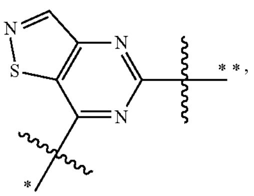
-continued
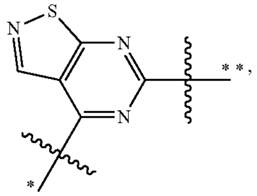
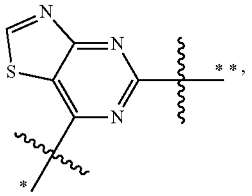
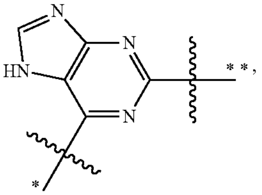
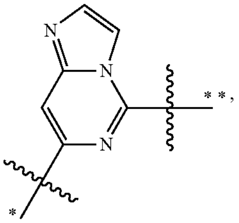
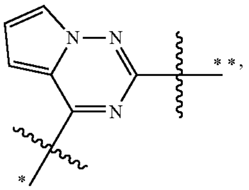
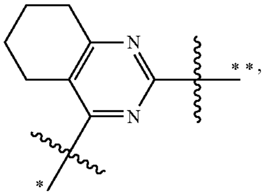
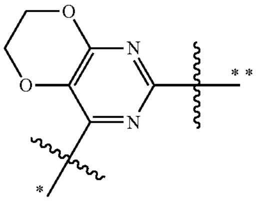
or
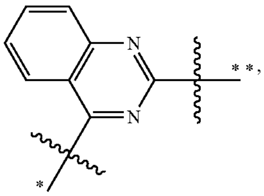
the above group is attached to Y at either of the two positions labeled * or **, and is attached to X at the other position.
In preferred embodiments, ring E is
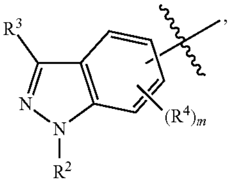
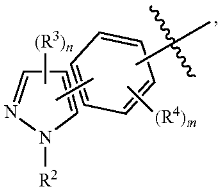
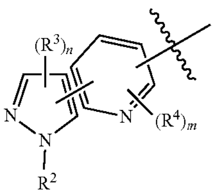
or
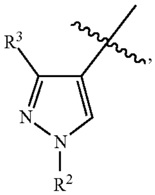
preferably

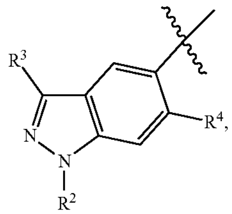
,
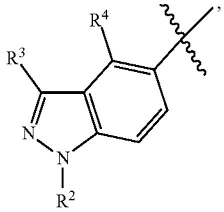
,
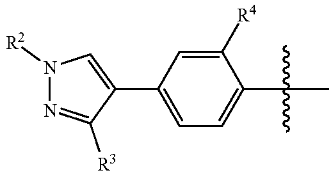
or
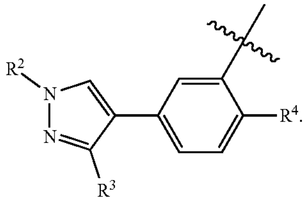
.
In some embodiments, $R^3$ and $R^4$, at each occurrence, are each independently selected from the group consisting of H, F, Cl, Br, I, —OH, methyl, ethyl, propyl, methoxy, $—NH_2$, $—N(CH_3)_2$, $—O\text{-ethylene-}N(CH_3)_2$.
In preferred embodiments, ring E is
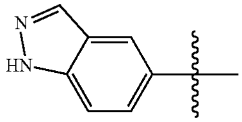
,
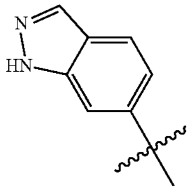
,
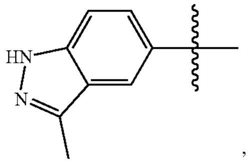
,
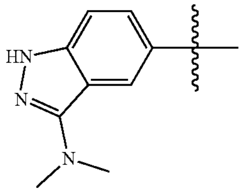
,
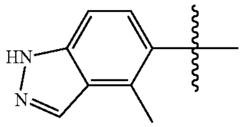
,
-continued
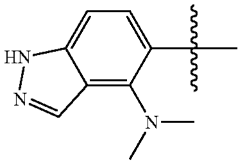
,
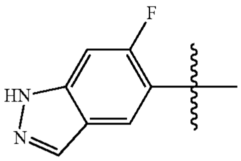
,
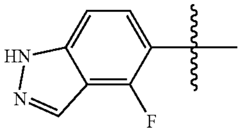
,
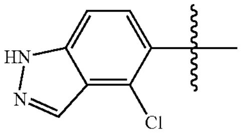
,
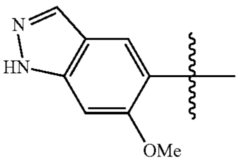
,
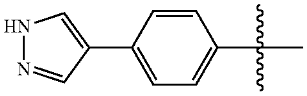
,
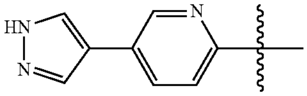
,
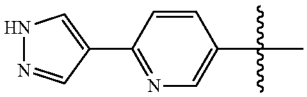
,
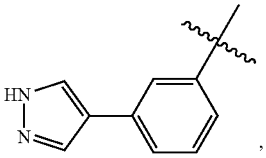
,
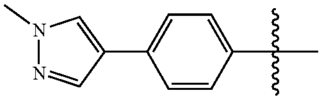
,
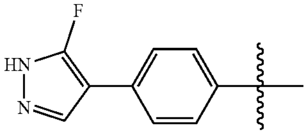
,
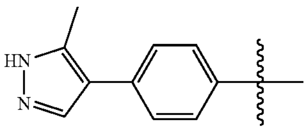
,
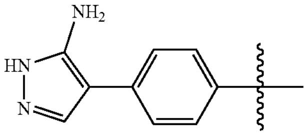
,
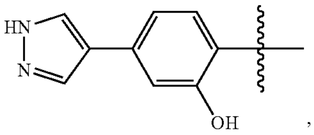
, -continued
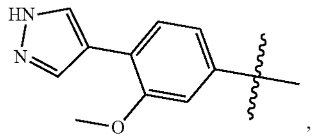
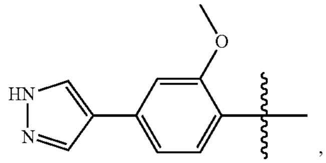
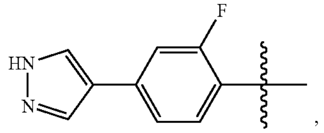
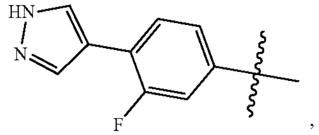
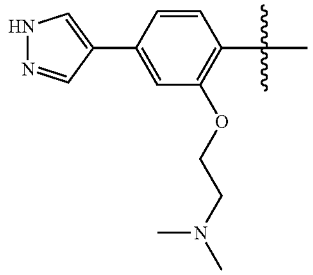
or
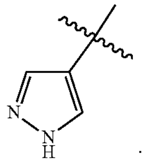
In preferred embodiments $R^1$ is methyl, $—CH_2OH$,
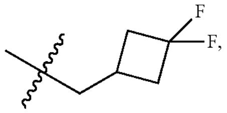
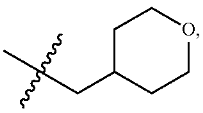
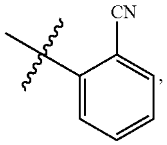
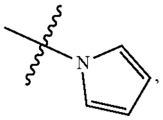
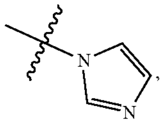
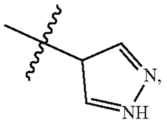
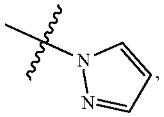
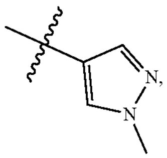
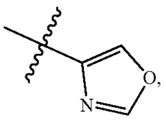
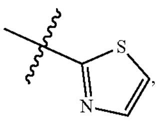
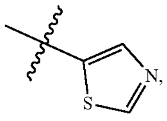
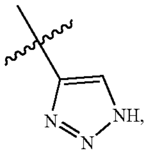
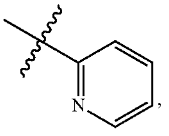
-continued
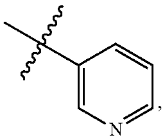
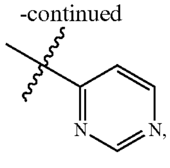
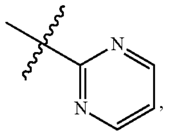
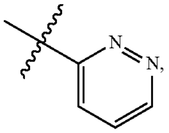
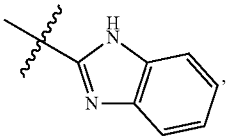
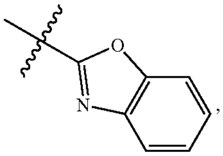
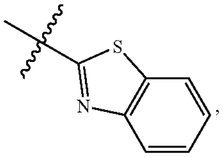
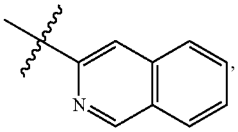
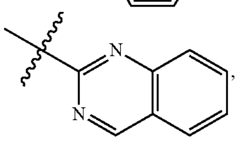
$—C({=}O)CF_3$, $—C({=}O)CH_2CF_3$, $—C({=}O)CH_2CN$, $—C({=}O)OCH_3$, $—C({=}O)OC(CH_3)_3$,
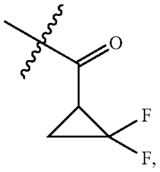
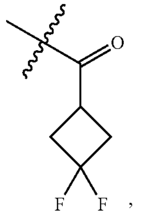
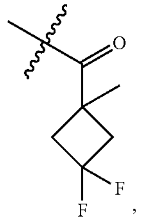
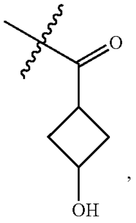
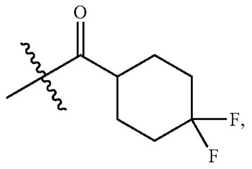
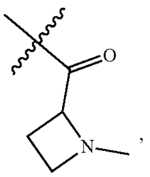
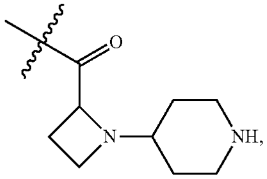
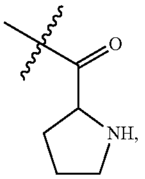
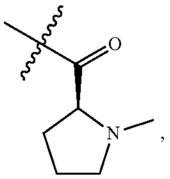
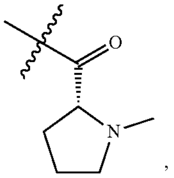
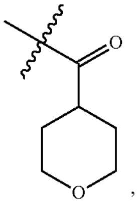

-continued
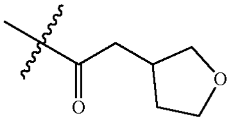,
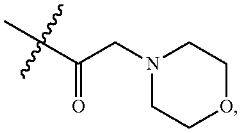
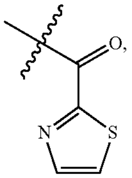
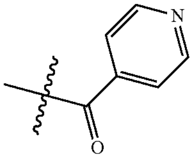,
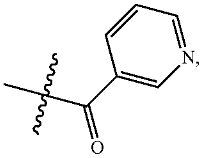
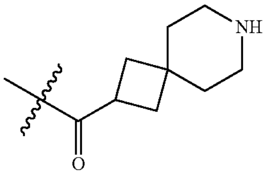,
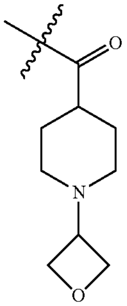,
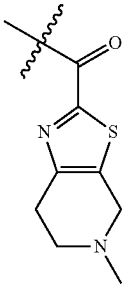,
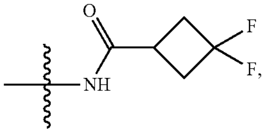
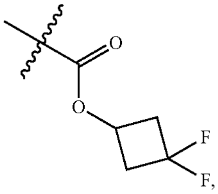
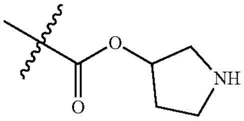,
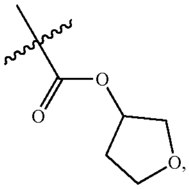
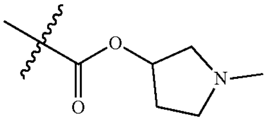,
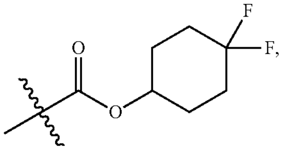
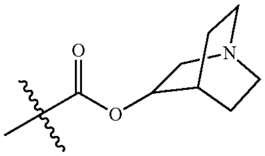,
-continued
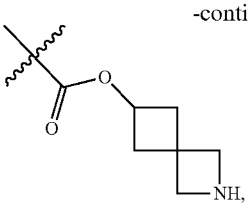
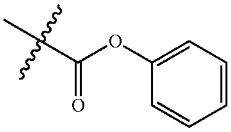,
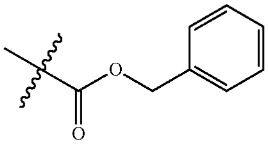,
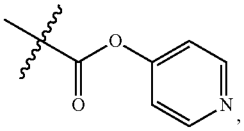, $—S(=O)_2CH_2CH_3$,
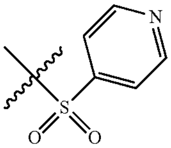
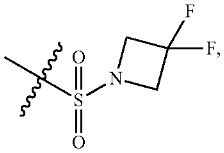
$—C(=O)CH_2N(CH_3)_2$,
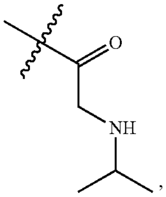,
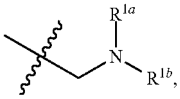
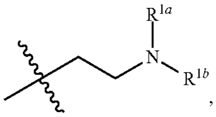,
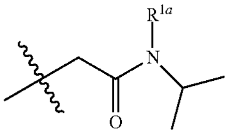 or 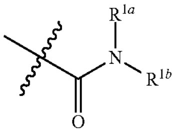
(e.g., 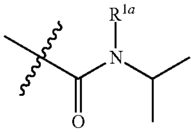 or
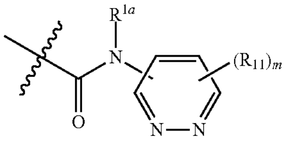),
more preferably
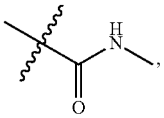
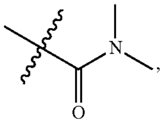
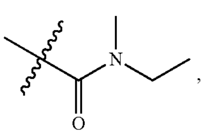,
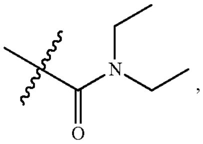, -continued

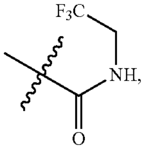
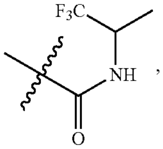
,
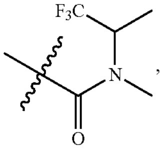
,
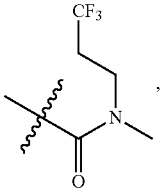
,
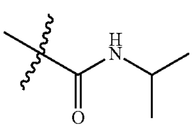
, or
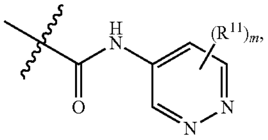

wherein $R^{11}$ is H, halogen, amino, cyano, nitro, $C_{1-6}$ alkyl, $C_{2-6}$ alkenyl, $C_{2-6}$ alkynyl, $C_{3-10}$ cyclic hydrocarbyl, 3- to 10-membered heterocyclyl, $C_{6-10}$ aryl, 5- to 14-membered heteroaryl, $C_{6-12}$ aralkyl, —C(═O)$R^5$, —OC(═O)$R^5$, —C(═O)O$R^5$, —O$R^5$, —S$R^5$, —S(═O)$R^5$, —S(═O)$_2R^5$, —S(═O)$_2$N$R^5R^6$, —N$R^5R^6$, —C(═O)N$R^5R^6$, —N$R^5$—C(═O)$R^6$, —N$R^5$—C(═O)O$R^6$, —N$R^5$—S(═O)$_2$—$R^6$, —N$R^5$—C(═O)—N$R^5R^6$, —$C_{1-6}$ alkylene-N$R^5R^6$ or —O—$C_{1-6}$ alkylene-N$R^5R^6$.

In preferred embodiments, $R^{1a}$ and $R^{1b}$ are each independently selected from the group consisting of H, methyl, —$CF_3$, ethyl, —$CH_2CF_3$, —$CH_2CH_2CF_3$, —$CH(CH_3)CF_3$, n-propyl, isopropyl, cyclopropyl, cyclobutyl, cyclopentyl, cyclohexyl, -ethylene-O-methyl, —$CH_2CN$, —$CH_2CH_2CN$, —$CH_2CH_2OH$,

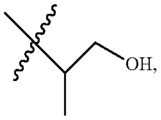
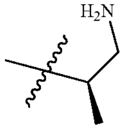
,
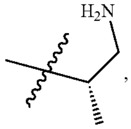
,
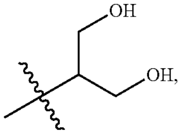
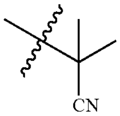
,
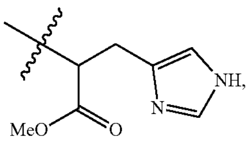
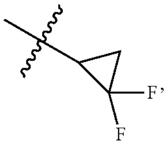
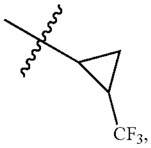
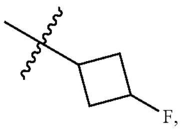
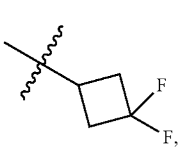
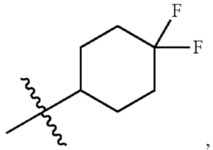
, -continued

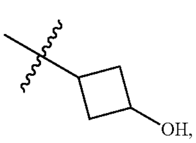
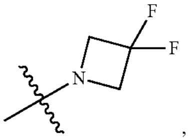
,
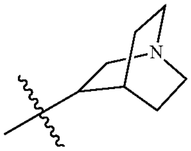
,
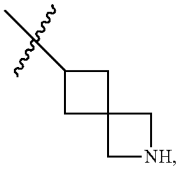
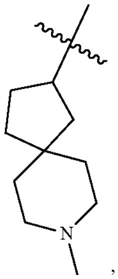
,
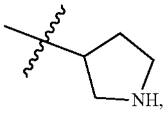
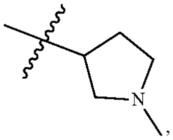
,
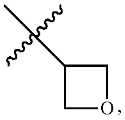
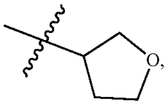
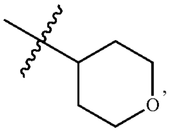
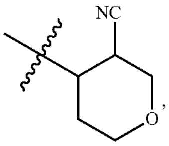
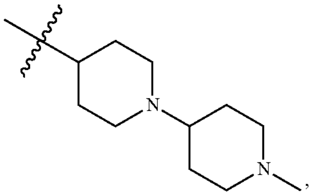
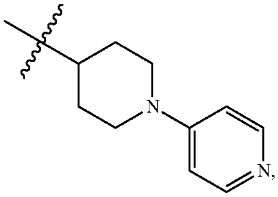
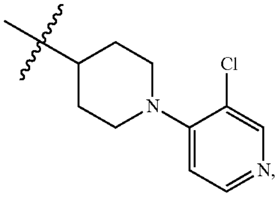
,
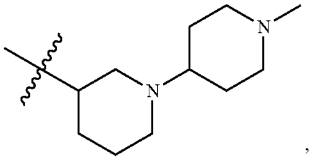
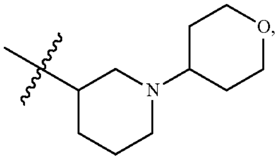

-continued
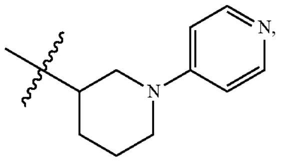
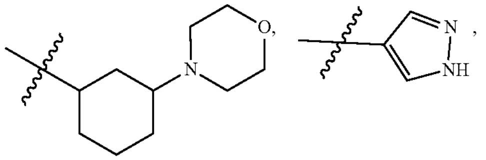
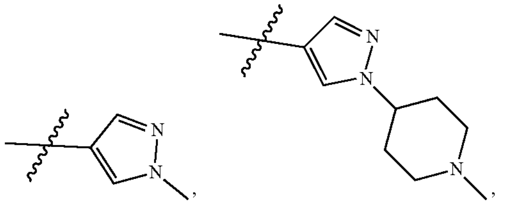
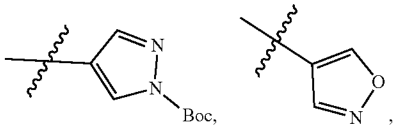
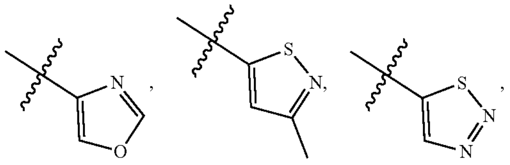
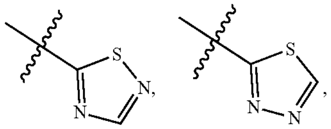
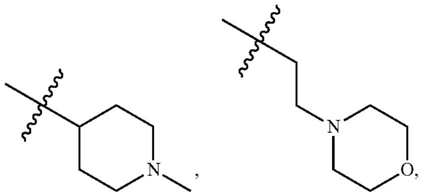
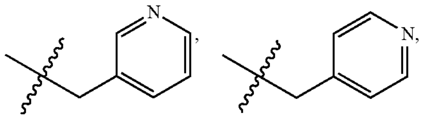
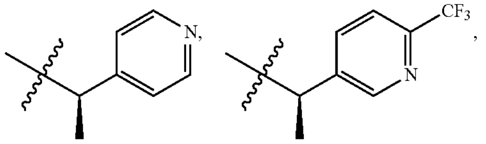
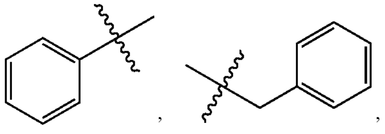
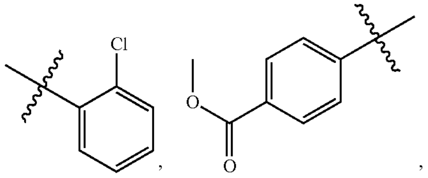
-continued
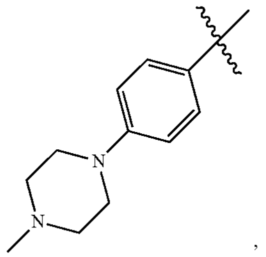
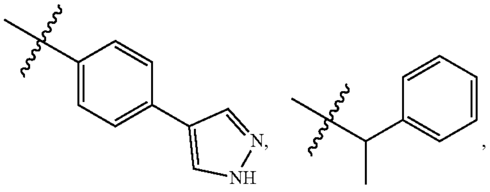
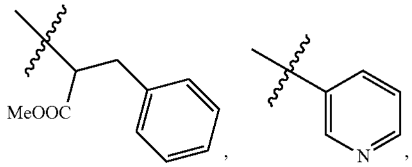
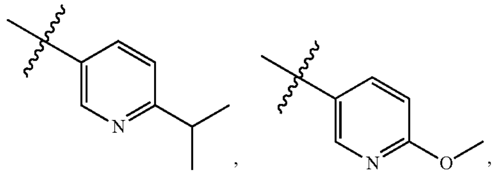
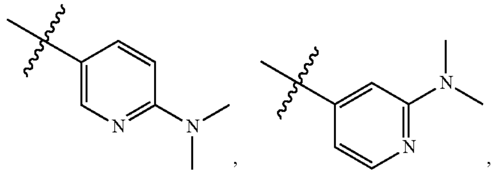
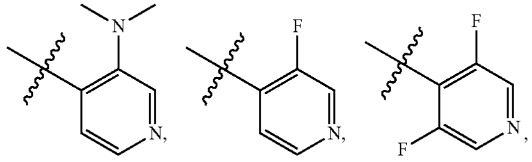
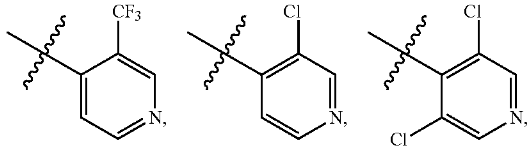
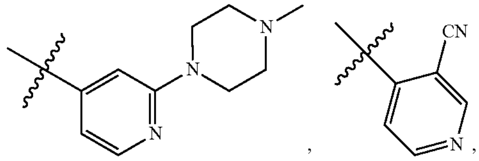
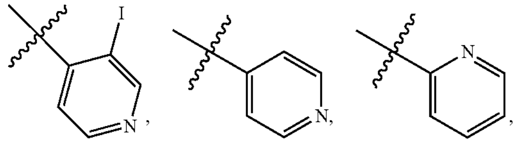
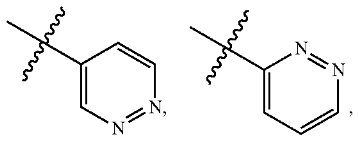

-continued
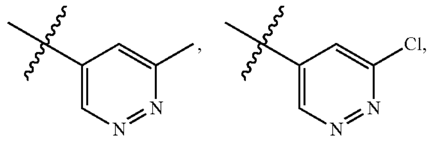
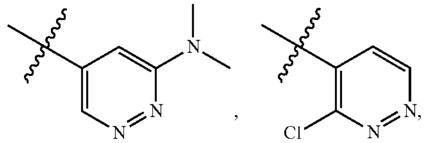
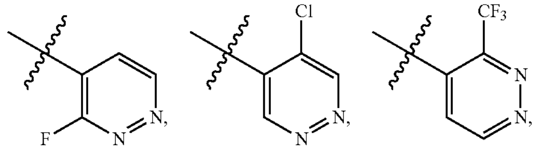
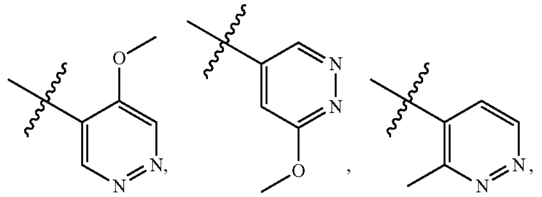
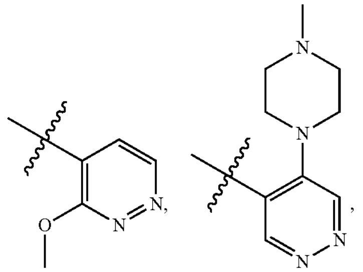
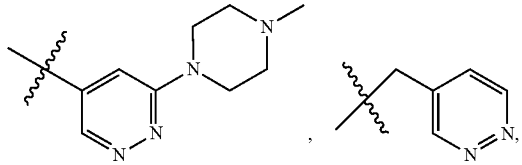
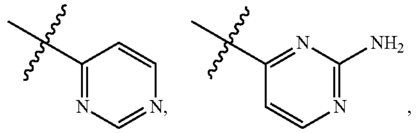
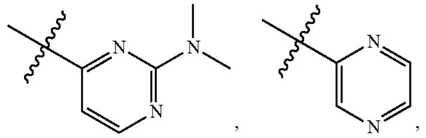
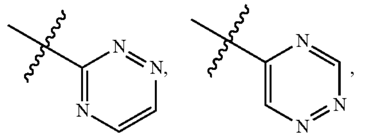
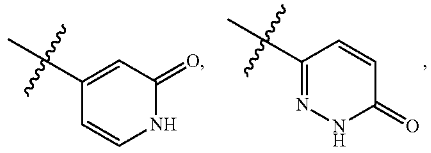
-continued
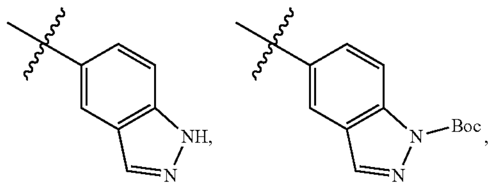
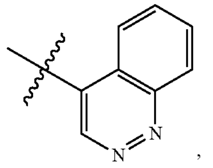
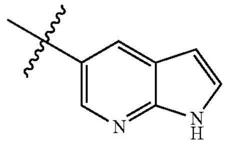
and
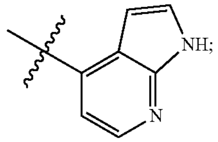
or $R^{1a}$ and $R^{1b}$ together with the atom to which they are attached form the following group:
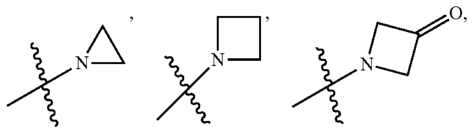
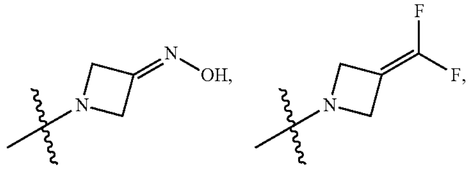
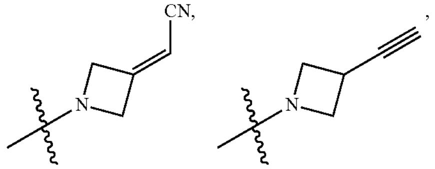
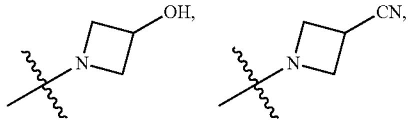
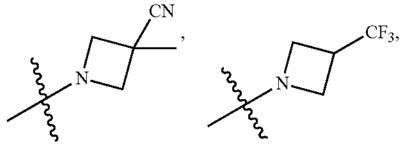
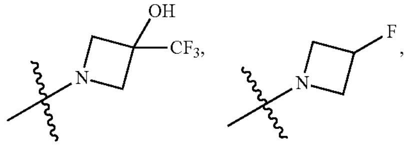
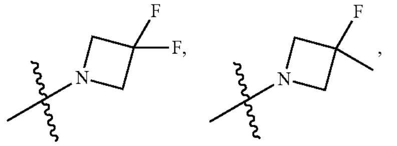

-continued
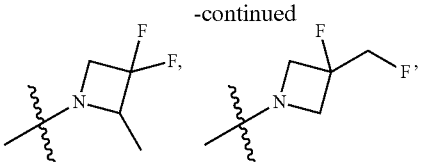
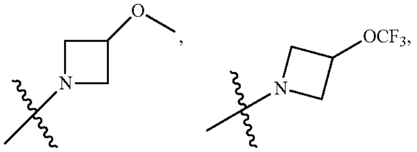
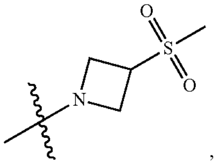
,
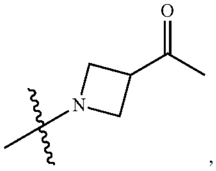
,
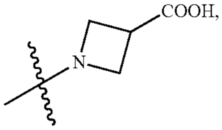
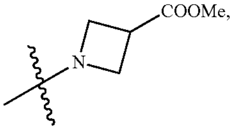
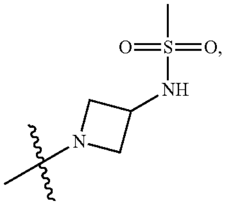
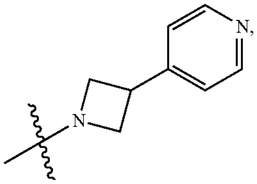
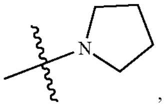
,
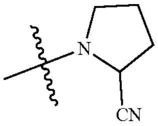
,
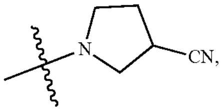
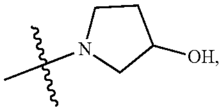
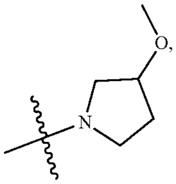
,
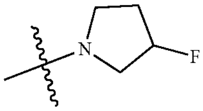
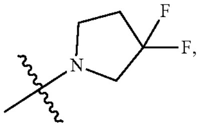
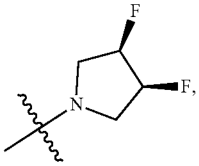
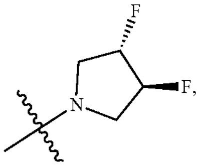
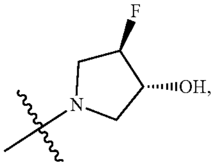
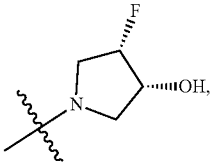
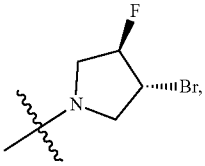
-continued
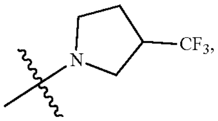
(e.g.,
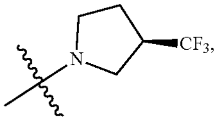
or
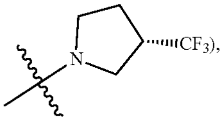
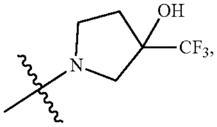
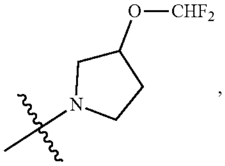
,
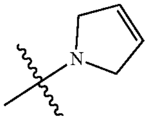
,
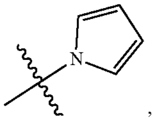
,
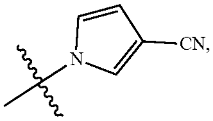
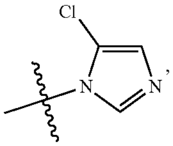
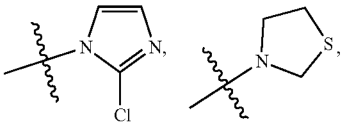
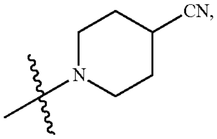
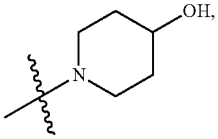
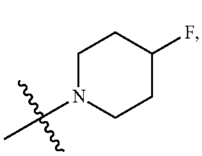
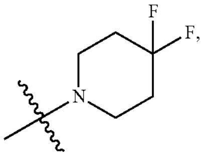
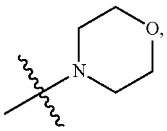
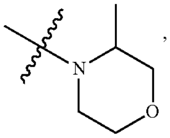
,
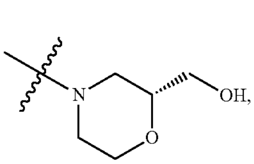
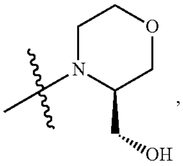
,
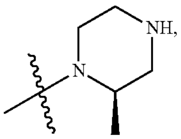
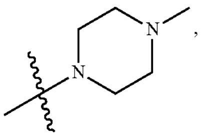
, -continued
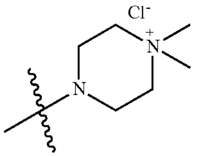
,
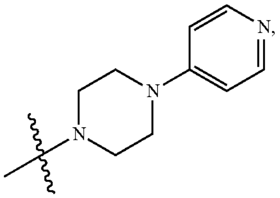
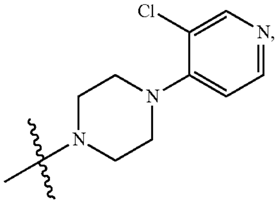
,
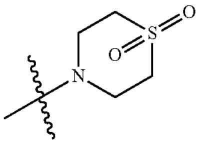
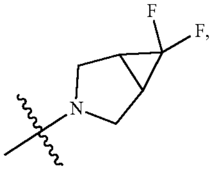
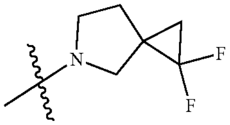
,
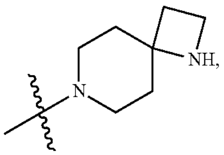
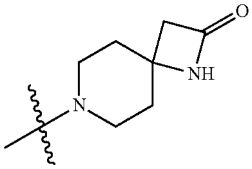
,
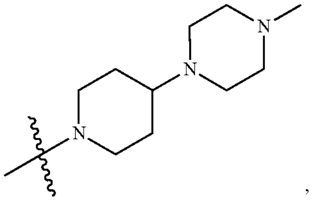
,
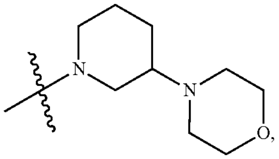
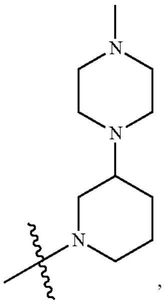
,
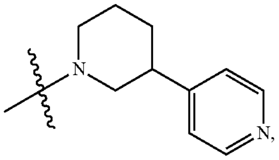
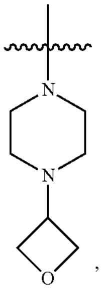
,
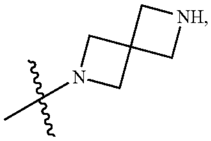
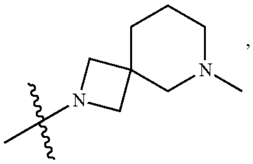
,
-continued
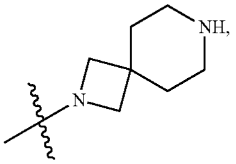
,
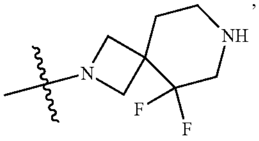
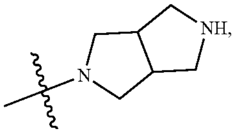
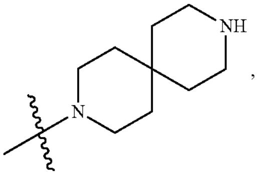
,
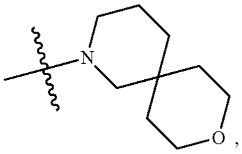
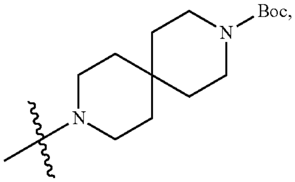
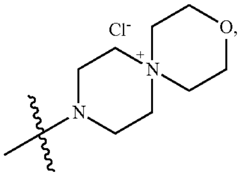
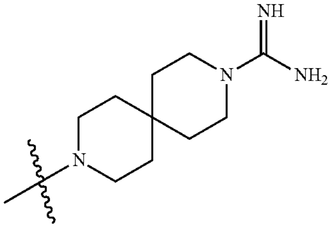
or
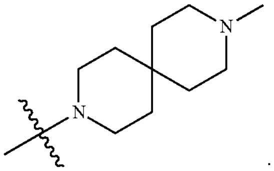
.
In preferred embodiments, the compound has the structure of any of the following formulae:
(II)
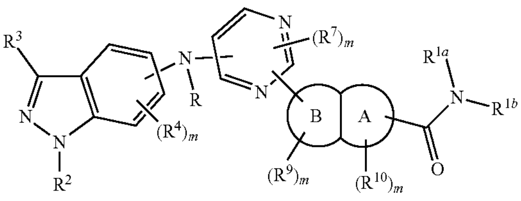
, -continued
(II')
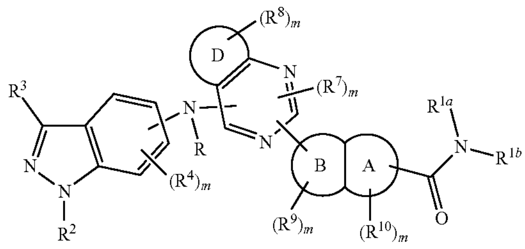
,
(III)
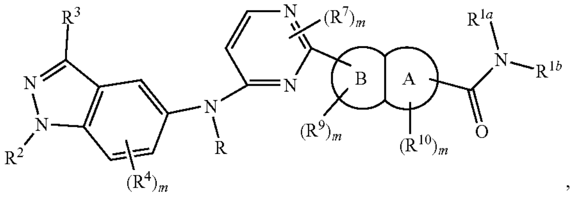
,
(III')
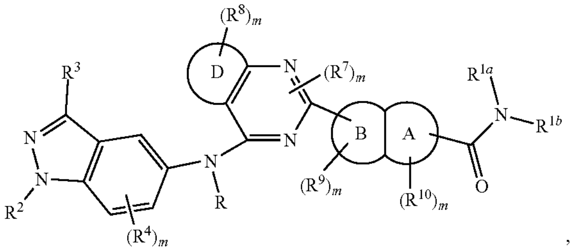
,
(IV)
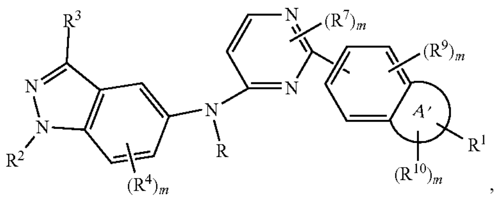
,
(IV')
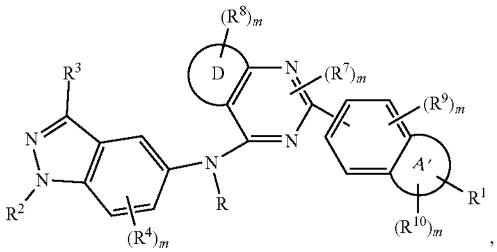
,
(V)
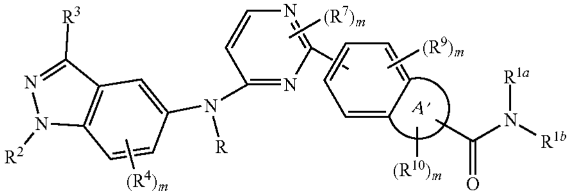
,
-continued
(V')
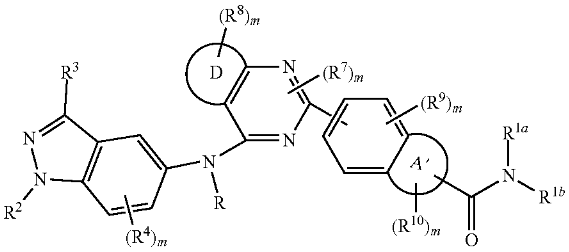
,
(VI)
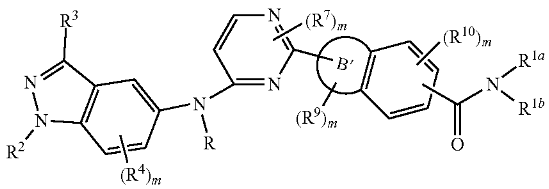
,
(VI')
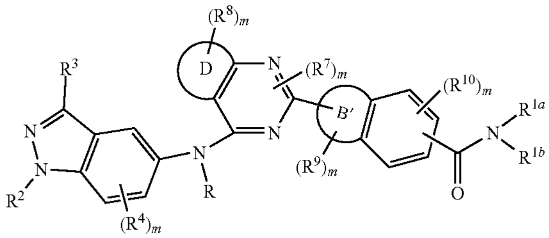
,
(VII)
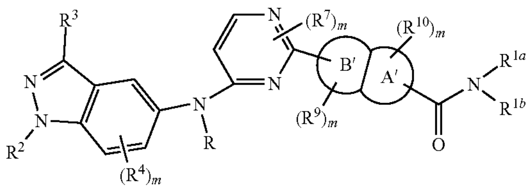
,
(VII')
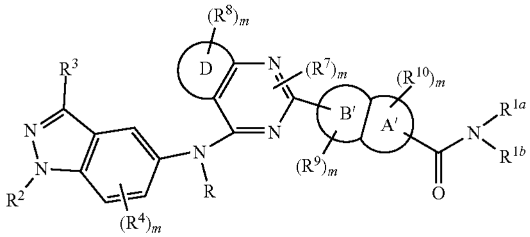
,
(VIII)
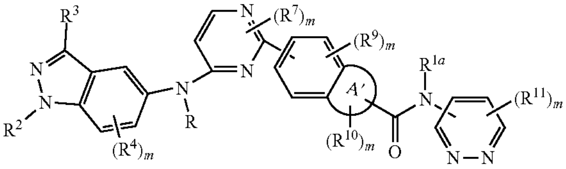
, -continued
(VIII')
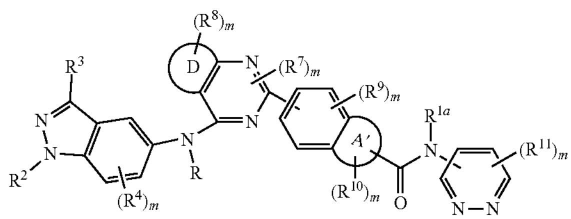
,
(IX)
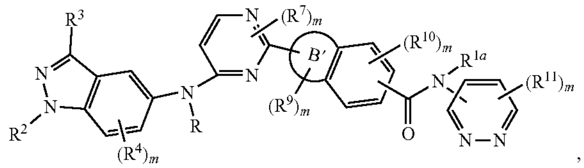
,
(IX')
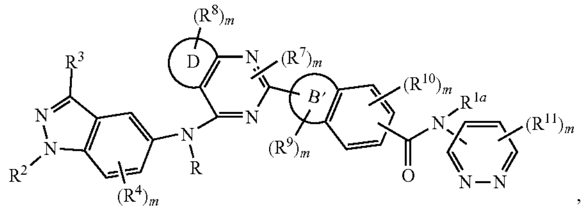
,
(X)
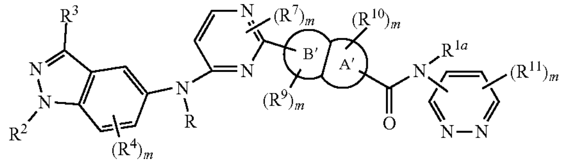
,
(X')
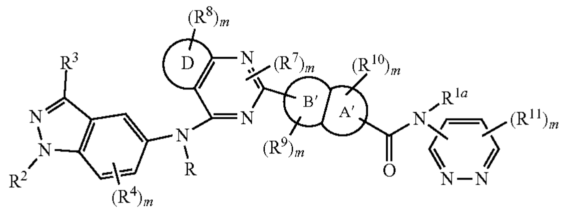
,
(XI)
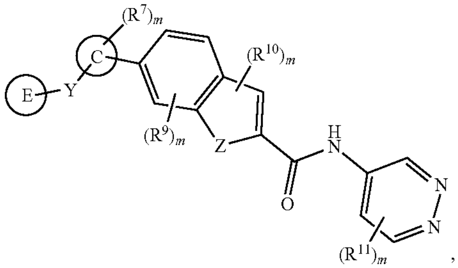
,
-continued
(XI')
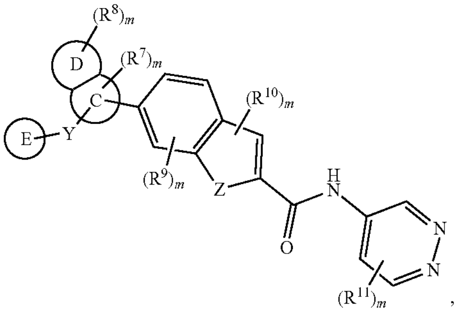
,
(XII)
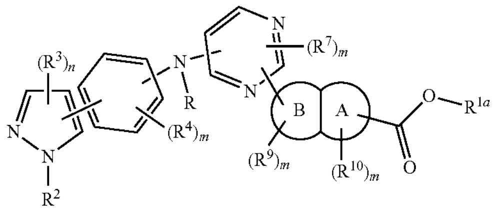
,
(XII')
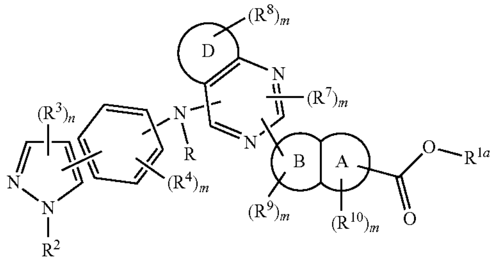
,
(XIII)
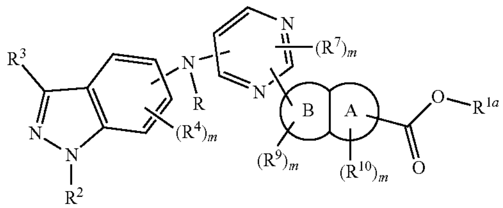
,
(XIII')
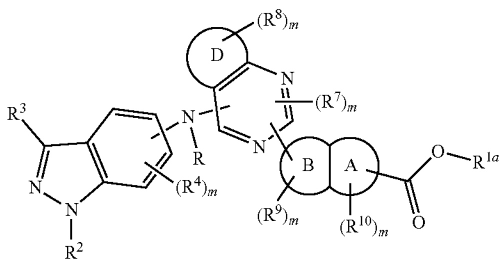
,
(XIV)
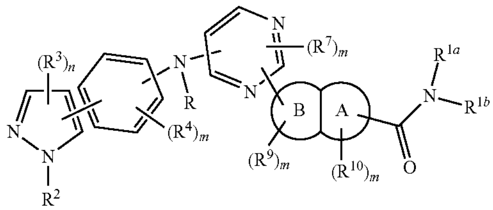
, -continued (XIV')

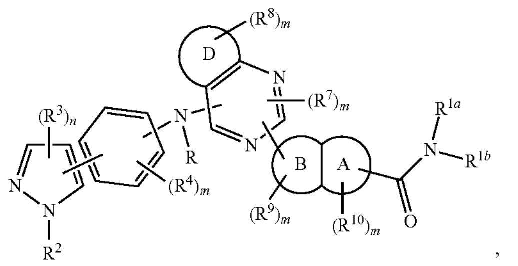

, (XV)

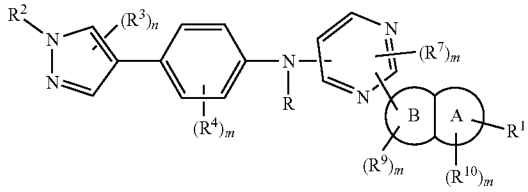

, (XV')

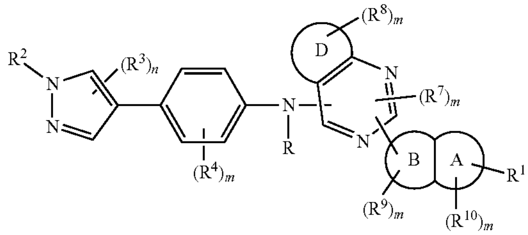

, (XV)-1

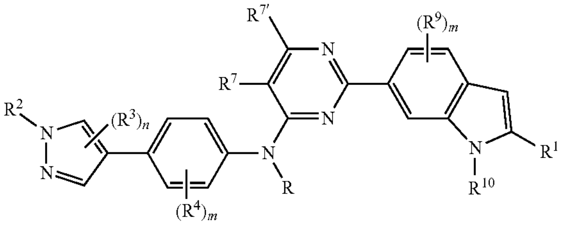

, (XV')-2

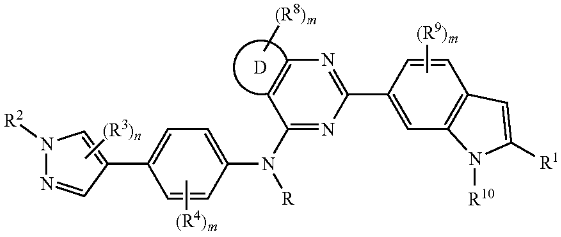

, (XV)-3

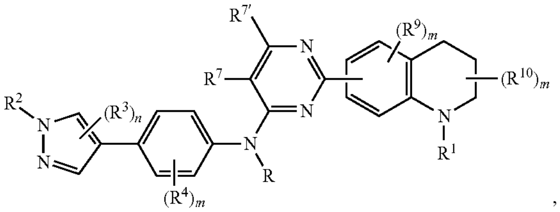

,

-continued (XV')-4

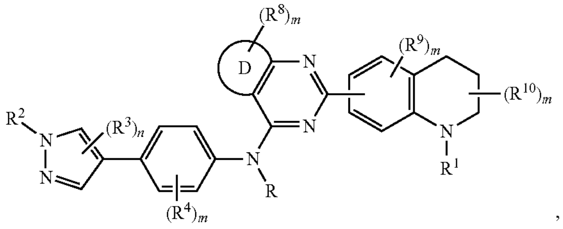

, (XVI)

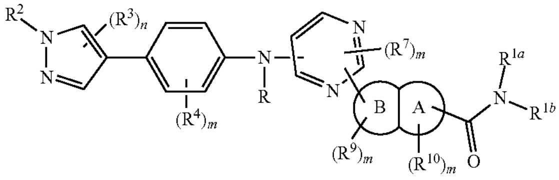

, (XVI')

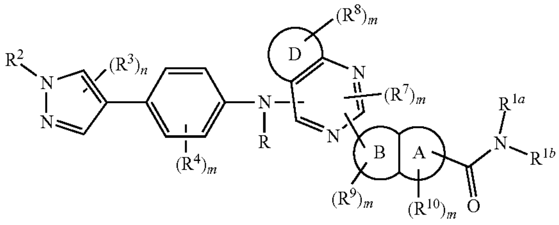

;

wherein:

Z is selected from the group consisting of O, S(=O)$_i$ and NR;

each of the remaining groups is as defined above.

In preferred embodiments, the compound has the structure of formula (XVII) or formula (XVII'):

(XVII)

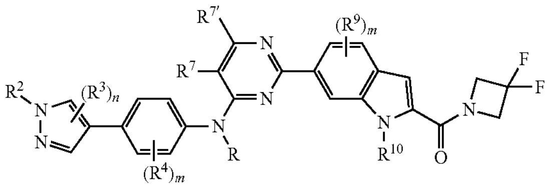

or (XVII')

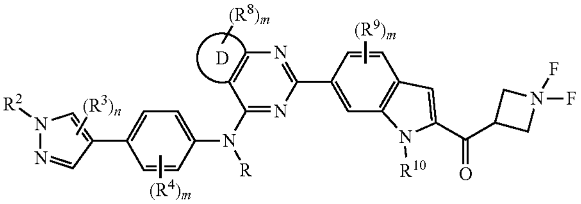

wherein:

R is selected from the group consisting of H and $C_{1-6}$ alkyl;

ring D is saturated or partially unsaturated 3- to 10-membered heterocycle, $C_{6-10}$ aryl or 5- to 10-membered heteroaromatic ring, preferably

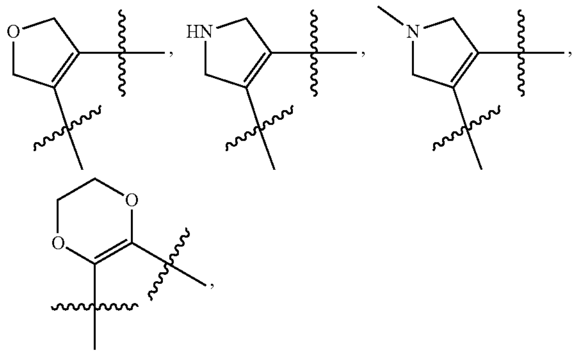

phenyl ring, N-methylpyrrole ring, furan ring or thiophene ring;

$R^2$ is selected from the group consisting of H and $C_{1-6}$ alkyl;

$R^3$, $R^4$, $R^7$, $R^{7'}$ and $R^8$, at each occurrence, are each independently selected from the group consisting of H, halogen, —$NH_2$, —OH, $C_{1-6}$ alkyl and —$OR^5$;

$R^9$ and $R^{10}$, at each occurrence, are each independently selected from the group consisting of H, halogen, $C_{1-6}$ alkyl, $C_{2-6}$ alkenyl, $C_{3-10}$ cyclic hydrocarbyl, 3- to 10-membered heterocyclyl, $C_{6-10}$ aryl, 5- to 14-membered heteroaryl, $C_{6-12}$ aralkyl, —C(=O)$R^5$ and —$C_{1-6}$ alkylene-O(P=O)$(OH)_2$;

the above alkyl, alkenyl, cyclic hydrocarbyl, heterocyclyl, aryl, heteroaryl, heteroaromatic ring and aralkyl, at each occurrence, are each optionally substituted with one or more substituents independently selected from the group consisting of halogen, $C_{1-6}$ alkyl and —OR';

$R^5$ and $R^6$, at each occurrence, are each independently selected from the group consisting of H, $C_{1-6}$ alkyl, $C_{3-10}$ cyclic hydrocarbyl, 3- to 10-membered heterocyclyl, $C_{6-10}$ aryl, 5- to 14-membered heteroaryl and $C_{6-12}$ aralkyl;

m, at each occurrence, is each independently an integer of 0, 1, 2 or 3;

n is an integer of 0, 1 or 2.

In preferred embodiments, $R^5$ and $R^6$, at each occurrence, are each independently selected from the group consisting of H, methyl and ethyl.

In preferred embodiments, $R^3$, $R^4$, $R^7$, $R^{7'}$ and $R^8$, at each occurrence, are each independently selected from the group consisting of H, F, Cl, Br, —$NH_2$, —OH, methyl, trifluoromethyl, —$CH_2$-Ph, methoxy, ethoxy and —$CH_2OCH_3$.

In preferred embodiments, $R^9$ and $R^{10}$, at each occurrence, are each independently selected from the group consisting of H, F, Cl, Br, methyl, ethyl, n-propyl, isopropyl, vinyl, cyclopropyl, cyclobutyl, cyclopentyl, oxetanyl, monofluoromethyl, difluoromethyl, trifluoromethyl, acetyl, —$CH_2CHF_2$, —$CH_2OH$, —$CH_2OCH_3$, —$CH_2CH_2OCH_3$, —$CH_2$—O(P=O)$(OH)_2$,

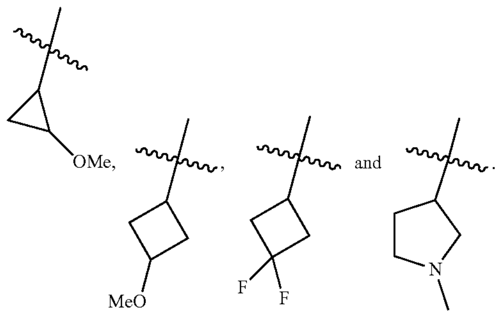

Technical solutions obtained by any combination of the various embodiments is encompassed by the present disclosure.

In preferred embodiments, the compound has the following structure:

| No. | Structure |
|---|---|
| 1. | 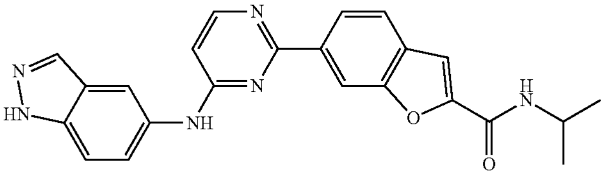 |
| 2. | 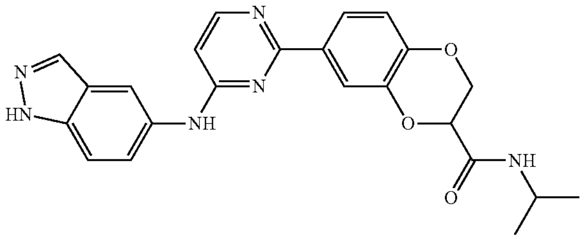 |
| 3. | 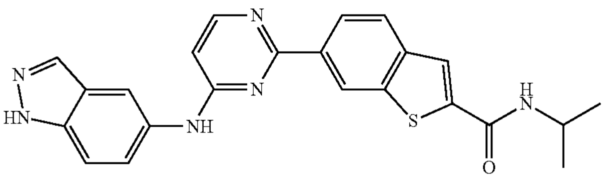 [SMILES: CC(C)NC(=O)c1cc2ccc(-c3nccc(Nc4ccc5[nH]ncc5c4)n3)cc2o1] |

-continued
| No. | Structure |
|---|---|
| 4. | 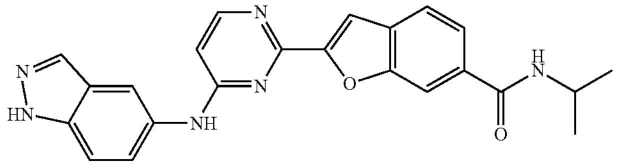 [SMILES: CC(C)NC(=O)c1ccc2cc(-c3nccc(Nc4ccc5[nH]ncc5c4)n3)oc2c1] |
| 5. | 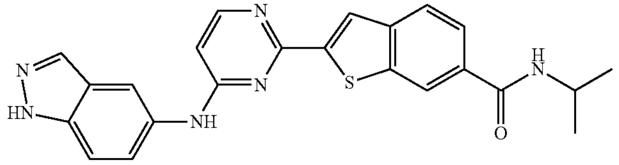 [SMILES: CC(C)NC(=O)c1ccc2cc(-c3nccc(Nc4ccc5[nH]ncc5c4)n3)sc2c1] |
| 6. | 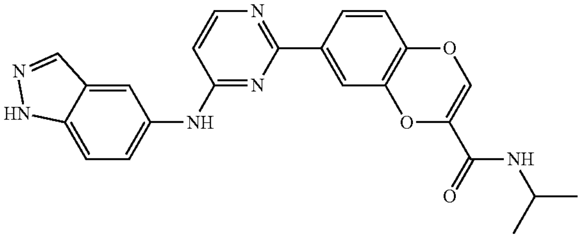 |
| 7. | 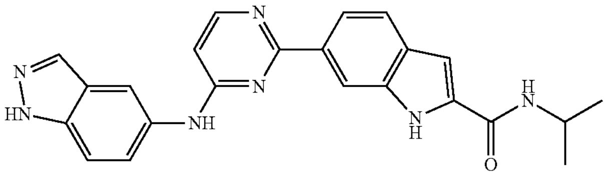 [SMILES: CC(C)NC(=O)c1cc2ccc(-c3nccc(Nc4ccc5[nH]ncc5c4)n3)cc2[nH]1] |
| 8. | 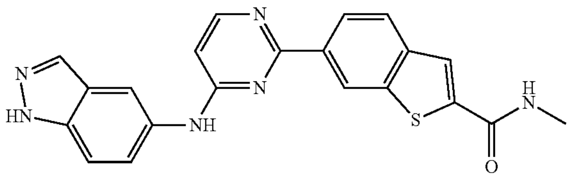 [SMILES: CNC(=O)c1cc2ccc(-c3nccc(Nc4ccc5[nH]ncc5c4)n3)cc2s1] |
| 9. | 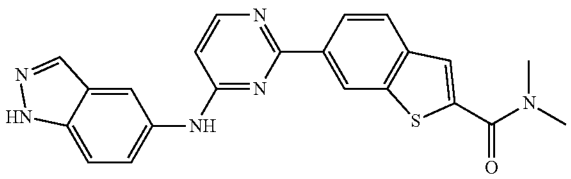 [SMILES: CN(C)C(=O)c1cc2ccc(-c3nccc(Nc4ccc5[nH]ncc5c4)n3)cc2s1] |
| 10. | 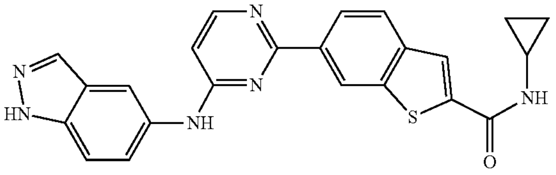 [SMILES: O=C(NC1CC1)c1cc2ccc(-c3nccc(Nc4ccc5[nH]ncc5c4)n3)cc2s1] |
| 11. | 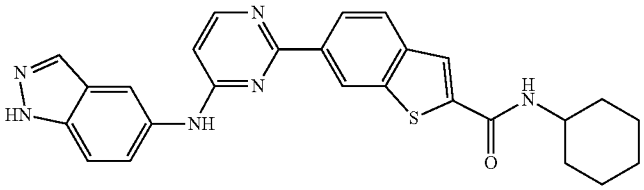 [SMILES: O=C(NC1CCCCC1)c1cc2ccc(-c3nccc(Nc4ccc5[nH]ncc5c4)n3)cc2s1] |

-continued
| No. | Structure |
| --- | --- |
| 12. | 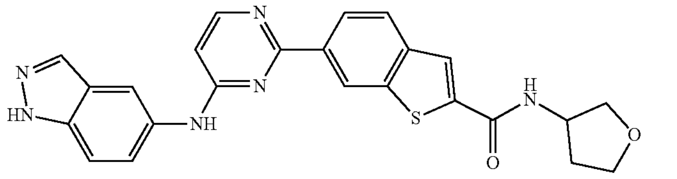 [SMILES: O=C(NC1CCOC1)c1cc2ccc(-c3nccc(Nc4ccc5[nH]ncc5c4)n3)cc2s1] |
| 13. | 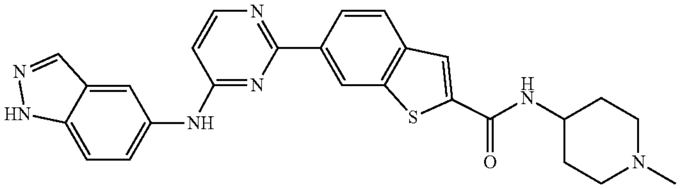 [SMILES: CN1CCC(NC(=O)c2cc3ccc(-c4nccc(Nc5ccc6[nH]ncc6c5)n4)cc3s2)CC1] |
| 14. | 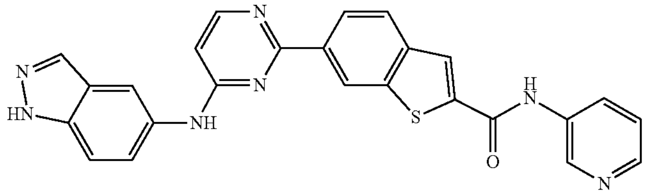 [SMILES: O=C(Nc1cccnc1)c1cc2ccc(-c3nccc(Nc4ccc5[nH]ncc5c4)n3)cc2s1] |
| 15. | 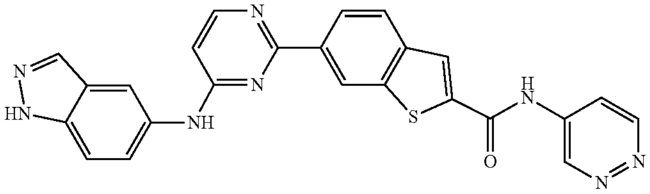 [SMILES: O=C(Nc1ccnnc1)c1cc2ccc(-c3nccc(Nc4ccc5[nH]ncc5c4)n3)cc2s1] |
| 16. | 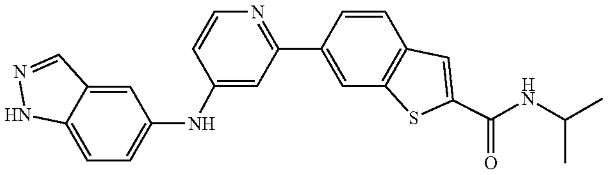 [SMILES: CC(C)NC(=O)c1cc2ccc(-c3cc(Nc4ccc5[nH]ncc5c4)ccn3)cc2s1] |
| 17. | 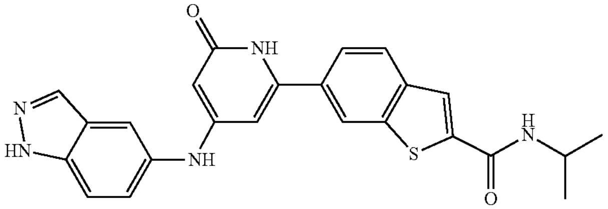 [SMILES: CC(C)NC(=O)c1cc2ccc(-c3cc(Nc4ccc5[nH]ncc5c4)cc(=O)[nH]3)cc2s1] |
| 18. | 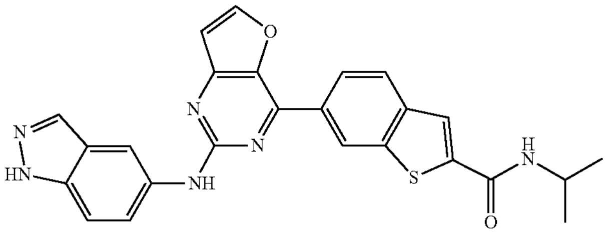 [SMILES: CC(C)NC(=O)c1cc2ccc(-c3nc(Nc4ccc5[nH]ncc5c4)nc4ccoc34)cc2s1] |

-continued
| No. | Structure |
| --- | --- |
| 19. | 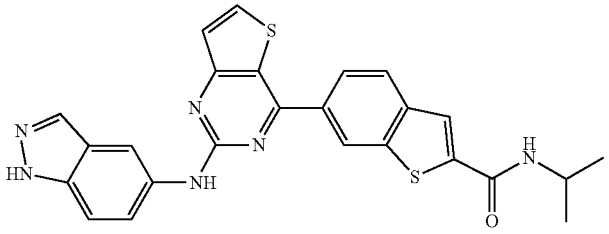 [SMILES: CC(C)NC(=O)c1cc2ccc(-c3nc(Nc4ccc5[nH]ncc5c4)nc4ccsc34)cc2s1] |
| 20. | 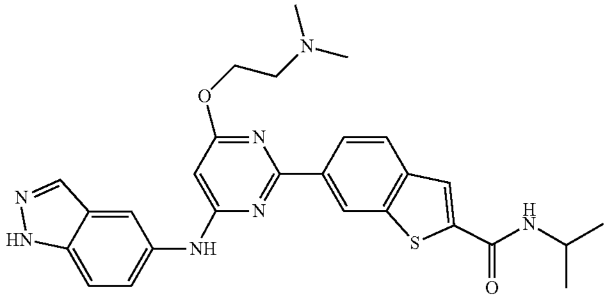 [SMILES: CC(C)NC(=O)c1cc2ccc(-c3nc(Nc4ccc5[nH]ncc5c4)cc(OCCN(C)C)n3)cc2s1] |
| 21. | 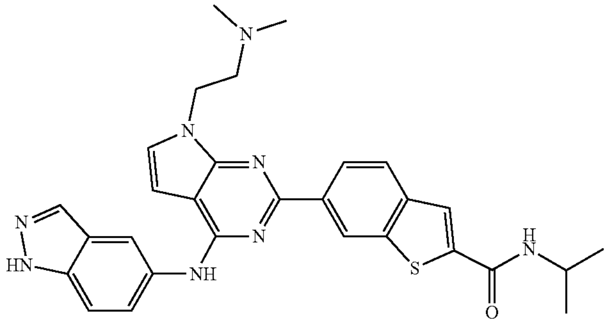 [SMILES: CC(C)NC(=O)c1cc2ccc(-c3nc(Nc4ccc5[nH]ncc5c4)c4ccn(CCN(C)C)c4n3)cc2s1] |
| 22. | 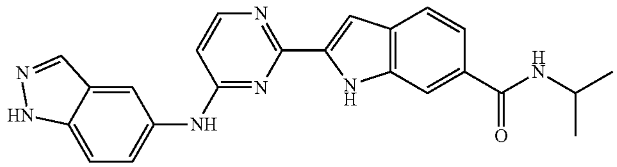 [SMILES: CC(C)NC(=O)c1ccc2cc(-c3nccc(Nc4ccc5[nH]ncc5c4)n3)[nH]c2c1] |
| 23. | 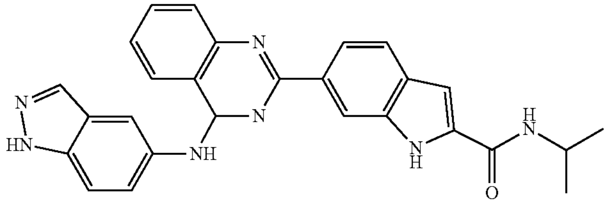 [SMILES: CC(C)NC(=O)c1cc2ccc(C3=Nc4ccccc4C(Nc4ccc5[nH]ncc5c4)N3)cc2[nH]1] |
| 24. | 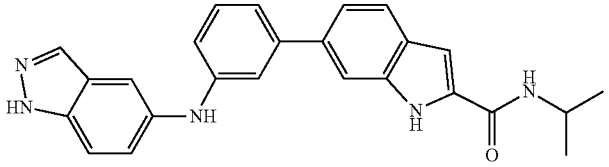 [SMILES: CC(C)NC(=O)c1cc2ccc(-c3cccc(Nc4ccc5[nH]ncc5c4)c3)cc2[nH]1] |

-continued
| No. | Structure |
|---|---|
| 25. | 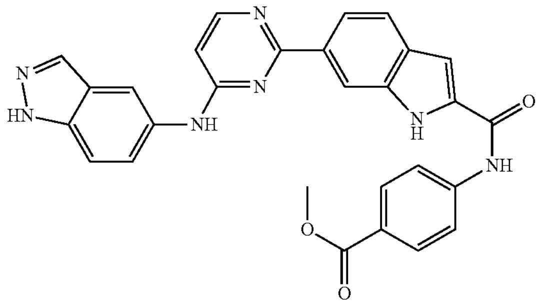 [SMILES: COC(=O)c1ccc(NC(=O)c2cc3ccc(-c4nccc(Nc5ccc6[nH]ncc6c5)n4)cc3[nH]2)cc1] |
| 26. | 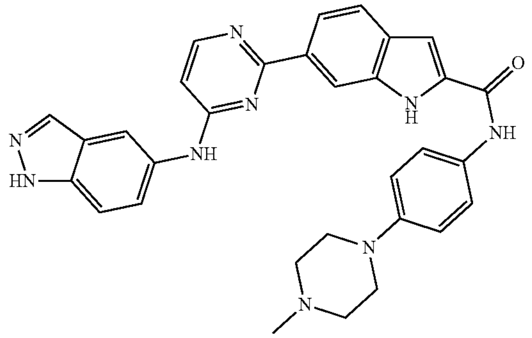 [SMILES: CN1CCN(c2ccc(NC(=O)c3cc4ccc(-c5nccc(Nc6ccc7[nH]ncc7c6)n5)cc4[nH]3)cc2)CC1] |
| 27. | 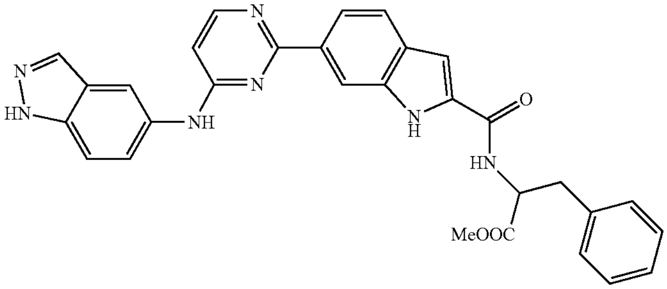 [SMILES: COC(=O)C(Cc1ccccc1)NC(=O)c1cc2ccc(-c3nccc(Nc4ccc5[nH]ncc5c4)n3)cc2[nH]1] |
| 28. | 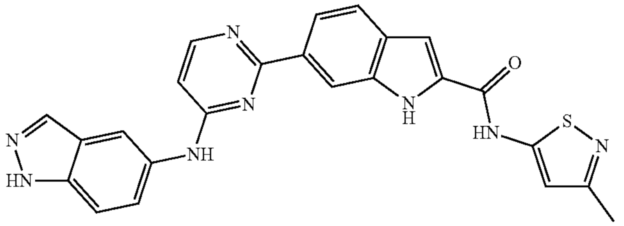 [SMILES: Cc1cc(NC(=O)c2cc3ccc(-c4nccc(Nc5ccc6[nH]ncc6c5)n4)cc3[nH]2)sn1] |
| 29. | 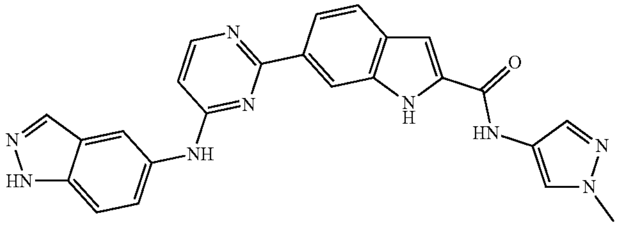 [SMILES: Cn1cc(NC(=O)c2cc3ccc(-c4nccc(Nc5ccc6[nH]ncc6c5)n4)cc3[nH]2)cn1] |

-continued
| No. | Structure |
| --- | --- |
| 30. | 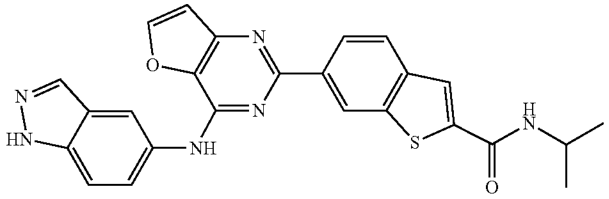 [SMILES: CC(C)NC(=O)c1cc2ccc(-c3nc(Nc4ccc5[nH]ncc5c4)c4occc4n3)cc2s1] |
| 31. | 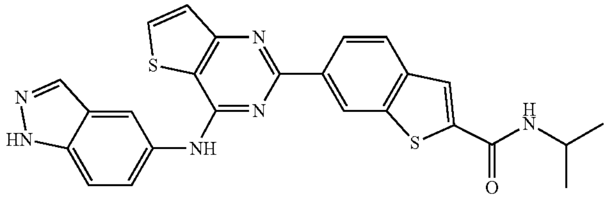 [SMILES: CC(C)NC(=O)c1cc2ccc(-c3nc(Nc4ccc5[nH]ncc5c4)c4sccc4n3)cc2s1] |
| 32. | 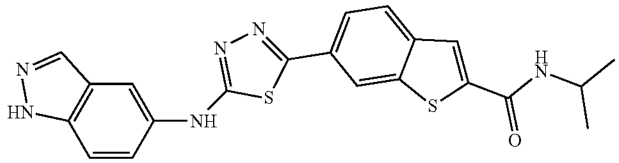 [SMILES: CC(C)NC(=O)c1cc2ccc(-c3nnc(Nc4ccc5[nH]ncc5c4)s3)cc2s1] |
| 33. | 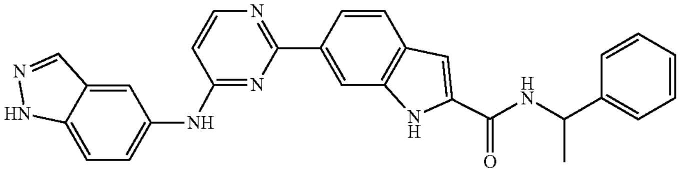 [SMILES: CC(NC(=O)c1cc2ccc(-c3nccc(Nc4ccc5[nH]ncc5c4)n3)cc2[nH]1)c1ccccc1] |
| 34. | 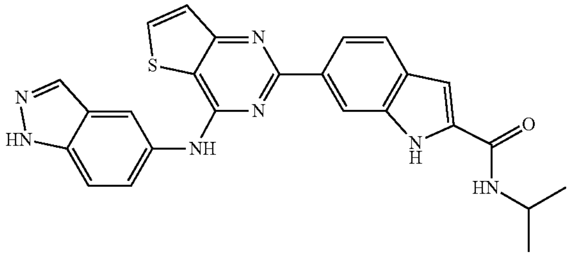 [SMILES: CC(C)NC(=O)c1cc2ccc(-c3nc(Nc4ccc5[nH]ncc5c4)c4sccc4n3)cc2[nH]1] |
| 35. | 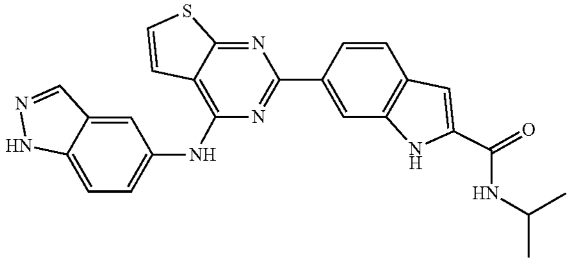 [SMILES: CC(C)NC(=O)c1cc2ccc(-c3nc(Nc4ccc5[nH]ncc5c4)c4ccsc4n3)cc2[nH]1] |
| 36. | 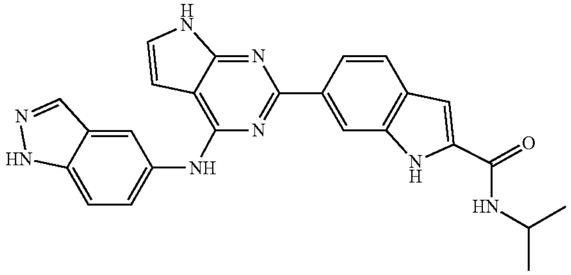 [SMILES: CC(C)NC(=O)c1cc2ccc(-c3nc(Nc4ccc5[nH]ncc5c4)c4cc[nH]c4n3)cc2[nH]1] |

-continued
| No. | Structure |
|---|---|
| 37. | 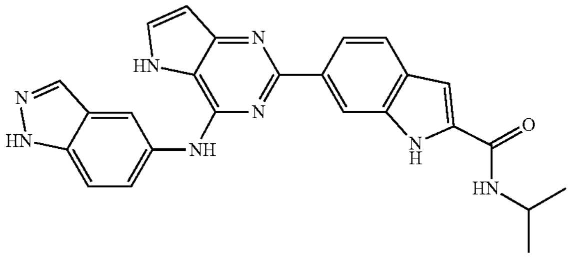 [SMILES: CC(C)NC(=O)c1cc2ccc(-c3nc(Nc4ccc5[nH]ncc5c4)c4[nH]ccc4n3)cc2[nH]1] |
| 38. | 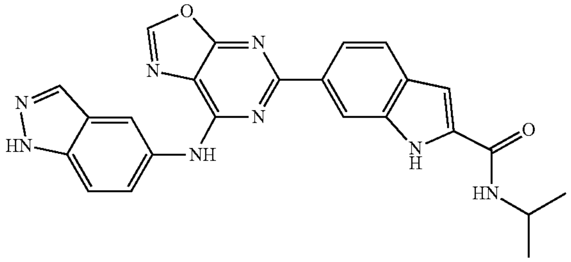 [SMILES: CC(C)NC(=O)c1cc2ccc(-c3nc(Nc4ccc5[nH]ncc5c4)c4ncoc4n3)cc2[nH]1] |
| 39. | 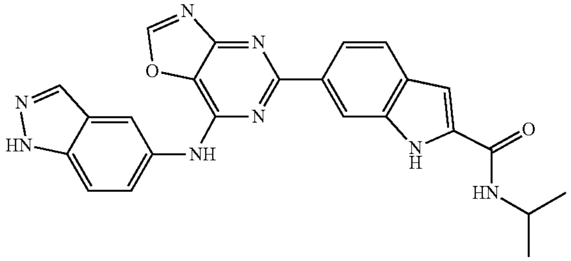 [SMILES: CC(C)NC(=O)c1cc2ccc(-c3nc(Nc4ccc5[nH]ncc5c4)c4ocnc4n3)cc2[nH]1] |
| 40. | 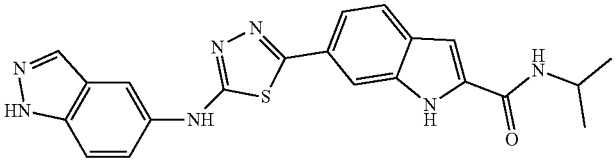 [SMILES: CC(C)NC(=O)c1cc2ccc(-c3nnc(Nc4ccc5[nH]ncc5c4)s3)cc2[nH]1] |
| 41. | 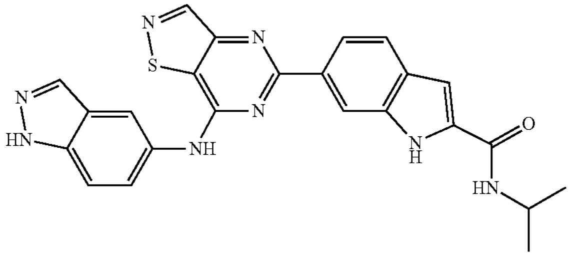 |
| 42. | 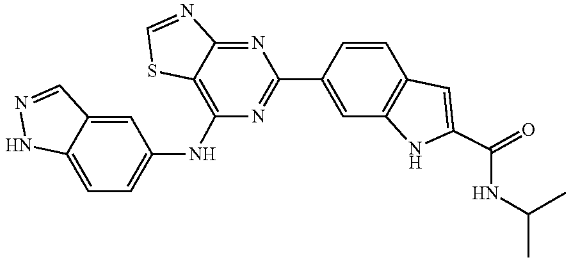 |

-continued
| No. | Structure |
|---|---|
| 43. | 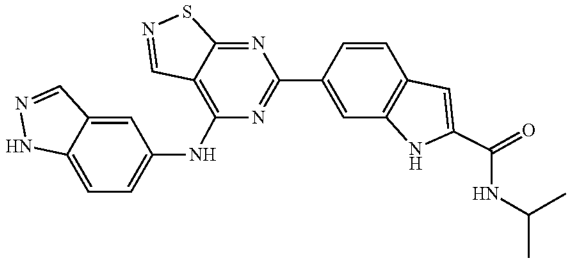 [SMILES: CC(C)NC(=O)c1cc2ccc(-c3nc(Nc4ccc5[nH]ncc5c4)c4cnsc4n3)cc2[nH]1] |
| 44. | 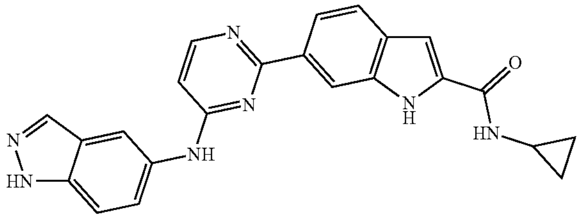 [SMILES: O=C(NC1CC1)c1cc2ccc(-c3nccc(Nc4ccc5[nH]ncc5c4)n3)cc2[nH]1] |
| 45. | 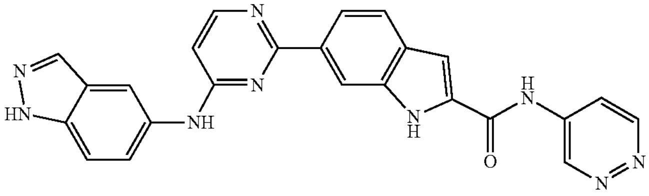 [SMILES: O=C(Nc1ccnnc1)c1cc2ccc(-c3nccc(Nc4ccc5[nH]ncc5c4)n3)cc2[nH]1] |
| 46. | 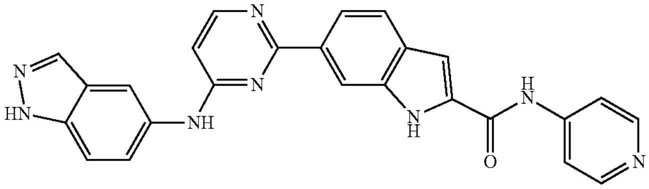 |
| 47. | 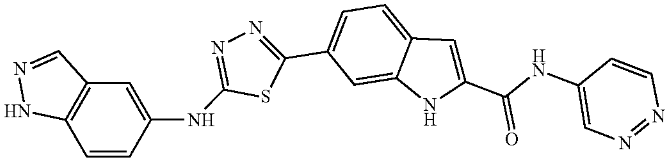 [SMILES: O=C(Nc1ccnnc1)c1cc2ccc(-c3nnc(Nc4ccc5[nH]ncc5c4)s3)cc2[nH]1] |
| 48. | 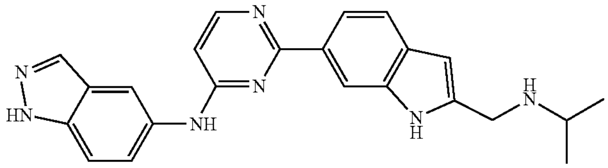 [SMILES: CC(C)NCc1cc2ccc(-c3nccc(Nc4ccc5[nH]ncc5c4)n3)cc2[nH]1] |
| 49. | 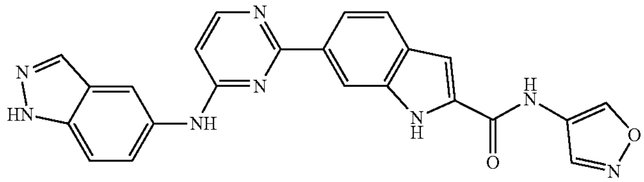 [SMILES: O=C(Nc1cnoc1)c1cc2ccc(-c3nccc(Nc4ccc5[nH]ncc5c4)n3)cc2[nH]1] |

-continued
| No. | Structure |
| --- | --- |
| 50. | 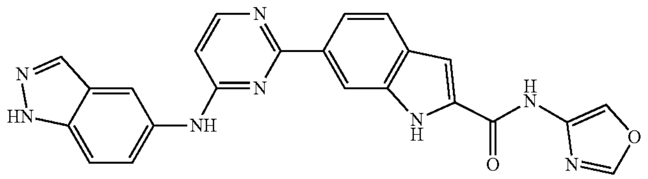 [SMILES: O=C(Nc1cocn1)c1cc2ccc(-c3nccc(Nc4ccc5[nH]ncc5c4)n3)cc2[nH]1] |
| 51. | 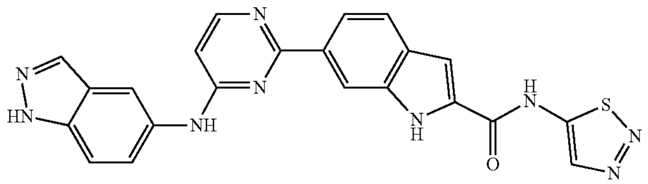 [SMILES: O=C(Nc1cnns1)c1cc2ccc(-c3nccc(Nc4ccc5[nH]ncc5c4)n3)cc2[nH]1] |
| 52. | 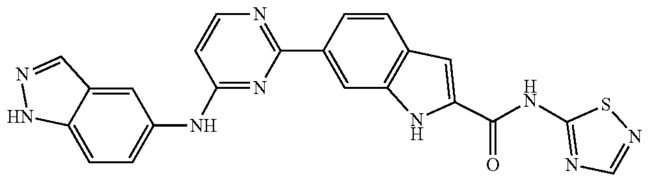 [SMILES: O=C(Nc1ncns1)c1cc2ccc(-c3nccc(Nc4ccc5[nH]ncc5c4)n3)cc2[nH]1] |
| 53. | 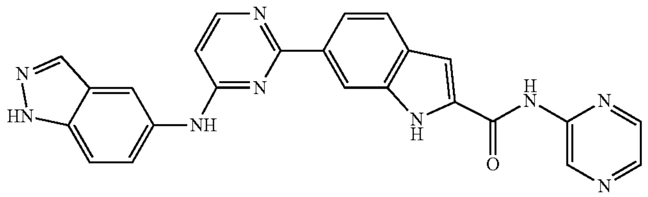 [SMILES: O=C(Nc1cnccn1)c1cc2ccc(-c3nccc(Nc4ccc5[nH]ncc5c4)n3)cc2[nH]1] |
| 54. | 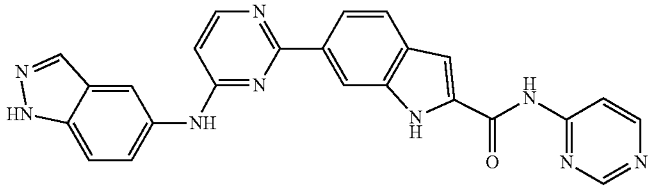 [SMILES: O=C(Nc1ccncn1)c1cc2ccc(-c3nccc(Nc4ccc5[nH]ncc5c4)n3)cc2[nH]1] |
| 55. | 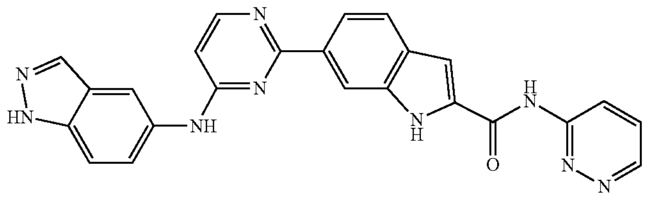 |
| 56. | 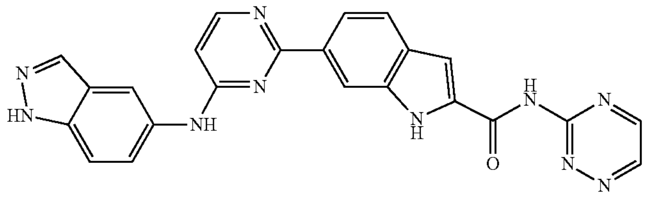 [SMILES: O=C(Nc1nccnn1)c1cc2ccc(-c3nccc(Nc4ccc5[nH]ncc5c4)n3)cc2[nH]1] |

-continued
| No. | Structure |
| --- | --- |
| 57. | 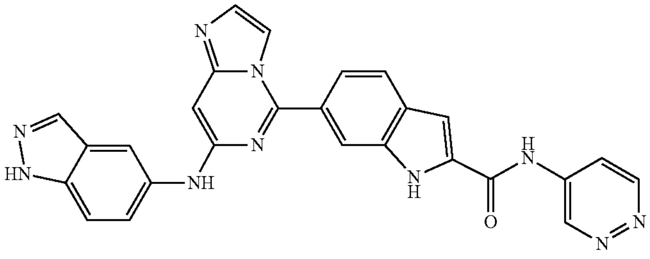 [SMILES: O=C(Nc1ccnnc1)c1cc2ccc(-c3nc(Nc4ccc5[nH]ncc5c4)cc4nccn34)cc2[nH]1] |
| 58. | 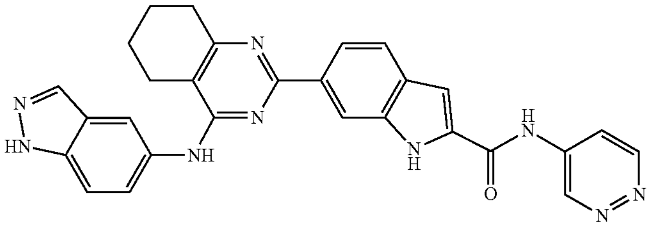 [SMILES: O=C(Nc1ccnnc1)c1cc2ccc(-c3nc4c(c(Nc5ccc6[nH]ncc6c5)n3)CCCC4)cc2[nH]1] |
| 59. | 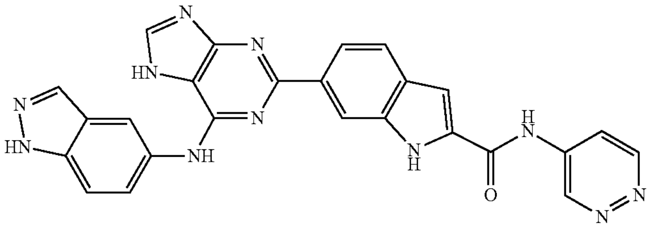 [SMILES: O=C(Nc1ccnnc1)c1cc2ccc(-c3nc(Nc4ccc5[nH]ncc5c4)c4[nH]cnc4n3)cc2[nH]1] |
| 60. | 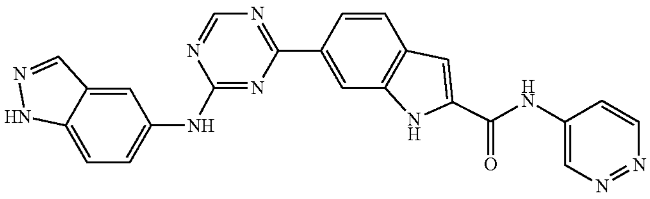 |
| 61. | 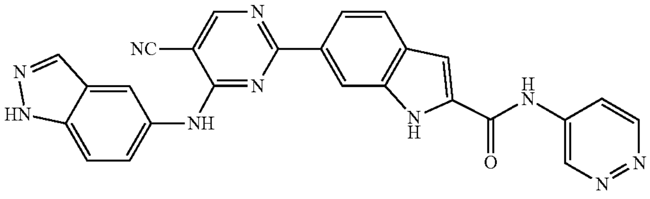 [SMILES: N#Cc1cnc(-c2ccc3cc(C(=O)Nc4ccnnc4)[nH]c3c2)nc1Nc1ccc2[nH]ncc2c1] |
| 62. | 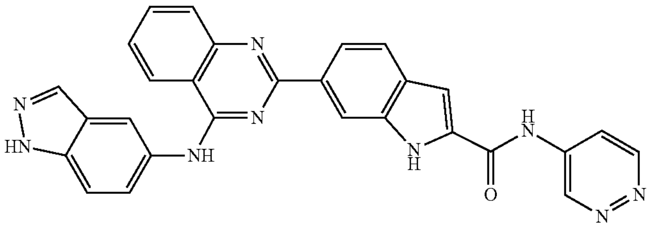 [SMILES: O=C(Nc1ccnnc1)c1cc2ccc(-c3nc(Nc4ccc5[nH]ncc5c4)c4ccccc4n3)cc2[nH]1] |
| 63. | 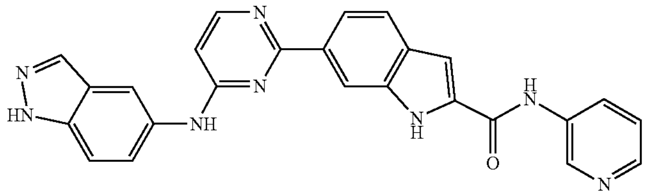 |

-continued
| No. | Structure |
| --- | --- |
| 64. | 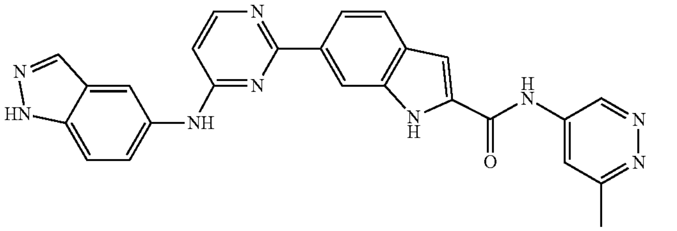 [SMILES: Cc1cc(NC(=O)c2cc3ccc(-c4nccc(Nc5ccc6[nH]ncc6c5)n4)cc3[nH]2)cnn1] |
| 65. | 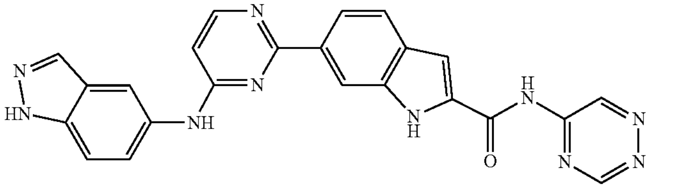 [SMILES: O=C(Nc1cnncn1)c1cc2ccc(-c3nccc(Nc4ccc5[nH]ncc5c4)n3)cc2[nH]1] |
| 66. | 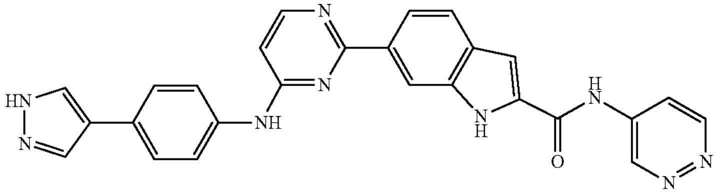 [SMILES: O=C(Nc1ccnnc1)c1cc2ccc(-c3nccc(Nc4ccc(-c5cn[nH]c5)cc4)n3)cc2[nH]1] |
| 67. | 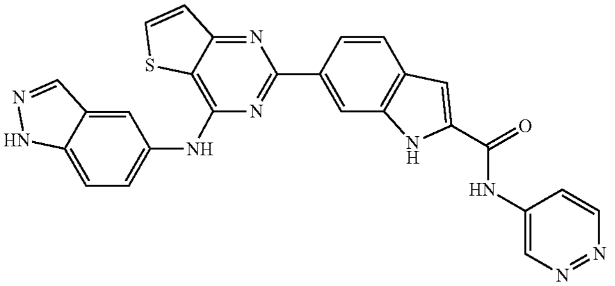 [SMILES: O=C(Nc1ccnnc1)c1cc2ccc(-c3nc(Nc4ccc5[nH]ncc5c4)c4sccc4n3)cc2[nH]1] |
| 68. | 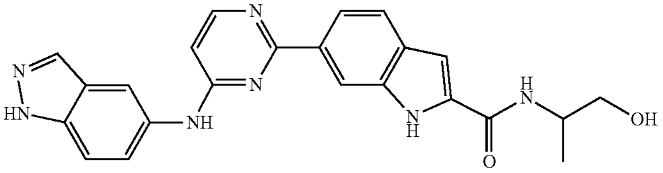 [SMILES: CC(CO)NC(=O)c1cc2ccc(-c3nccc(Nc4ccc5[nH]ncc5c4)n3)cc2[nH]1] |
| 69. | 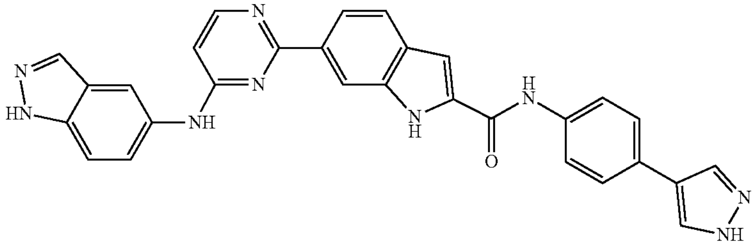 [SMILES: O=C(Nc1ccc(-c2cn[nH]c2)cc1)c1cc2ccc(-c3nccc(Nc4ccc5[nH]ncc5c4)n3)cc2[nH]1] |
| 70. | 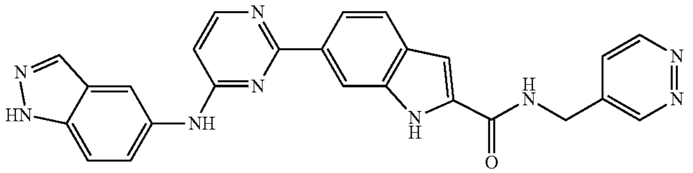 [SMILES: O=C(NCc1ccnnc1)c1cc2ccc(-c3nccc(Nc4ccc5[nH]ncc5c4)n3)cc2[nH]1] |

-continued
| No. | Structure |
|---|---|
| 71. | 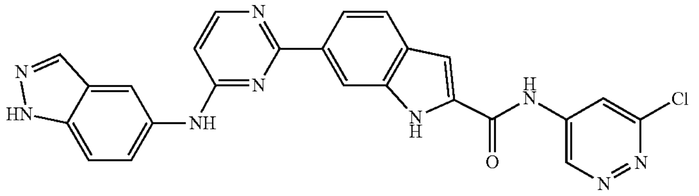 [SMILES: O=C(Nc1cnnc(Cl)c1)c1cc2ccc(-c3nccc(Nc4ccc5[nH]ncc5c4)n3)cc2[nH]1] |
| 72. | 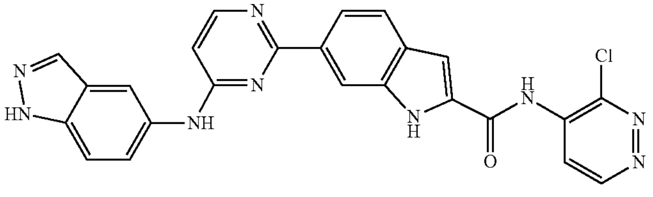 [SMILES: O=C(Nc1ccnnc1Cl)c1cc2ccc(-c3nccc(Nc4ccc5[nH]ncc5c4)n3)cc2[nH]1] |
| 73. | 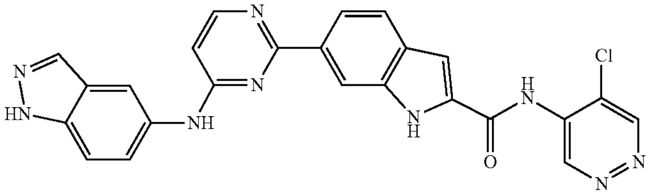 [SMILES: O=C(Nc1cnncc1Cl)c1cc2ccc(-c3nccc(Nc4ccc5[nH]ncc5c4)n3)cc2[nH]1] |
| 74. | 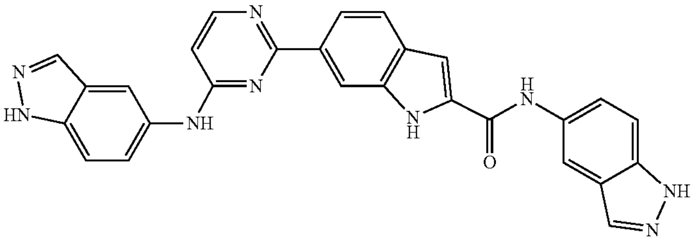 [SMILES: O=C(Nc1ccc2[nH]ncc2c1)c1cc2ccc(-c3nccc(Nc4ccc5[nH]ncc5c4)n3)cc2[nH]1] |
| 75. | 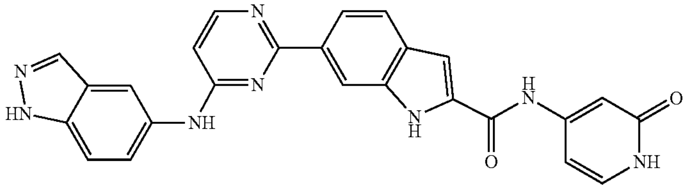 [SMILES: O=C(Nc1cc[nH]c(=O)c1)c1cc2ccc(-c3nccc(Nc4ccc5[nH]ncc5c4)n3)cc2[nH]1] |
| 76. | 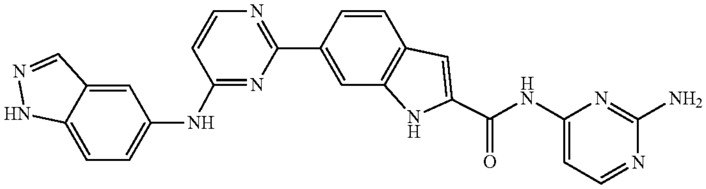 [SMILES: Nc1nccc(NC(=O)c2cc3ccc(-c4nccc(Nc5ccc6[nH]ncc6c5)n4)cc3[nH]2)n1] |
| 77. | 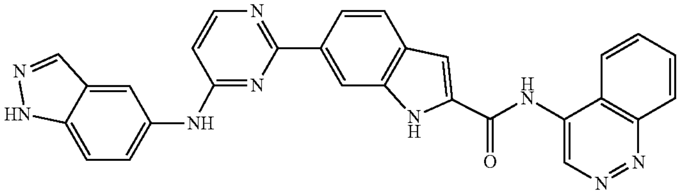 [SMILES: O=C(Nc1cnnc2ccccc12)c1cc2ccc(-c3nccc(Nc4ccc5[nH]ncc5c4)n3)cc2[nH]1] |

-continued
| No. | Structure |
|---|---|
| 78. | 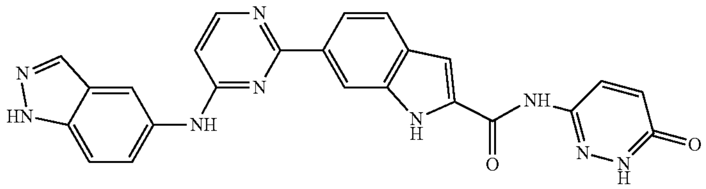 |
| 79. | 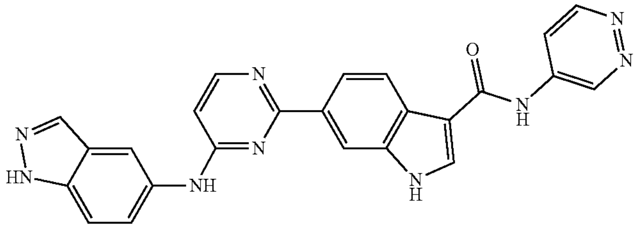 [SMILES: O=C(Nc1ccnnc1)c1c[nH]c2cc(-c3nccc(Nc4ccc5[nH]ncc5c4)n3)ccc12] |
| 80. | 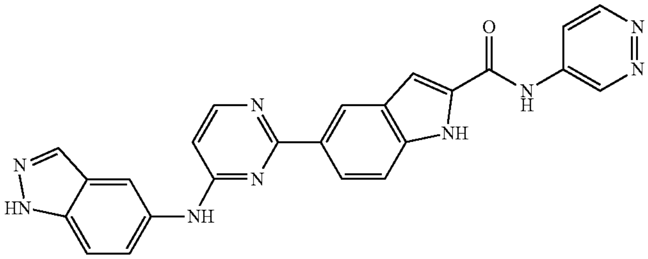 [SMILES: O=C(Nc1ccnnc1)c1cc2cc(-c3nccc(Nc4ccc5[nH]ncc5c4)n3)ccc2[nH]1] |
| 81. | 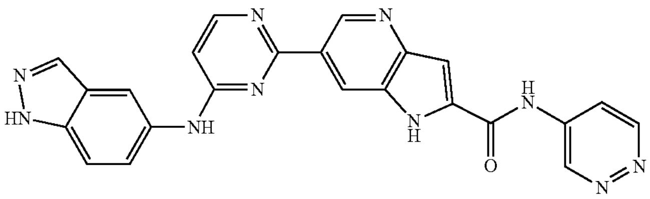 |
| 82. | 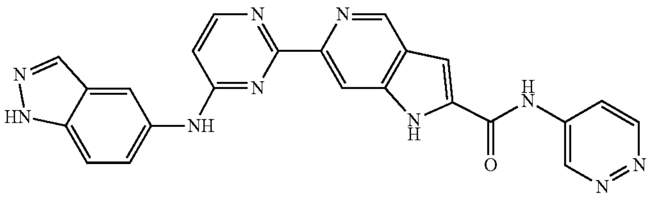 [SMILES: O=C(Nc1ccnnc1)c1cc2cnc(-c3nccc(Nc4ccc5[nH]ncc5c4)n3)cc2[nH]1] |
| 83. | 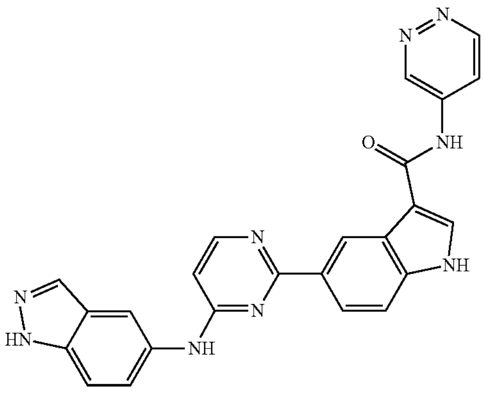 [SMILES: O=C(Nc1ccnnc1)c1c[nH]c2ccc(-c3nccc(Nc4ccc5[nH]ncc5c4)n3)cc12] |

-continued
| No. | Structure |
| --- | --- |
| 84. | 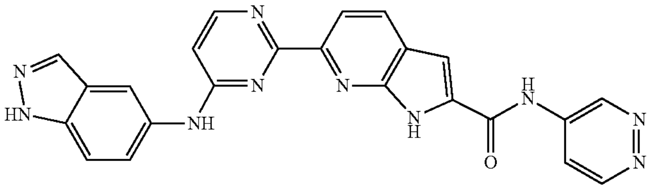 [SMILES: O=C(Nc1ccnnc1)c1cc2ccc(-c3nccc(Nc4ccc5[nH]ncc5c4)n3)nc2[nH]1] |
| 85. | 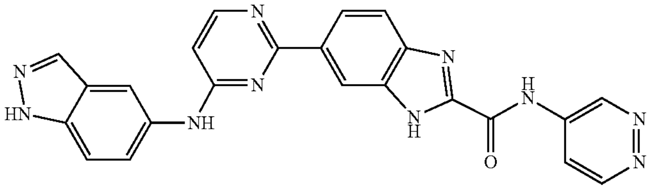 |
| 86. | 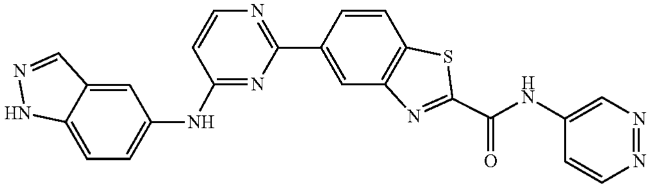 [SMILES: O=C(Nc1ccnnc1)c1nc2cc(-c3nccc(Nc4ccc5[nH]ncc5c4)n3)ccc2s1] |
| 87. | 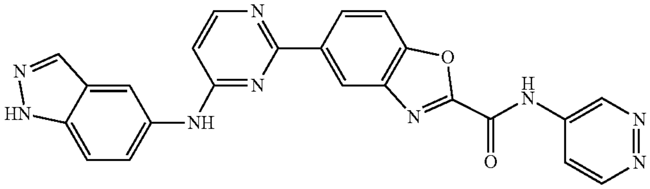 [SMILES: O=C(Nc1ccnnc1)c1nc2cc(-c3nccc(Nc4ccc5[nH]ncc5c4)n3)ccc2o1] |
| 88. | 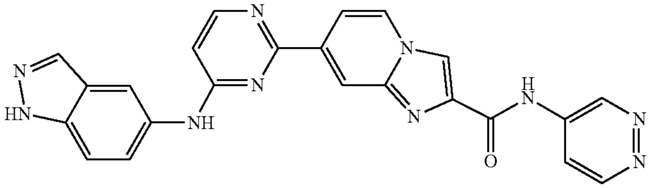 [SMILES: O=C(Nc1ccnnc1)c1cn2ccc(-c3nccc(Nc4ccc5[nH]ncc5c4)n3)cc2n1] |
| 89. | 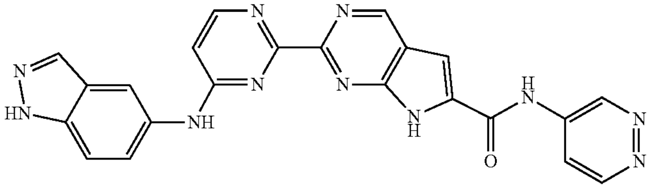 |
| 90. | 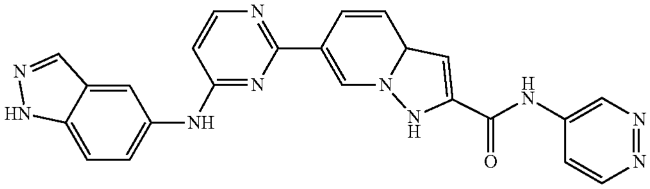 |
| 91. | 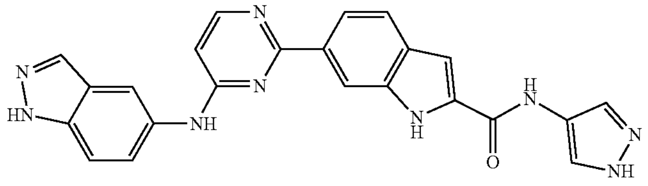 [SMILES: O=C(Nc1cn[nH]c1)c1cc2ccc(-c3nccc(Nc4ccc5[nH]ncc5c4)n3)cc2[nH]1] |

-continued
| No. | Structure |
| --- | --- |
| 92. | 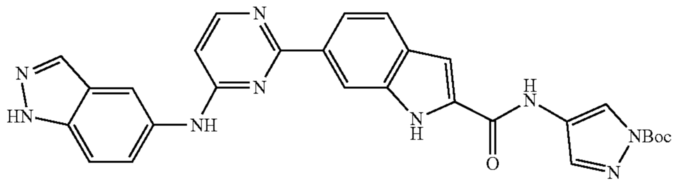 [SMILES: CC(C)(C)OC(=O)n1cc(NC(=O)c2cc3ccc(-c4nccc(Nc5ccc6[nH]ncc6c5)n4)cc3[nH]2)cn1] |
| 93. | 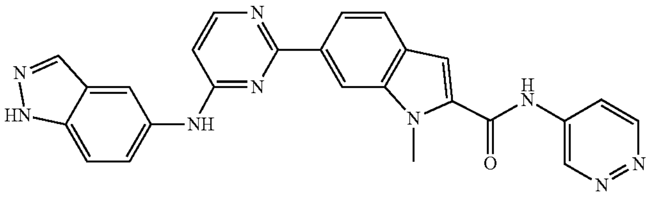 [SMILES: Cn1c(C(=O)Nc2ccnnc2)cc2ccc(-c3nccc(Nc4ccc5[nH]ncc5c4)n3)cc21] |
| 94. | 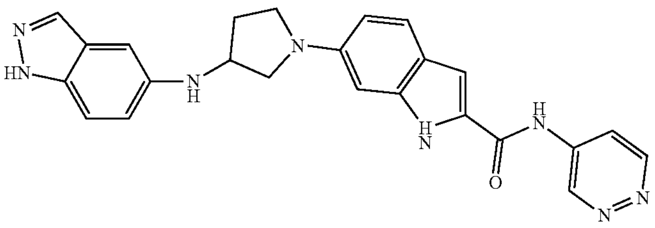 [SMILES: O=C(Nc1ccnnc1)c1cc2ccc(N3CCC(Nc4ccc5[nH]ncc5c4)C3)cc2[nH]1] |
| 95. | 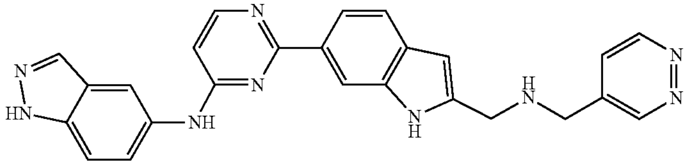 [SMILES: c1cc(CNCc2cc3ccc(-c4nccc(Nc5ccc6[nH]ncc6c5)n4)cc3[nH]2)cnn1] |
| 96. | 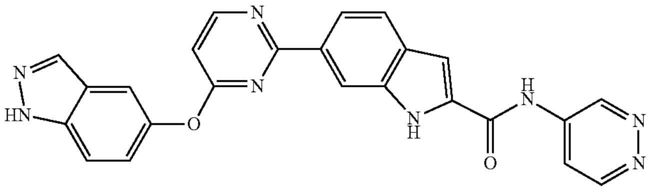 [SMILES: O=C(Nc1ccnnc1)c1cc2ccc(-c3nccc(Oc4ccc5[nH]ncc5c4)n3)cc2[nH]1] |
| 97. | 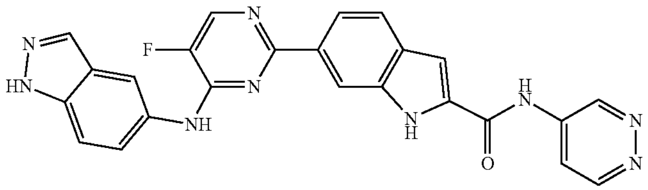 [SMILES: O=C(Nc1ccnnc1)c1cc2ccc(-c3ncc(F)c(Nc4ccc5[nH]ncc5c4)n3)cc2[nH]1] |
| 98. | 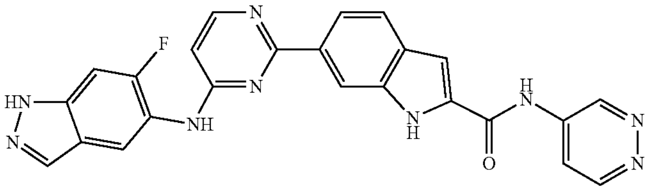 [SMILES: O=C(Nc1ccnnc1)c1cc2ccc(-c3nccc(Nc4cc5cn[nH]c5cc4F)n3)cc2[nH]1] |
| 99. | 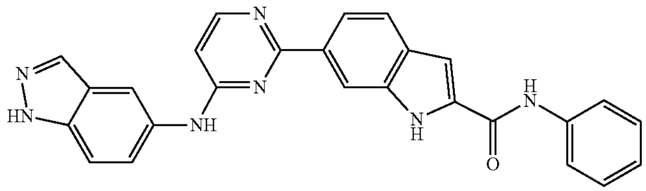 [SMILES: O=C(Nc1ccccc1)c1cc2ccc(-c3nccc(Nc4ccc5[nH]ncc5c4)n3)cc2[nH]1] |

-continued
| No. | Structure |
| --- | --- |
| 100. | 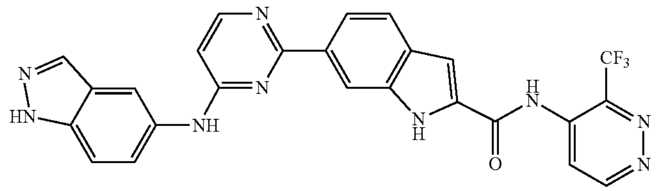 [SMILES: O=C(Nc1ccnnc1C(F)(F)F)c1cc2ccc(-c3nccc(Nc4ccc5[nH]ncc5c4)n3)cc2[nH]1] |
| 101. | 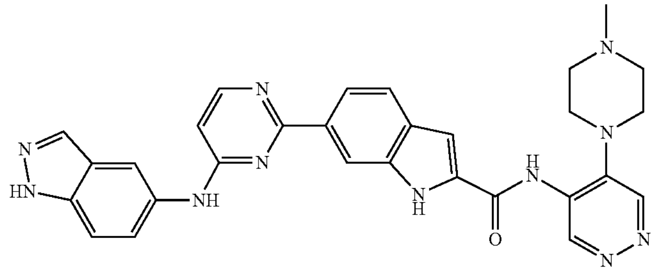 [SMILES: CN1CCN(c2cnncc2NC(=O)c2cc3ccc(-c4nccc(Nc5ccc6[nH]ncc6c5)n4)cc3[nH]2)CC1] |
| 102. | 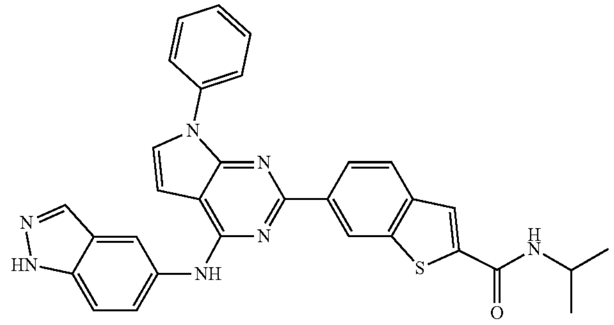 [SMILES: CC(C)NC(=O)c1cc2ccc(-c3nc(Nc4ccc5[nH]ncc5c4)c4ccn(-c5ccccc5)c4n3)cc2s1] |
| 103. | 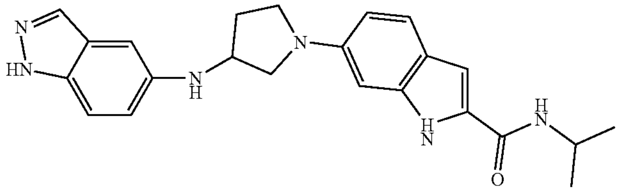 [SMILES: CC(C)NC(=O)c1cc2ccc(N3CCC(Nc4ccc5[nH]ncc5c4)C3)cc2[nH]1] |
| 104. | 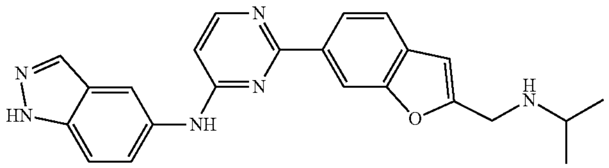 [SMILES: CC(C)NCc1cc2ccc(-c3nccc(Nc4ccc5[nH]ncc5c4)n3)cc2o1] |
| 105. | 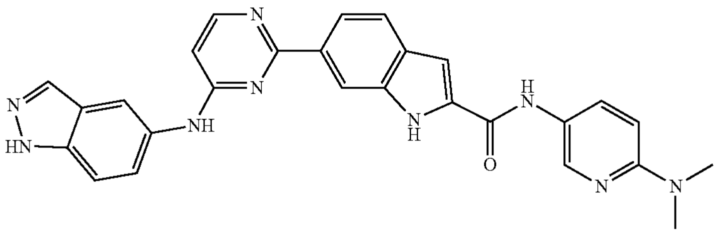 [SMILES: CN(C)c1ccc(NC(=O)c2cc3ccc(-c4nccc(Nc5ccc6[nH]ncc6c5)n4)cc3[nH]2)cn1] |

-continued
| No. | Structure |
|---|---|
| 106. | 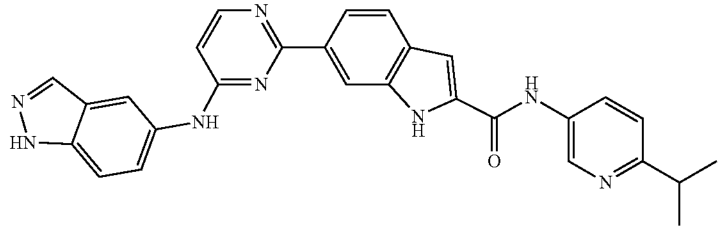 [SMILES: CC(C)c1ccc(NC(=O)c2cc3ccc(-c4nccc(Nc5ccc6[nH]ncc6c5)n4)cc3[nH]2)cn1] |
| 107. | 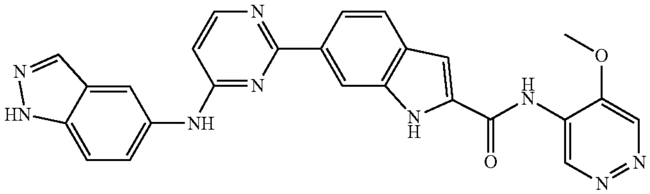 [SMILES: COc1cnncc1NC(=O)c1cc2ccc(-c3nccc(Nc4ccc5[nH]ncc5c4)n3)cc2[nH]1] |
| 108. | 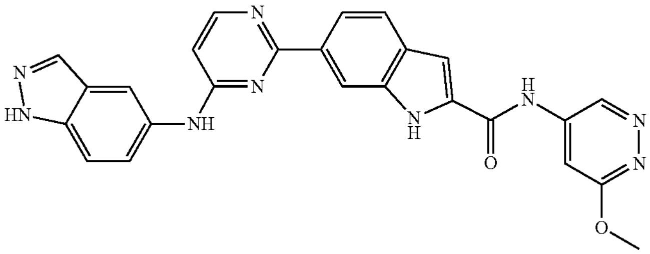 [SMILES: COc1cc(NC(=O)c2cc3ccc(-c4nccc(Nc5ccc6[nH]ncc6c5)n4)cc3[nH]2)cnn1] |
| 109. | 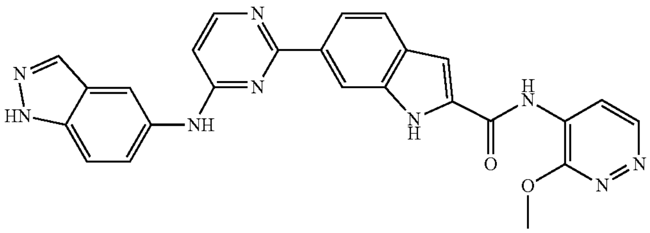 [SMILES: COc1nnccc1NC(=O)c1cc2ccc(-c3nccc(Nc4ccc5[nH]ncc5c4)n3)cc2[nH]1] |
| 110. | 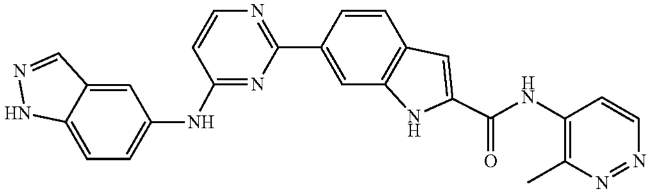 [SMILES: Cc1nnccc1NC(=O)c1cc2ccc(-c3nccc(Nc4ccc5[nH]ncc5c4)n3)cc2[nH]1] |
| 111. | 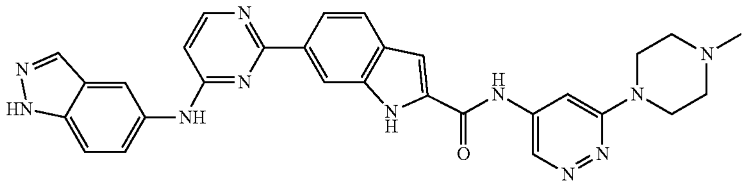 [SMILES: CN1CCN(c2cc(NC(=O)c3cc4ccc(-c5nccc(Nc6ccc7[nH]ncc7c6)n5)cc4[nH]3)cnn2)CC1] |
| 112. | 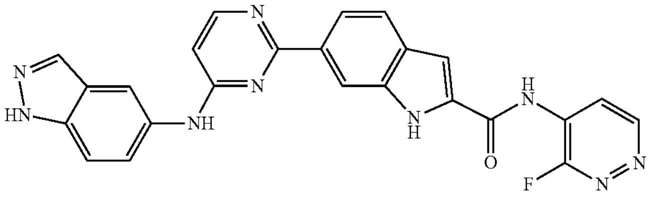 [SMILES: O=C(Nc1ccnnc1F)c1cc2ccc(-c3nccc(Nc4ccc5[nH]ncc5c4)n3)cc2[nH]1] |

-continued
| No. | Structure |
|---|---|
| 113. | 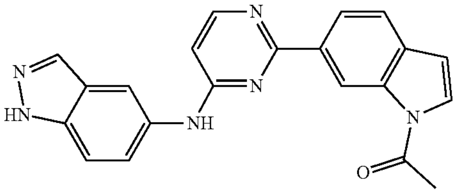 [SMILES: CC(=O)n1ccc2ccc(-c3nccc(Nc4ccc5[nH]ncc5c4)n3)cc21] |
| 114. | 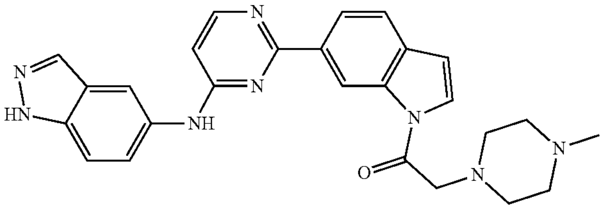 [SMILES: CN1CCN(CC(=O)n2ccc3ccc(-c4nccc(Nc5ccc6[nH]ncc6c5)n4)cc32)CC1] |
| 115. | 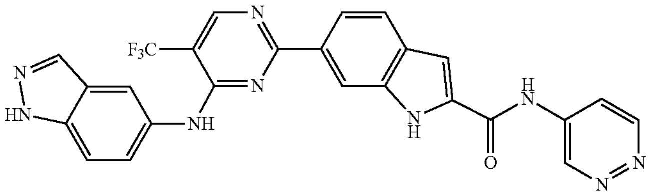 [SMILES: O=C(Nc1ccnnc1)c1cc2ccc(-c3ncc(C(F)(F)F)c(Nc4ccc5[nH]ncc5c4)n3)cc2[nH]1] |
| 116. | 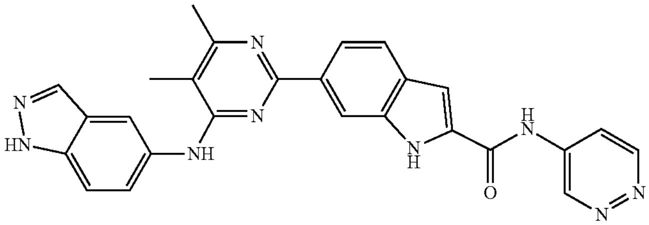 [SMILES: Cc1nc(-c2ccc3cc(C(=O)Nc4ccnnc4)[nH]c3c2)nc(Nc2ccc3[nH]ncc3c2)c1C] |
| 117. | 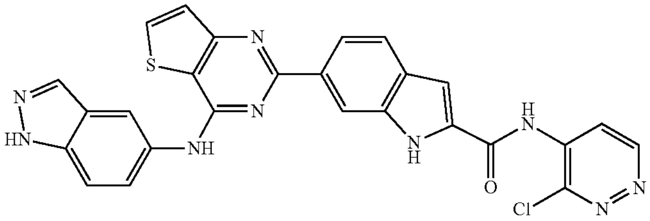 [SMILES: O=C(Nc1ccnnc1Cl)c1cc2ccc(-c3nc(Nc4ccc5[nH]ncc5c4)c4sccc4n3)cc2[nH]1] |
| 118. | 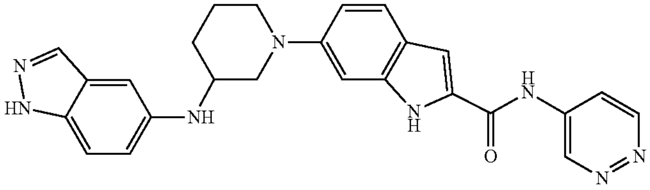 [SMILES: O=C(Nc1ccnnc1)c1cc2ccc(N3CCCC(Nc4ccc5[nH]ncc5c4)C3)cc2[nH]1] |
| 119. | 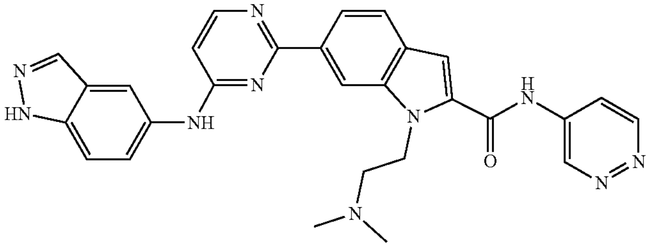 [SMILES: CN(C)CCn1c(C(=O)Nc2ccnnc2)cc2ccc(-c3nccc(Nc4ccc5[nH]ncc5c4)n3)cc21] |

-continued
| No. | Structure |
| --- | --- |
| 120. | 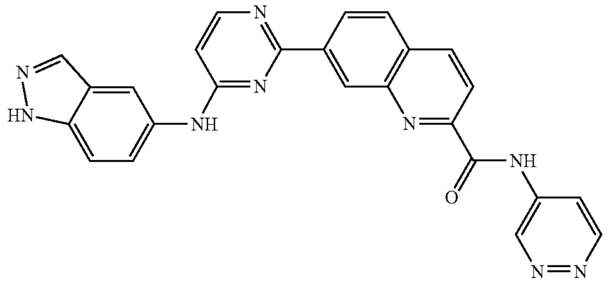 [SMILES: O=C(Nc1ccnnc1)c1ccc2ccc(-c3nccc(Nc4ccc5[nH]ncc5c4)n3)cc2n1] |
| 121. | 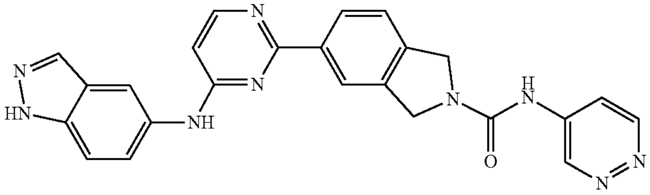 [SMILES: O=C(Nc1ccnnc1)N1Cc2ccc(-c3nccc(Nc4ccc5[nH]ncc5c4)n3)cc2C1] |
| 122. | 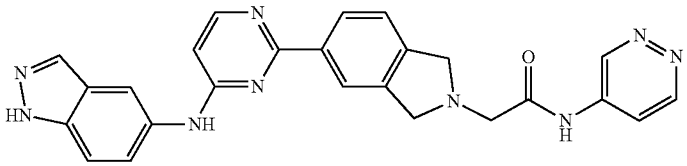 [SMILES: O=C(CN1Cc2ccc(-c3nccc(Nc4ccc5[nH]ncc5c4)n3)cc2C1)Nc1ccnnc1] |
| 123. | 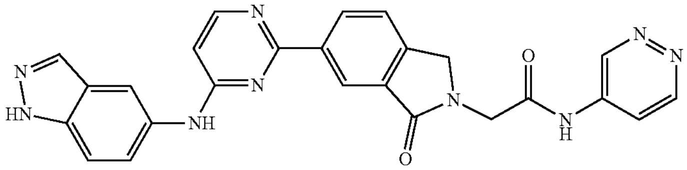 [SMILES: O=C(CN1Cc2ccc(-c3nccc(Nc4ccc5[nH]ncc5c4)n3)cc2C1=O)Nc1ccnnc1] |
| 124. | 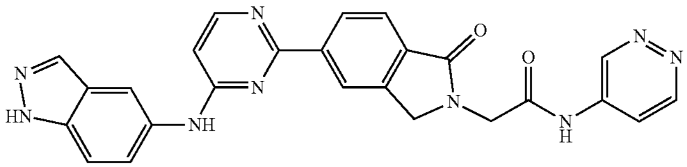 [SMILES: O=C(CN1Cc2cc(-c3nccc(Nc4ccc5[nH]ncc5c4)n3)ccc2C1=O)Nc1ccnnc1] |
| 125. | 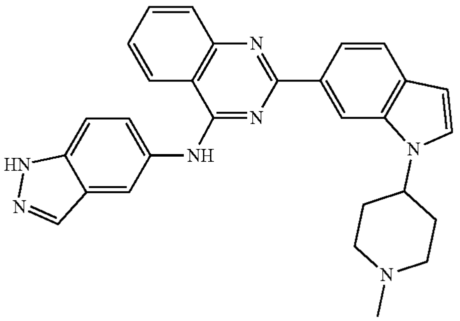 [SMILES: CN1CCC(n2ccc3ccc(-c4nc(Nc5ccc6[nH]ncc6c5)c5ccccc5n4)cc32)CC1] |
| 126. | 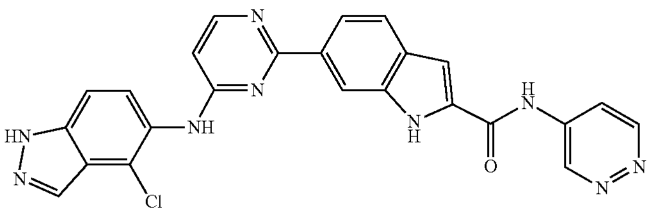 |

-continued
| No. | Structure |
|---|---|
| 127. | 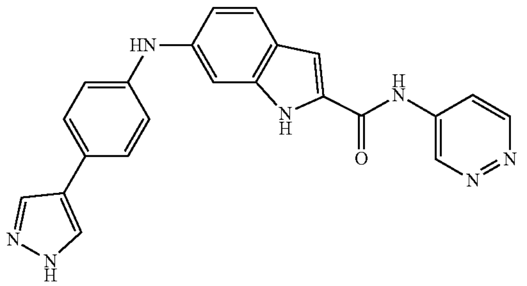 [SMILES: O=C(Nc1ccnnc1)c1cc2ccc(Nc3ccc(-c4cn[nH]c4)cc3)cc2[nH]1] |
| 128. | 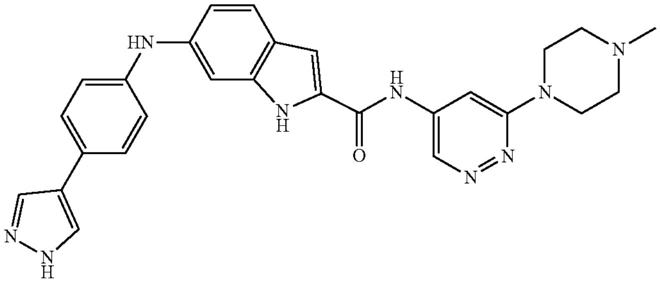 [SMILES: CN1CCN(c2cc(NC(=O)c3cc4ccc(Nc5ccc(-c6cn[nH]c6)cc5)cc4[nH]3)cnn2)CC1] |
| 129. | 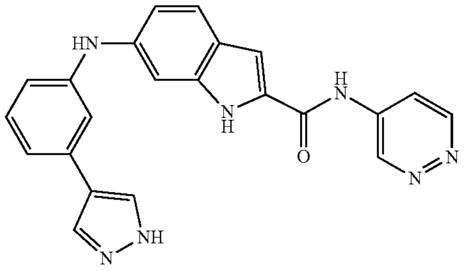 [SMILES: O=C(Nc1ccnnc1)c1cc2ccc(Nc3cccc(-c4cn[nH]c4)c3)cc2[nH]1] |
| 130. | 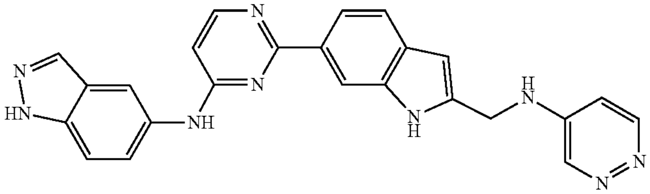 [SMILES: c1cc(NCc2cc3ccc(-c4nccc(Nc5ccc6[nH]ncc6c5)n4)cc3[nH]2)cnn1] |
| 131. | 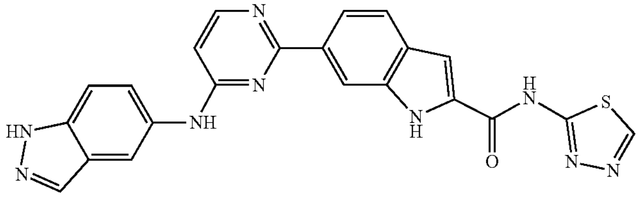 [SMILES: O=C(Nc1nncs1)c1cc2ccc(-c3nccc(Nc4ccc5[nH]ncc5c4)n3)cc2[nH]1] |
| 132. | 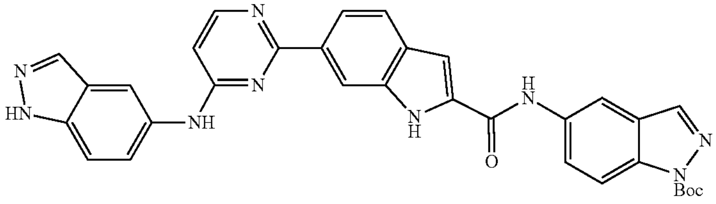 [SMILES: CC(C)(C)OC(=O)n1ncc2cc(NC(=O)c3cc4ccc(-c5nccc(Nc6ccc7[nH]ncc7c6)n5)cc4[nH]3)ccc21] |

-continued
| No. | Structure |
|---|---|
| 133. | 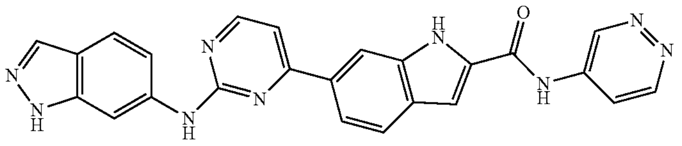 [SMILES: O=C(Nc1ccnnc1)c1cc2ccc(-c3ccnc(Nc4ccc5cn[nH]c5c4)n3)cc2[nH]1] |
| 134. | 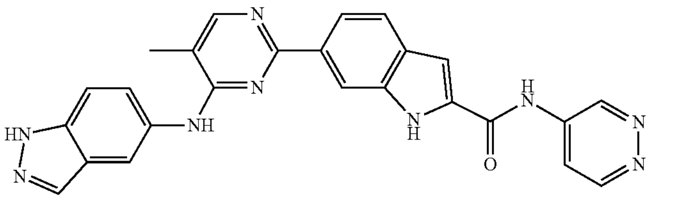 [SMILES: Cc1cnc(-c2ccc3cc(C(=O)Nc4ccnnc4)[nH]c3c2)nc1Nc1ccc2[nH]ncc2c1] |
| 135. | 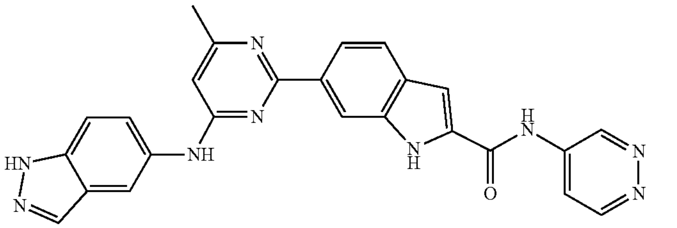 |
| 136. | 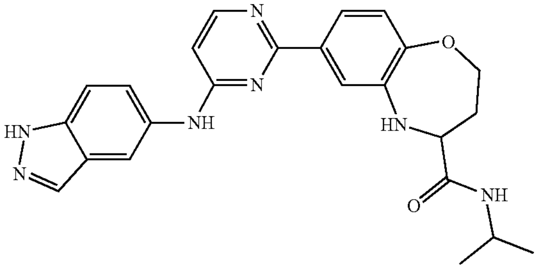 [SMILES: CC(C)NC(=O)C1CCOc2ccc(-c3nccc(Nc4ccc5[nH]ncc5c4)n3)cc2N1] |
| 137. | 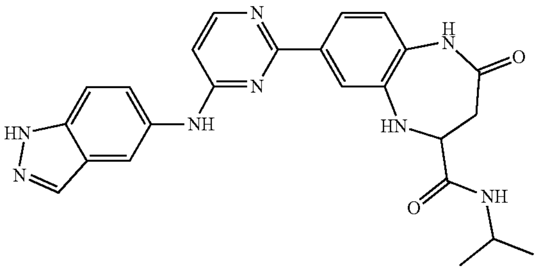 [SMILES: CC(C)NC(=O)C1CC(=O)Nc2ccc(-c3nccc(Nc4ccc5[nH]ncc5c4)n3)cc2N1] |
| 138. | 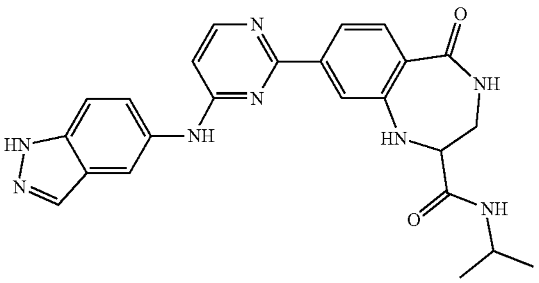 [SMILES: CC(C)NC(=O)C1CNC(=O)c2ccc(-c3nccc(Nc4ccc5[nH]ncc5c4)n3)cc2N1] |

-continued
| No. | Structure |
| --- | --- |
| 139. | 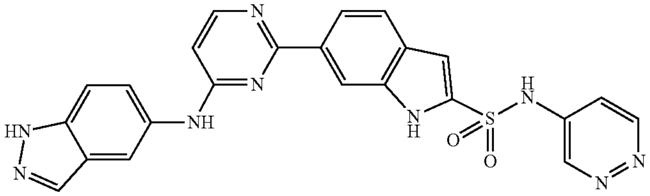 [SMILES: O=S(=O)(Nc1ccnnc1)c1cc2ccc(-c3nccc(Nc4ccc5[nH]ncc5c4)n3)cc2[nH]1] |
| 140. | 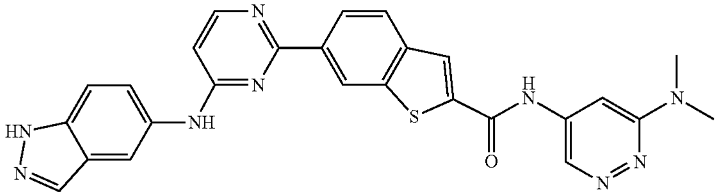 [SMILES: CN(C)c1cc(NC(=O)c2cc3ccc(-c4nccc(Nc5ccc6[nH]ncc6c5)n4)cc3s2)cnn1] |
| 141. | 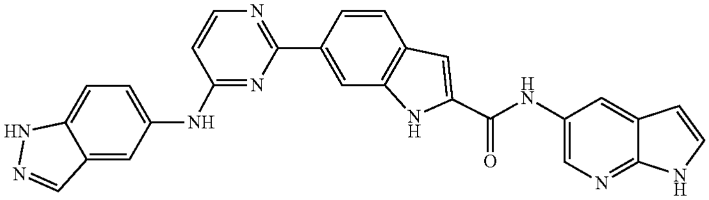 [SMILES: O=C(Nc1cnc2[nH]ccc2c1)c1cc2ccc(-c3nccc(Nc4ccc5[nH]ncc5c4)n3)cc2[nH]1] |
| 142. | 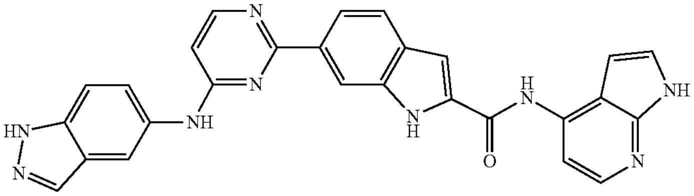 [SMILES: O=C(Nc1ccnc2[nH]ccc12)c1cc2ccc(-c3nccc(Nc4ccc5[nH]ncc5c4)n3)cc2[nH]1] |
| 143. | 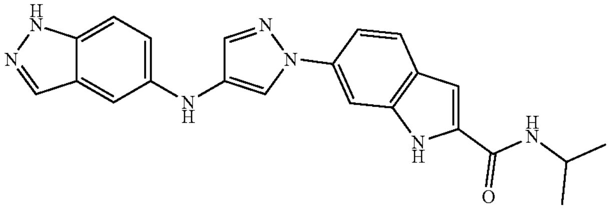 [SMILES: CC(C)NC(=O)c1cc2ccc(-n3cc(Nc4ccc5[nH]ncc5c4)cn3)cc2[nH]1] |
| 144. | 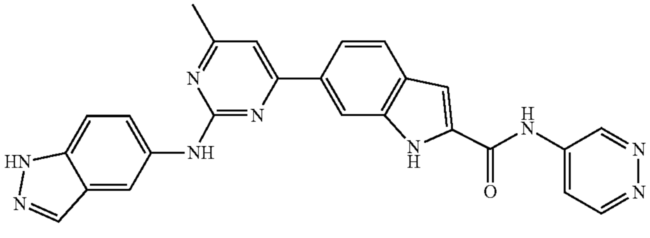 [SMILES: Cc1cc(-c2ccc3cc(C(=O)Nc4ccnnc4)[nH]c3c2)nc(Nc2ccc3[nH]ncc3c2)n1] |
| 145. | 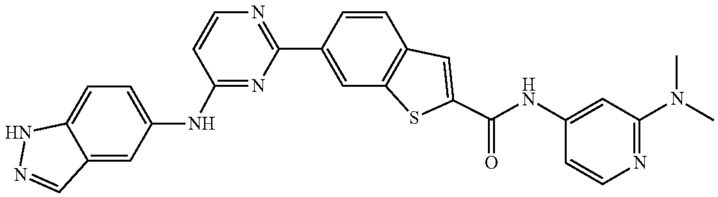 [SMILES: CN(C)c1cc(NC(=O)c2cc3ccc(-c4nccc(Nc5ccc6[nH]ncc6c5)n4)cc3s2)ccn1] |

-continued
| No. | Structure |
| --- | --- |
| 146. | 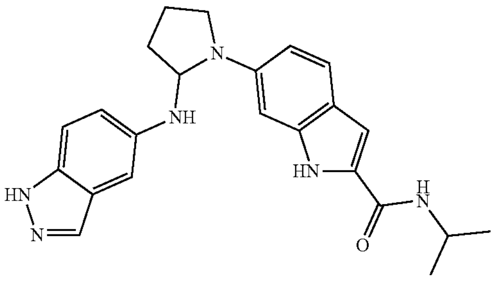 [SMILES: CC(C)NC(=O)c1cc2ccc(N3CCCC3Nc3ccc4[nH]ncc4c3)cc2[nH]1] |
| 147. | 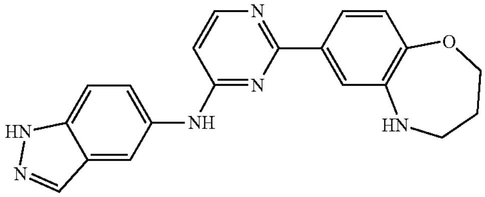 [SMILES: c1cc(Nc2ccc3[nH]ncc3c2)nc(-c2ccc3c(c2)NCCCO3)n1] |
| 148. | 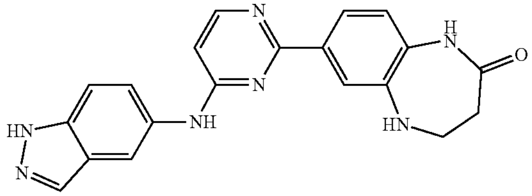 [SMILES: O=C1CCNc2cc(-c3nccc(Nc4ccc5[nH]ncc5c4)n3)ccc2N1] |
| 149. | 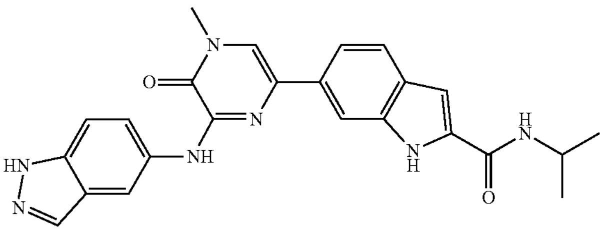 [SMILES: CC(C)NC(=O)c1cc2ccc(-c3cn(C)c(=O)c(Nc4ccc5[nH]ncc5c4)n3)cc2[nH]1] |
| 150. | 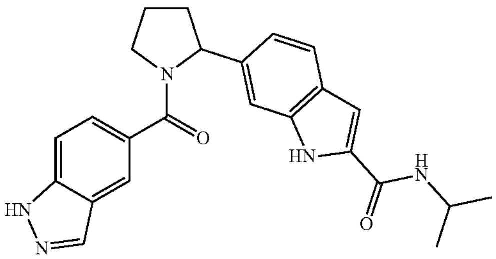 [SMILES: CC(C)NC(=O)c1cc2ccc(C3CCCN3C(=O)c3ccc4[nH]ncc4c3)cc2[nH]1] |
| 151. | 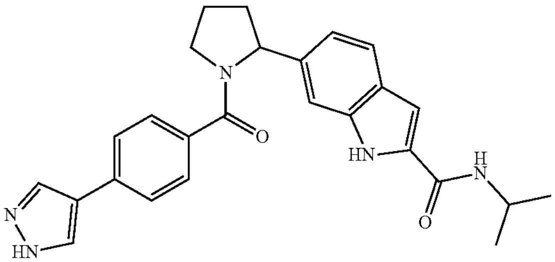 [SMILES: CC(C)NC(=O)c1cc2ccc(C3CCCN3C(=O)c3ccc(-c4cn[nH]c4)cc3)cc2[nH]1] |

-continued
| No. | Structure |
|---|---|
| 152. | 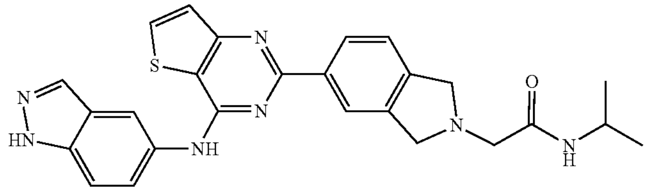 [SMILES: CC(C)NC(=O)CN1Cc2ccc(-c3nc(Nc4ccc5[nH]ncc5c4)c4sccc4n3)cc2C1] |
| 153. | 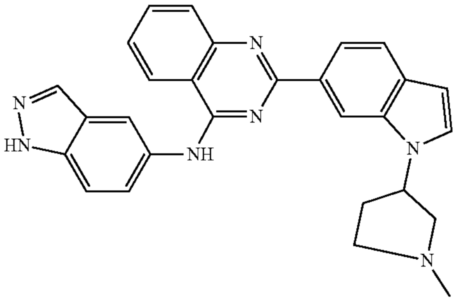 [SMILES: CN1CCC(n2ccc3ccc(-c4nc(Nc5ccc6[nH]ncc6c5)c5ccccc5n4)cc32)C1] |
| 154. | 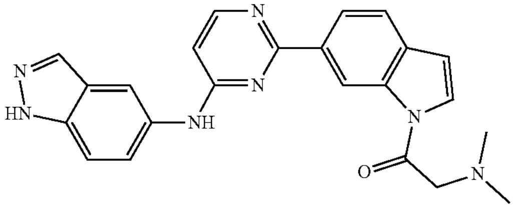 [SMILES: CN(C)CC(=O)n1ccc2ccc(-c3nccc(Nc4ccc5[nH]ncc5c4)n3)cc21] |
| 155. | 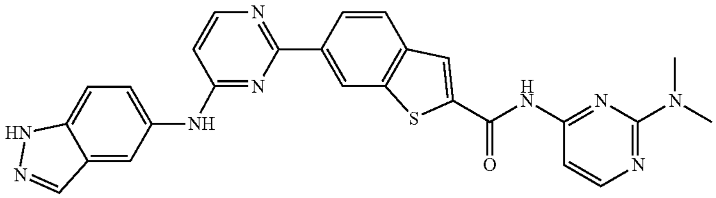 [SMILES: CN(C)c1nccc(NC(=O)c2cc3ccc(-c4nccc(Nc5ccc6[nH]ncc6c5)n4)cc3s2)n1] |
| 156. | 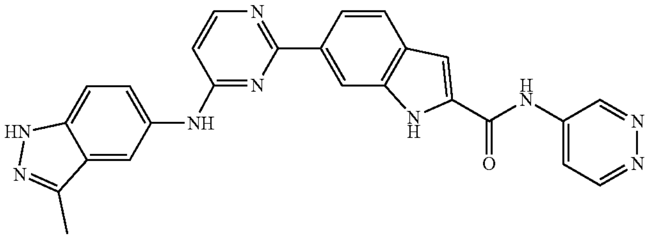 [SMILES: Cc1n[nH]c2ccc(Nc3ccnc(-c4ccc5cc(C(=O)Nc6ccnnc6)[nH]c5c4)n3)cc12] |
| 157. | 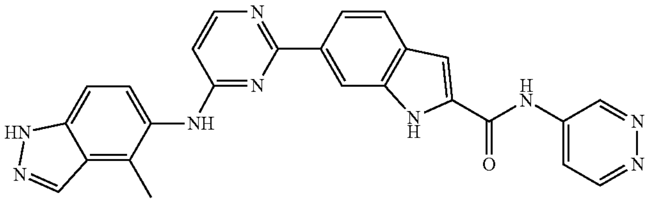 [SMILES: Cc1c(Nc2ccnc(-c3ccc4cc(C(=O)Nc5ccnnc5)[nH]c4c3)n2)ccc2[nH]ncc12] |
| 158. | 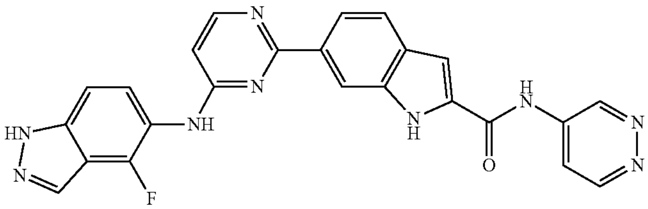 [SMILES: O=C(Nc1ccnnc1)c1cc2ccc(-c3nccc(Nc4ccc5[nH]ncc5c4F)n3)cc2[nH]1] |

-continued
| No. | Structure |
| --- | --- |
| 159. | 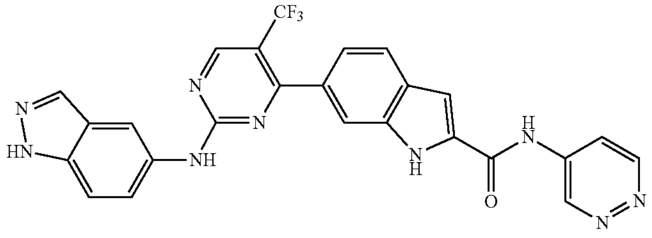 [SMILES: O=C(Nc1ccnnc1)c1cc2ccc(-c3nc(Nc4ccc5[nH]ncc5c4)ncc3C(F)(F)F)cc2[nH]1] |
| 160. | 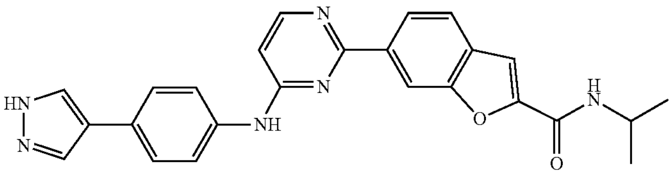 [SMILES: CC(C)NC(=O)c1cc2ccc(-c3nccc(Nc4ccc(-c5cn[nH]c5)cc4)n3)cc2o1] |
| 161. | 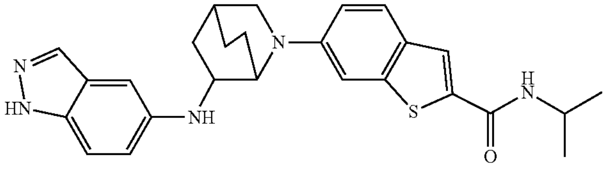 [SMILES: CC(C)NC(=O)c1cc2ccc(N3CC4CCC3C(Nc3ccc5[nH]ncc5c3)C4)cc2s1] |
| 162. | 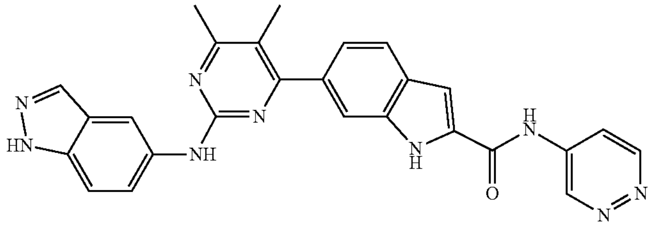 [SMILES: Cc1nc(Nc2ccc3[nH]ncc3c2)nc(-c2ccc3cc(C(=O)Nc4ccnnc4)[nH]c3c2)c1C] |
| 163. | 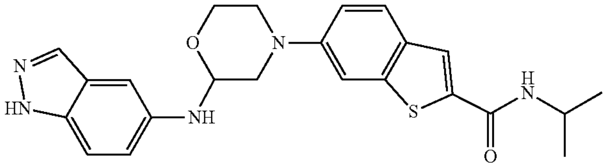 [SMILES: CC(C)NC(=O)c1cc2ccc(N3CCOC(Nc4ccc5[nH]ncc5c4)C3)cc2s1] |
| 164. | 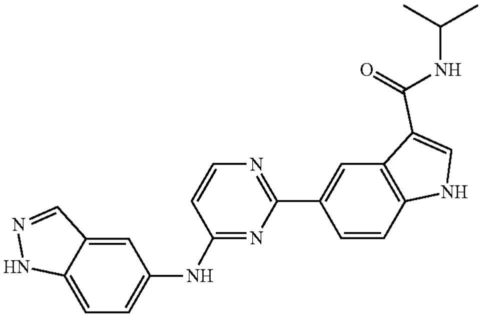 [SMILES: CC(C)NC(=O)c1c[nH]c2ccc(-c3nccc(Nc4ccc5[nH]ncc5c4)n3)cc12] |

-continued
| No. | Structure |
|---|---|
| 165. | 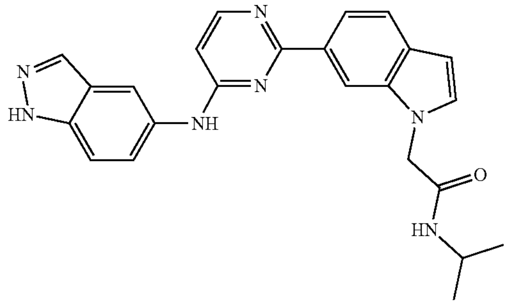 [SMILES: CC(C)NC(=O)Cn1ccc2ccc(-c3nccc(Nc4ccc5[nH]ncc5c4)n3)cc21] |
| 166. | 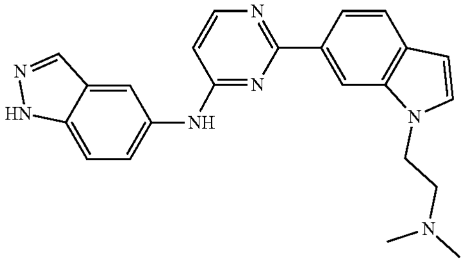 [SMILES: CN(C)CCn1ccc2ccc(-c3nccc(Nc4ccc5[nH]ncc5c4)n3)cc21] |
| 167. | 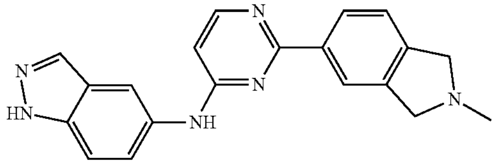 [SMILES: CN1Cc2ccc(-c3nccc(Nc4ccc5[nH]ncc5c4)n3)cc2C1] |
| 168. | 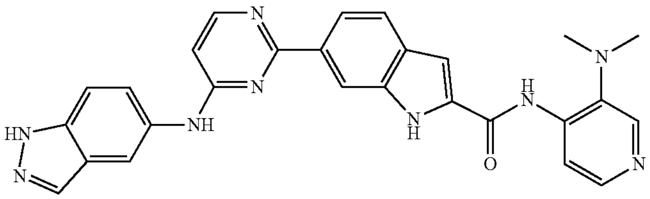 [SMILES: CN(C)c1cnccc1NC(=O)c1cc2ccc(-c3nccc(Nc4ccc5[nH]ncc5c4)n3)cc2[nH]1] |
| 169. | 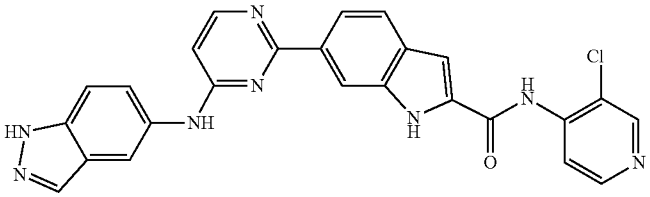 [SMILES: O=C(Nc1ccncc1Cl)c1cc2ccc(-c3nccc(Nc4ccc5[nH]ncc5c4)n3)cc2[nH]1] |
| 170. | 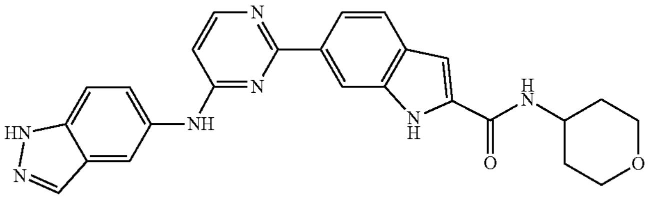 [SMILES: O=C(NC1CCOCC1)c1cc2ccc(-c3nccc(Nc4ccc5[nH]ncc5c4)n3)cc2[nH]1] |
| 171. | 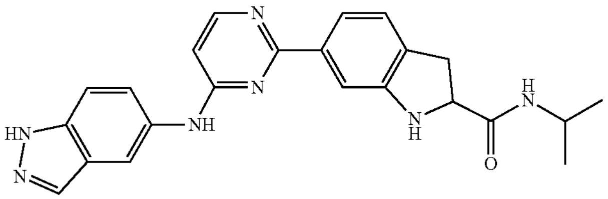 [SMILES: CC(C)NC(=O)C1Cc2ccc(-c3nccc(Nc4ccc5[nH]ncc5c4)n3)cc2N1] |

-continued
| No. | Structure |
|---|---|
| 172. | 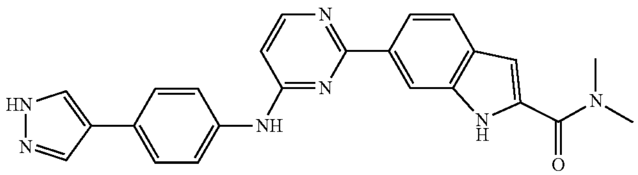 |
| 173. | 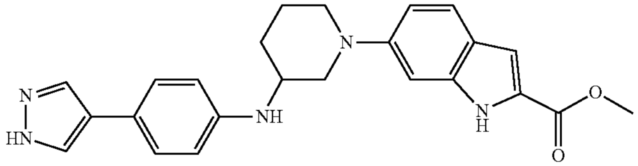 [SMILES: COC(=O)c1cc2ccc(N3CCCC(Nc4ccc(-c5cn[nH]c5)cc4)C3)cc2[nH]1] |
| 174. | 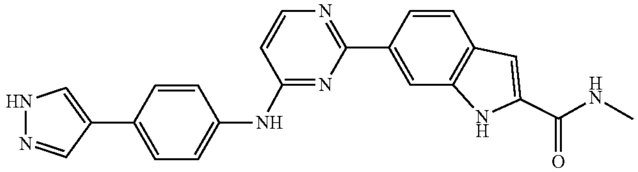 |
| 175. | 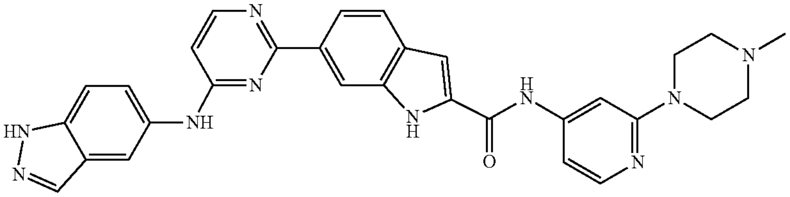 [SMILES: CN1CCN(c2cc(NC(=O)c3cc4ccc(-c5nccc(Nc6ccc7[nH]ncc7c6)n5)cc4[nH]3)ccn2)CC1] |
| 176. | 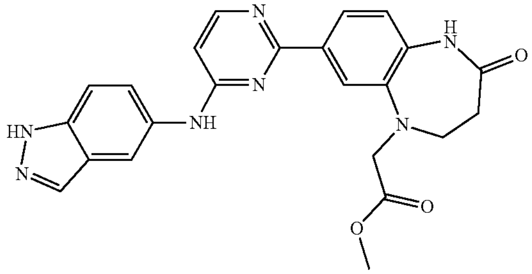 [SMILES: COC(=O)CN1CCC(=O)Nc2ccc(-c3nccc(Nc4ccc5[nH]ncc5c4)n3)cc21] |
| 177. | 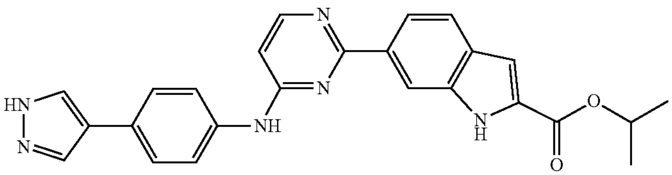 [SMILES: CC(C)OC(=O)c1cc2ccc(-c3nccc(Nc4ccc(-c5cn[nH]c5)cc4)n3)cc2[nH]1] |
| 178. | 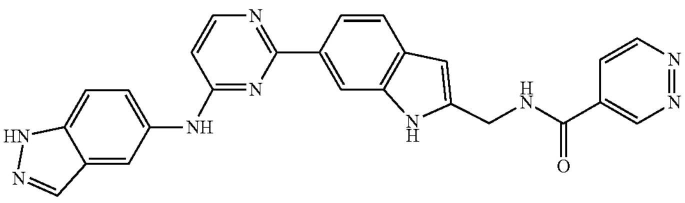 [SMILES: O=C(NCc1cc2ccc(-c3nccc(Nc4ccc5[nH]ncc5c4)n3)cc2[nH]1)c1ccnnc1] |

-continued
| No. | Structure |
|---|---|
| 179. | 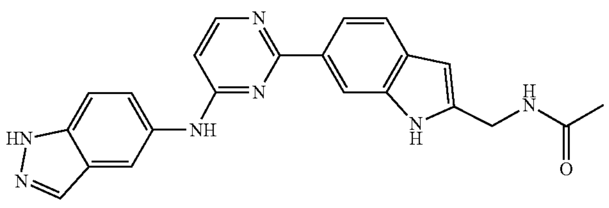 [SMILES: CC(=O)NCc1cc2ccc(-c3nccc(Nc4ccc5[nH]ncc5c4)n3)cc2[nH]1] |
| 180. | 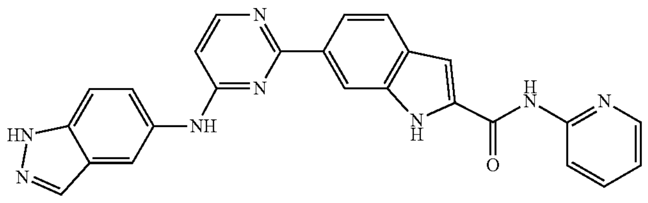 [SMILES: O=C(Nc1ccccn1)c1cc2ccc(-c3nccc(Nc4ccc5[nH]ncc5c4)n3)cc2[nH]1] |
| 181. | 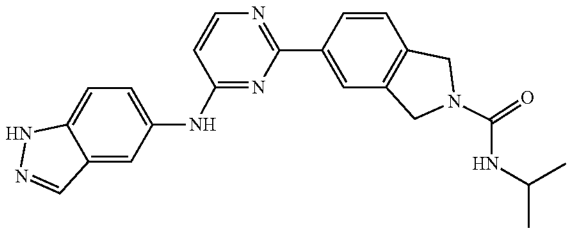 [SMILES: CC(C)NC(=O)N1Cc2ccc(-c3nccc(Nc4ccc5[nH]ncc5c4)n3)cc2C1] |
| 182. | 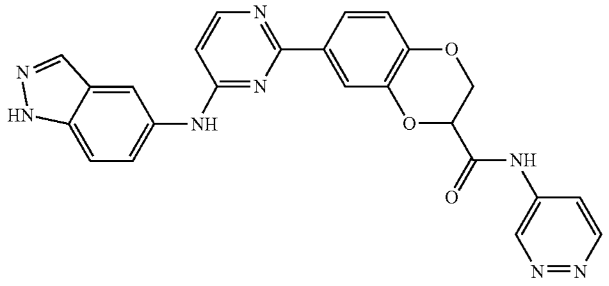 [SMILES: O=C(Nc1ccnnc1)C1COc2ccc(-c3nccc(Nc4ccc5[nH]ncc5c4)n3)cc2O1] |
| 183. | 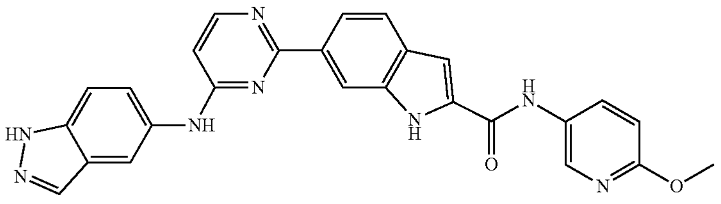 [SMILES: COc1ccc(NC(=O)c2cc3ccc(-c4nccc(Nc5ccc6[nH]ncc6c5)n4)cc3[nH]2)cn1] |
| 184. | 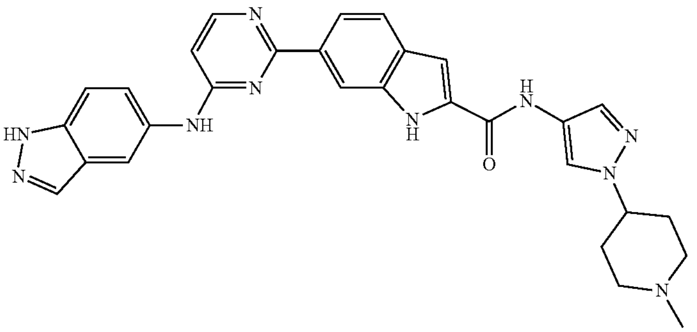 [SMILES: CN1CCC(n2cc(NC(=O)c3cc4ccc(-c5nccc(Nc6ccc7[nH]ncc7c6)n5)cc4[nH]3)cn2)CC1] |

-continued
| No. | Structure |
|---|---|
| 185. | 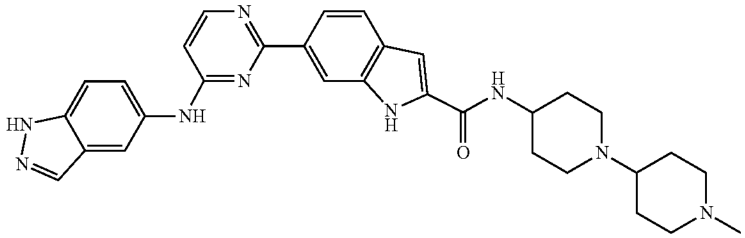 [SMILES: CN1CCC(N2CCC(NC(=O)c3cc4ccc(-c5nccc(Nc6ccc7[nH]ncc7c6)n5)cc4[nH]3)CC2)CC1] |
| 186. | 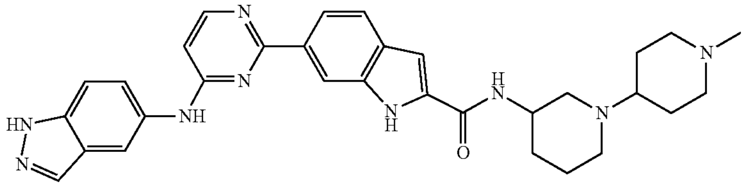 [SMILES: CN1CCC(N2CCCC(NC(=O)c3cc4ccc(-c5nccc(Nc6ccc7[nH]ncc7c6)n5)cc4[nH]3)C2)CC1] |
| 187. | 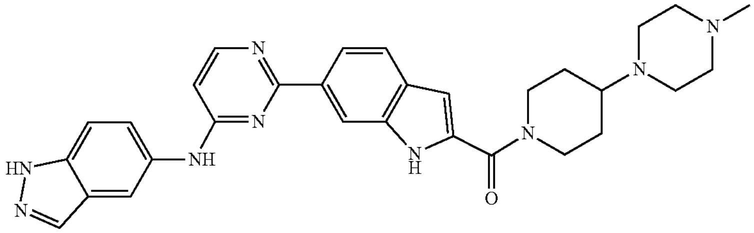 [SMILES: CN1CCN(C2CCN(C(=O)c3cc4ccc(-c5nccc(Nc6ccc7[nH]ncc7c6)n5)cc4[nH]3)CC2)CC1] |
| 188. | 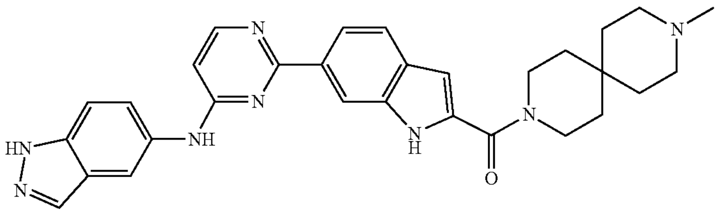 [SMILES: CN1CCC2(CC1)CCN(C(=O)c1cc3ccc(-c4nccc(Nc5ccc6[nH]ncc6c5)n4)cc3[nH]1)CC2] |
| 189. | 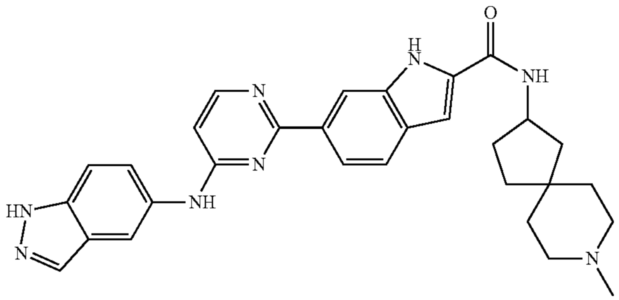 [SMILES: CN1CCC2(CCC(NC(=O)c3cc4ccc(-c5nccc(Nc6ccc7[nH]ncc7c6)n5)cc4[nH]3)C2)CC1] |
| 190. | 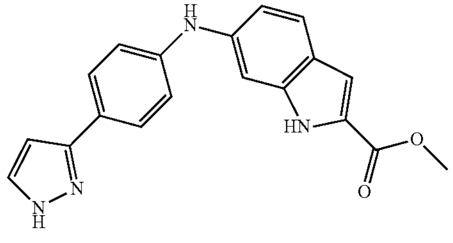 [SMILES: COC(=O)c1cc2ccc(Nc3ccc(-c4cc[nH]n4)cc3)cc2[nH]1] |

-continued
| No. | Structure |
|---|---|
| 191. | 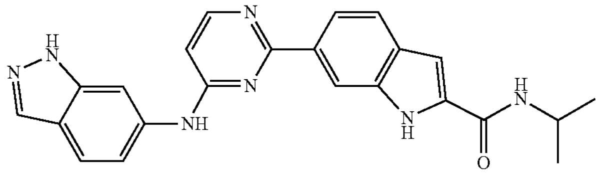 [SMILES: CC(C)NC(=O)c1cc2ccc(-c3nccc(Nc4ccc5cn[nH]c5c4)n3)cc2[nH]1] |
| 192. | 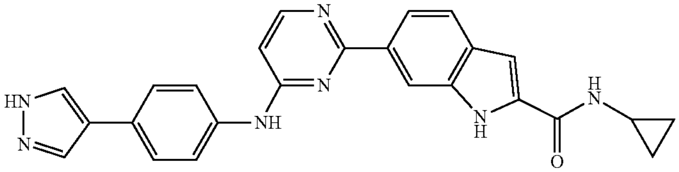 [SMILES: O=C(NC1CC1)c1cc2ccc(-c3nccc(Nc4ccc(-c5cn[nH]c5)cc4)n3)cc2[nH]1] |
| 193. | 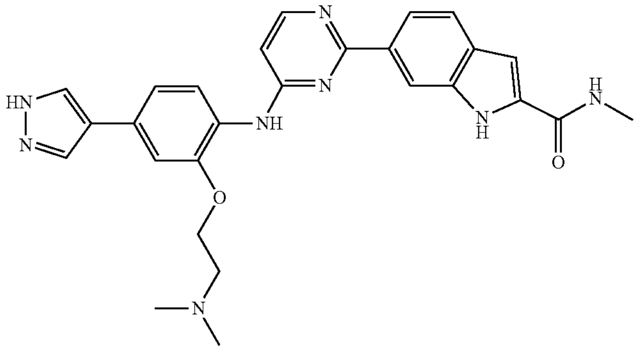 [SMILES: CNC(=O)c1cc2ccc(-c3nccc(Nc4ccc(-c5cn[nH]c5)cc4OCCN(C)C)n3)cc2[nH]1] |
| 194. | 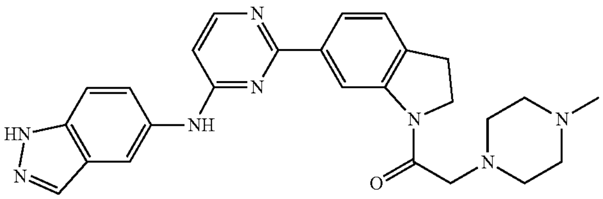 [SMILES: CN1CCN(CC(=O)N2CCc3ccc(-c4nccc(Nc5ccc6[nH]ncc6c5)n4)cc32)CC1] |
| 195. | 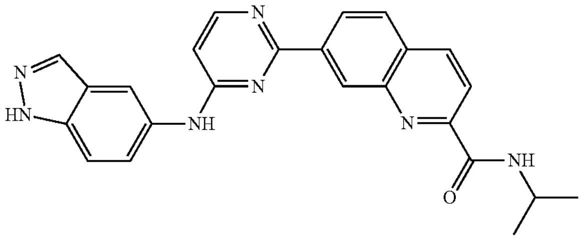 [SMILES: CC(C)NC(=O)c1ccc2ccc(-c3nccc(Nc4ccc5[nH]ncc5c4)n3)cc2n1] |
| 196. | 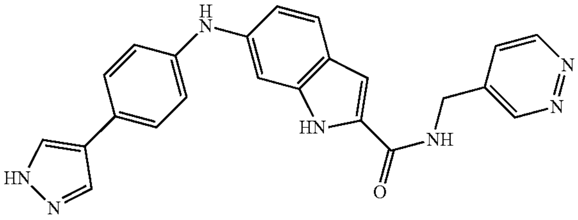 [SMILES: O=C(NCc1ccnnc1)c1cc2ccc(Nc3ccc(-c4cn[nH]c4)cc3)cc2[nH]1] |
| 197. | 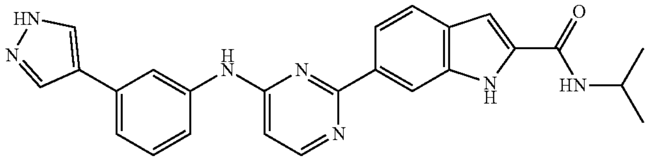 [SMILES: CC(C)NC(=O)c1cc2ccc(-c3nccc(Nc4cccc(-c5cn[nH]c5)c4)n3)cc2[nH]1] |

-continued
| No. | Structure |
| --- | --- |
| 198. | 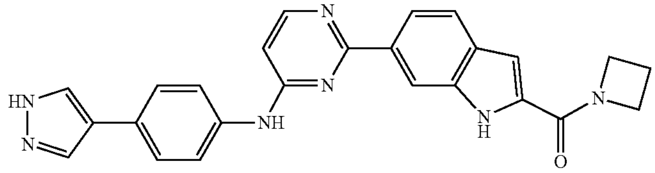 [SMILES: O=C(c1cc2ccc(-c3nccc(Nc4ccc(-c5cn[nH]c5)cc4)n3)cc2[nH]1)N1CCC1] |
| 199. | 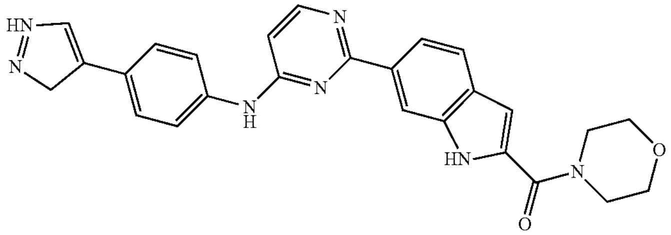 [SMILES: O=C(c1cc2ccc(-c3nccc(Nc4ccc(C5=CN=NC5)cc4)n3)cc2[nH]1)N1CCOCC1] |
| 200. | 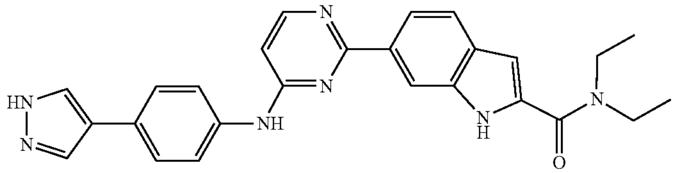 [SMILES: CCN(CC)C(=O)c1cc2ccc(-c3nccc(Nc4ccc(-c5cn[nH]c5)cc4)n3)cc2[nH]1] |
| 201. | 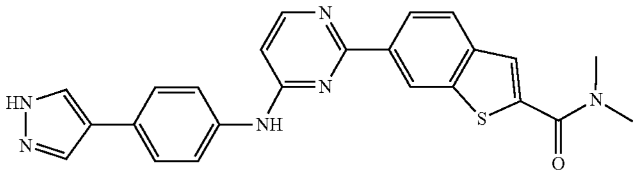 |
| 202. | 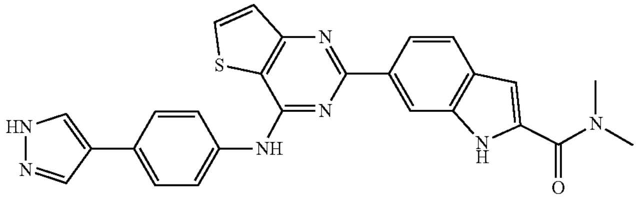 [SMILES: CN(C)C(=O)c1cc2ccc(-c3nc(Nc4ccc(-c5cn[nH]c5)cc4)c4sccc4n3)cc2[nH]1] |
| 203. | 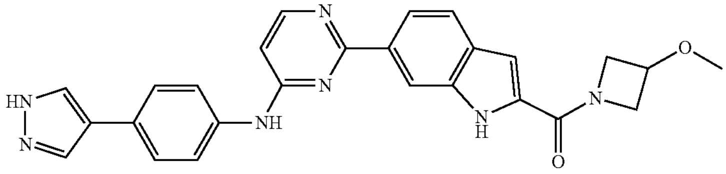 [SMILES: COC1CN(C(=O)c2cc3ccc(-c4nccc(Nc5ccc(-c6cn[nH]c6)cc5)n4)cc3[nH]2)C1] |
| 204. | 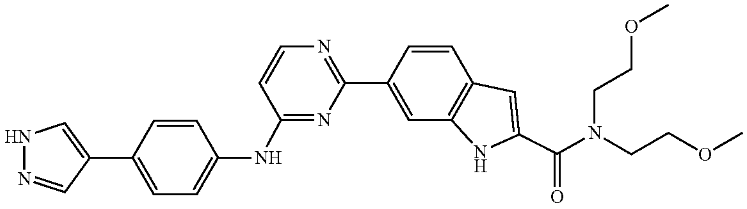 [SMILES: COCCN(CCOC)C(=O)c1cc2ccc(-c3nccc(Nc4ccc(-c5cn[nH]c5)cc4)n3)cc2[nH]1] |
| 205. | 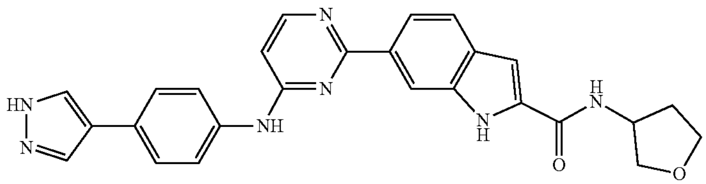 |

-continued
| No. | Structure |
|---|---|
| 206. | 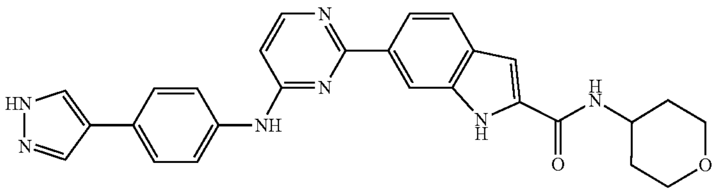 [SMILES: O=C(NC1CCOCC1)c1cc2ccc(-c3nccc(Nc4ccc(-c5cn[nH]c5)cc4)n3)cc2[nH]1] |
| 207. | 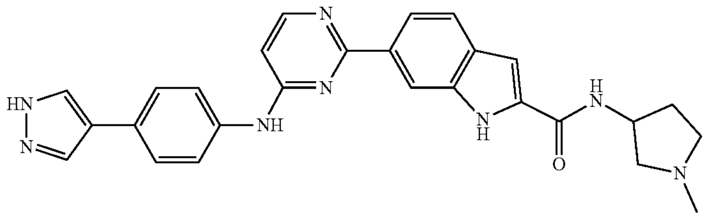 [SMILES: CN1CCC(NC(=O)c2cc3ccc(-c4nccc(Nc5ccc(-c6cn[nH]c6)cc5)n4)cc3[nH]2)C1] |
| 208. | 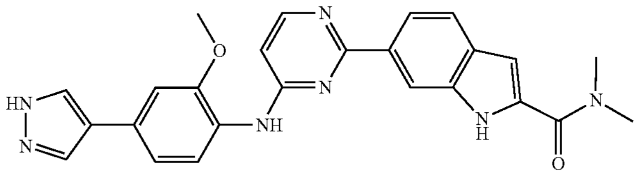 [SMILES: COc1cc(-c2cn[nH]c2)ccc1Nc1ccnc(-c2ccc3cc(C(=O)N(C)C)[nH]c3c2)n1] |
| 209. | 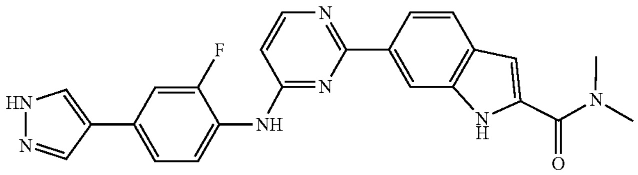 [SMILES: CN(C)C(=O)c1cc2ccc(-c3nccc(Nc4ccc(-c5cn[nH]c5)cc4F)n3)cc2[nH]1] |
| 210. | 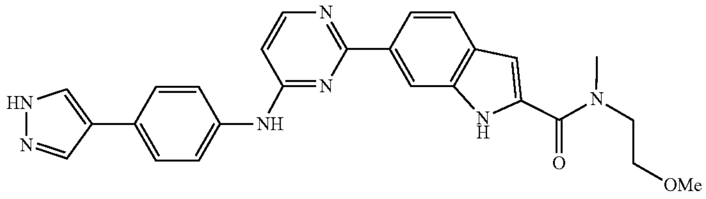 [SMILES: COCCN(C)C(=O)c1cc2ccc(-c3nccc(Nc4ccc(-c5cn[nH]c5)cc4)n3)cc2[nH]1] |
| 211. | 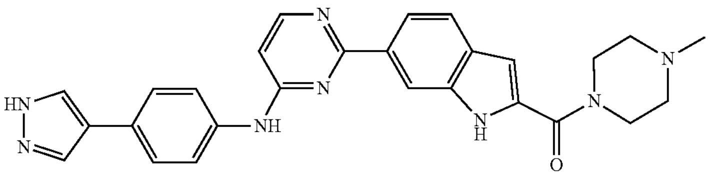 [SMILES: CN1CCN(C(=O)c2cc3ccc(-c4nccc(Nc5ccc(-c6cn[nH]c6)cc5)n4)cc3[nH]2)CC1] |
| 212. | 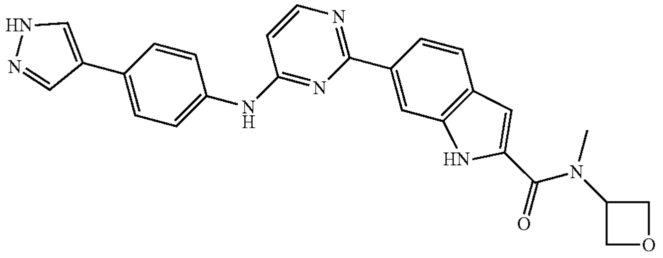 [SMILES: CN(C(=O)c1cc2ccc(-c3nccc(Nc4ccc(-c5cn[nH]c5)cc4)n3)cc2[nH]1)C1COC1] |

-continued
| No. | Structure |
| --- | --- |
| 213. | 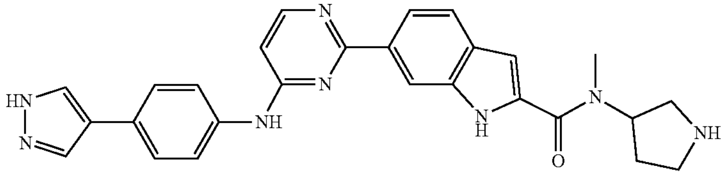 [SMILES: CN(C(=O)c1cc2ccc(-c3nccc(Nc4ccc(-c5cn[nH]c5)cc4)n3)cc2[nH]1)C1CCNC1] |
| 214. | 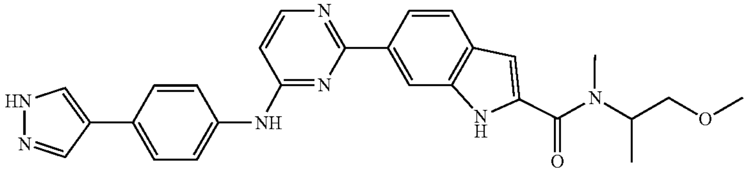 [SMILES: COCC(C)N(C)C(=O)c1cc2ccc(-c3nccc(Nc4ccc(-c5cn[nH]c5)cc4)n3)cc2[nH]1] |
| 215. | 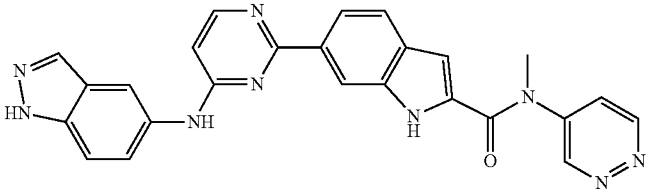 [SMILES: CN(C(=O)c1cc2ccc(-c3nccc(Nc4ccc5[nH]ncc5c4)n3)cc2[nH]1)c1ccnnc1] |
| 216. | 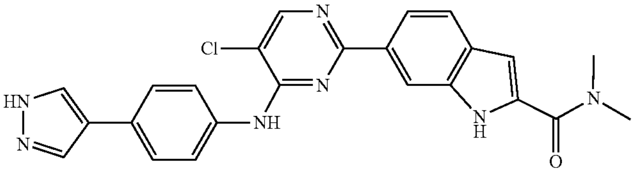 |
| 217. | 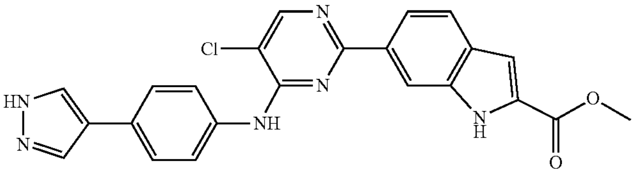 [SMILES: COC(=O)c1cc2ccc(-c3ncc(Cl)c(Nc4ccc(-c5cn[nH]c5)cc4)n3)cc2[nH]1] |
| 218. | 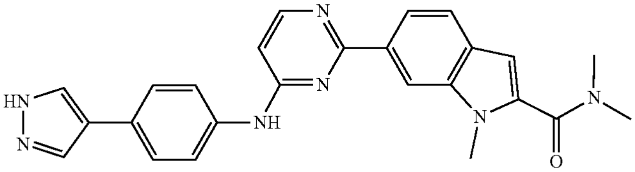 [SMILES: CN(C)C(=O)c1cc2ccc(-c3nccc(Nc4ccc(-c5cn[nH]c5)cc4)n3)cc2n1C] |
| 219. | 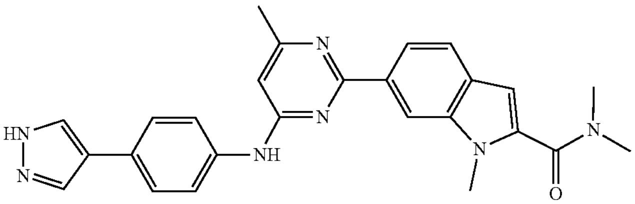 [SMILES: Cc1cc(Nc2ccc(-c3cn[nH]c3)cc2)nc(-c2ccc3cc(C(=O)N(C)C)n(C)c3c2)n1] |
| 220. | 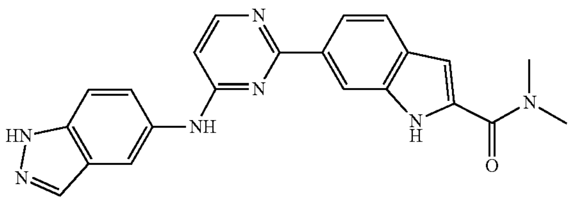 [SMILES: CN(C)C(=O)c1cc2ccc(-c3nccc(Nc4ccc5[nH]ncc5c4)n3)cc2[nH]1] |

-continued
| No. | Structure |
| --- | --- |
| 221. | 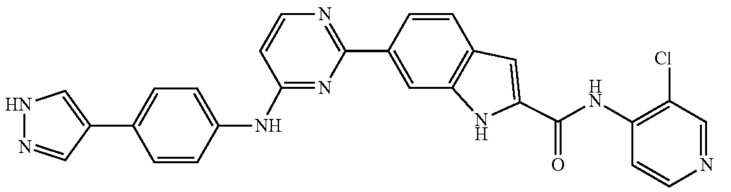 [SMILES: O=C(Nc1ccncc1Cl)c1cc2ccc(-c3nccc(Nc4ccc(-c5cn[nH]c5)cc4)n3)cc2[nH]1] |
| 222. | 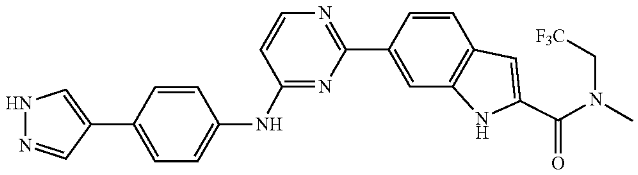 [SMILES: CN(CC(F)(F)F)C(=O)c1cc2ccc(-c3nccc(Nc4ccc(-c5cn[nH]c5)cc4)n3)cc2[nH]1] |
| 223. | 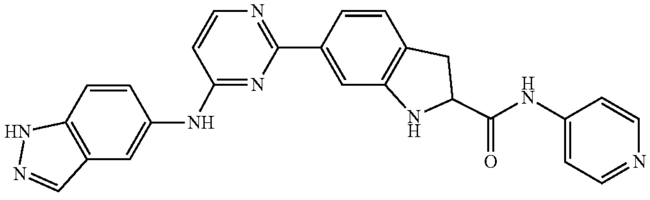 [SMILES: O=C(Nc1ccncc1)C1Cc2ccc(-c3nccc(Nc4ccc5[nH]ncc5c4)n3)cc2N1] |
| 224. | 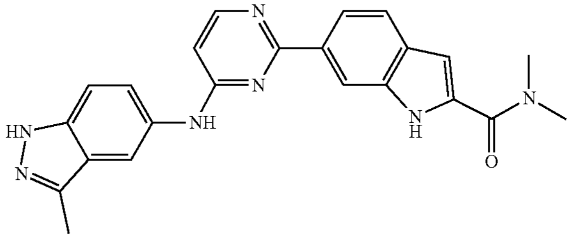 [SMILES: Cc1n[nH]c2ccc(Nc3ccnc(-c4ccc5cc(C(=O)N(C)C)[nH]c5c4)n3)cc12] |
| 225. | 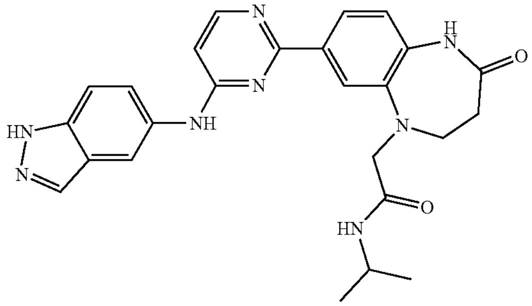 [SMILES: CC(C)NC(=O)CN1CCC(=O)Nc2ccc(-c3nccc(Nc4ccc5[nH]ncc5c4)n3)cc21] |
| 226. | 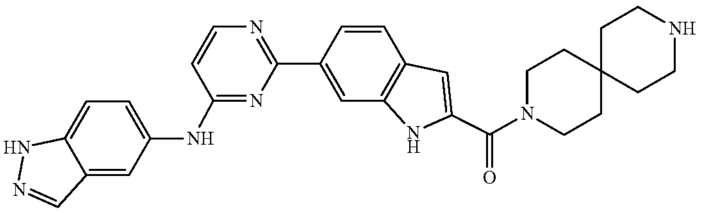 [SMILES: O=C(c1cc2ccc(-c3nccc(Nc4ccc5[nH]ncc5c4)n3)cc2[nH]1)N1CCC2(CCNCC2)CC1] |
| 227. | 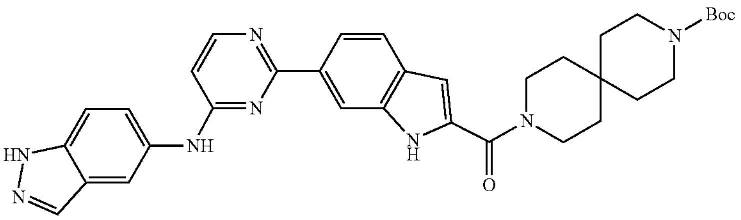 [SMILES: CC(C)(C)OC(=O)N1CCC2(CC1)CCN(C(=O)c1cc3ccc(-c4nccc(Nc5ccc6[nH]ncc6c5)n4)cc3[nH]1)CC2] |

-continued
| No. | Structure |
|---|---|
| 228. | 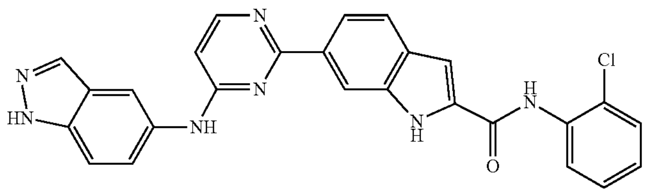 [SMILES: O=C(Nc1ccccc1Cl)c1cc2ccc(-c3nccc(Nc4ccc5[nH]ncc5c4)n3)cc2[nH]1] |
| 229. | 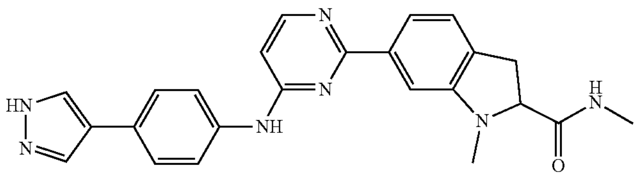 [SMILES: CNC(=O)C1Cc2ccc(-c3nccc(Nc4ccc(-c5cn[nH]c5)cc4)n3)cc2N1C] |
| 230. | 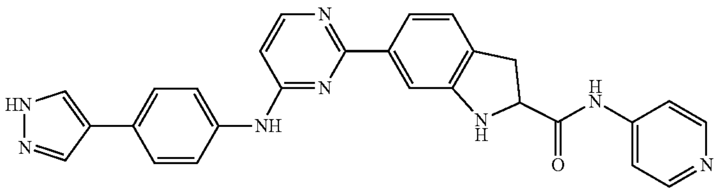 [SMILES: O=C(Nc1ccncc1)C1Cc2ccc(-c3nccc(Nc4ccc(-c5cn[nH]c5)cc4)n3)cc2N1] |
| 231. | 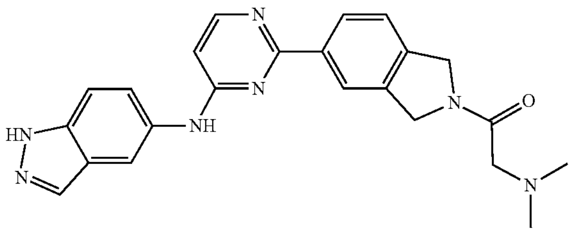 [SMILES: CN(C)CC(=O)N1Cc2ccc(-c3nccc(Nc4ccc5[nH]ncc5c4)n3)cc2C1] |
| 232. | 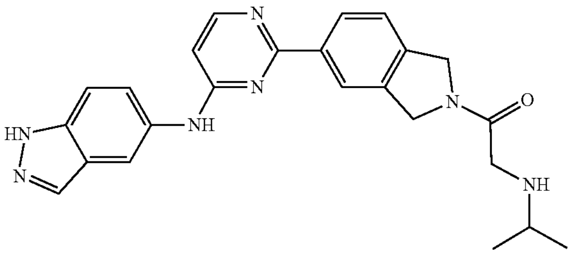 [SMILES: CC(C)NCC(=O)N1Cc2ccc(-c3nccc(Nc4ccc5[nH]ncc5c4)n3)cc2C1] |
| 233. | 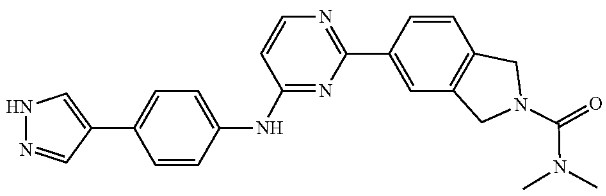 [SMILES: CN(C)C(=O)N1Cc2ccc(-c3nccc(Nc4ccc(-c5cn[nH]c5)cc4)n3)cc2C1] |
| 234. | 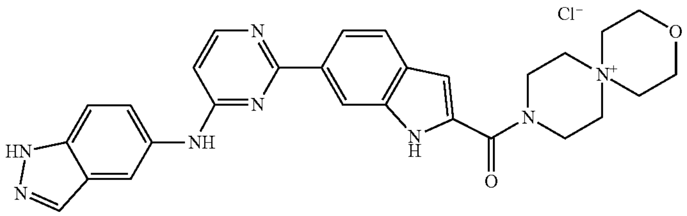 [SMILES: O=C(c1cc2ccc(-c3nccc(Nc4ccc5[nH]ncc5c4)n3)cc2[nH]1)N1CC[N+]2(CCOCC2)CC1 ; [Cl-]] |

-continued
| No. | Structure |
|---|---|
| 235. | 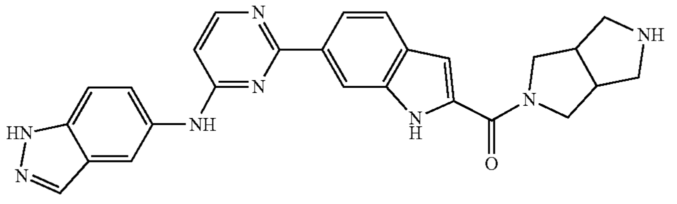 [SMILES: O=C(c1cc2ccc(-c3nccc(Nc4ccc5[nH]ncc5c4)n3)cc2[nH]1)N1CC2CNCC2C1] |
| 236. | 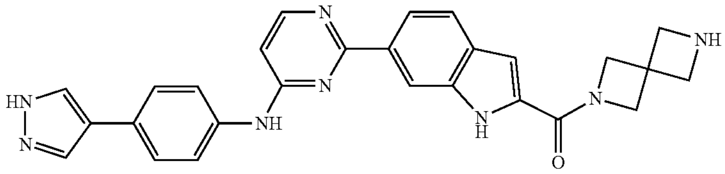 [SMILES: O=C(c1cc2ccc(-c3nccc(Nc4ccc(-c5cn[nH]c5)cc4)n3)cc2[nH]1)N1CC2(CNC2)C1] |
| 237. | 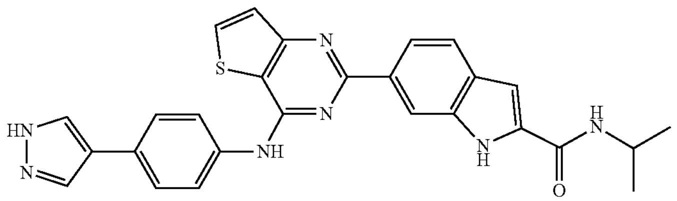 |
| 238. | 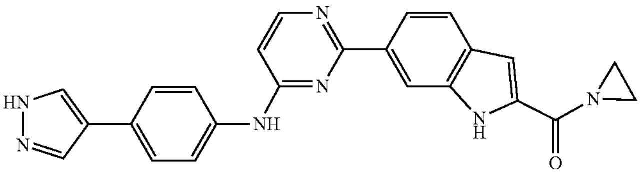 [SMILES: O=C(c1cc2ccc(-c3nccc(Nc4ccc(-c5cn[nH]c5)cc4)n3)cc2[nH]1)N1CC1] |
| 239. | 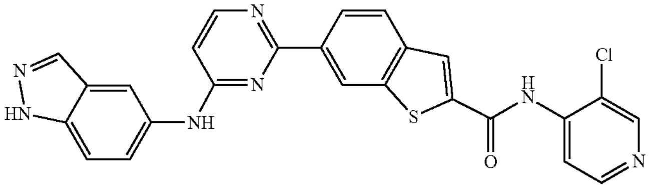 |
| 240. | 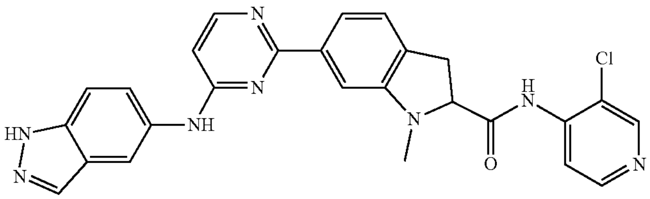 |
| 241. | 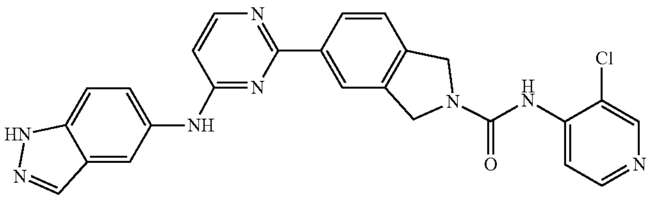 [SMILES: O=C(Nc1ccncc1Cl)N1Cc2ccc(-c3nccc(Nc4ccc5[nH]ncc5c4)n3)cc2C1] |

-continued
| No. | Structure |
| --- | --- |
| 242. | 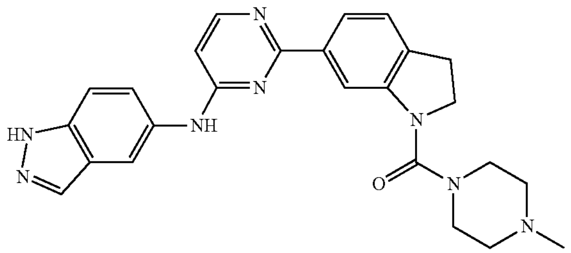 [SMILES: CN1CCN(C(=O)N2CCc3ccc(-c4nccc(Nc5ccc6[nH]ncc6c5)n4)cc32)CC1] |
| 243. | 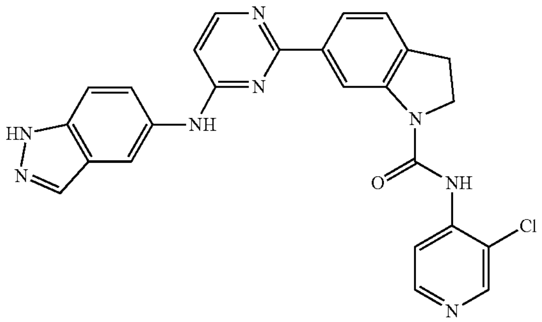 [SMILES: O=C(Nc1ccncc1Cl)N1CCc2ccc(-c3nccc(Nc4ccc5[nH]ncc5c4)n3)cc21] |
| 244. | 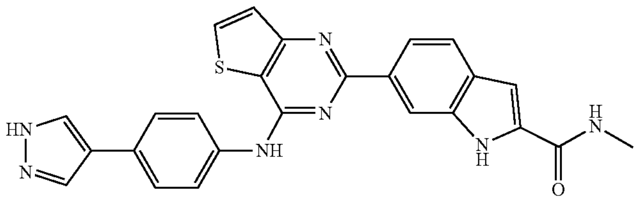 [SMILES: CNC(=O)c1cc2ccc(-c3nc(Nc4ccc(-c5cn[nH]c5)cc4)c4sccc4n3)cc2[nH]1] |
| 245. | 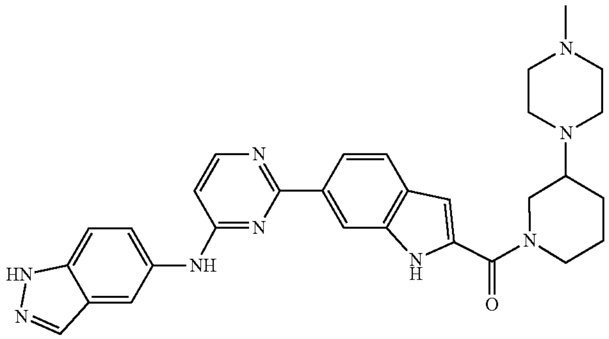 [SMILES: CN1CCN(C2CCCN(C(=O)c3cc4ccc(-c5nccc(Nc6ccc7[nH]ncc7c6)n5)cc4[nH]3)C2)CC1] |
| 246. | 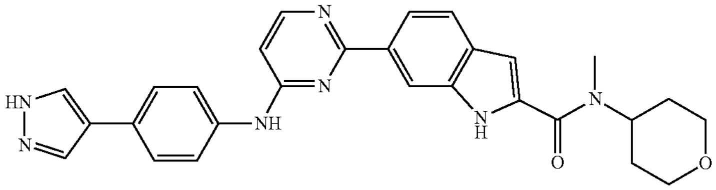 [SMILES: CN(C(=O)c1cc2ccc(-c3nccc(Nc4ccc(-c5cn[nH]c5)cc4)n3)cc2[nH]1)C1CCOCC1] |
| 247. | 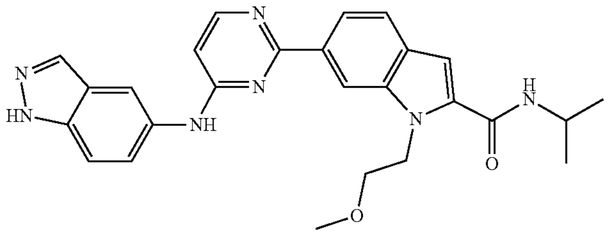 [SMILES: COCCn1c(C(=O)NC(C)C)cc2ccc(-c3nccc(Nc4ccc5[nH]ncc5c4)n3)cc21] |

-continued
| No. | Structure |
| --- | --- |
| 248. | 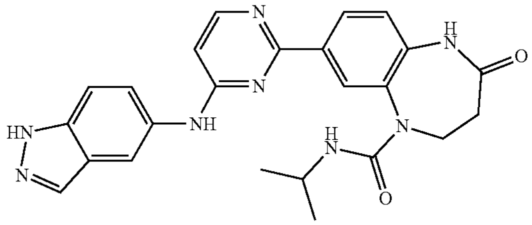 [SMILES: CC(C)NC(=O)N1CCC(=O)Nc2ccc(-c3nccc(Nc4ccc5[nH]ncc5c4)n3)cc21] |
| 249. | 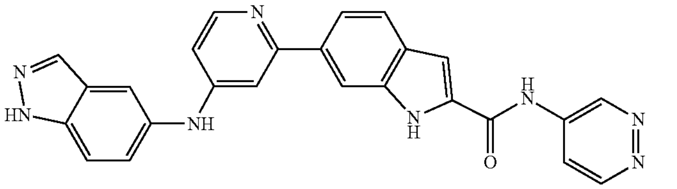 |
| 250. | 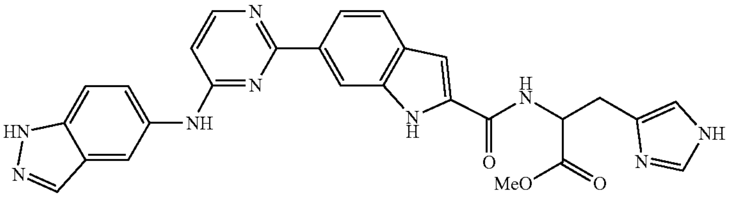 [SMILES: COC(=O)C(Cc1c[nH]cn1)NC(=O)c1cc2ccc(-c3nccc(Nc4ccc5[nH]ncc5c4)n3)cc2[nH]1] |
| 251. | 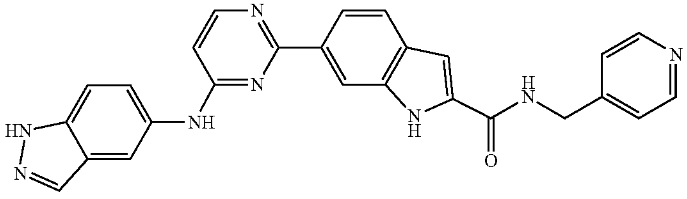 [SMILES: O=C(NCc1ccncc1)c1cc2ccc(-c3nccc(Nc4ccc5[nH]ncc5c4)n3)cc2[nH]1] |
| 252. | 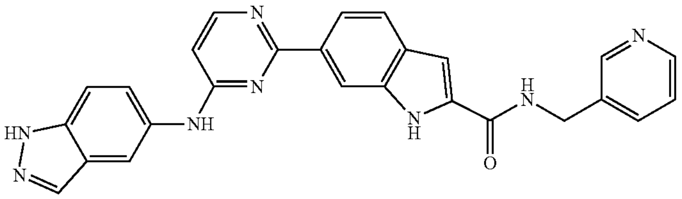 [SMILES: O=C(NCc1cccnc1)c1cc2ccc(-c3nccc(Nc4ccc5[nH]ncc5c4)n3)cc2[nH]1] |
| 253. | 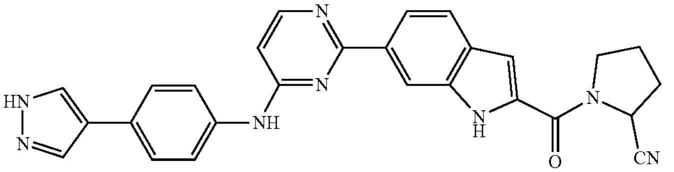 [SMILES: N#CC1CCCN1C(=O)c1cc2ccc(-c3nccc(Nc4ccc(-c5cn[nH]c5)cc4)n3)cc2[nH]1] |
| 254. | 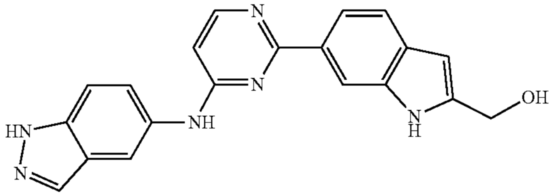 [SMILES: OCc1cc2ccc(-c3nccc(Nc4ccc5[nH]ncc5c4)n3)cc2[nH]1] |

-continued
| No. | Structure |
| --- | --- |
| 255. | 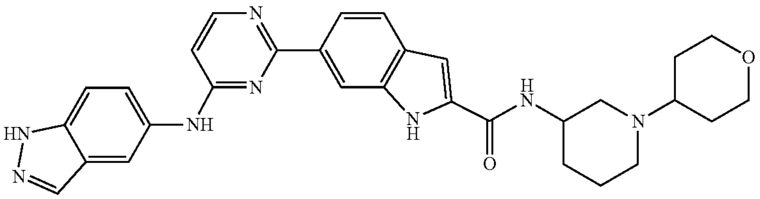 [SMILES: O=C(NC1CCCN(C2CCOCC2)C1)c1cc2ccc(-c3nccc(Nc4ccc5[nH]ncc5c4)n3)cc2[nH]1] |
| 256. | 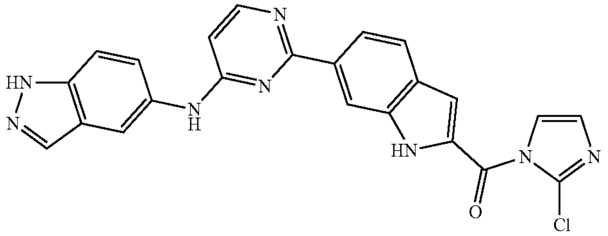 [SMILES: O=C(c1cc2ccc(-c3nccc(Nc4ccc5[nH]ncc5c4)n3)cc2[nH]1)n1ccnc1Cl] |
| 257. | 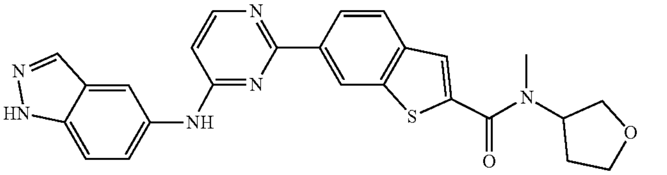 |
| 258. | 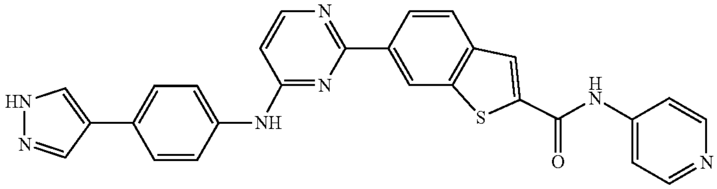 [SMILES: O=C(Nc1ccncc1)c1cc2ccc(-c3nccc(Nc4ccc(-c5cn[nH]c5)cc4)n3)cc2s1] |
| 259. | 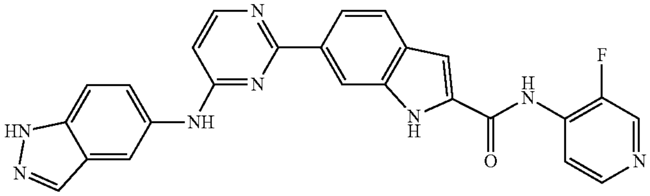 [SMILES: O=C(Nc1ccncc1F)c1cc2ccc(-c3nccc(Nc4ccc5[nH]ncc5c4)n3)cc2[nH]1] |
| 260. | 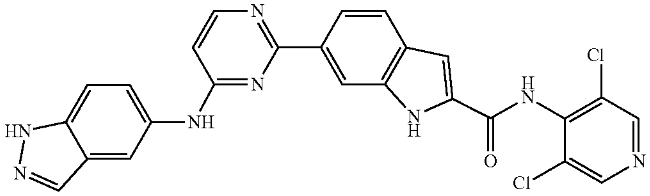 [SMILES: O=C(Nc1c(Cl)cncc1Cl)c1cc2ccc(-c3nccc(Nc4ccc5[nH]ncc5c4)n3)cc2[nH]1] |
| 261. | 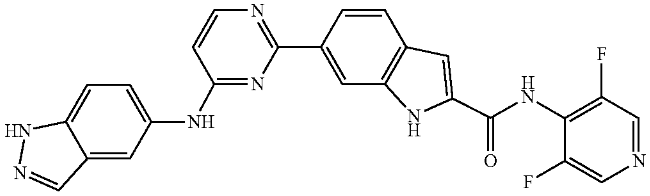 [SMILES: O=C(Nc1c(F)cncc1F)c1cc2ccc(-c3nccc(Nc4ccc5[nH]ncc5c4)n3)cc2[nH]1] |

-continued
| No. | Structure |
|---|---|
| 262. | 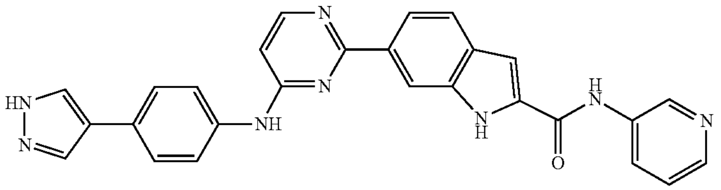 [SMILES: O=C(Nc1cccnc1)c1cc2ccc(-c3nccc(Nc4ccc(-c5cn[nH]c5)cc4)n3)cc2[nH]1] |
| 263. | 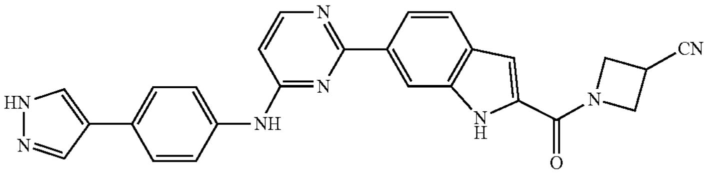 [SMILES: N#CC1CN(C(=O)c2cc3ccc(-c4nccc(Nc5ccc(-c6cn[nH]c6)cc5)n4)cc3[nH]2)C1] |
| 264. | 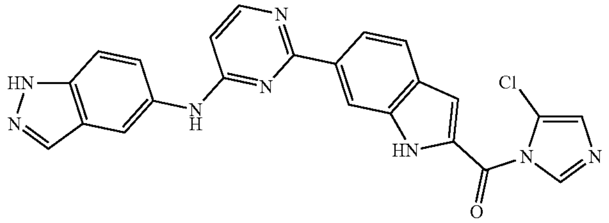 [SMILES: O=C(c1cc2ccc(-c3nccc(Nc4ccc5[nH]ncc5c4)n3)cc2[nH]1)n1cncc1Cl] |
| 265. | 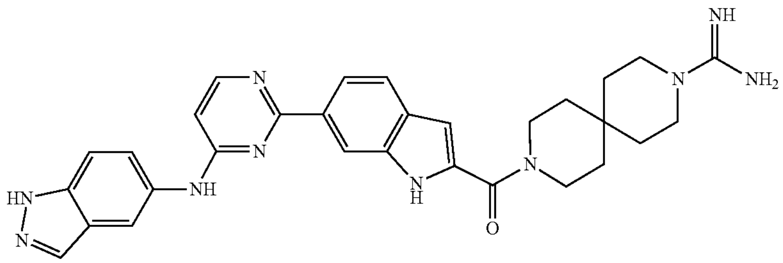 [SMILES: N=C(N)N1CCC2(CC1)CCN(C(=O)c1cc3ccc(-c4nccc(Nc5ccc6[nH]ncc6c5)n4)cc3[nH]1)CC2] |
| 266. | 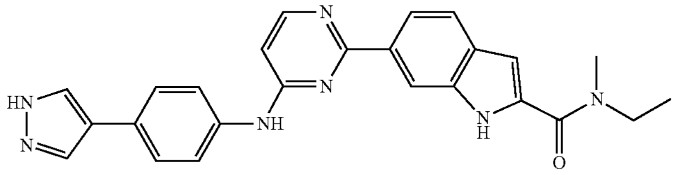 |
| 267. | 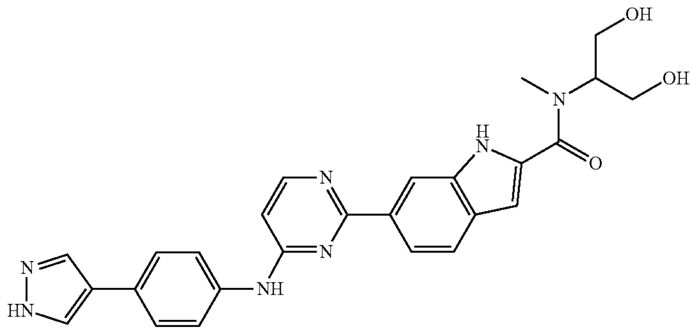 [SMILES: CN(C(=O)c1cc2ccc(-c3nccc(Nc4ccc(-c5cn[nH]c5)cc4)n3)cc2[nH]1)C(CO)CO] |
| 268. | 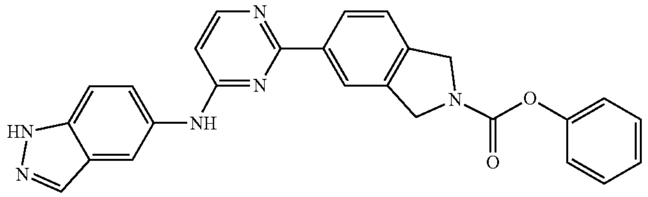 [SMILES: O=C(Oc1ccccc1)N1Cc2ccc(-c3nccc(Nc4ccc5[nH]ncc5c4)n3)cc2C1] |

-continued
| No. | Structure |
| --- | --- |
| 269. | 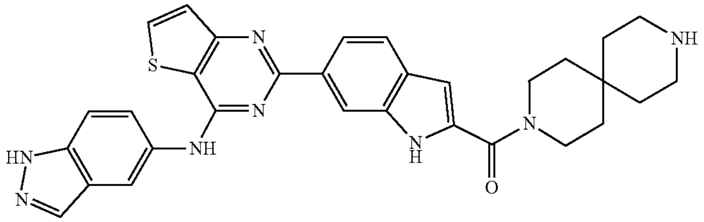 [SMILES: O=C(c1cc2ccc(-c3nc(Nc4ccc5[nH]ncc5c4)c4sccc4n3)cc2[nH]1)N1CCC2(CCNCC2)CC1] |
| 270. | 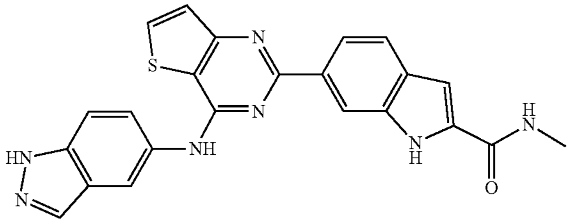 [SMILES: CNC(=O)c1cc2ccc(-c3nc(Nc4ccc5[nH]ncc5c4)c4sccc4n3)cc2[nH]1] |
| 271. | 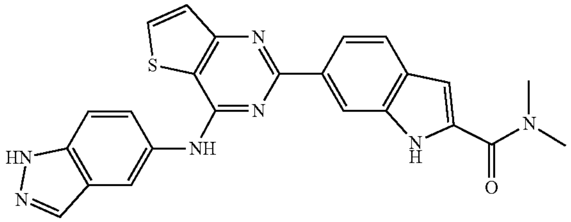 [SMILES: CN(C)C(=O)c1cc2ccc(-c3nc(Nc4ccc5[nH]ncc5c4)c4sccc4n3)cc2[nH]1] |
| 272. | 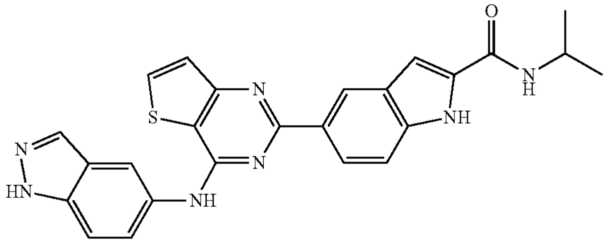 [SMILES: CC(C)NC(=O)c1cc2cc(-c3nc(Nc4ccc5[nH]ncc5c4)c4sccc4n3)ccc2[nH]1] |
| 273. | 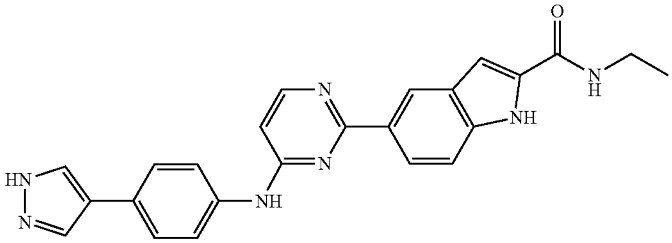 [SMILES: CCNC(=O)c1cc2cc(-c3nccc(Nc4ccc(-c5cn[nH]c5)cc4)n3)ccc2[nH]1] |
| 274. | 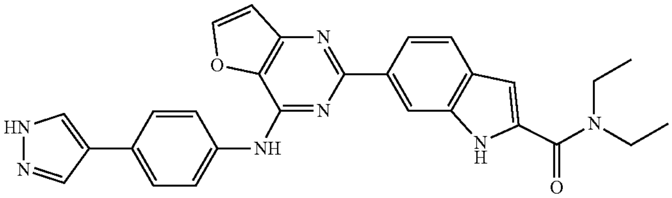 |

-continued
| No. | Structure |
|---|---|
| 275. | 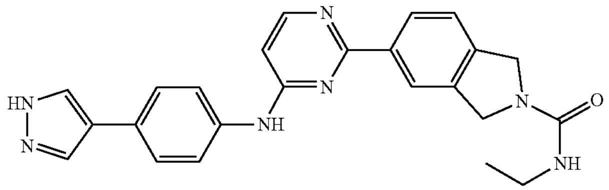 [SMILES: CCNC(=O)N1Cc2ccc(-c3nccc(Nc4ccc(-c5cn[nH]c5)cc4)n3)cc2C1] |
| 276. | 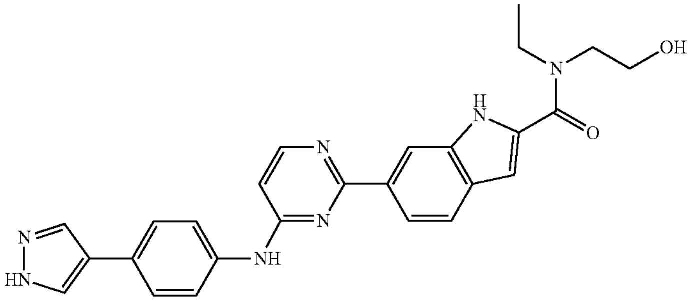 [SMILES: CCN(CCO)C(=O)c1cc2ccc(-c3nccc(Nc4ccc(-c5cn[nH]c5)cc4)n3)cc2[nH]1] |
| 277. | 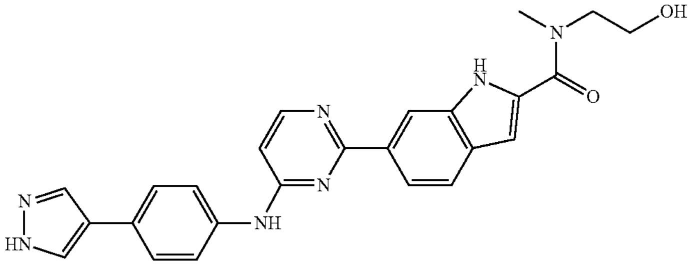 [SMILES: CN(CCO)C(=O)c1cc2ccc(-c3nccc(Nc4ccc(-c5cn[nH]c5)cc4)n3)cc2[nH]1] |
| 278. | 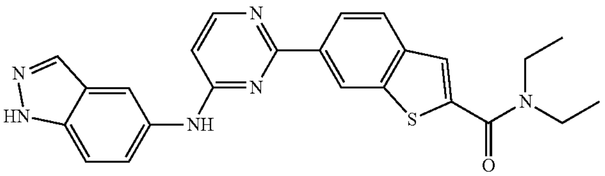 [SMILES: CCN(CC)C(=O)c1cc2ccc(-c3nccc(Nc4ccc5[nH]ncc5c4)n3)cc2s1] |
| 279. | 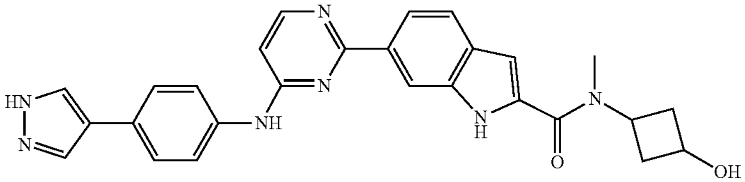 [SMILES: CN(C(=O)c1cc2ccc(-c3nccc(Nc4ccc(-c5cn[nH]c5)cc4)n3)cc2[nH]1)C1CC(O)C1] |
| 280. | 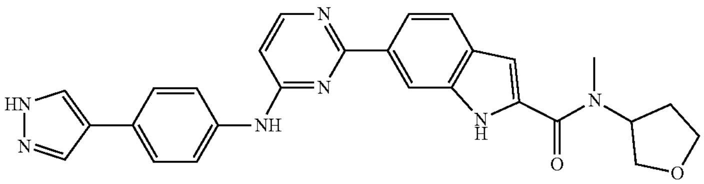 |
| 281. | 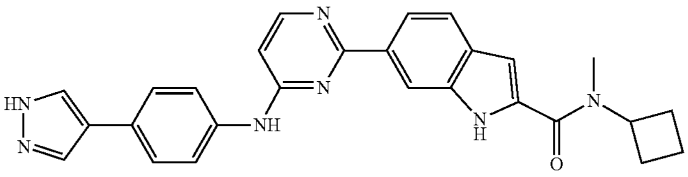 [SMILES: CN(C(=O)c1cc2ccc(-c3nccc(Nc4ccc(-c5cn[nH]c5)cc4)n3)cc2[nH]1)C1CCC1] |

-continued
| No. | Structure |
| --- | --- |
| 282. | 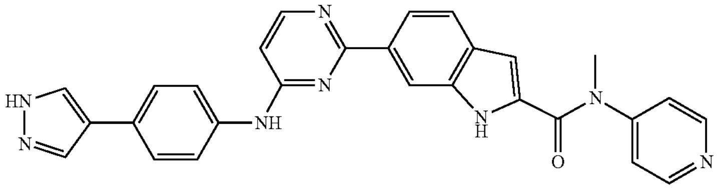 [SMILES: CN(C(=O)c1cc2ccc(-c3nccc(Nc4ccc(-c5cn[nH]c5)cc4)n3)cc2[nH]1)c1ccncc1] |
| 283. | 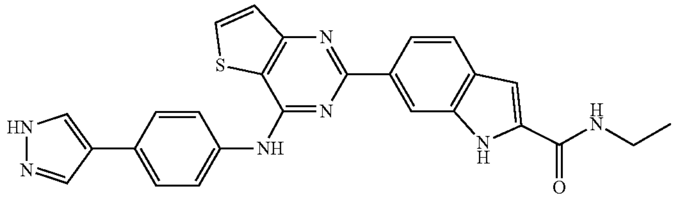 |
| 284. | 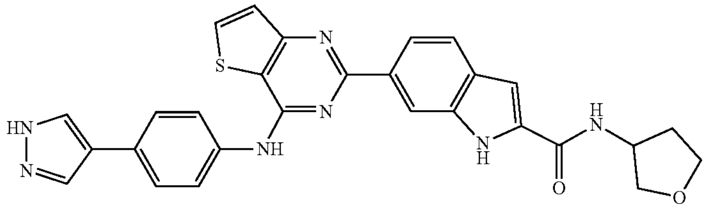 [SMILES: O=C(NC1CCOC1)c1cc2ccc(-c3nc(Nc4ccc(-c5cn[nH]c5)cc4)c4sccc4n3)cc2[nH]1] |
| 285. | 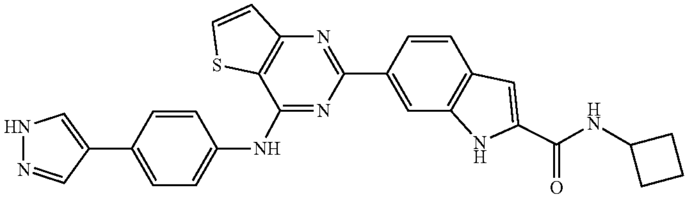 [SMILES: O=C(NC1CCC1)c1cc2ccc(-c3nc(Nc4ccc(-c5cn[nH]c5)cc4)c4sccc4n3)cc2[nH]1] |
| 286. | 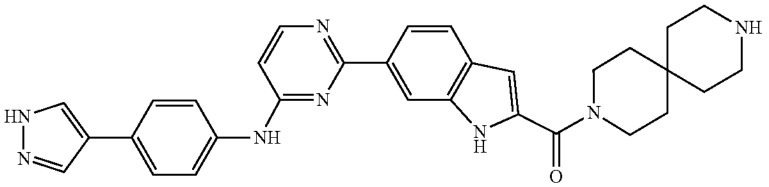 [SMILES: O=C(c1cc2ccc(-c3nccc(Nc4ccc(-c5cn[nH]c5)cc4)n3)cc2[nH]1)N1CCC2(CCNCC2)CC1] |
| 287. | 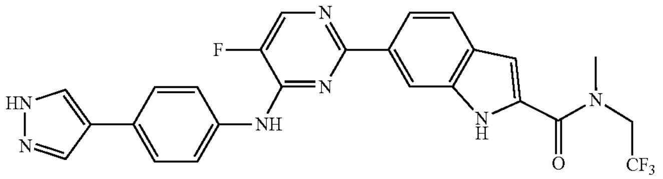 [SMILES: CN(CC(F)(F)F)C(=O)c1cc2ccc(-c3ncc(F)c(Nc4ccc(-c5cn[nH]c5)cc4)n3)cc2[nH]1] |
| 288. | 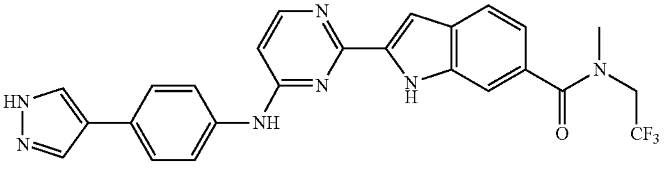 [SMILES: CN(CC(F)(F)F)C(=O)c1ccc2cc(-c3nccc(Nc4ccc(-c5cn[nH]c5)cc4)n3)[nH]c2c1] |
| 289. | 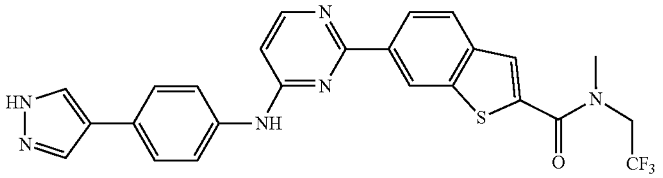 |

-continued
| No. | Structure |
|---|---|
| 290. | 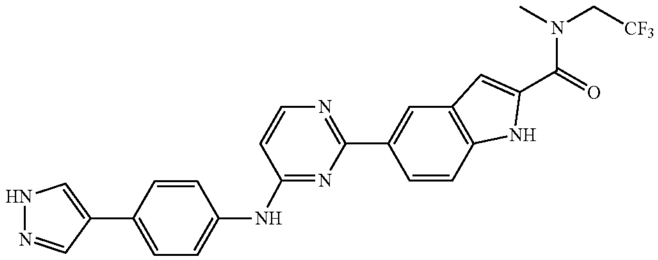 [SMILES: CN(CC(F)(F)F)C(=O)c1cc2cc(-c3nccc(Nc4ccc(-c5cn[nH]c5)cc4)n3)ccc2[nH]1] |
| 291. | 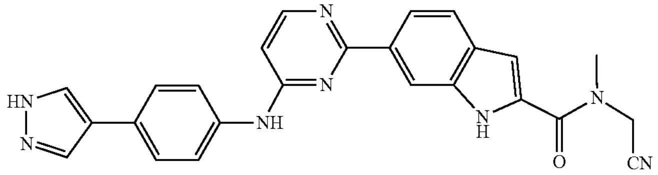 [SMILES: CN(CC#N)C(=O)c1cc2ccc(-c3nccc(Nc4ccc(-c5cn[nH]c5)cc4)n3)cc2[nH]1] |
| 292. | 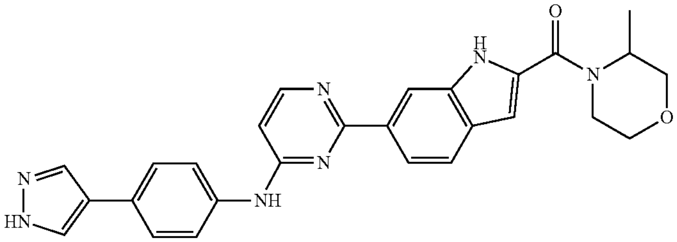 [SMILES: CC1COCCN1C(=O)c1cc2ccc(-c3nccc(Nc4ccc(-c5cn[nH]c5)cc4)n3)cc2[nH]1] |
| 293. | 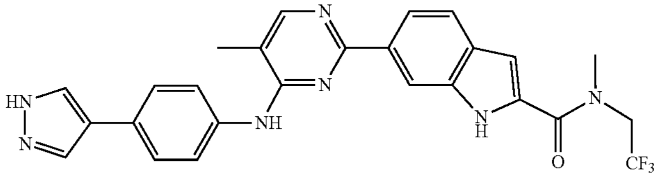 |
| 294. | 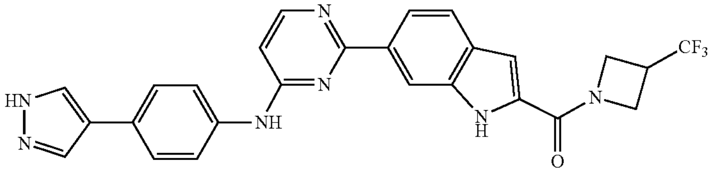 [SMILES: O=C(c1cc2ccc(-c3nccc(Nc4ccc(-c5cn[nH]c5)cc4)n3)cc2[nH]1)N1CC(C(F)(F)F)C1] |
| 295. | 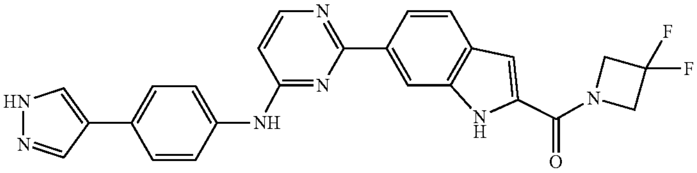 [SMILES: O=C(c1cc2ccc(-c3nccc(Nc4ccc(-c5cn[nH]c5)cc4)n3)cc2[nH]1)N1CC(F)(F)C1] |
| 296. | 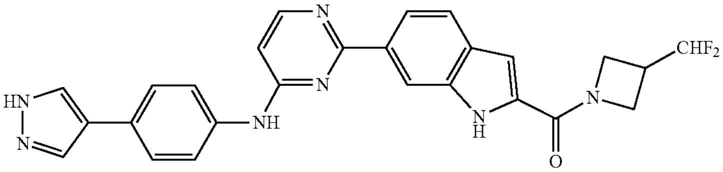 [SMILES: O=C(c1cc2ccc(-c3nccc(Nc4ccc(-c5cn[nH]c5)cc4)n3)cc2[nH]1)N1CC(C(F)F)C1] |

-continued
| No. | Structure |
| --- | --- |
| 297. | 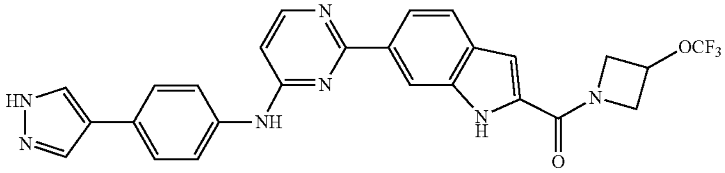 [SMILES: O=C(c1cc2ccc(-c3nccc(Nc4ccc(-c5cn[nH]c5)cc4)n3)cc2[nH]1)N1CC(OC(F)(F)F)C1] |
| 298. | 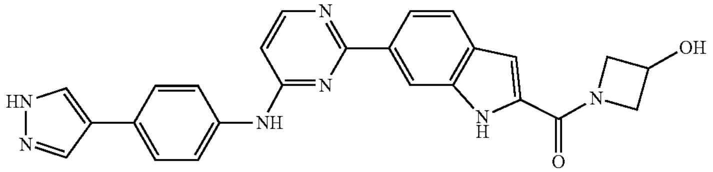 [SMILES: O=C(c1cc2ccc(-c3nccc(Nc4ccc(-c5cn[nH]c5)cc4)n3)cc2[nH]1)N1CC(O)C1] |
| 299. | 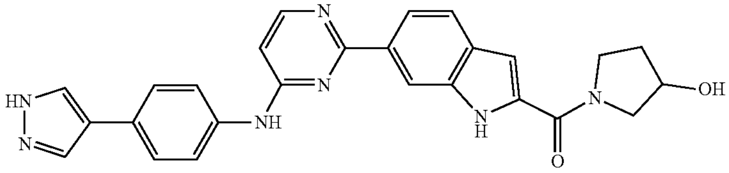 |
| 300. | 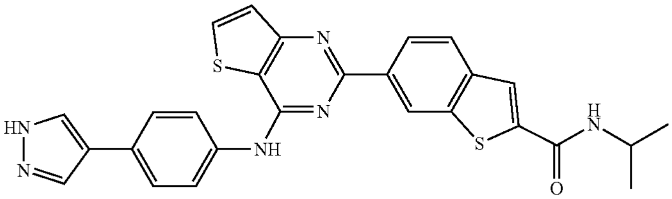 [SMILES: CC(C)NC(=O)c1cc2ccc(-c3nc(Nc4ccc(-c5cn[nH]c5)cc4)c4sccc4n3)cc2s1] |
| 301. | 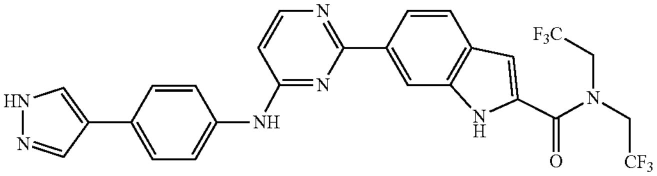 [SMILES: O=C(c1cc2ccc(-c3nccc(Nc4ccc(-c5cn[nH]c5)cc4)n3)cc2[nH]1)N(CC(F)(F)F)CC(F)(F)F] |
| 302. | 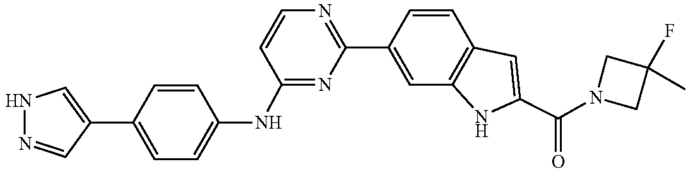 [SMILES: CC1(F)CN(C(=O)c2cc3ccc(-c4nccc(Nc5ccc(-c6cn[nH]c6)cc5)n4)cc3[nH]2)C1] |
| 303. | 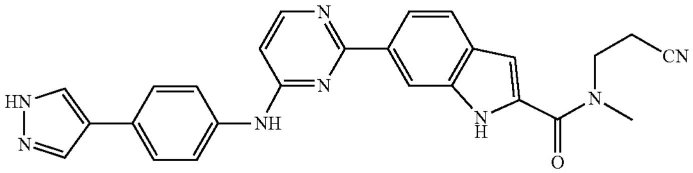 [SMILES: CN(CCC#N)C(=O)c1cc2ccc(-c3nccc(Nc4ccc(-c5cn[nH]c5)cc4)n3)cc2[nH]1] |
| 304. | 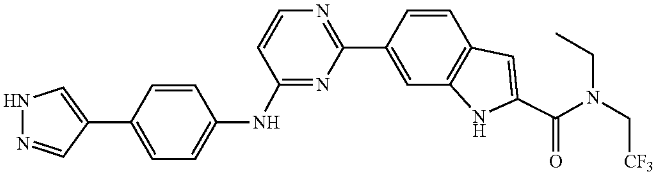 [SMILES: CCN(CC(F)(F)F)C(=O)c1cc2ccc(-c3nccc(Nc4ccc(-c5cn[nH]c5)cc4)n3)cc2[nH]1] |

-continued
| No. | Structure |
|---|---|
| 305. | 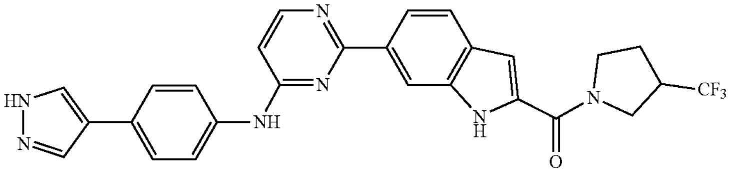 [SMILES: O=C(c1cc2ccc(-c3nccc(Nc4ccc(-c5cn[nH]c5)cc4)n3)cc2[nH]1)N1CCC(C(F)(F)F)C1] |
| 306. | 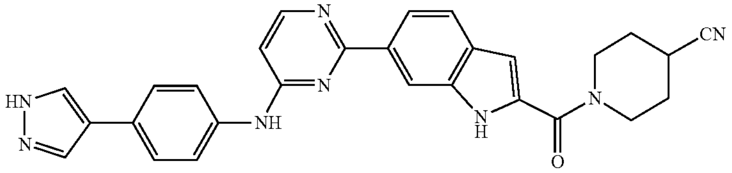 [SMILES: N#CC1CCN(C(=O)c2cc3ccc(-c4nccc(Nc5ccc(-c6cn[nH]c6)cc5)n4)cc3[nH]2)CC1] |
| 307. | 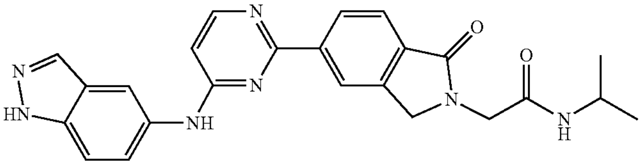 [SMILES: CC(C)NC(=O)CN1Cc2cc(-c3nccc(Nc4ccc5[nH]ncc5c4)n3)ccc2C1=O] |
| 308. | 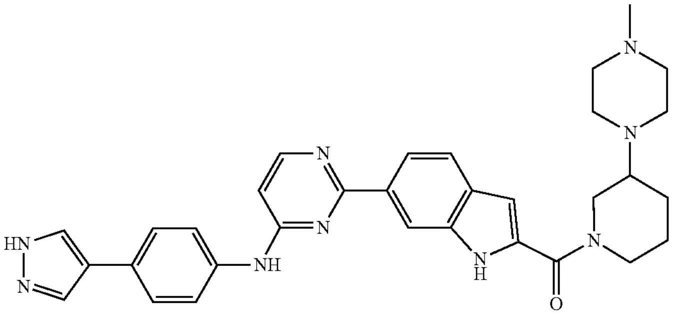 [SMILES: CN1CCN(C2CCCN(C(=O)c3cc4ccc(-c5nccc(Nc6ccc(-c7cn[nH]c7)cc6)n5)cc4[nH]3)C2)CC1] |
| 309. | 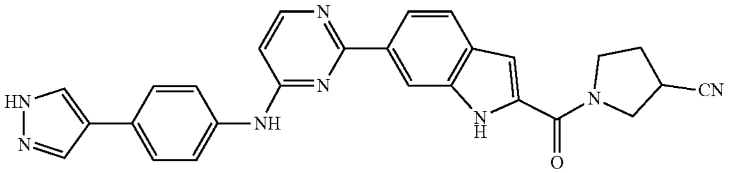 [SMILES: N#CC1CCN(C(=O)c2cc3ccc(-c4nccc(Nc5ccc(-c6cn[nH]c6)cc5)n4)cc3[nH]2)C1] |
| 310. | 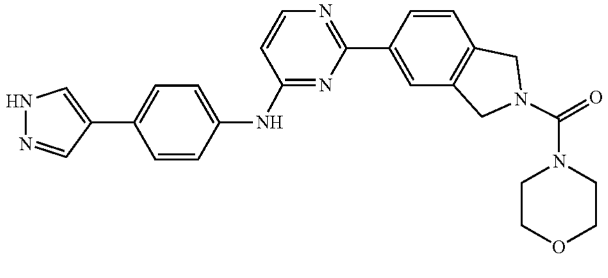 |
| 311. | 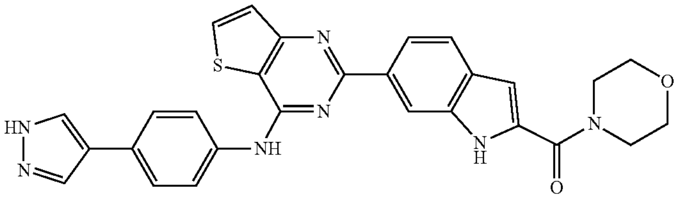 [SMILES: O=C(c1cc2ccc(-c3nc(Nc4ccc(-c5cn[nH]c5)cc4)c4sccc4n3)cc2[nH]1)N1CCOCC1] |

-continued
| No. | Structure |
|---|---|
| 312. | 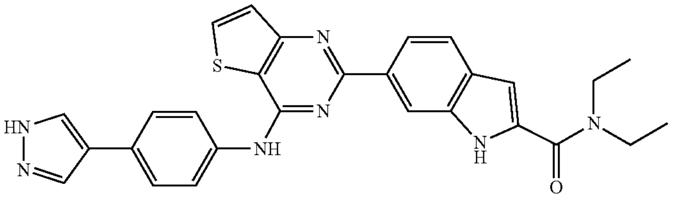 |
| 313. | 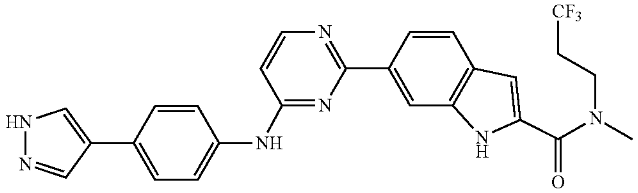 [SMILES: CN(CCC(F)(F)F)C(=O)c1cc2ccc(-c3nccc(Nc4ccc(-c5cn[nH]c5)cc4)n3)cc2[nH]1] |
| 314. | 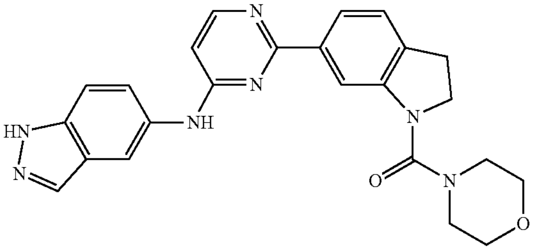 [SMILES: O=C(N1CCOCC1)N1CCc2ccc(-c3nccc(Nc4ccc5[nH]ncc5c4)n3)cc21] |
| 315. | 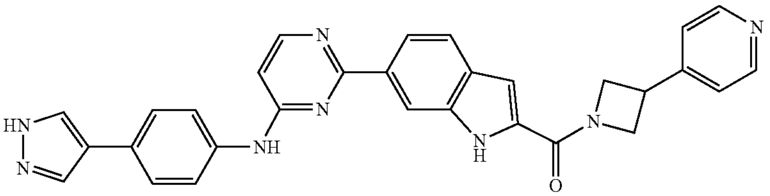 [SMILES: O=C(c1cc2ccc(-c3nccc(Nc4ccc(-c5cn[nH]c5)cc4)n3)cc2[nH]1)N1CC(c2ccncc2)C1] |
| 316. | 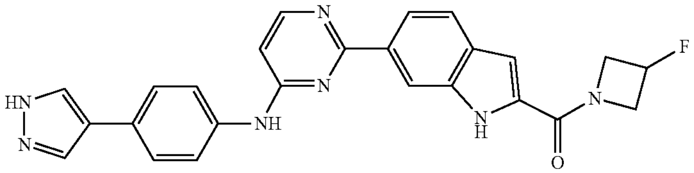 [SMILES: O=C(c1cc2ccc(-c3nccc(Nc4ccc(-c5cn[nH]c5)cc4)n3)cc2[nH]1)N1CC(F)C1] |
| 317. | 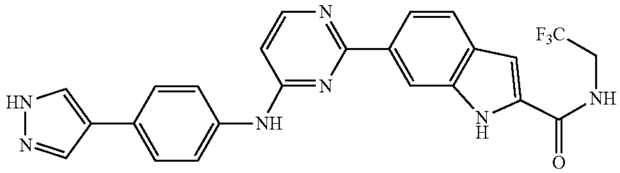 [SMILES: O=C(NCC(F)(F)F)c1cc2ccc(-c3nccc(Nc4ccc(-c5cn[nH]c5)cc4)n3)cc2[nH]1] |
| 318. | 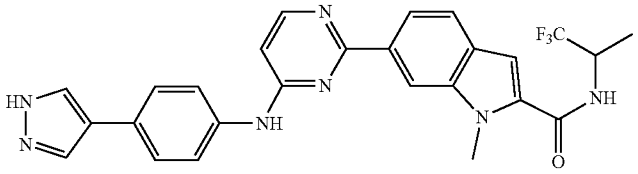 [SMILES: CC(NC(=O)c1cc2ccc(-c3nccc(Nc4ccc(-c5cn[nH]c5)cc4)n3)cc2n1C)C(F)(F)F] |
| 319. | 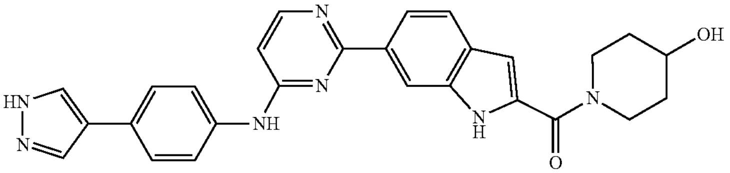 [SMILES: O=C(c1cc2ccc(-c3nccc(Nc4ccc(-c5cn[nH]c5)cc4)n3)cc2[nH]1)N1CCC(O)CC1] |

-continued
| No. | Structure |
| --- | --- |
| 320. | 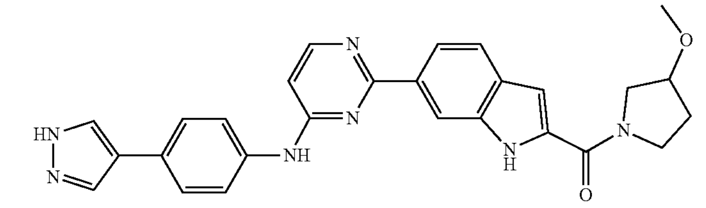 [SMILES: COC1CCN(C(=O)c2cc3ccc(-c4nccc(Nc5ccc(-c6cn[nH]c6)cc5)n4)cc3[nH]2)C1] |
| 321. | 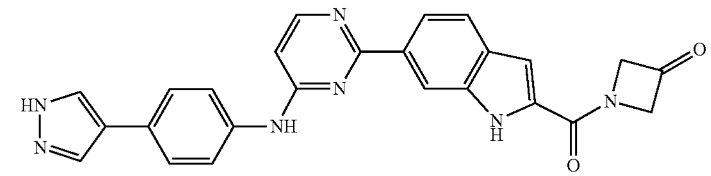 [SMILES: O=C1CN(C(=O)c2cc3ccc(-c4nccc(Nc5ccc(-c6cn[nH]c6)cc5)n4)cc3[nH]2)C1] |
| 322. | 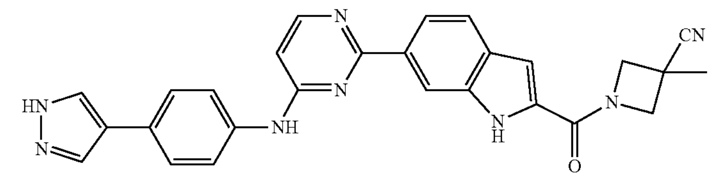 [SMILES: CC1(C#N)CN(C(=O)c2cc3ccc(-c4nccc(Nc5ccc(-c6cn[nH]c6)cc5)n4)cc3[nH]2)C1] |
| 323. | 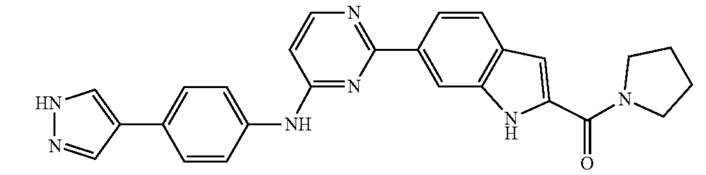 [SMILES: O=C(c1cc2ccc(-c3nccc(Nc4ccc(-c5cn[nH]c5)cc4)n3)cc2[nH]1)N1CCCC1] |
| 324. | 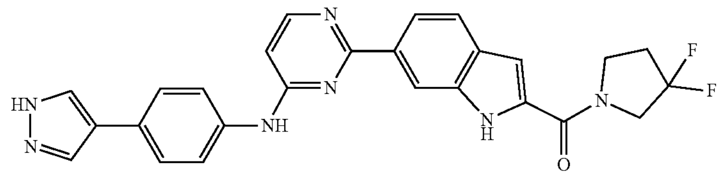 |
| 325. | 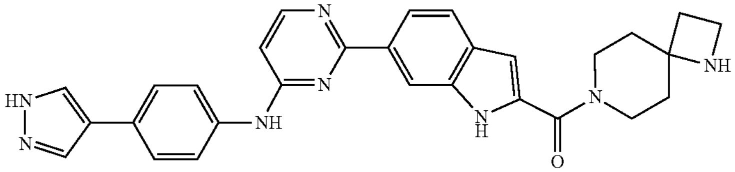 [SMILES: O=C(c1cc2ccc(-c3nccc(Nc4ccc(-c5cn[nH]c5)cc4)n3)cc2[nH]1)N1CCC2(CCN2)CC1] |
| 326. | 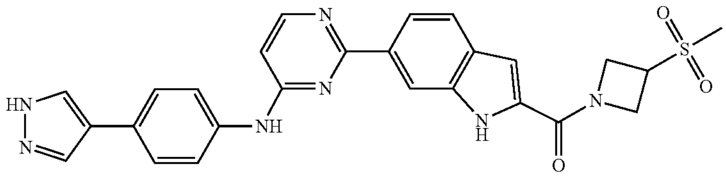 [SMILES: CS(=O)(=O)C1CN(C(=O)c2cc3ccc(-c4nccc(Nc5ccc(-c6cn[nH]c6)cc5)n4)cc3[nH]2)C1] |
| 327. | 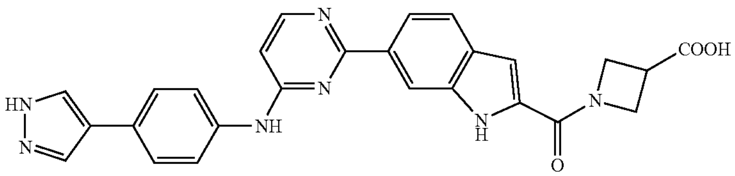 [SMILES: O=C(O)C1CN(C(=O)c2cc3ccc(-c4nccc(Nc5ccc(-c6cn[nH]c6)cc5)n4)cc3[nH]2)C1] |

-continued
| No. | Structure |
|---|---|
| 328. | 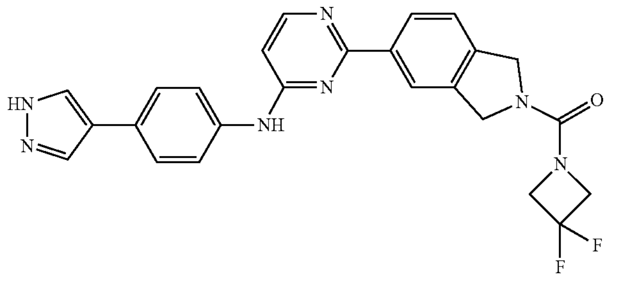 |
| 329. | 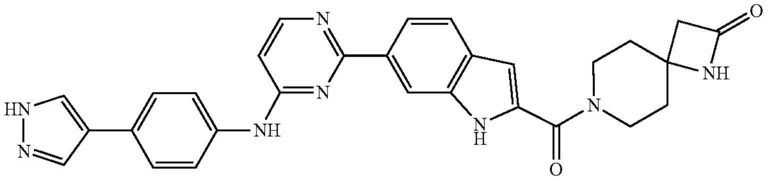 [SMILES: O=C1CC2(CCN(C(=O)c3cc4ccc(-c5nccc(Nc6ccc(-c7cn[nH]c7)cc6)n5)cc4[nH]3)CC2)N1] |
| 330. | 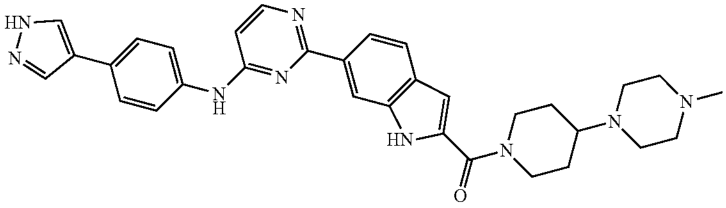 [SMILES: CN1CCN(C2CCN(C(=O)c3cc4ccc(-c5nccc(Nc6ccc(-c7cn[nH]c7)cc6)n5)cc4[nH]3)CC2)CC1] |
| 331. | 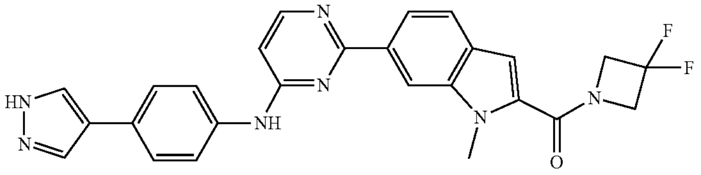 [SMILES: Cn1c(C(=O)N2CC(F)(F)C2)cc2ccc(-c3nccc(Nc4ccc(-c5cn[nH]c5)cc4)n3)cc21] |
| 332. | 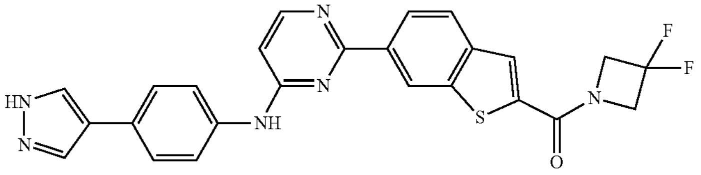 [SMILES: O=C(c1cc2ccc(-c3nccc(Nc4ccc(-c5cn[nH]c5)cc4)n3)cc2s1)N1CC(F)(F)C1] |
| 333. | 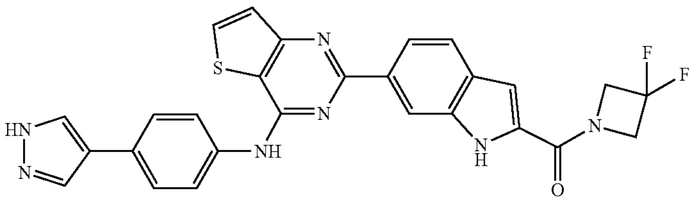 [SMILES: O=C(c1cc2ccc(-c3nc(Nc4ccc(-c5cn[nH]c5)cc4)c4sccc4n3)cc2[nH]1)N1CC(F)(F)C1] |
| 334. | 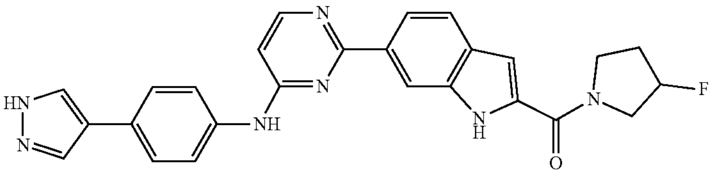 [SMILES: O=C(c1cc2ccc(-c3nccc(Nc4ccc(-c5cn[nH]c5)cc4)n3)cc2[nH]1)N1CCC(F)C1] |

-continued
| No. | Structure |
|---|---|
| 335. | 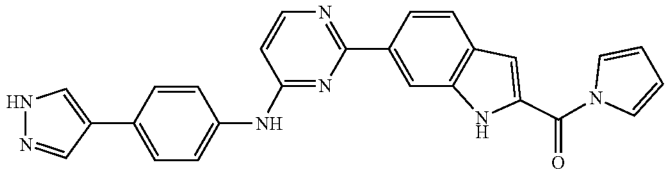 [SMILES: O=C(c1cc2ccc(-c3nccc(Nc4ccc(-c5cn[nH]c5)cc4)n3)cc2[nH]1)n1cccc1] |
| 336. | 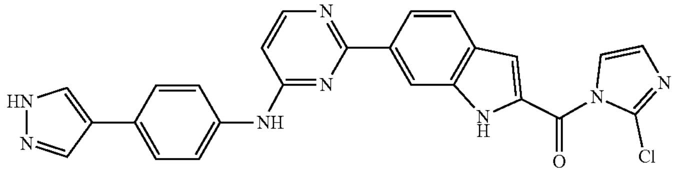 [SMILES: O=C(c1cc2ccc(-c3nccc(Nc4ccc(-c5cn[nH]c5)cc4)n3)cc2[nH]1)n1ccnc1Cl] |
| 337. | 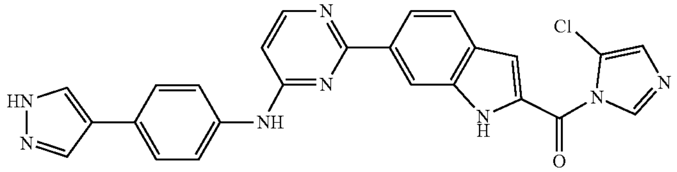 [SMILES: O=C(c1cc2ccc(-c3nccc(Nc4ccc(-c5cn[nH]c5)cc4)n3)cc2[nH]1)n1cncc1Cl] |
| 338. | 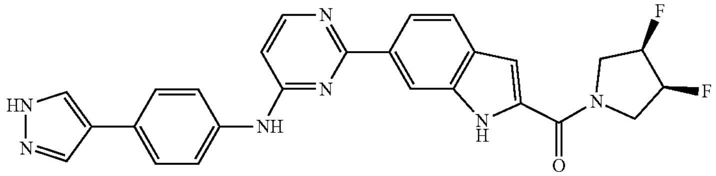 [SMILES: O=C(c1cc2ccc(-c3nccc(Nc4ccc(-c5cn[nH]c5)cc4)n3)cc2[nH]1)N1C[C@@H](F)[C@@H](F)C1] |
| 339. | 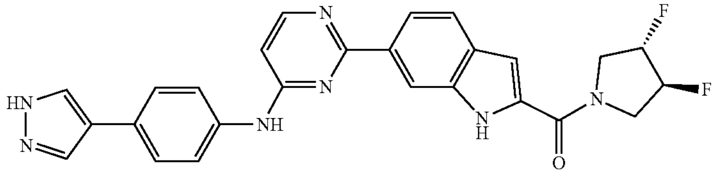 [SMILES: O=C(c1cc2ccc(-c3nccc(Nc4ccc(-c5cn[nH]c5)cc4)n3)cc2[nH]1)N1C[C@H](F)[C@@H](F)C1] |
| 340. | 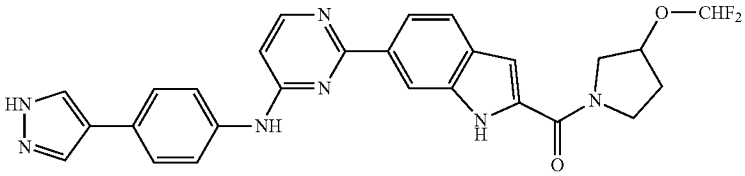 [SMILES: O=C(c1cc2ccc(-c3nccc(Nc4ccc(-c5cn[nH]c5)cc4)n3)cc2[nH]1)N1CCC(OC(F)F)C1] |
| 341. | 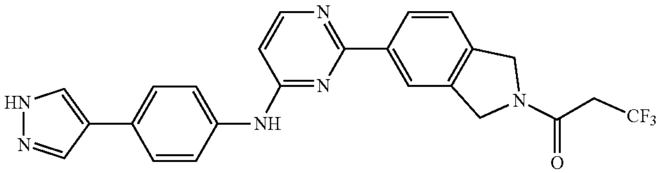 [SMILES: O=C(CC(F)(F)F)N1Cc2ccc(-c3nccc(Nc4ccc(-c5cn[nH]c5)cc4)n3)cc2C1] |
| 342. | 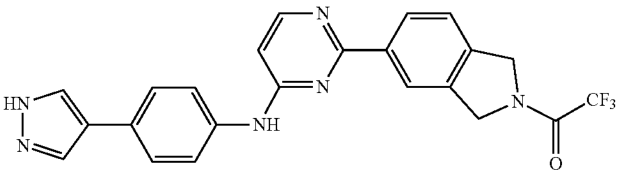 [SMILES: O=C(N1Cc2ccc(-c3nccc(Nc4ccc(-c5cn[nH]c5)cc4)n3)cc2C1)C(F)(F)F] |

-continued
| No. | Structure |
|---|---|
| 343. | 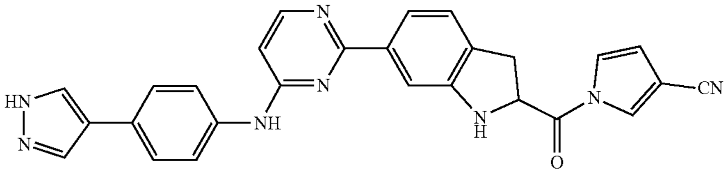 [SMILES: N#Cc1ccn(C(=O)C2Cc3ccc(-c4nccc(Nc5ccc(-c6cn[nH]c6)cc5)n4)cc3N2)c1] |
| 344. | 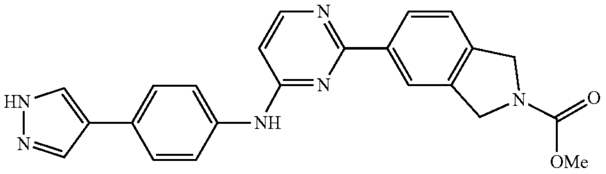 [SMILES: COC(=O)N1Cc2ccc(-c3nccc(Nc4ccc(-c5cn[nH]c5)cc4)n3)cc2C1] |
| 345. | 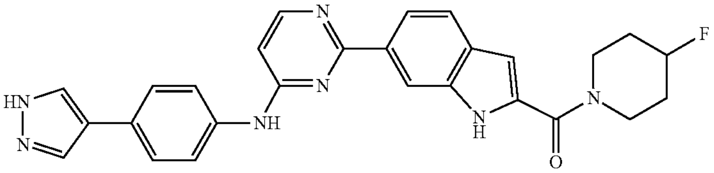 [SMILES: O=C(c1cc2ccc(-c3nccc(Nc4ccc(-c5cn[nH]c5)cc4)n3)cc2[nH]1)N1CCC(F)CC1] |
| 346. | 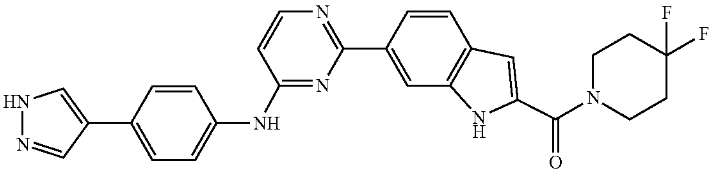 [SMILES: O=C(c1cc2ccc(-c3nccc(Nc4ccc(-c5cn[nH]c5)cc4)n3)cc2[nH]1)N1CCC(F)(F)CC1] |
| 347. | 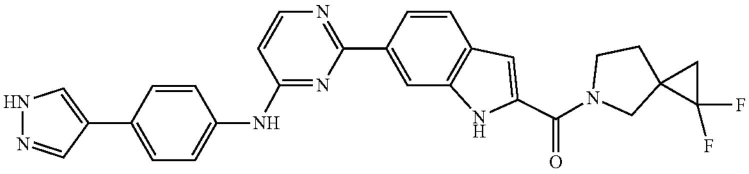 [SMILES: O=C(c1cc2ccc(-c3nccc(Nc4ccc(-c5cn[nH]c5)cc4)n3)cc2[nH]1)N1CCC2(C1)CC2(F)F] |
| 348. | 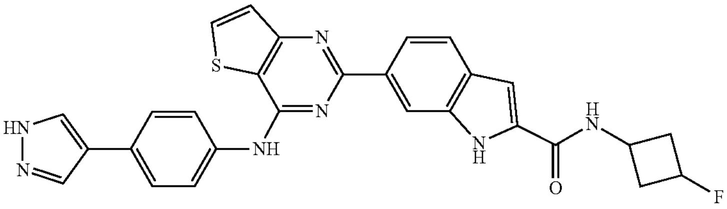 [SMILES: O=C(NC1CC(F)C1)c1cc2ccc(-c3nc(Nc4ccc(-c5cn[nH]c5)cc4)c4sccc4n3)cc2[nH]1] |
| 349. | 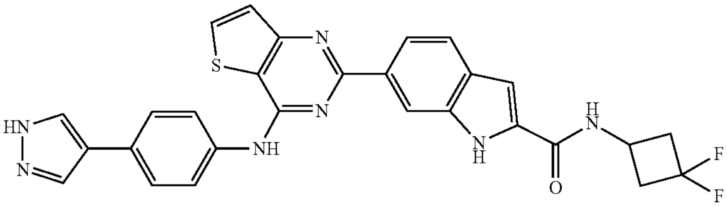 [SMILES: O=C(NC1CC(F)(F)C1)c1cc2ccc(-c3nc(Nc4ccc(-c5cn[nH]c5)cc4)c4sccc4n3)cc2[nH]1] |
| 350. | 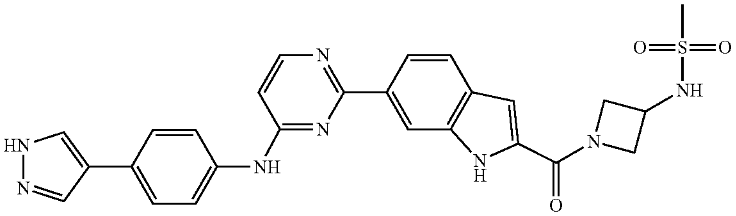 [SMILES: CS(=O)(=O)NC1CN(C(=O)c2cc3ccc(-c4nccc(Nc5ccc(-c6cn[nH]c6)cc5)n4)cc3[nH]2)C1] |

-continued
| No. | Structure |
|---|---|
| 351. | 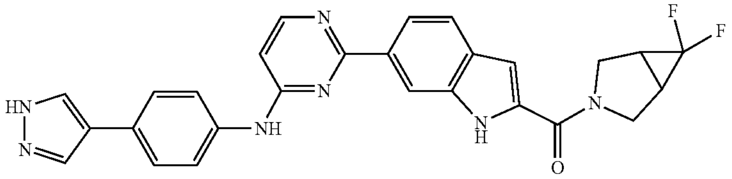 [SMILES: O=C(c1cc2ccc(-c3nccc(Nc4ccc(-c5cn[nH]c5)cc4)n3)cc2[nH]1)N1CC2C(C1)C2(F)F] |
| 352. | 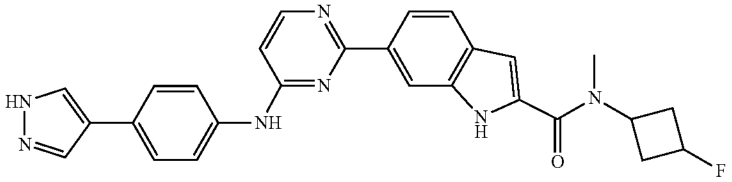 [SMILES: CN(C(=O)c1cc2ccc(-c3nccc(Nc4ccc(-c5cn[nH]c5)cc4)n3)cc2[nH]1)C1CC(F)C1] |
| 353. | 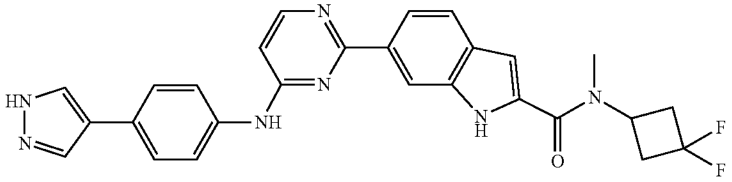 [SMILES: CN(C(=O)c1cc2ccc(-c3nccc(Nc4ccc(-c5cn[nH]c5)cc4)n3)cc2[nH]1)C1CC(F)(F)C1] |
| 354. | 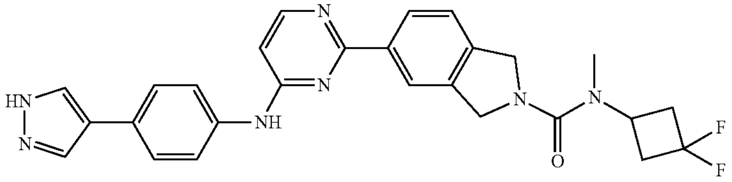 [SMILES: CN(C(=O)N1Cc2ccc(-c3nccc(Nc4ccc(-c5cn[nH]c5)cc4)n3)cc2C1)C1CC(F)(F)C1] |
| 355. | 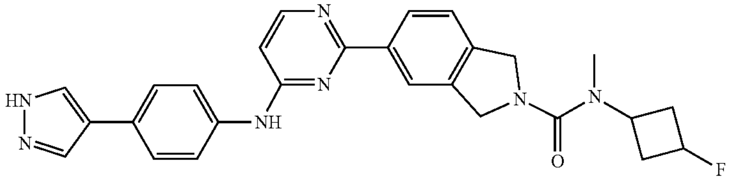 [SMILES: CN(C(=O)N1Cc2ccc(-c3nccc(Nc4ccc(-c5cn[nH]c5)cc4)n3)cc2C1)C1CC(F)C1] |
| 356. | 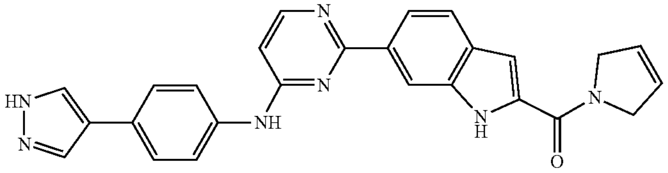 [SMILES: O=C(c1cc2ccc(-c3nccc(Nc4ccc(-c5cn[nH]c5)cc4)n3)cc2[nH]1)N1CC=CC1] |
| 357. | 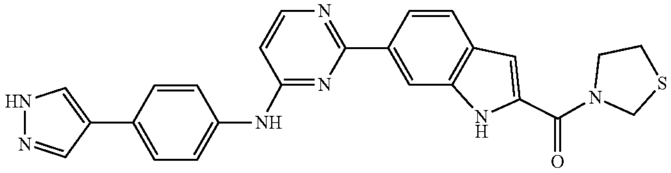 [SMILES: O=C(c1cc2ccc(-c3nccc(Nc4ccc(-c5cn[nH]c5)cc4)n3)cc2[nH]1)N1CCSC1] |
| 358. | 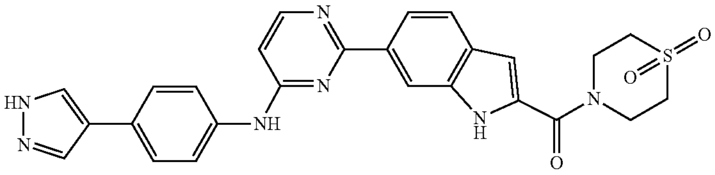 |

-continued
| No. | Structure |
|---|---|
| 359. | 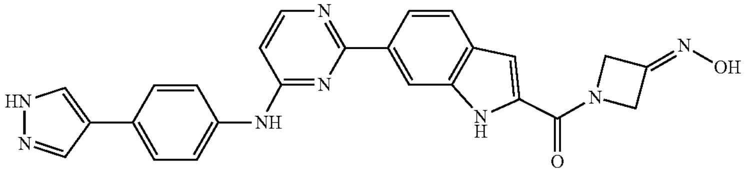 [SMILES: O=C(c1cc2ccc(-c3nccc(Nc4ccc(-c5cn[nH]c5)cc4)n3)cc2[nH]1)N1CC(=NO)C1] |
| 360. | 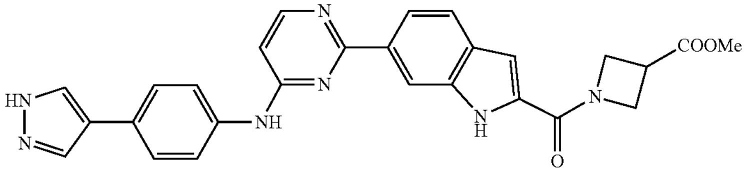 [SMILES: COC(=O)C1CN(C(=O)c2cc3ccc(-c4nccc(Nc5ccc(-c6cn[nH]c6)cc5)n4)cc3[nH]2)C1] |
| 361. | 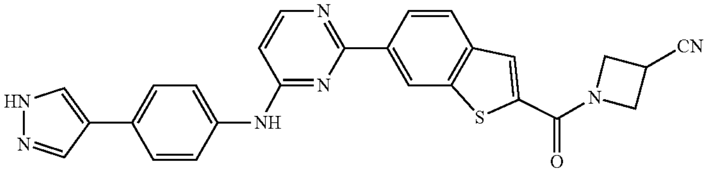 [SMILES: N#CC1CN(C(=O)c2cc3ccc(-c4nccc(Nc5ccc(-c6cn[nH]c6)cc5)n4)cc3s2)C1] |
| 362. | 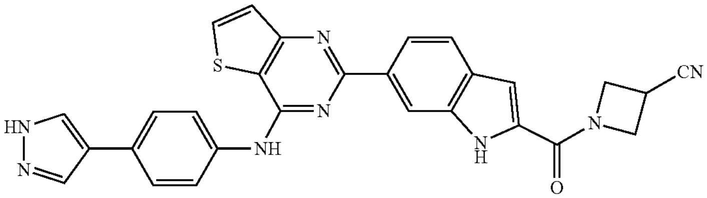 [SMILES: N#CC1CN(C(=O)c2cc3ccc(-c4nc(Nc5ccc(-c6cn[nH]c6)cc5)c5sccc5n4)cc3[nH]2)C1] |
| 363. | 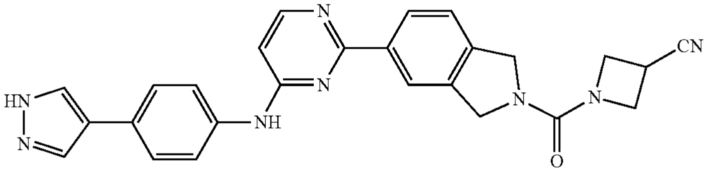 [SMILES: N#CC1CN(C(=O)N2Cc3ccc(-c4nccc(Nc5ccc(-c6cn[nH]c6)cc5)n4)cc3C2)C1] |
| 364. | 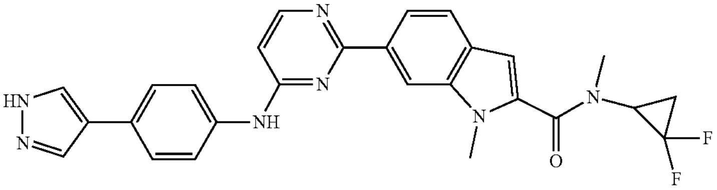 [SMILES: CN(C(=O)c1cc2ccc(-c3nccc(Nc4ccc(-c5cn[nH]c5)cc4)n3)cc2n1C)C1CC1(F)F] |
| 365. | 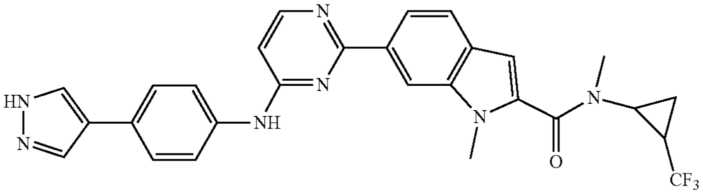 [SMILES: CN(C(=O)c1cc2ccc(-c3nccc(Nc4ccc(-c5cn[nH]c5)cc4)n3)cc2n1C)C1CC1C(F)(F)F] |
| 366. | 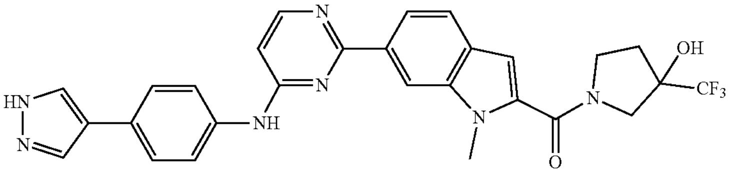 [SMILES: Cn1c(C(=O)N2CCC(O)(C(F)(F)F)C2)cc2ccc(-c3nccc(Nc4ccc(-c5cn[nH]c5)cc4)n3)cc21] |

-continued
| No. | Structure |
| --- | --- |
| 367. | 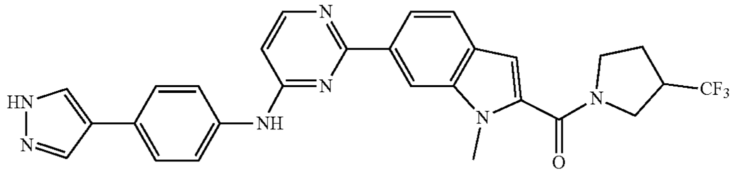 [SMILES: Cn1c(C(=O)N2CCC(C(F)(F)F)C2)cc2ccc(-c3nccc(Nc4ccc(-c5cn[nH]c5)cc4)n3)cc21] |
| 368. | 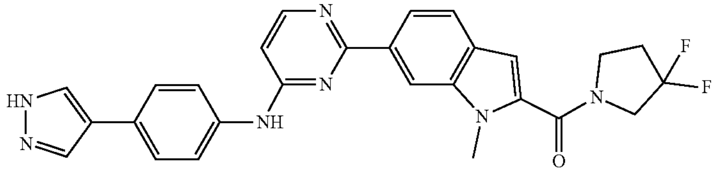 [SMILES: Cn1c(C(=O)N2CCC(F)(F)C2)cc2ccc(-c3nccc(Nc4ccc(-c5cn[nH]c5)cc4)n3)cc21] |
| 369. | 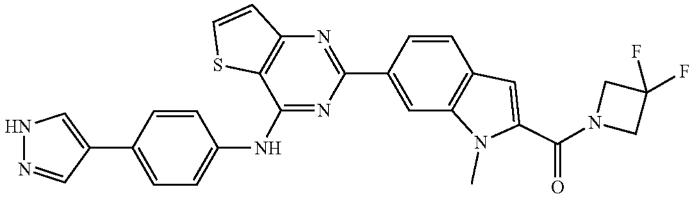 [SMILES: Cn1c(C(=O)N2CC(F)(F)C2)cc2ccc(-c3nc(Nc4ccc(-c5cn[nH]c5)cc4)c4sccc4n3)cc21] |
| 370. | 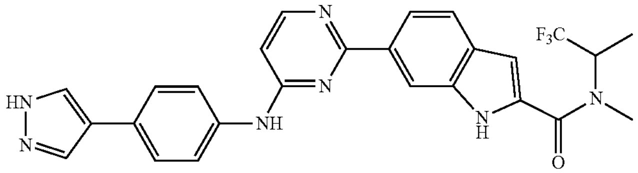 [SMILES: CC(N(C)C(=O)c1cc2ccc(-c3nccc(Nc4ccc(-c5cn[nH]c5)cc4)n3)cc2[nH]1)C(F)(F)F] |
| 371. | 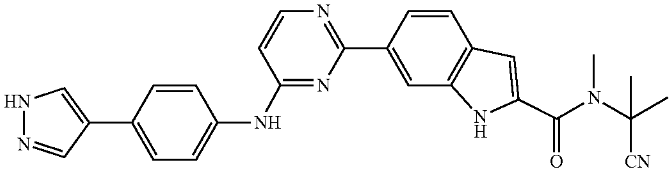 [SMILES: CN(C(=O)c1cc2ccc(-c3nccc(Nc4ccc(-c5cn[nH]c5)cc4)n3)cc2[nH]1)C(C)(C)C#N] |
| 372. | 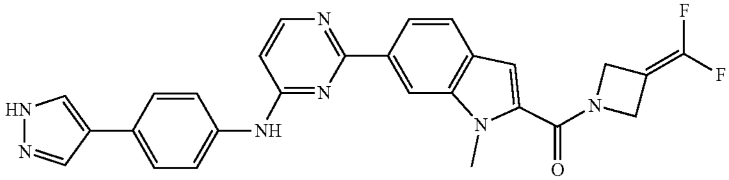 [SMILES: Cn1c(C(=O)N2CC(=C(F)F)C2)cc2ccc(-c3nccc(Nc4ccc(-c5cn[nH]c5)cc4)n3)cc21] |
| 373. | 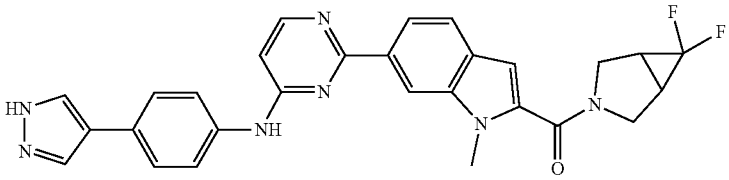 [SMILES: Cn1c(C(=O)N2CC3C(C2)C3(F)F)cc2ccc(-c3nccc(Nc4ccc(-c5cn[nH]c5)cc4)n3)cc21] |
| 374. | 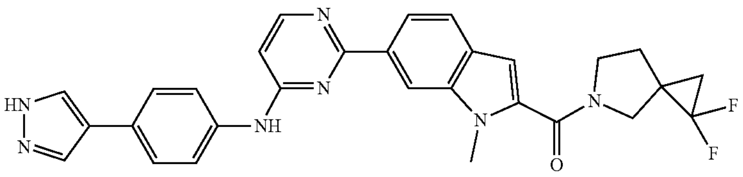 [SMILES: Cn1c(C(=O)N2CCC3(C2)CC3(F)F)cc2ccc(-c3nccc(Nc4ccc(-c5cn[nH]c5)cc4)n3)cc21] |

-continued
| No. | Structure |
| --- | --- |
| 375. | 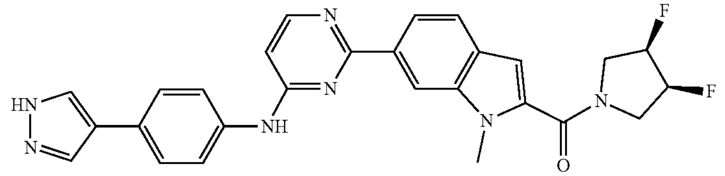 [SMILES: Cn1c(C(=O)N2C[C@@H](F)[C@@H](F)C2)cc2ccc(-c3nccc(Nc4ccc(-c5cn[nH]c5)cc4)n3)cc21] |
| 376. | 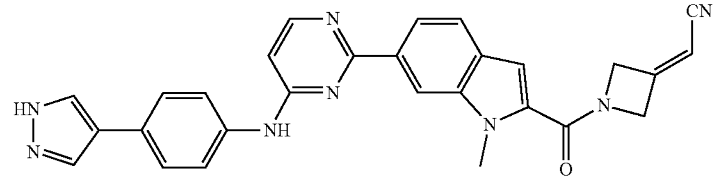 [SMILES: Cn1c(C(=O)N2CC(=CC#N)C2)cc2ccc(-c3nccc(Nc4ccc(-c5cn[nH]c5)cc4)n3)cc21] |
| 377. | 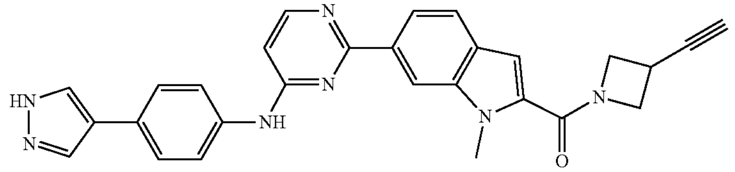 [SMILES: C#CC1CN(C(=O)c2cc3ccc(-c4nccc(Nc5ccc(-c6cn[nH]c6)cc5)n4)cc3n2C)C1] |
| 378. | 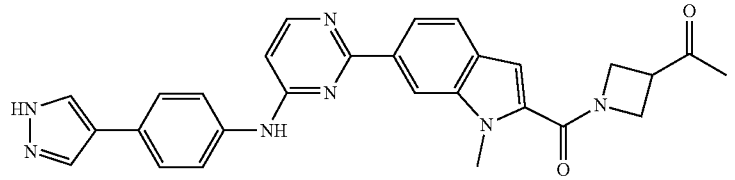 [SMILES: CC(=O)C1CN(C(=O)c2cc3ccc(-c4nccc(Nc5ccc(-c6cn[nH]c6)cc5)n4)cc3n2C)C1] |
| 379. | 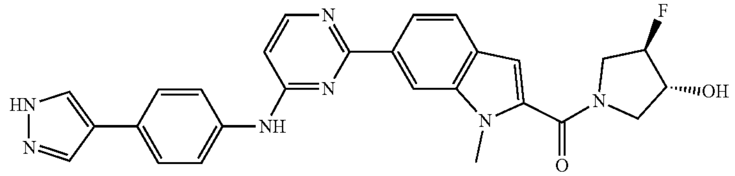 [SMILES: Cn1c(C(=O)N2C[C@@H](O)[C@H](F)C2)cc2ccc(-c3nccc(Nc4ccc(-c5cn[nH]c5)cc4)n3)cc21] |
| 380. | 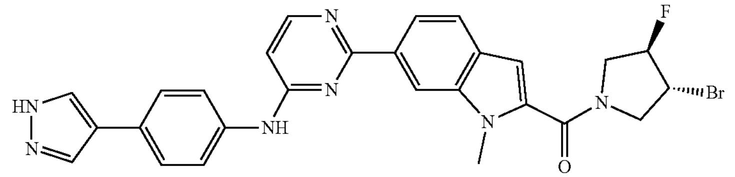 [SMILES: Cn1c(C(=O)N2C[C@@H](F)[C@H](Br)C2)cc2ccc(-c3nccc(Nc4ccc(-c5cn[nH]c5)cc4)n3)cc21] |
| 381. | 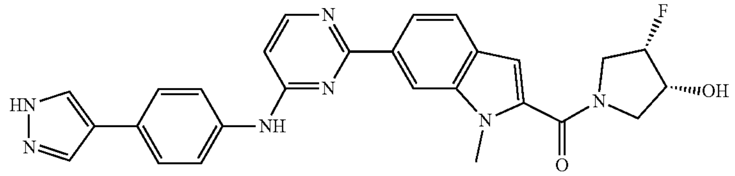 [SMILES: Cn1c(C(=O)N2C[C@@H](O)[C@@H](F)C2)cc2ccc(-c3nccc(Nc4ccc(-c5cn[nH]c5)cc4)n3)cc21] |
| 382. | 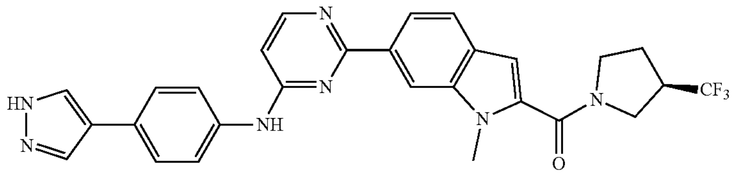 [SMILES: Cn1c(C(=O)N2CC[C@@H](C(F)(F)F)C2)cc2ccc(-c3nccc(Nc4ccc(-c5cn[nH]c5)cc4)n3)cc21] |

-continued
| No. | Structure |
|---|---|
| 383. | 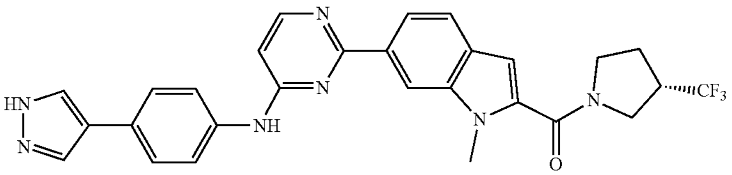 [SMILES: Cn1c(C(=O)N2CC[C@H](C(F)(F)F)C2)cc2ccc(-c3nccc(Nc4ccc(-c5cn[nH]c5)cc4)n3)cc21] |
| 384. | 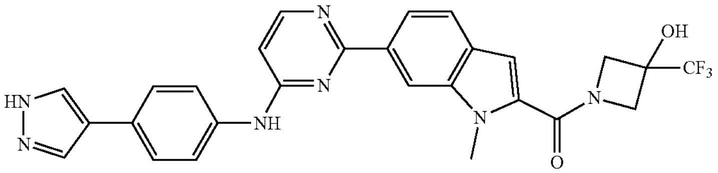 [SMILES: Cn1c(C(=O)N2CC(O)(C(F)(F)F)C2)cc2ccc(-c3nccc(Nc4ccc(-c5cn[nH]c5)cc4)n3)cc21] |
| 385. | 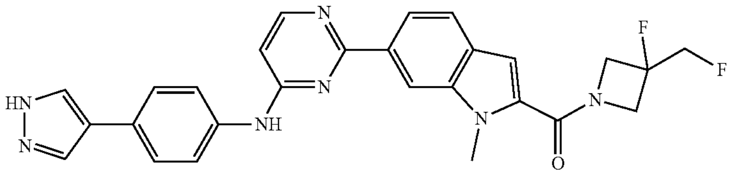 [SMILES: Cn1c(C(=O)N2CC(F)(CF)C2)cc2ccc(-c3nccc(Nc4ccc(-c5cn[nH]c5)cc4)n3)cc21] |
| 386. | 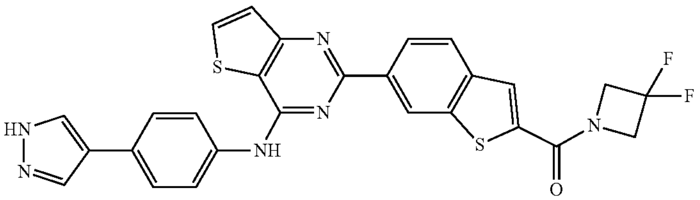 [SMILES: O=C(c1cc2ccc(-c3nc(Nc4ccc(-c5cn[nH]c5)cc4)c4sccc4n3)cc2s1)N1CC(F)(F)C1] |
| 387. | 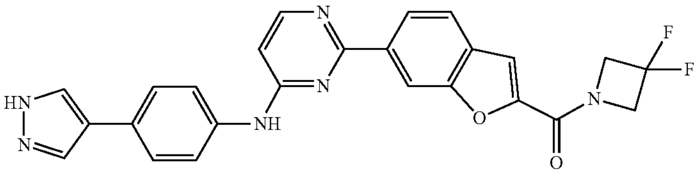 |
| 388. | 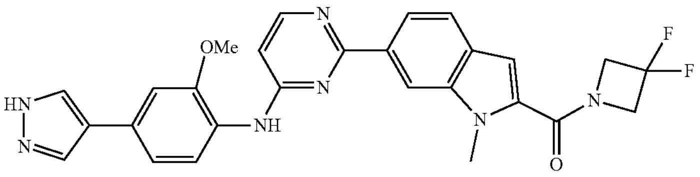 |
| 389. | 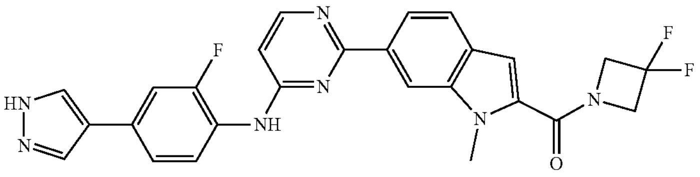 [SMILES: Cn1c(C(=O)N2CC(F)(F)C2)cc2ccc(-c3nccc(Nc4ccc(-c5cn[nH]c5)cc4F)n3)cc21] |
| 390. | 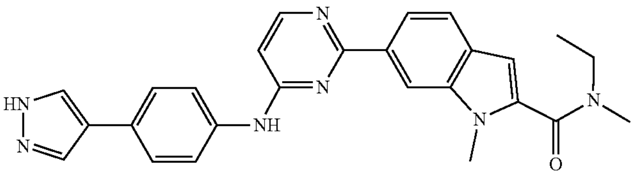 [SMILES: CCN(C)C(=O)c1cc2ccc(-c3nccc(Nc4ccc(-c5cn[nH]c5)cc4)n3)cc2n1C] |

-continued
| No. | Structure |
| --- | --- |
| 391. | 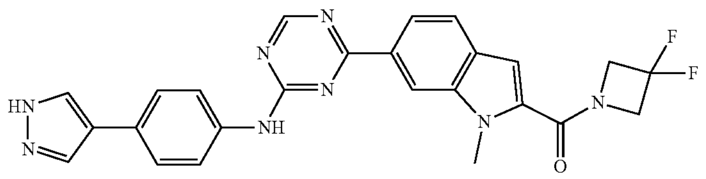 [SMILES: Cn1c(C(=O)N2CC(F)(F)C2)cc2ccc(-c3ncnc(Nc4ccc(-c5cn[nH]c5)cc4)n3)cc21] |
| 392. | 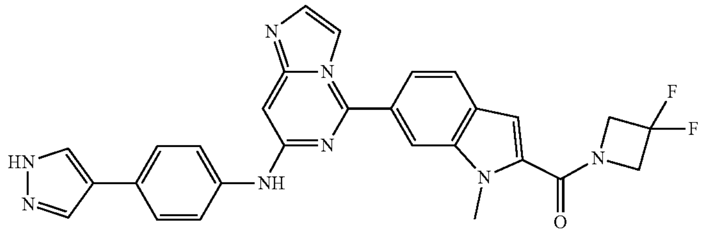 |
| 393. | 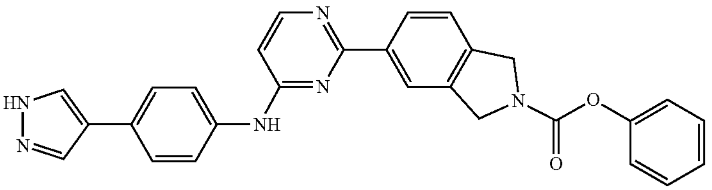 [SMILES: O=C(Oc1ccccc1)N1Cc2ccc(-c3nccc(Nc4ccc(-c5cn[nH]c5)cc4)n3)cc2C1] |
| 394. | 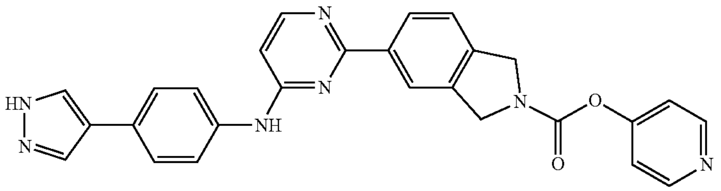 [SMILES: O=C(Oc1ccncc1)N1Cc2ccc(-c3nccc(Nc4ccc(-c5cn[nH]c5)cc4)n3)cc2C1] |
| 395. | 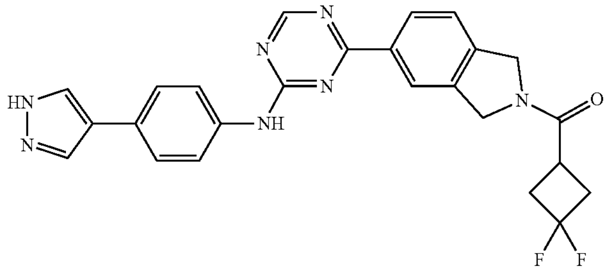 [SMILES: O=C(C1CC(F)(F)C1)N1Cc2ccc(-c3ncnc(Nc4ccc(-c5cn[nH]c5)cc4)n3)cc2C1] |
| 396. | 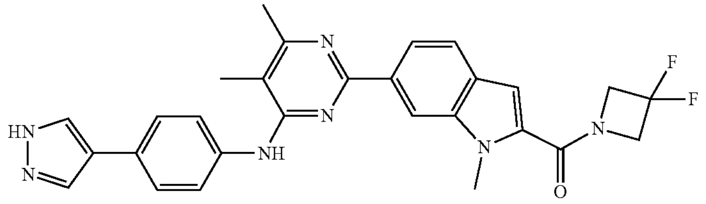 [SMILES: Cc1nc(-c2ccc3cc(C(=O)N4CC(F)(F)C4)n(C)c3c2)nc(Nc2ccc(-c3cn[nH]c3)cc2)c1C] |
| 397. | 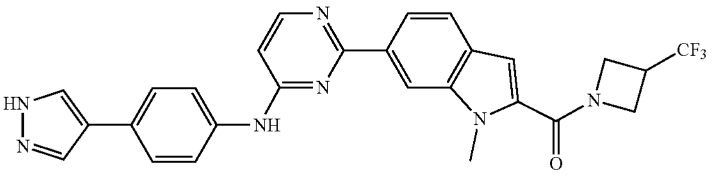 [SMILES: Cn1c(C(=O)N2CC(C(F)(F)F)C2)cc2ccc(-c3nccc(Nc4ccc(-c5cn[nH]c5)cc4)n3)cc21] |

-continued
| No. | Structure |
| --- | --- |
| 398. | 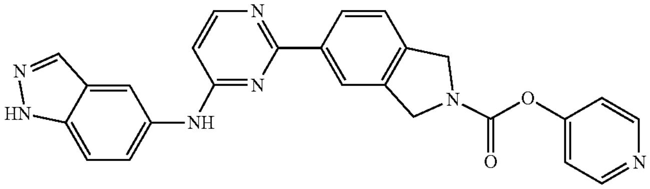 [SMILES: O=C(Oc1ccncc1)N1Cc2ccc(-c3nccc(Nc4ccc5[nH]ncc5c4)n3)cc2C1] |
| 399. | 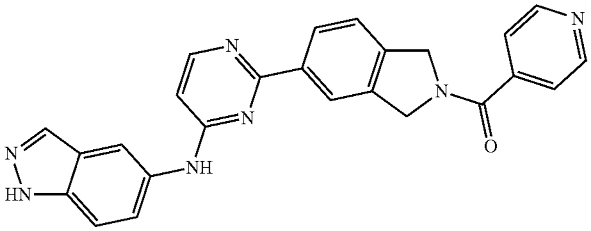 [SMILES: O=C(c1ccncc1)N1Cc2ccc(-c3nccc(Nc4ccc5[nH]ncc5c4)n3)cc2C1] |
| 400. | 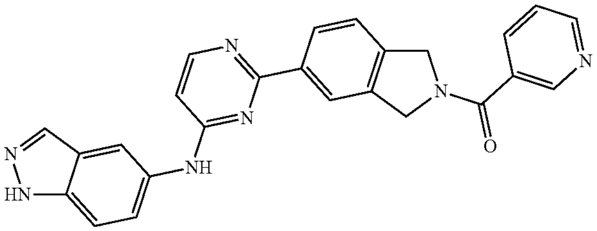 [SMILES: O=C(c1cccnc1)N1Cc2ccc(-c3nccc(Nc4ccc5[nH]ncc5c4)n3)cc2C1] |
| 401. | 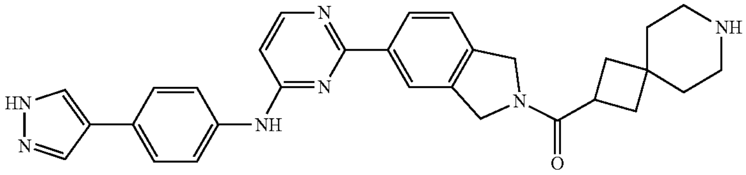 [SMILES: O=C(C1CC2(CCNCC2)C1)N1Cc2ccc(-c3nccc(Nc4ccc(-c5cn[nH]c5)cc4)n3)cc2C1] |
| 402. | 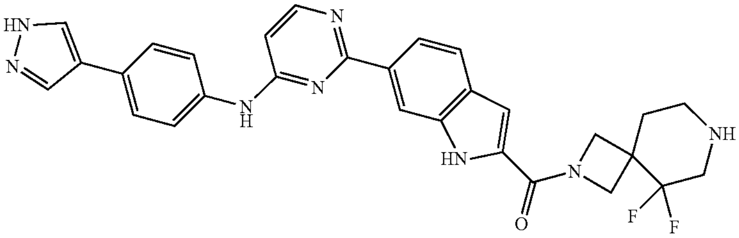 [SMILES: O=C(c1cc2ccc(-c3nccc(Nc4ccc(-c5cn[nH]c5)cc4)n3)cc2[nH]1)N1CC2(CCNCC2(F)F)C1] |
| 403. | 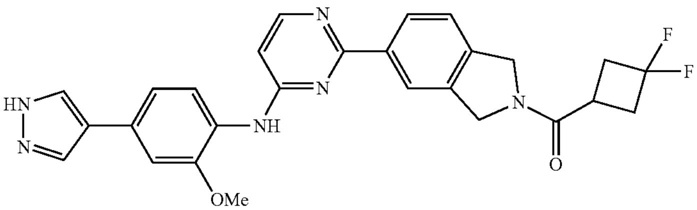 [SMILES: COc1cc(-c2cn[nH]c2)ccc1Nc1ccnc(-c2ccc3c(c2)CN(C(=O)C2CC(F)(F)C2)C3)n1] |
| 404. | 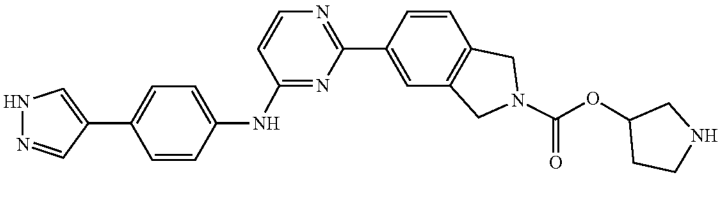 [SMILES: O=C(OC1CCNC1)N1Cc2ccc(-c3nccc(Nc4ccc(-c5cn[nH]c5)cc4)n3)cc2C1] |

-continued
| No. | Structure |
|---|---|
| 405. | 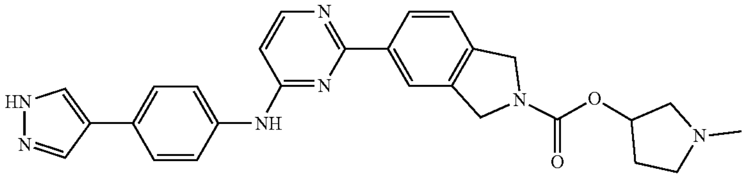 [SMILES: CN1CCC(OC(=O)N2Cc3ccc(-c4nccc(Nc5ccc(-c6cn[nH]c6)cc5)n4)cc3C2)C1] |
| 406. | 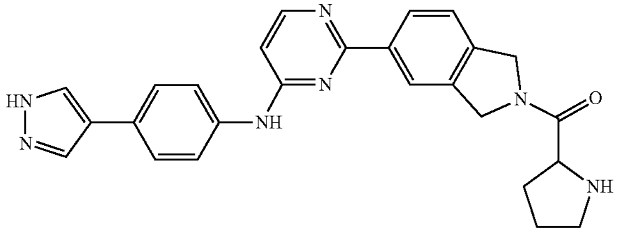 [SMILES: O=C(C1CCCN1)N1Cc2ccc(-c3nccc(Nc4ccc(-c5cn[nH]c5)cc4)n3)cc2C1] |
| 407. | 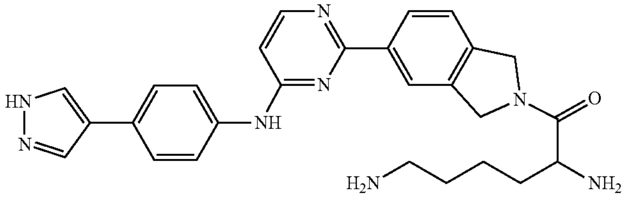 [SMILES: NCCCCC(N)C(=O)N1Cc2ccc(-c3nccc(Nc4ccc(-c5cn[nH]c5)cc4)n3)cc2C1] |
| 408. | 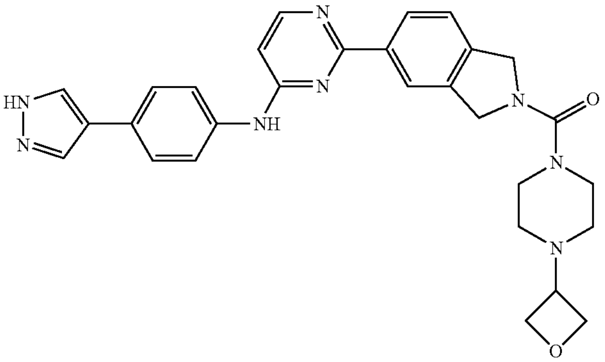 [SMILES: O=C(N1CCN(C2COC2)CC1)N1Cc2ccc(-c3nccc(Nc4ccc(-c5cn[nH]c5)cc4)n3)cc2C1] |
| 409. | 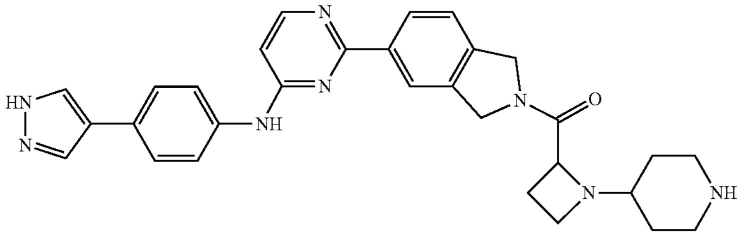 [SMILES: O=C(C1CCN1C1CCNCC1)N1Cc2ccc(-c3nccc(Nc4ccc(-c5cn[nH]c5)cc4)n3)cc2C1] |
| 410. | 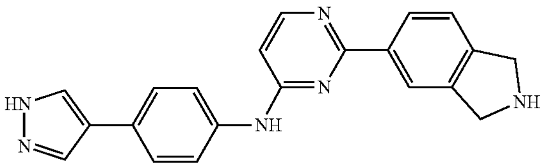 [SMILES: c1cc(Nc2ccc(-c3cn[nH]c3)cc2)nc(-c2ccc3c(c2)CNC3)n1] |
| 411. | 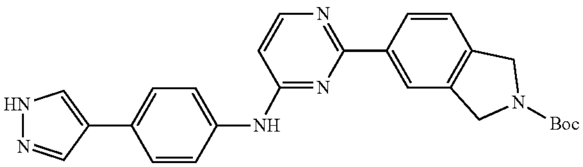 [SMILES: CC(C)(C)OC(=O)N1Cc2ccc(-c3nccc(Nc4ccc(-c5cn[nH]c5)cc4)n3)cc2C1] |

-continued
| No. | Structure |
| --- | --- |
| 412. | 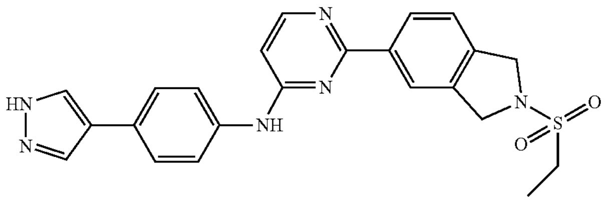 [SMILES: CCS(=O)(=O)N1Cc2ccc(-c3nccc(Nc4ccc(-c5cn[nH]c5)cc4)n3)cc2C1] |
| 413. | 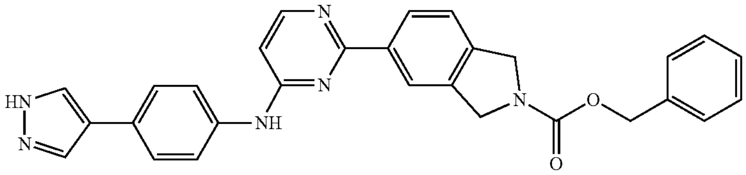 [SMILES: O=C(OCc1ccccc1)N1Cc2ccc(-c3nccc(Nc4ccc(-c5cn[nH]c5)cc4)n3)cc2C1] |
| 414. | 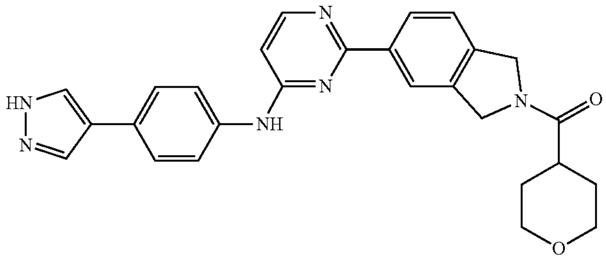 |
| 415. | 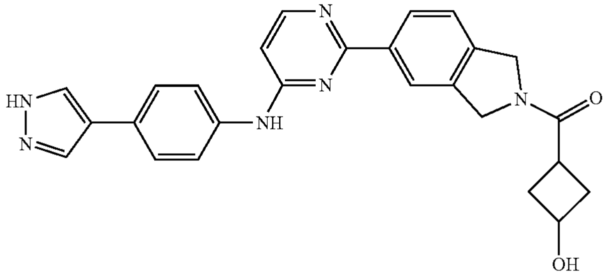 [SMILES: O=C(C1CC(O)C1)N1Cc2ccc(-c3nccc(Nc4ccc(-c5cn[nH]c5)cc4)n3)cc2C1] |
| 416. | 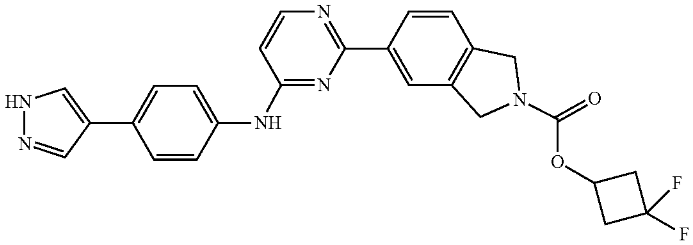 [SMILES: O=C(OC1CC(F)(F)C1)N1Cc2ccc(-c3nccc(Nc4ccc(-c5cn[nH]c5)cc4)n3)cc2C1] |
| 417. | 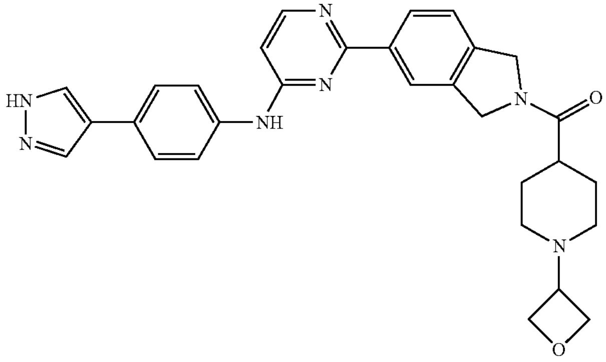 [SMILES: O=C(C1CCN(C2COC2)CC1)N1Cc2ccc(-c3nccc(Nc4ccc(-c5cn[nH]c5)cc4)n3)cc2C1] |

-continued
| No. | Structure |
| --- | --- |
| 418. | 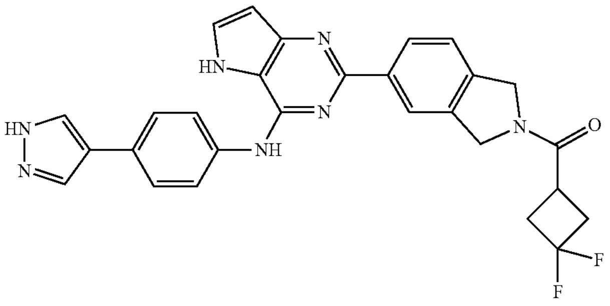 [SMILES: O=C(C1CC(F)(F)C1)N1Cc2ccc(-c3nc(Nc4ccc(-c5cn[nH]c5)cc4)c4[nH]ccc4n3)cc2C1] |
| 419. | 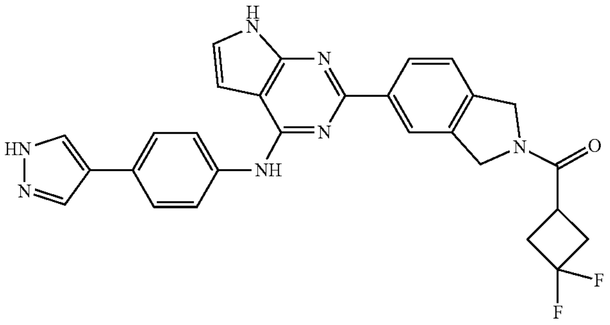 [SMILES: O=C(C1CC(F)(F)C1)N1Cc2ccc(-c3nc(Nc4ccc(-c5cn[nH]c5)cc4)c4cc[nH]c4n3)cc2C1] |
| 420. | 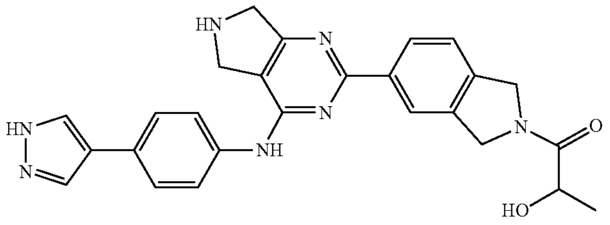 [SMILES: CC(O)C(=O)N1Cc2ccc(-c3nc4c(c(Nc5ccc(-c6cn[nH]c6)cc5)n3)CNC4)cc2C1] |
| 421. | 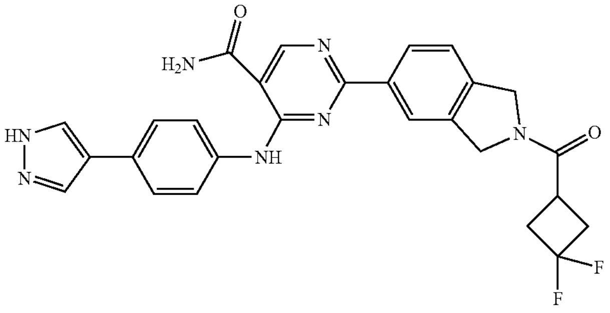 [SMILES: NC(=O)c1cnc(-c2ccc3c(c2)CN(C(=O)C2CC(F)(F)C2)C3)nc1Nc1ccc(-c2cn[nH]c2)cc1] |
| 422. | 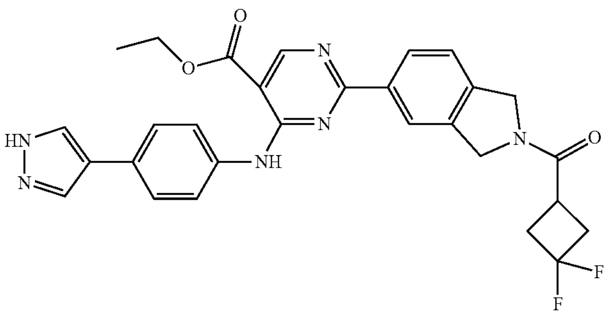 [SMILES: CCOC(=O)c1cnc(-c2ccc3c(c2)CN(C(=O)C2CC(F)(F)C2)C3)nc1Nc1ccc(-c2cn[nH]c2)cc1] |

-continued
| No. | Structure |
| --- | --- |
| 423. | 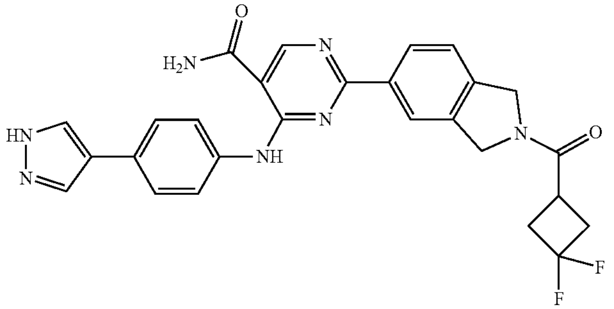 [SMILES: NC(=O)c1cnc(-c2ccc3c(c2)CN(C(=O)C2CC(F)(F)C2)C3)nc1Nc1ccc(-c2cn[nH]c2)cc1] |
| 424. | 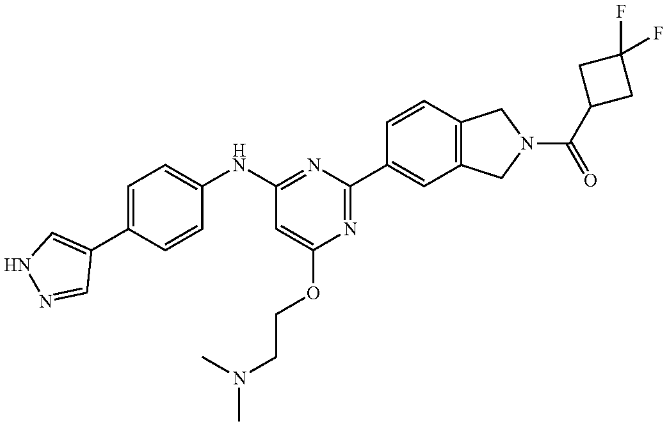 [SMILES: CN(C)CCOc1cc(Nc2ccc(-c3cn[nH]c3)cc2)nc(-c2ccc3c(c2)CN(C(=O)C2CC(F)(F)C2)C3)n1] |
| 425. | 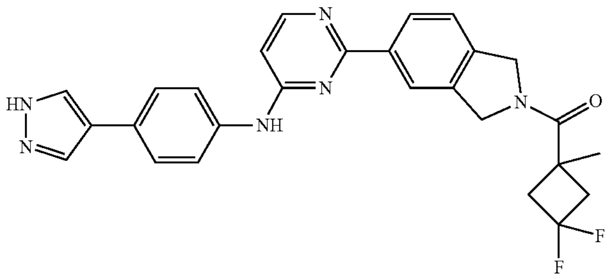 [SMILES: CC1(C(=O)N2Cc3ccc(-c4nccc(Nc5ccc(-c6cn[nH]c6)cc5)n4)cc3C2)CC(F)(F)C1] |
| 426. | 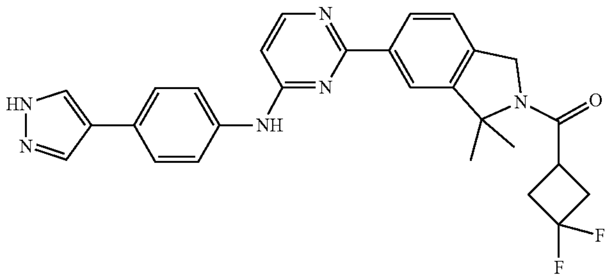 [SMILES: CC1(C)c2cc(-c3nccc(Nc4ccc(-c5cn[nH]c5)cc4)n3)ccc2CN1C(=O)C1CC(F)(F)C1] |
| 427. | 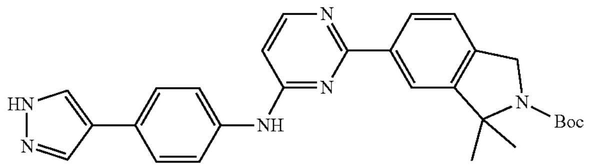 [SMILES: CC(C)(C)OC(=O)N1Cc2ccc(-c3nccc(Nc4ccc(-c5cn[nH]c5)cc4)n3)cc2C1(C)C] |

-continued
| No. | Structure |
| --- | --- |
| 428. | 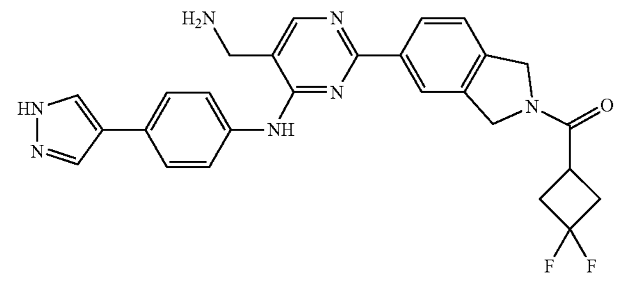 [SMILES: NCc1cnc(-c2ccc3c(c2)CN(C(=O)C2CC(F)(F)C2)C3)nc1Nc1ccc(-c2cn[nH]c2)cc1] |
| 429. | 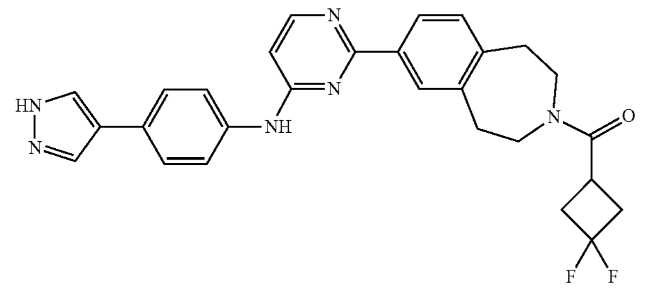 [SMILES: O=C(C1CC(F)(F)C1)N1CCc2ccc(-c3nccc(Nc4ccc(-c5cn[nH]c5)cc4)n3)cc2CC1] |
| 430. | 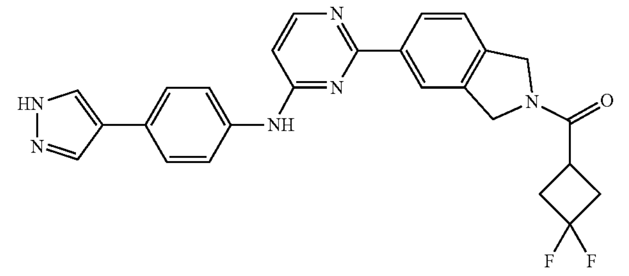 [SMILES: O=C(C1CC(F)(F)C1)N1Cc2ccc(-c3nccc(Nc4ccc(-c5cn[nH]c5)cc4)n3)cc2C1] |
| 431. | 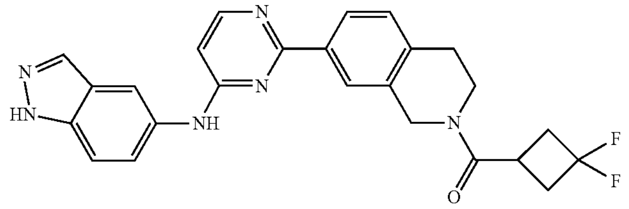 [SMILES: O=C(C1CC(F)(F)C1)N1CCc2ccc(-c3nccc(Nc4ccc5[nH]ncc5c4)n3)cc2C1] |
| 432. | 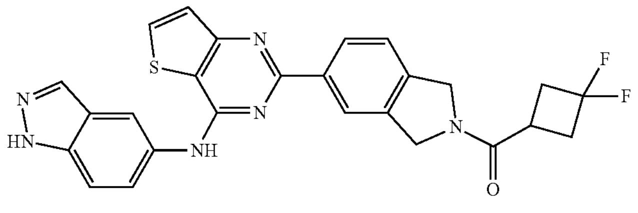 [SMILES: O=C(C1CC(F)(F)C1)N1Cc2ccc(-c3nc(Nc4ccc5[nH]ncc5c4)c4sccc4n3)cc2C1] |
| 433. | 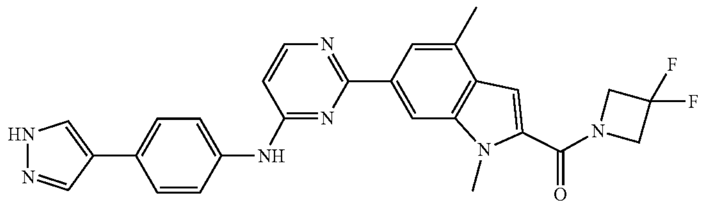 [SMILES: Cc1cc(-c2nccc(Nc3ccc(-c4cn[nH]c4)cc3)n2)cc2c1cc(C(=O)N1CC(F)(F)C1)n2C] |

-continued
| No. | Structure |
| --- | --- |
| 434. | 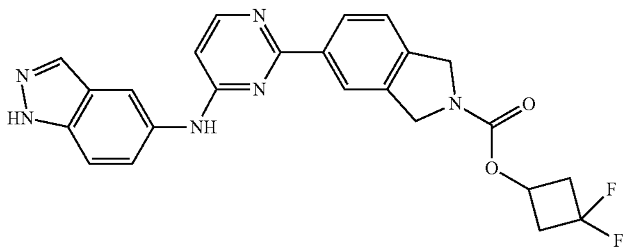 [SMILES: O=C(OC1CC(F)(F)C1)N1Cc2ccc(-c3nccc(Nc4ccc5[nH]ncc5c4)n3)cc2C1] |
| 435. | 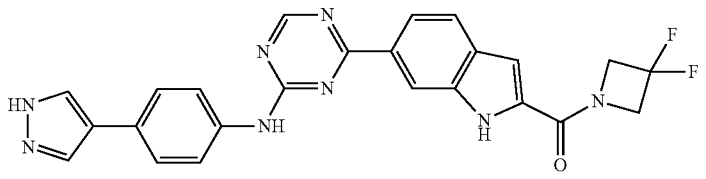 |
| 436. | 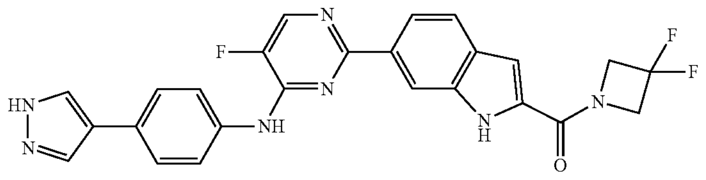 [SMILES: O=C(c1cc2ccc(-c3ncc(F)c(Nc4ccc(-c5cn[nH]c5)cc4)n3)cc2[nH]1)N1CC(F)(F)C1] |
| 437. | 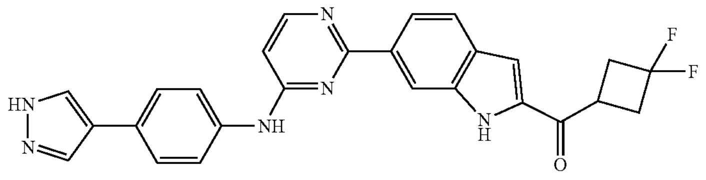 [SMILES: O=C(c1cc2ccc(-c3nccc(Nc4ccc(-c5cn[nH]c5)cc4)n3)cc2[nH]1)C1CC(F)(F)C1] |
| 438. | 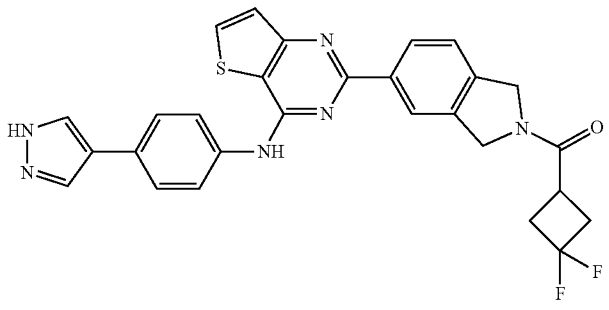 [SMILES: O=C(C1CC(F)(F)C1)N1Cc2ccc(-c3nc(Nc4ccc(-c5cn[nH]c5)cc4)c4sccc4n3)cc2C1] |
| 439. | 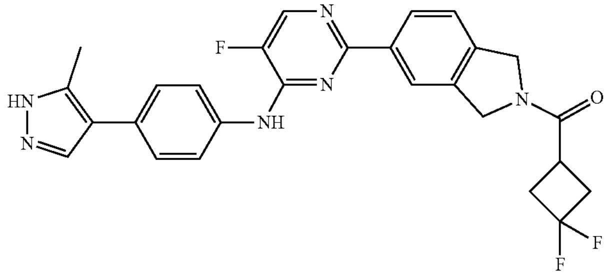 [SMILES: Cc1[nH]ncc1-c1ccc(Nc2nc(-c3ccc4c(c3)CN(C(=O)C3CC(F)(F)C3)C4)ncc2F)cc1] |

-continued
| No. | Structure |
|---|---|
| 440. | 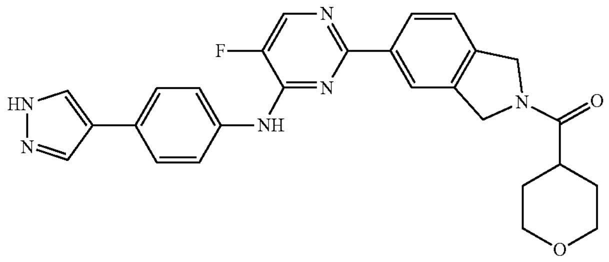 [SMILES: O=C(C1CCOCC1)N1Cc2ccc(-c3ncc(F)c(Nc4ccc(-c5cn[nH]c5)cc4)n3)cc2C1] |
| 441. | 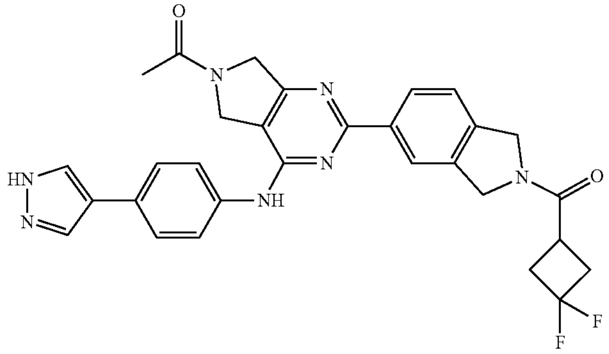 [SMILES: CC(=O)N1Cc2nc(-c3ccc4c(c3)CN(C(=O)C3CC(F)(F)C3)C4)nc(Nc3ccc(-c4cn[nH]c4)cc3)c2C1] |
| 442. | 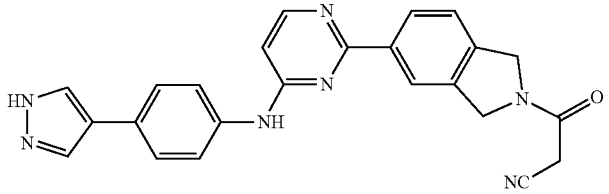 [SMILES: N#CCC(=O)N1Cc2ccc(-c3nccc(Nc4ccc(-c5cn[nH]c5)cc4)n3)cc2C1] |
| 443. | 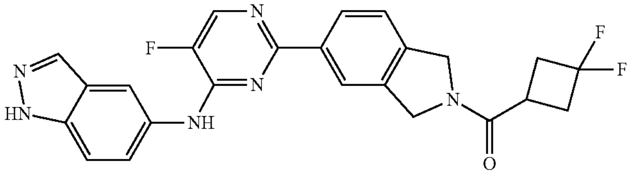 [SMILES: O=C(C1CC(F)(F)C1)N1Cc2ccc(-c3ncc(F)c(Nc4ccc5[nH]ncc5c4)n3)cc2C1] |
| 444. | 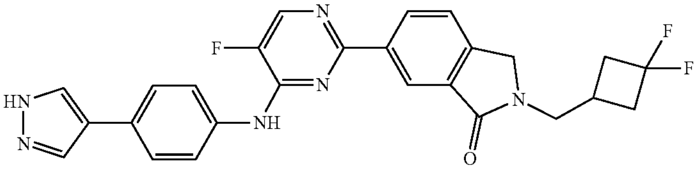 [SMILES: O=C1c2cc(-c3ncc(F)c(Nc4ccc(-c5cn[nH]c5)cc4)n3)ccc2CN1CC1CC(F)(F)C1] |
| 445. | 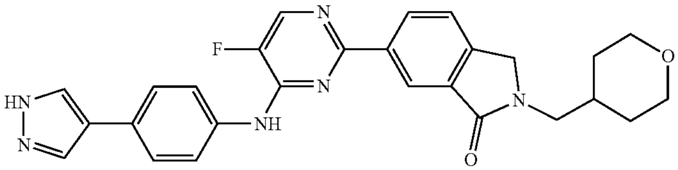 [SMILES: O=C1c2cc(-c3ncc(F)c(Nc4ccc(-c5cn[nH]c5)cc4)n3)ccc2CN1CC1CCOCC1] |

-continued
| No. | Structure |
|---|---|
| 446. | 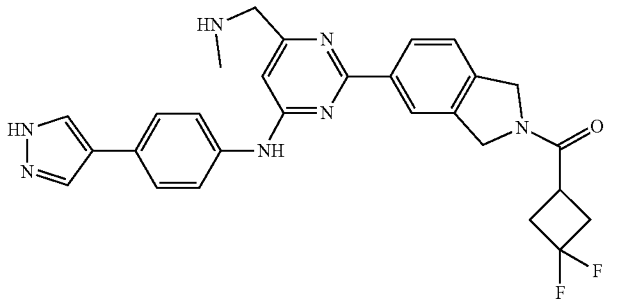 [SMILES: CNCc1cc(Nc2ccc(-c3cn[nH]c3)cc2)nc(-c2ccc3c(c2)CN(C(=O)C2CC(F)(F)C2)C3)n1] |
| 447. | 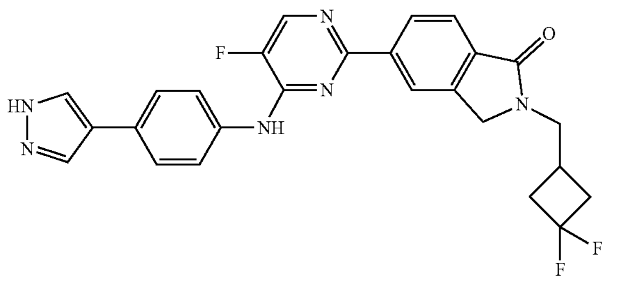 [SMILES: O=C1c2ccc(-c3ncc(F)c(Nc4ccc(-c5cn[nH]c5)cc4)n3)cc2CN1CC1CC(F)(F)C1] |
| 448. | 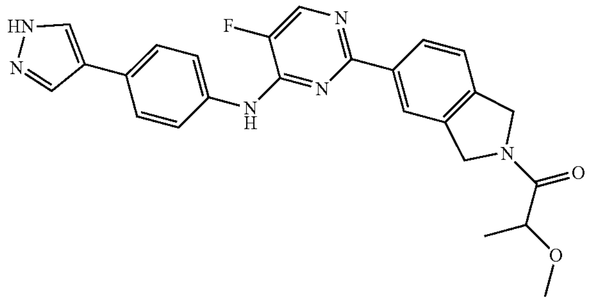 [SMILES: COC(C)C(=O)N1Cc2ccc(-c3ncc(F)c(Nc4ccc(-c5cn[nH]c5)cc4)n3)cc2C1] |
| 449. | 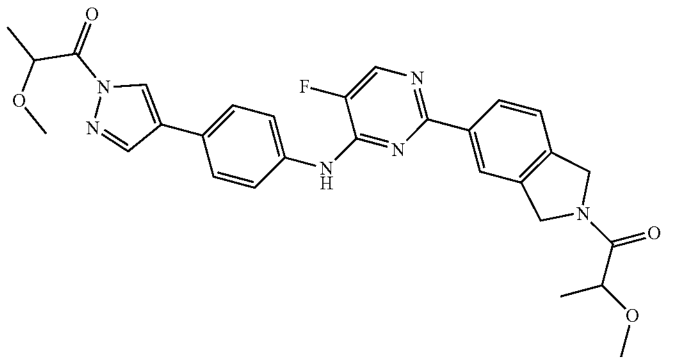 [SMILES: COC(C)C(=O)N1Cc2ccc(-c3ncc(F)c(Nc4ccc(-c5cnn(C(=O)C(C)OC)c5)cc4)n3)cc2C1] |
| 450. | 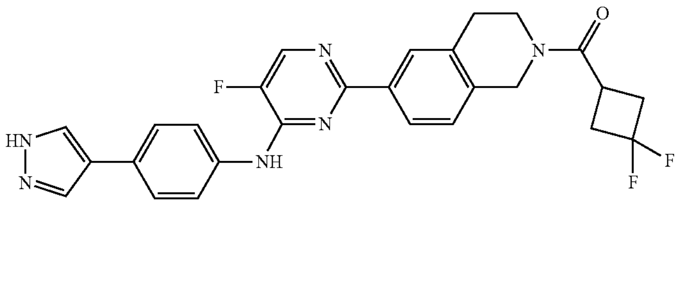 [SMILES: O=C(C1CC(F)(F)C1)N1CCc2cc(-c3ncc(F)c(Nc4ccc(-c5cn[nH]c5)cc4)n3)ccc2C1] |

-continued
| No. | Structure |
| --- | --- |
| 451. | 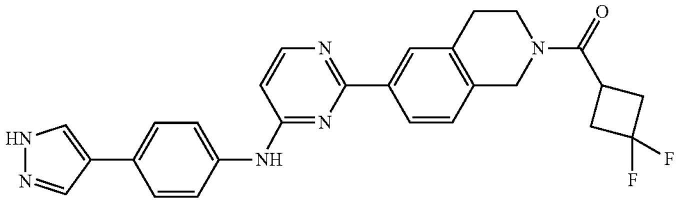 [SMILES: O=C(C1CC(F)(F)C1)N1CCc2cc(-c3nccc(Nc4ccc(-c5cn[nH]c5)cc4)n3)ccc2C1] |
| 452. | 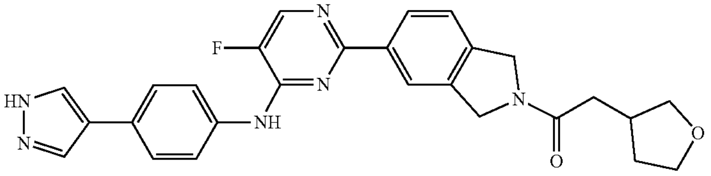 [SMILES: O=C(CC1CCOC1)N1Cc2ccc(-c3ncc(F)c(Nc4ccc(-c5cn[nH]c5)cc4)n3)cc2C1] |
| 453. | 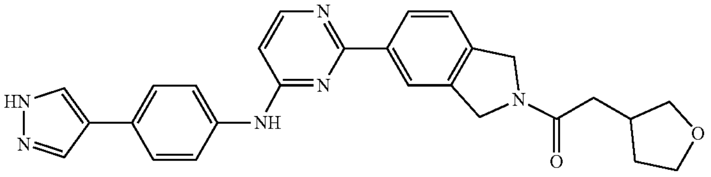 [SMILES: O=C(CC1CCOC1)N1Cc2ccc(-c3nccc(Nc4ccc(-c5cn[nH]c5)cc4)n3)cc2C1] |
| 454. | 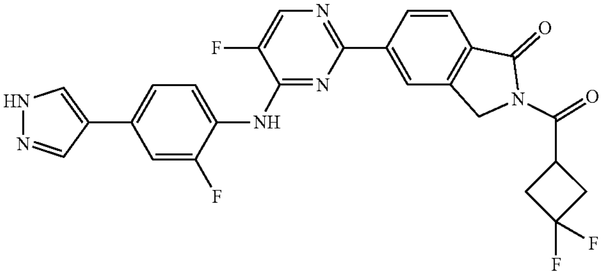 [SMILES: O=C1c2ccc(-c3ncc(F)c(Nc4ccc(-c5cn[nH]c5)cc4F)n3)cc2CN1C(=O)C1CC(F)(F)C1] |
| 455. | 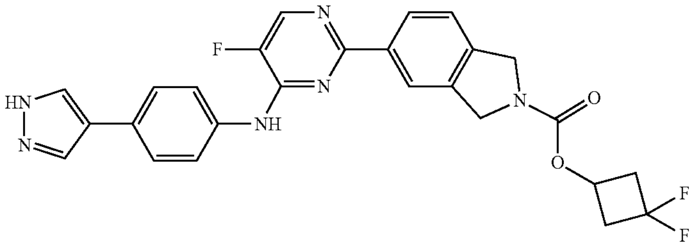 [SMILES: O=C(OC1CC(F)(F)C1)N1Cc2ccc(-c3ncc(F)c(Nc4ccc(-c5cn[nH]c5)cc4)n3)cc2C1] |
| 456. | 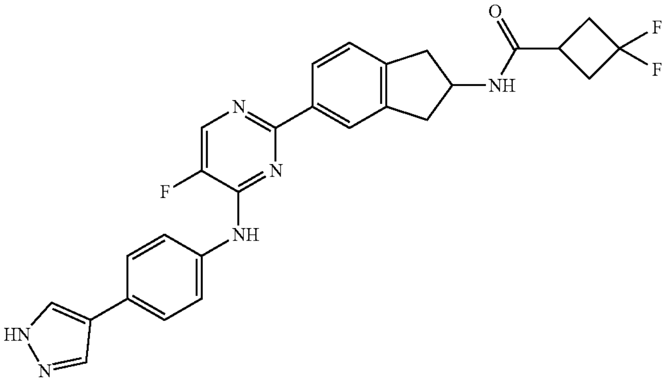 [SMILES: O=C(NC1Cc2ccc(-c3ncc(F)c(Nc4ccc(-c5cn[nH]c5)cc4)n3)cc2C1)C1CC(F)(F)C1] |

-continued
| No. | Structure |
| --- | --- |
| 457. | 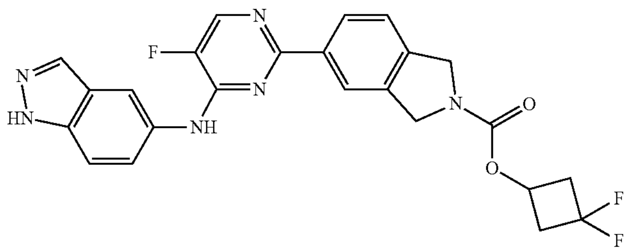 [SMILES: O=C(OC1CC(F)(F)C1)N1Cc2ccc(-c3ncc(F)c(Nc4ccc5[nH]ncc5c4)n3)cc2C1] |
| 458. | 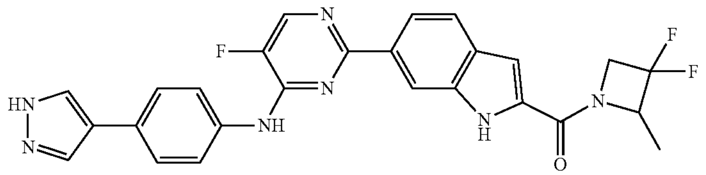 [SMILES: CC1N(C(=O)c2cc3ccc(-c4ncc(F)c(Nc5ccc(-c6cn[nH]c6)cc5)n4)cc3[nH]2)CC1(F)F] |
| 459. | 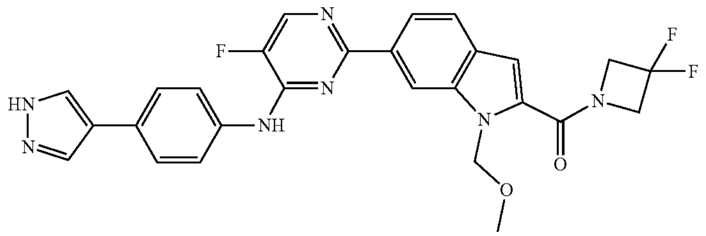 [SMILES: COCn1c(C(=O)N2CC(F)(F)C2)cc2ccc(-c3ncc(F)c(Nc4ccc(-c5cn[nH]c5)cc4)n3)cc21] |
| 460. | 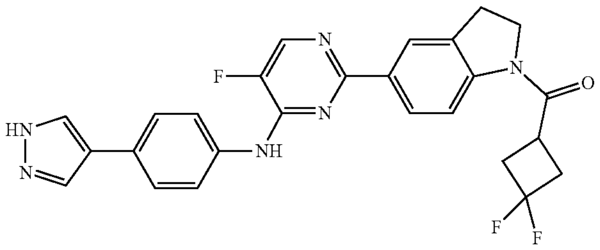 [SMILES: O=C(C1CC(F)(F)C1)N1CCc2cc(-c3ncc(F)c(Nc4ccc(-c5cn[nH]c5)cc4)n3)ccc21] |
| 461. | 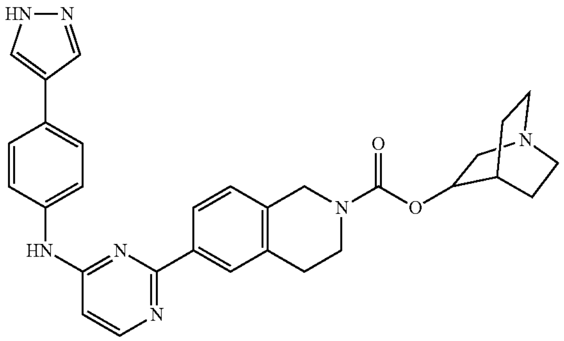 [SMILES: O=C(OC1CN2CCC1CC2)N1CCc2cc(-c3nccc(Nc4ccc(-c5cn[nH]c5)cc4)n3)ccc2C1] |

-continued
| No. | Structure |
|---|---|
| 462. | 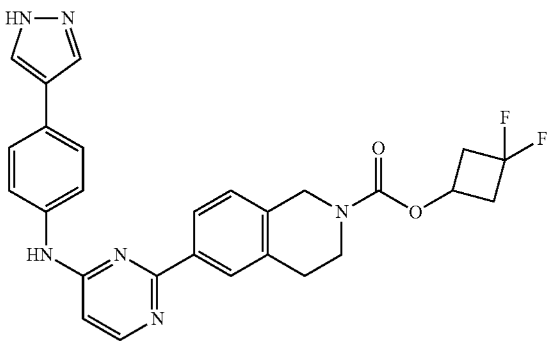 [SMILES: O=C(OC1CC(F)(F)C1)N1CCc2cc(-c3nccc(Nc4ccc(-c5cn[nH]c5)cc4)n3)ccc2C1] |
| 463. | 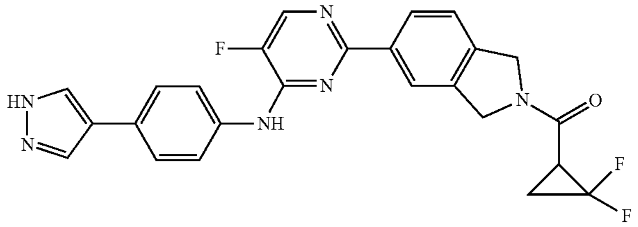 [SMILES: O=C(C1CC1(F)F)N1Cc2ccc(-c3ncc(F)c(Nc4ccc(-c5cn[nH]c5)cc4)n3)cc2C1] |
| 464. | 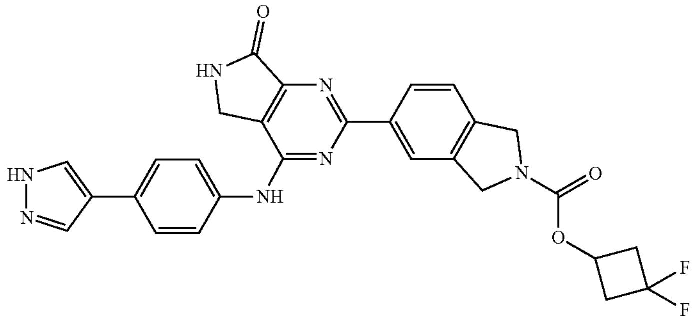 [SMILES: O=C1NCc2c(Nc3ccc(-c4cn[nH]c4)cc3)nc(-c3ccc4c(c3)CN(C(=O)OC3CC(F)(F)C3)C4)nc21] |
| 465. | 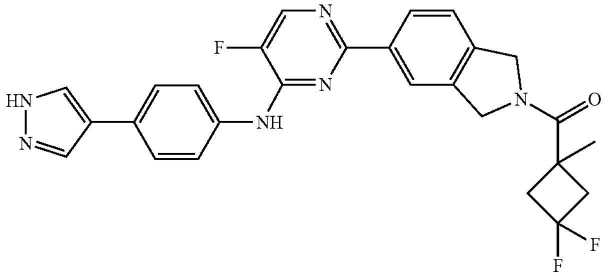 [SMILES: CC1(C(=O)N2Cc3ccc(-c4ncc(F)c(Nc5ccc(-c6cn[nH]c6)cc5)n4)cc3C2)CC(F)(F)C1] |
| 466. | 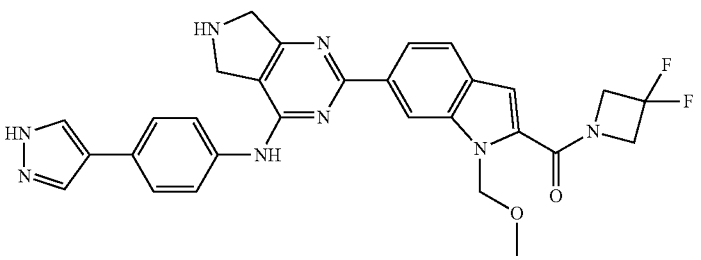 [SMILES: COCn1c(C(=O)N2CC(F)(F)C2)cc2ccc(-c3nc4c(c(Nc5ccc(-c6cn[nH]c6)cc5)n3)CNC4)cc21] |

-continued
| No. | Structure |
| --- | --- |
| 467. | 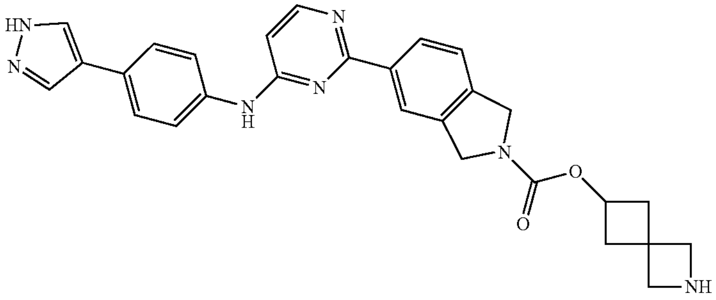 [SMILES: O=C(OC1CC2(CNC2)C1)N1Cc2ccc(-c3nccc(Nc4ccc(-c5cn[nH]c5)cc4)n3)cc2C1] |
| 468. | 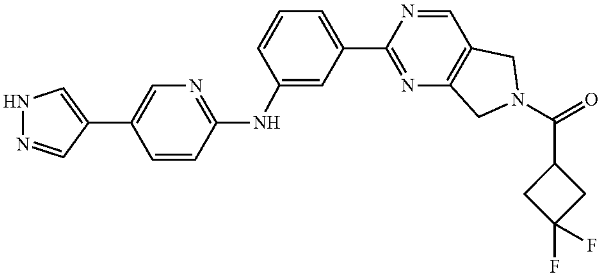 [SMILES: O=C(C1CC(F)(F)C1)N1Cc2cnc(-c3cccc(Nc4ccc(-c5cn[nH]c5)cn4)c3)nc2C1] |
| 469. | 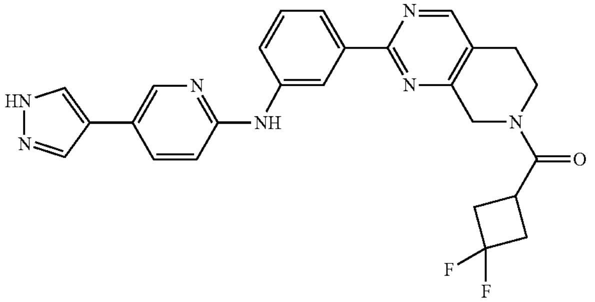 [SMILES: O=C(C1CC(F)(F)C1)N1CCc2cnc(-c3cccc(Nc4ccc(-c5cn[nH]c5)cn4)c3)nc2C1] |
| 470. | 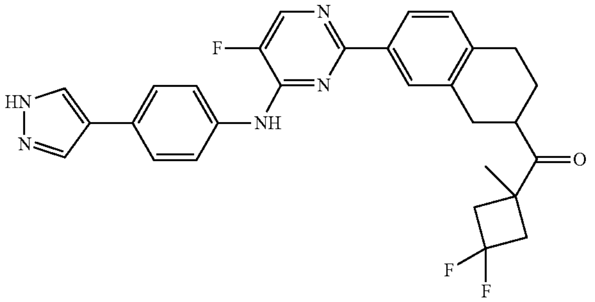 [SMILES: CC1(C(=O)C2CCc3ccc(-c4ncc(F)c(Nc5ccc(-c6cn[nH]c6)cc5)n4)cc3C2)CC(F)(F)C1] |
| 471. | 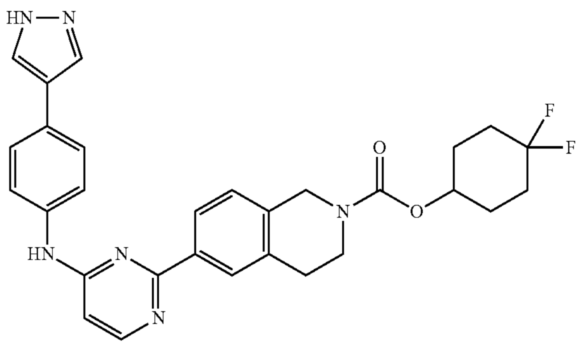 [SMILES: O=C(OC1CCC(F)(F)CC1)N1CCc2cc(-c3nccc(Nc4ccc(-c5cn[nH]c5)cc4)n3)ccc2C1] |

-continued
| No. | Structure |
| --- | --- |
| 472. | 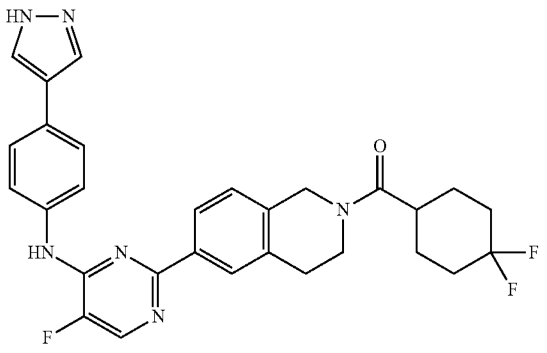 [SMILES: O=C(C1CCC(F)(F)CC1)N1CCc2cc(-c3ncc(F)c(Nc4ccc(-c5cn[nH]c5)cc4)n3)ccc2C1] |
| 473. | 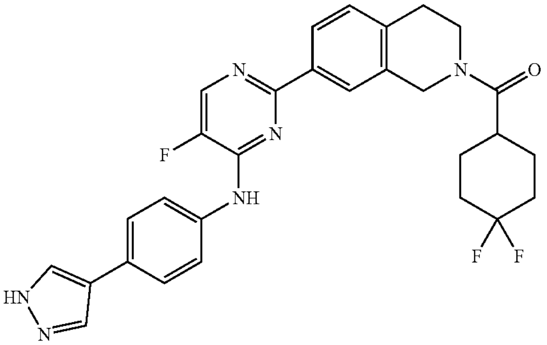 [SMILES: O=C(C1CCC(F)(F)CC1)N1CCc2ccc(-c3ncc(F)c(Nc4ccc(-c5cn[nH]c5)cc4)n3)cc2C1] |
| 474. | 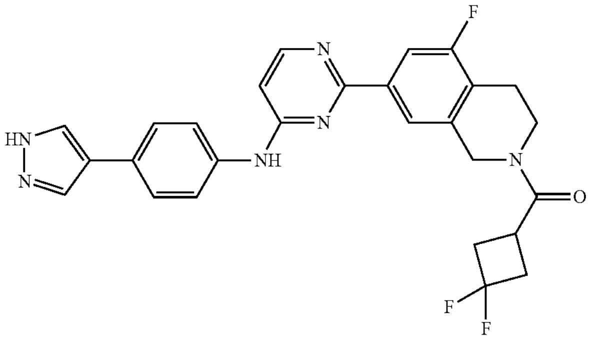 [SMILES: O=C(C1CC(F)(F)C1)N1CCc2c(F)cc(-c3nccc(Nc4ccc(-c5cn[nH]c5)cc4)n3)cc2C1] |
| 475. | 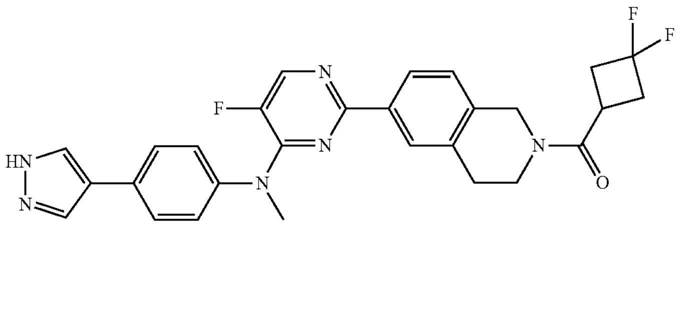 [SMILES: CN(c1ccc(-c2cn[nH]c2)cc1)c1nc(-c2ccc3c(c2)CCN(C(=O)C2CC(F)(F)C2)C3)ncc1F] |

-continued
| No. | Structure |
| --- | --- |
| 476. | 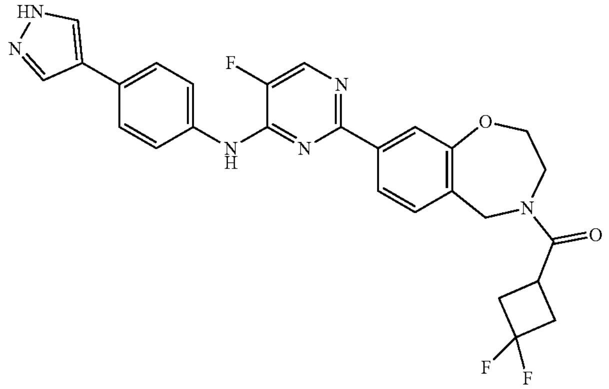 [SMILES: O=C(C1CC(F)(F)C1)N1CCOc2cc(-c3ncc(F)c(Nc4ccc(-c5cn[nH]c5)cc4)n3)ccc2C1] |
| 477. | 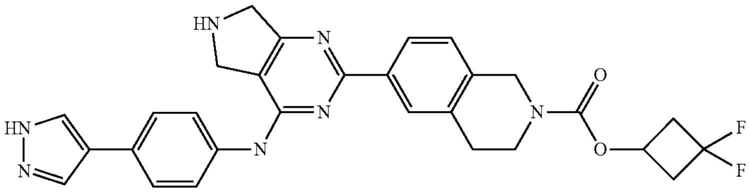 [SMILES: O=C(OC1CC(F)(F)C1)N1CCc2cc(-c3nc4c(c(Nc5ccc(-c6cn[nH]c6)cc5)n3)CNC4)ccc2C1] |
| 478. | 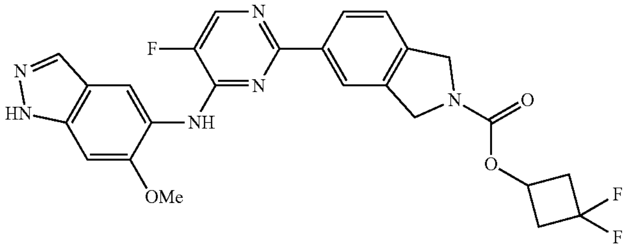 [SMILES: COc1cc2[nH]ncc2cc1Nc1nc(-c2ccc3c(c2)CN(C(=O)OC2CC(F)(F)C2)C3)ncc1F] |
| 479. | 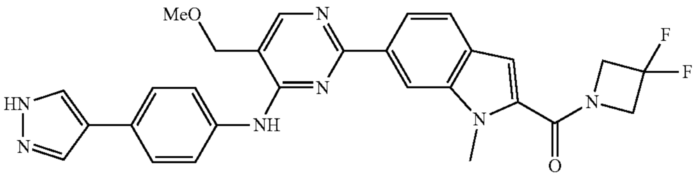 [SMILES: COCc1cnc(-c2ccc3cc(C(=O)N4CC(F)(F)C4)n(C)c3c2)nc1Nc1ccc(-c2cn[nH]c2)cc1] |
| 480. | 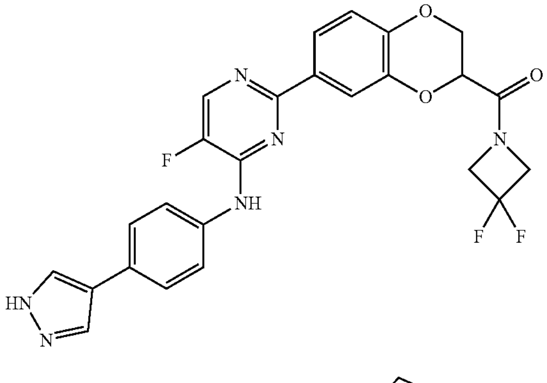 |
| 481. | 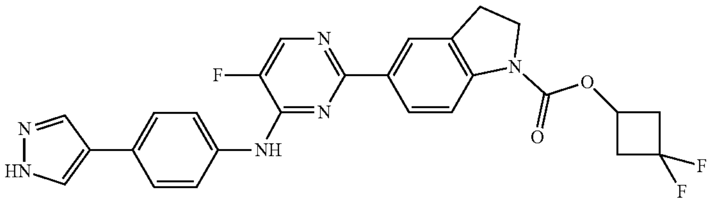 [SMILES: O=C(OC1CC(F)(F)C1)N1CCc2cc(-c3ncc(F)c(Nc4ccc(-c5cn[nH]c5)cc4)n3)ccc21] |

-continued
| No. | Structure |
|---|---|
| 482. | 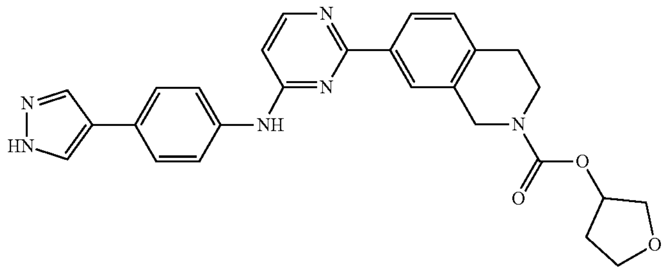 [SMILES: O=C(OC1CCOC1)N1CCc2ccc(-c3nccc(Nc4ccc(-c5cn[nH]c5)cc4)n3)cc2C1] |
| 483. | 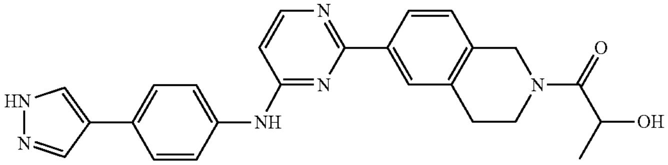 [SMILES: CC(O)C(=O)N1CCc2cc(-c3nccc(Nc4ccc(-c5cn[nH]c5)cc4)n3)ccc2C1] |
| 484. | 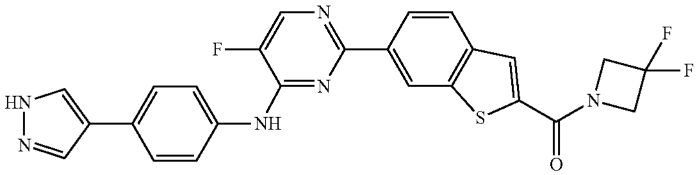 [SMILES: O=C(c1cc2ccc(-c3ncc(F)c(Nc4ccc(-c5cn[nH]c5)cc4)n3)cc2s1)N1CC(F)(F)C1] |
| 485. | 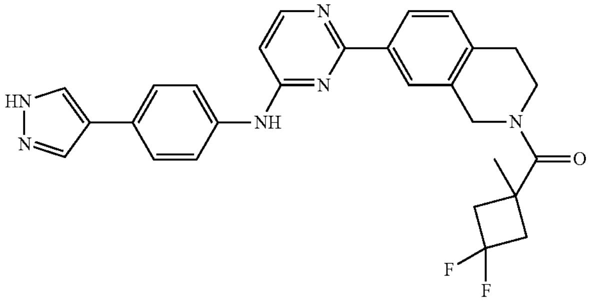 [SMILES: CC1(C(=O)N2CCc3ccc(-c4nccc(Nc5ccc(-c6cn[nH]c6)cc5)n4)cc3C2)CC(F)(F)C1] |
| 486. | 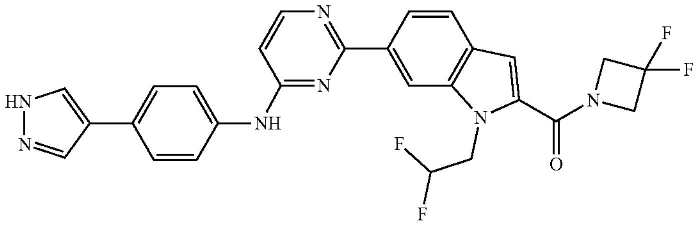 [SMILES: O=C(c1cc2ccc(-c3nccc(Nc4ccc(-c5cn[nH]c5)cc4)n3)cc2n1CC(F)F)N1CC(F)(F)C1] |
| 487. | 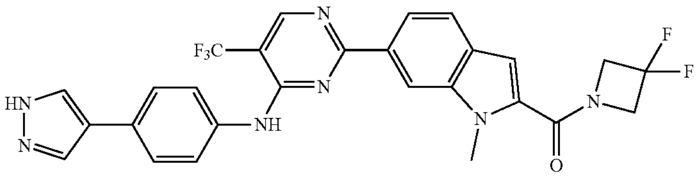 [SMILES: Cn1c(C(=O)N2CC(F)(F)C2)cc2ccc(-c3ncc(C(F)(F)F)c(Nc4ccc(-c5cn[nH]c5)cc4)n3)cc21] |

-continued
| No. | Structure |
|---|---|
| 488. | 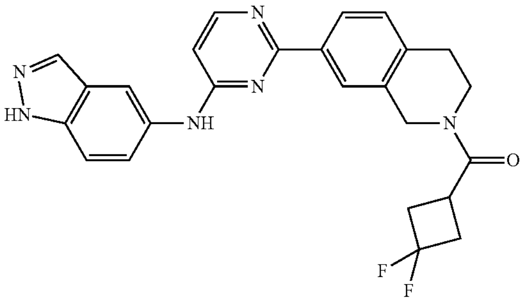 [SMILES: O=C(C1CC(F)(F)C1)N1CCc2ccc(-c3nccc(Nc4ccc5[nH]ncc5c4)n3)cc2C1] |
| 489. | 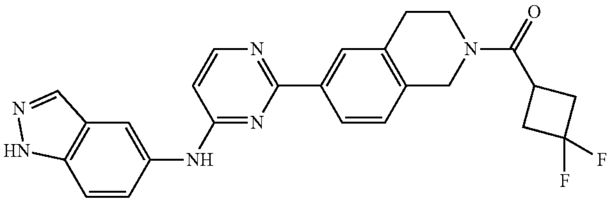 [SMILES: O=C(C1CC(F)(F)C1)N1CCc2cc(-c3nccc(Nc4ccc5[nH]ncc5c4)n3)ccc2C1] |
| 490. | 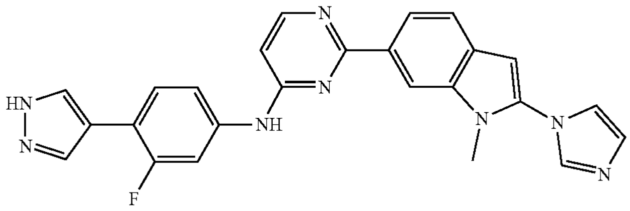 [SMILES: Cn1c(-n2ccnc2)cc2ccc(-c3nccc(Nc4ccc(-c5cn[nH]c5)c(F)c4)n3)cc21] |
| 491. | 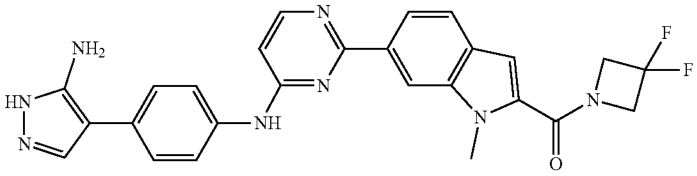 [SMILES: Cn1c(C(=O)N2CC(F)(F)C2)cc2ccc(-c3nccc(Nc4ccc(-c5cn[nH]c5N)cc4)n3)cc21] |
| 492. | 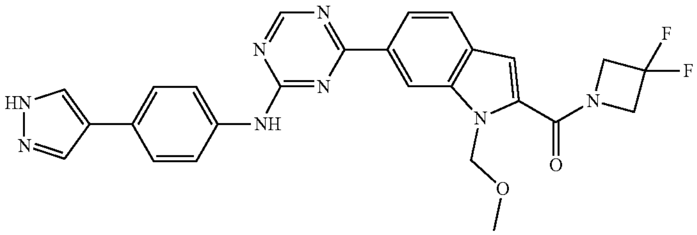 [SMILES: COCn1c(C(=O)N2CC(F)(F)C2)cc2ccc(-c3ncnc(Nc4ccc(-c5cn[nH]c5)cc4)n3)cc21] |
| 493. | 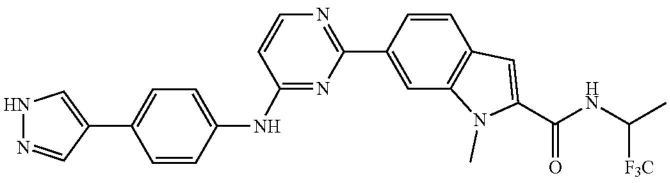 [SMILES: CC(NC(=O)c1cc2ccc(-c3nccc(Nc4ccc(-c5cn[nH]c5)cc4)n3)cc2n1C)C(F)(F)F] |

-continued
| No. | Structure |
|---|---|
| 494. | 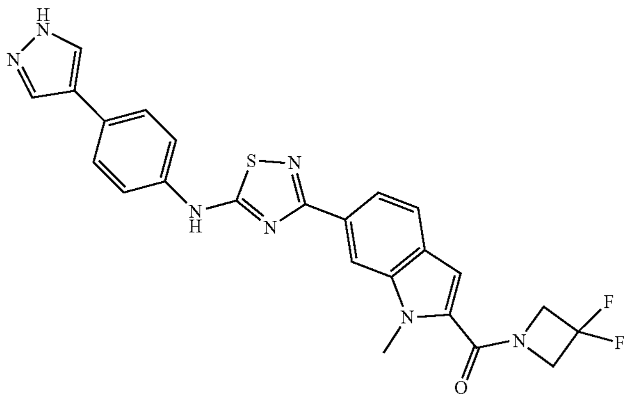 [SMILES: Cn1c(C(=O)N2CC(F)(F)C2)cc2ccc(-c3nsc(Nc4ccc(-c5cn[nH]c5)cc4)n3)cc21] |
| 495. | 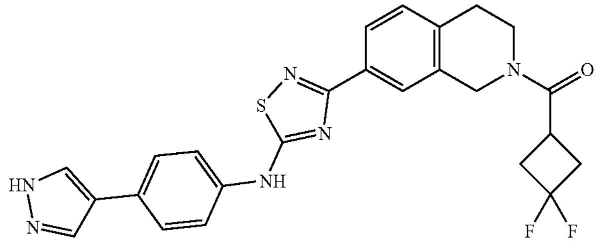 [SMILES: O=C(C1CC(F)(F)C1)N1CCc2ccc(-c3nsc(Nc4ccc(-c5cn[nH]c5)cc4)n3)cc2C1] |
| 496. | 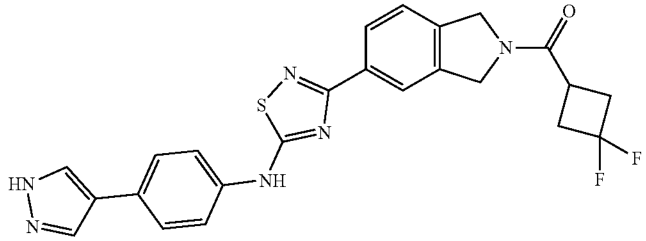 [SMILES: O=C(C1CC(F)(F)C1)N1Cc2ccc(-c3nsc(Nc4ccc(-c5cn[nH]c5)cc4)n3)cc2C1] |
| 497. | 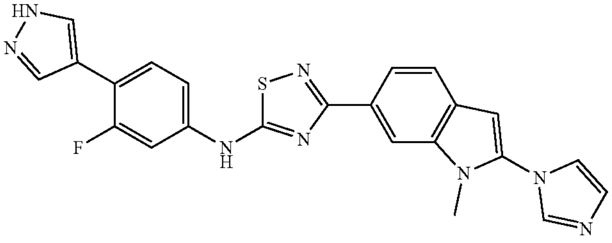 [SMILES: Cn1c(-n2ccnc2)cc2ccc(-c3nsc(Nc4ccc(-c5cn[nH]c5)c(F)c4)n3)cc21] |
| 498. | 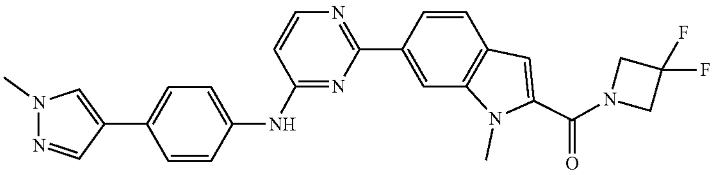 [SMILES: Cn1cc(-c2ccc(Nc3ccnc(-c4ccc5cc(C(=O)N6CC(F)(F)C6)n(C)c5c4)n3)cc2)cn1] |
| 499. | 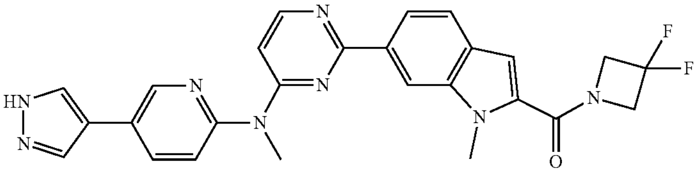 [SMILES: CN(c1ccc(-c2cn[nH]c2)cn1)c1ccnc(-c2ccc3cc(C(=O)N4CC(F)(F)C4)n(C)c3c2)n1] |

-continued
| No. | Structure |
| --- | --- |
| 500. | 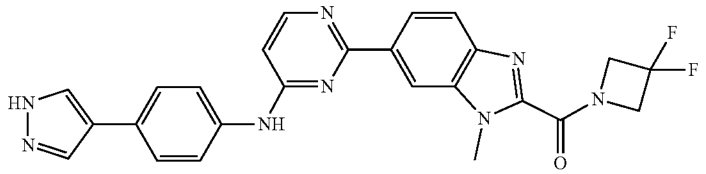 [SMILES: Cn1c(C(=O)N2CC(F)(F)C2)nc2ccc(-c3nccc(Nc4ccc(-c5cn[nH]c5)cc4)n3)cc21] |
| 501. | 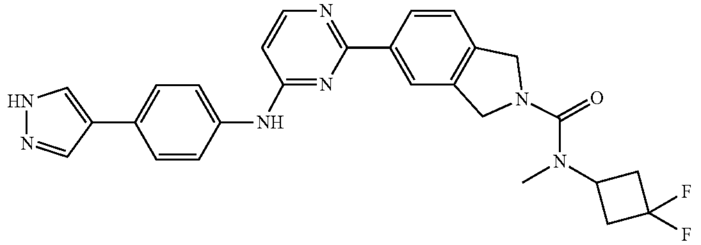 [SMILES: CN(C(=O)N1Cc2ccc(-c3nccc(Nc4ccc(-c5cn[nH]c5)cc4)n3)cc2C1)C1CC(F)(F)C1] |
| 502. | 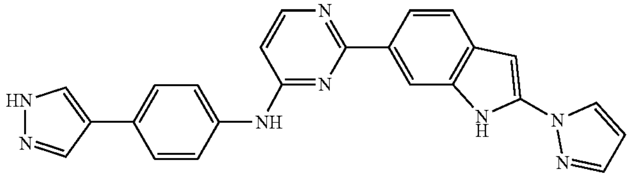 |
| 503. | 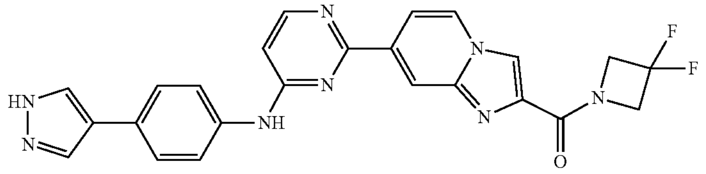 [SMILES: O=C(c1cn2ccc(-c3nccc(Nc4ccc(-c5cn[nH]c5)cc4)n3)cc2n1)N1CC(F)(F)C1] |
| 504. | 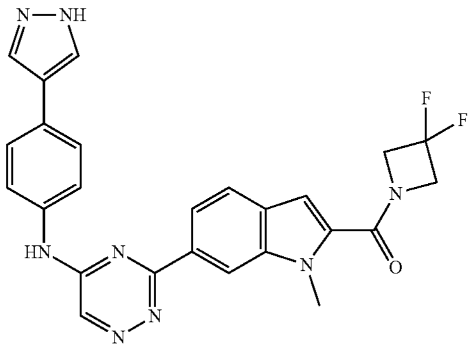 [SMILES: Cn1c(C(=O)N2CC(F)(F)C2)cc2ccc(-c3nncc(Nc4ccc(-c5cn[nH]c5)cc4)n3)cc21] |
| 505. | 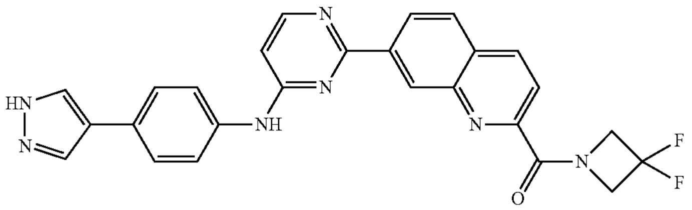 [SMILES: O=C(c1ccc2ccc(-c3nccc(Nc4ccc(-c5cn[nH]c5)cc4)n3)cc2n1)N1CC(F)(F)C1] |
| 506. | 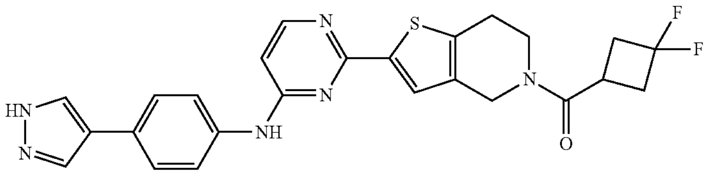 [SMILES: O=C(C1CC(F)(F)C1)N1CCc2sc(-c3nccc(Nc4ccc(-c5cn[nH]c5)cc4)n3)cc2C1] |

-continued
| No. | Structure |
| --- | --- |
| 507. | 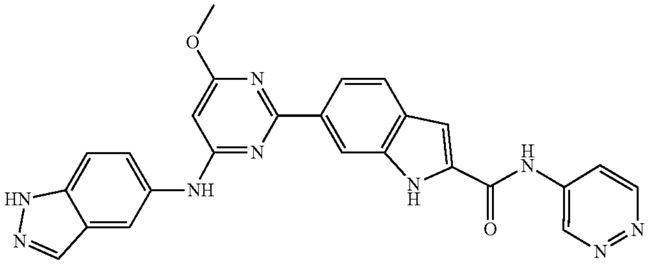 [SMILES: COc1cc(Nc2ccc3[nH]ncc3c2)nc(-c2ccc3cc(C(=O)Nc4ccnnc4)[nH]c3c2)n1] |
| 508. | 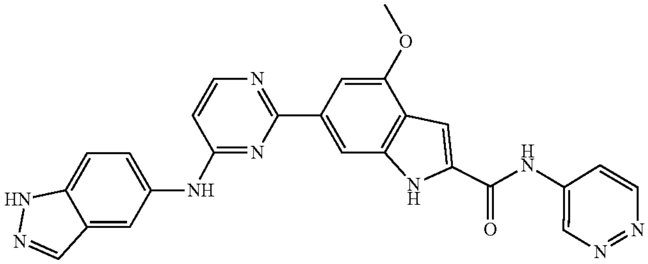 [SMILES: COc1cc(-c2nccc(Nc3ccc4[nH]ncc4c3)n2)cc2[nH]c(C(=O)Nc3ccnnc3)cc12] |
| 509. | 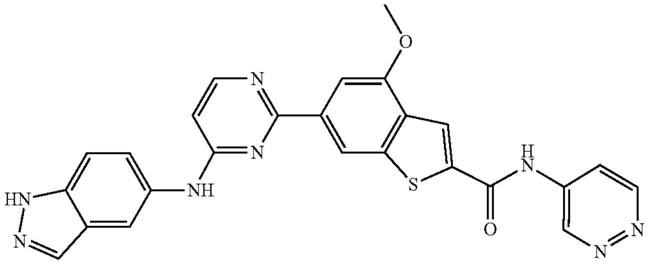 [SMILES: COc1cc(-c2nccc(Nc3ccc4[nH]ncc4c3)n2)cc2sc(C(=O)Nc3ccnnc3)cc12] |
| 510. | 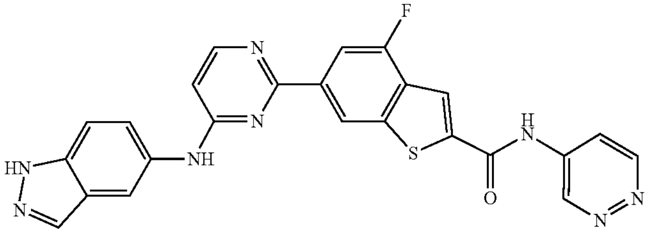 [SMILES: O=C(Nc1ccnnc1)c1cc2c(F)cc(-c3nccc(Nc4ccc5[nH]ncc5c4)n3)cc2s1] |
| 511. | 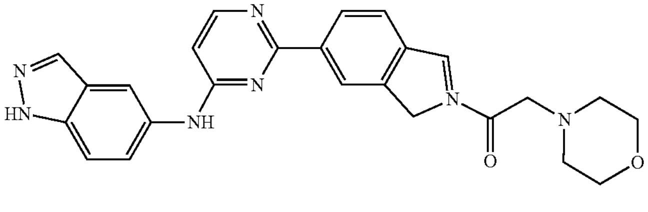 |
| 512. | 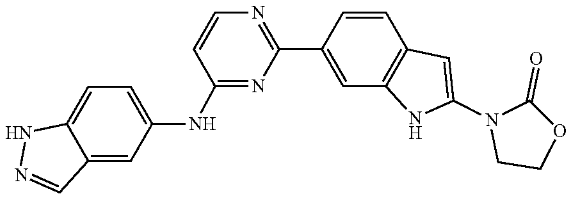 [SMILES: O=C1OCCN1c1cc2ccc(-c3nccc(Nc4ccc5[nH]ncc5c4)n3)cc2[nH]1] |

-continued
| No. | Structure |
|---|---|
| 513. | 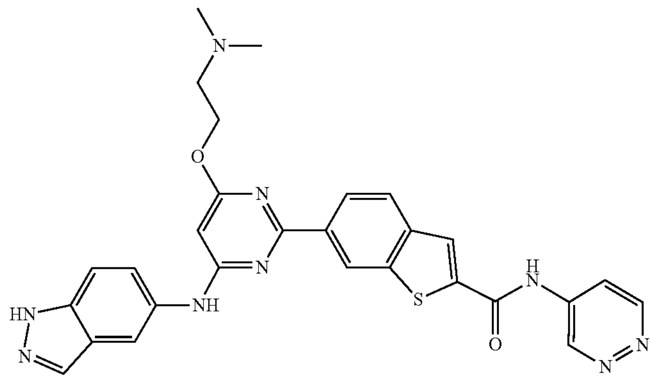 [SMILES: CN(C)CCOc1cc(Nc2ccc3[nH]ncc3c2)nc(-c2ccc3cc(C(=O)Nc4ccnnc4)sc3c2)n1] |
| 514. | 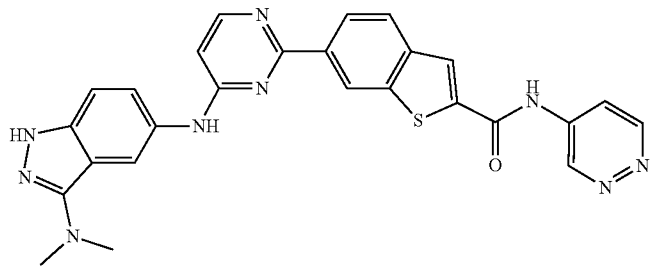 [SMILES: CN(C)c1n[nH]c2ccc(Nc3ccnc(-c4ccc5cc(C(=O)Nc6ccnnc6)sc5c4)n3)cc12] |
| 515. | 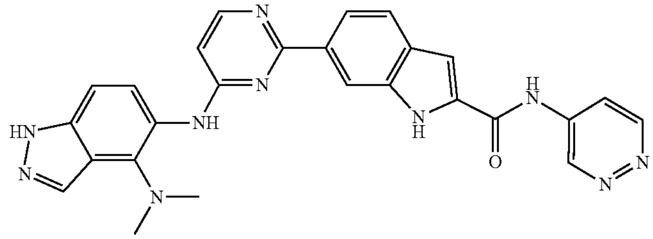 [SMILES: CN(C)c1c(Nc2ccnc(-c3ccc4cc(C(=O)Nc5ccnnc5)[nH]c4c3)n2)ccc2[nH]ncc12] |
| 516. | 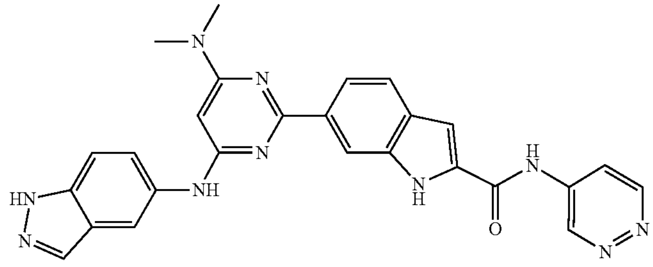 [SMILES: CN(C)c1cc(Nc2ccc3[nH]ncc3c2)nc(-c2ccc3cc(C(=O)Nc4ccnnc4)[nH]c3c2)n1] |
| 517. | 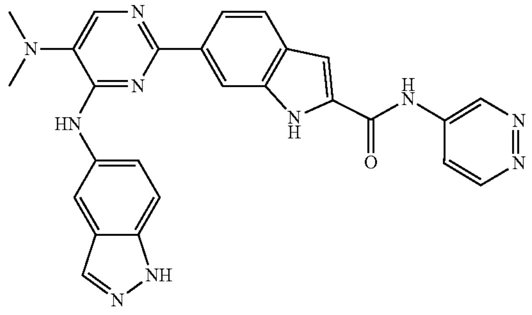 [SMILES: CN(C)c1cnc(-c2ccc3cc(C(=O)Nc4ccnnc4)[nH]c3c2)nc1Nc1ccc2[nH]ncc2c1] |

-continued
| No. | Structure |
|---|---|
| 518. | 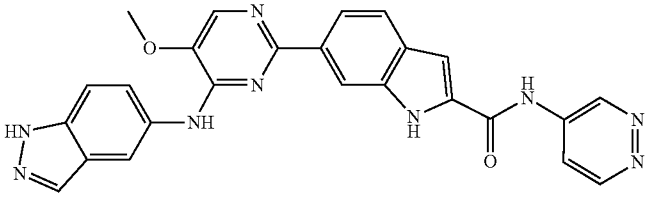 [SMILES: COc1cnc(-c2ccc3cc(C(=O)Nc4ccnnc4)[nH]c3c2)nc1Nc1ccc2[nH]ncc2c1] |
| 519. | 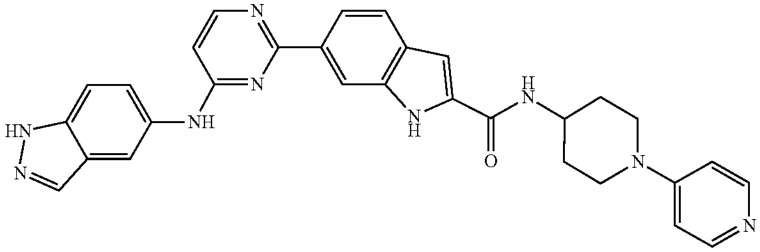 [SMILES: O=C(NC1CCN(c2ccncc2)CC1)c1cc2ccc(-c3nccc(Nc4ccc5[nH]ncc5c4)n3)cc2[nH]1] |
| 520. | 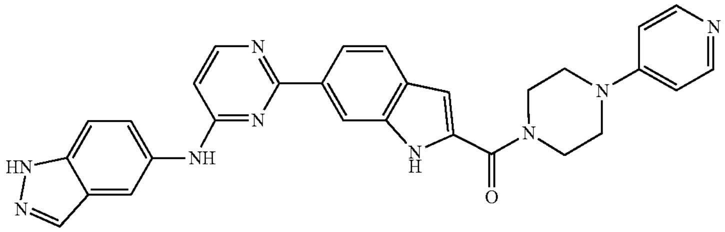 [SMILES: O=C(c1cc2ccc(-c3nccc(Nc4ccc5[nH]ncc5c4)n3)cc2[nH]1)N1CCN(c2ccncc2)CC1] |
| 521. | 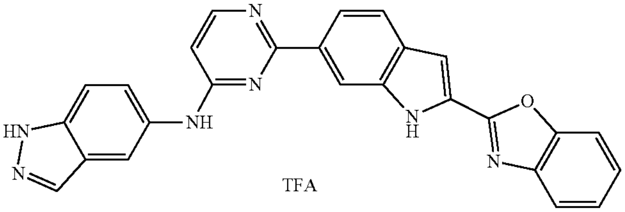 [SMILES: c1ccc2oc(-c3cc4ccc(-c5nccc(Nc6ccc7[nH]ncc7c6)n5)cc4[nH]3)nc2c1] TFA |
| 522. | 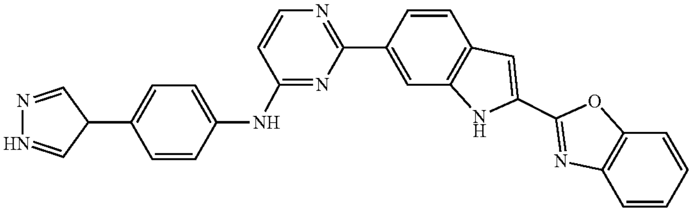 [SMILES: C1=NN=CC1c1ccc(Nc2ccnc(-c3ccc4cc(-c5nc6ccccc6o5)[nH]c4c3)n2)cc1] |
| 523. | 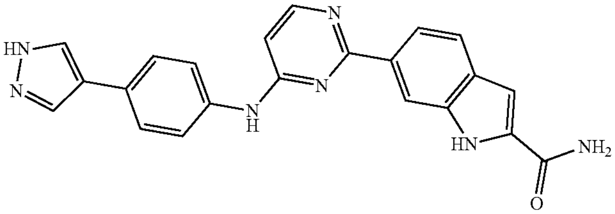 [SMILES: NC(=O)c1cc2ccc(-c3nccc(Nc4ccc(-c5cn[nH]c5)cc4)n3)cc2[nH]1] |
| 524. | 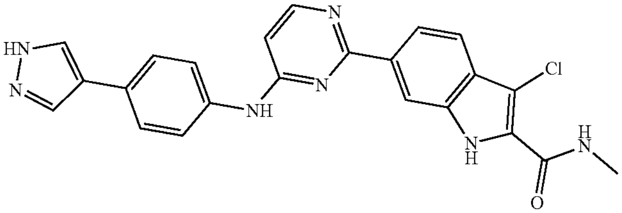 [SMILES: CNC(=O)c1[nH]c2cc(-c3nccc(Nc4ccc(-c5cn[nH]c5)cc4)n3)ccc2c1Cl] |

-continued
| No. | Structure |
|---|---|
| 525. | 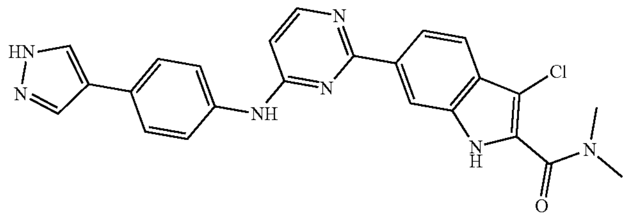 [SMILES: CN(C)C(=O)c1[nH]c2cc(-c3nccc(Nc4ccc(-c5cn[nH]c5)cc4)n3)ccc2c1Cl] |
| 526. | 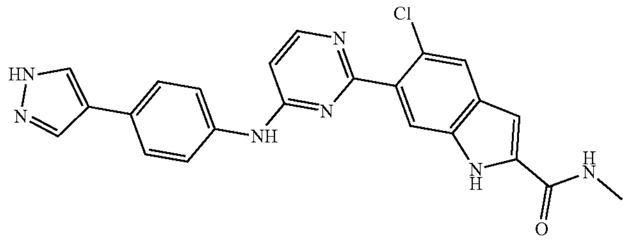 [SMILES: CNC(=O)c1cc2cc(Cl)c(-c3nccc(Nc4ccc(-c5cn[nH]c5)cc4)n3)cc2[nH]1] |
| 527. | 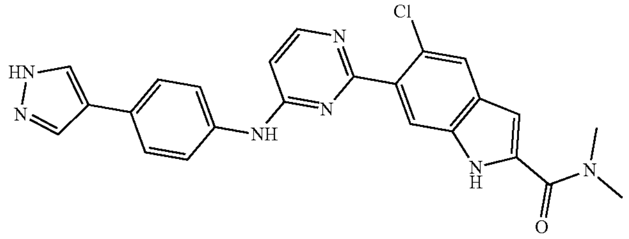 [SMILES: CN(C)C(=O)c1cc2cc(Cl)c(-c3nccc(Nc4ccc(-c5cn[nH]c5)cc4)n3)cc2[nH]1] |
| 528. | 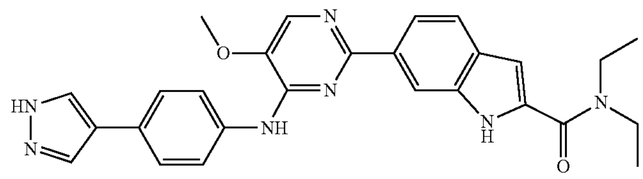 [SMILES: CCN(CC)C(=O)c1cc2ccc(-c3ncc(OC)c(Nc4ccc(-c5cn[nH]c5)cc4)n3)cc2[nH]1] |
| 529. | 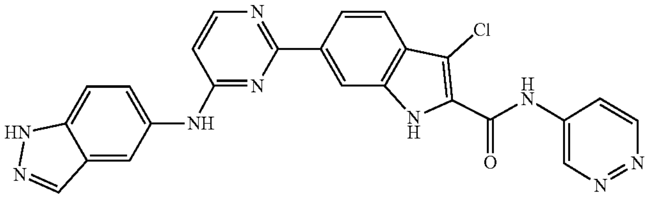 [SMILES: O=C(Nc1ccnnc1)c1[nH]c2cc(-c3nccc(Nc4ccc5[nH]ncc5c4)n3)ccc2c1Cl] |
| 530. | 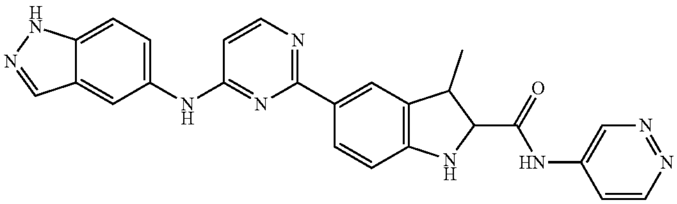 [SMILES: CC1c2cc(-c3nccc(Nc4ccc5[nH]ncc5c4)n3)ccc2NC1C(=O)Nc1ccnnc1] |

-continued
| No. | Structure |
|---|---|
| 531. | 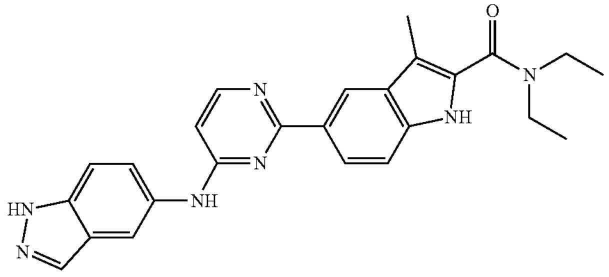 [SMILES: CCN(CC)C(=O)c1[nH]c2ccc(-c3nccc(Nc4ccc5[nH]ncc5c4)n3)cc2c1C] |
| 532. | 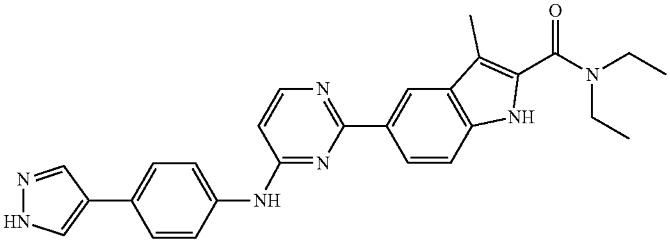 [SMILES: CCN(CC)C(=O)c1[nH]c2ccc(-c3nccc(Nc4ccc(-c5cn[nH]c5)cc4)n3)cc2c1C] |
| 533. | 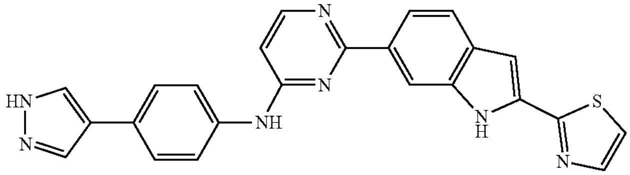 [SMILES: c1cc(Nc2ccc(-c3cn[nH]c3)cc2)nc(-c2ccc3cc(-c4nccs4)[nH]c3c2)n1] |
| 534. | 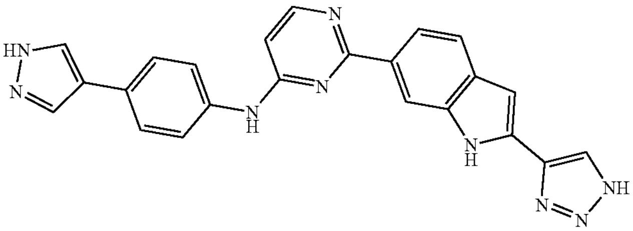 [SMILES: c1cc(Nc2ccc(-c3cn[nH]c3)cc2)nc(-c2ccc3cc(-c4c[nH]nn4)[nH]c3c2)n1] |
| 535. | 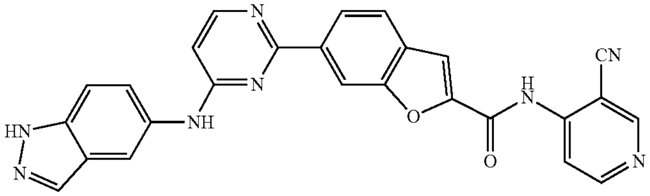 [SMILES: N#Cc1cnccc1NC(=O)c1cc2ccc(-c3nccc(Nc4ccc5[nH]ncc5c4)n3)cc2o1] |
| 536. | 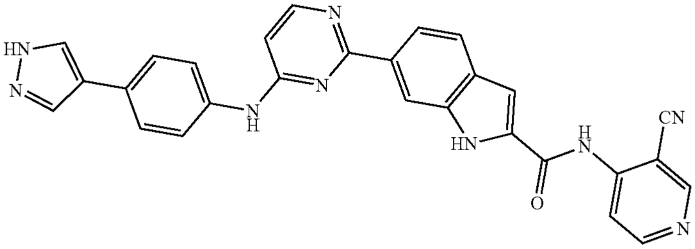 [SMILES: N#Cc1cnccc1NC(=O)c1cc2ccc(-c3nccc(Nc4ccc(-c5cn[nH]c5)cc4)n3)cc2[nH]1] |

-continued
| No. | Structure |
|---|---|
| 537. | 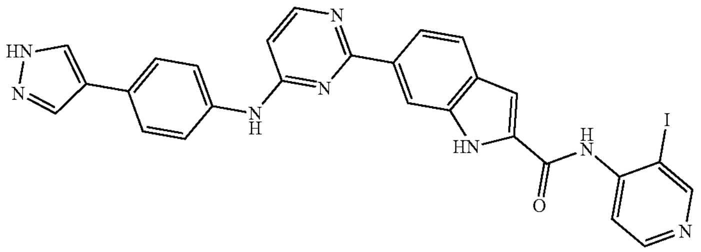 [SMILES: O=C(Nc1ccncc1I)c1cc2ccc(-c3nccc(Nc4ccc(-c5cn[nH]c5)cc4)n3)cc2[nH]1] |
| 538. | 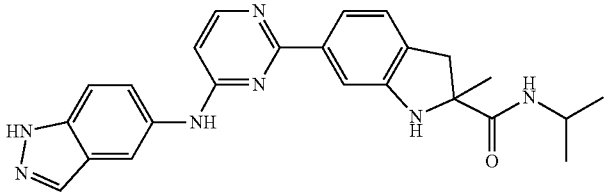 [SMILES: CC(C)NC(=O)C1(C)Cc2ccc(-c3nccc(Nc4ccc5[nH]ncc5c4)n3)cc2N1] |
| 539. | 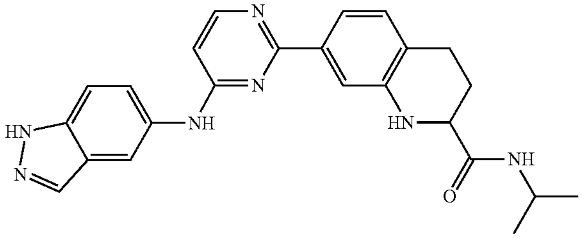 [SMILES: CC(C)NC(=O)C1CCc2ccc(-c3nccc(Nc4ccc5[nH]ncc5c4)n3)cc2N1] |
| 540. | 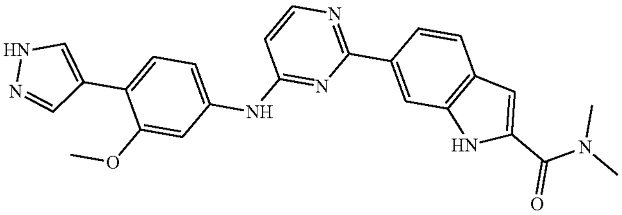 [SMILES: COc1cc(Nc2ccnc(-c3ccc4cc(C(=O)N(C)C)[nH]c4c3)n2)ccc1-c1cn[nH]c1] |
| 541. | 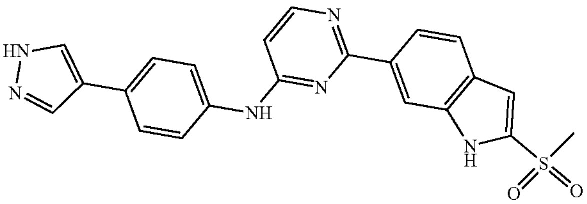 [SMILES: CS(=O)(=O)c1cc2ccc(-c3nccc(Nc4ccc(-c5cn[nH]c5)cc4)n3)cc2[nH]1] |
| 542. | 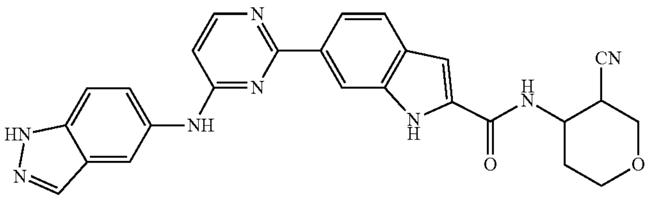 [SMILES: N#CC1COCCC1NC(=O)c1cc2ccc(-c3nccc(Nc4ccc5[nH]ncc5c4)n3)cc2[nH]1] |
| 543. | 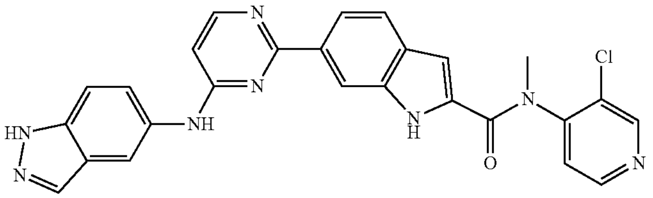 [SMILES: CN(C(=O)c1cc2ccc(-c3nccc(Nc4ccc5[nH]ncc5c4)n3)cc2[nH]1)c1ccncc1Cl] |

-continued
| No. | Structure |
|---|---|
| 544. | 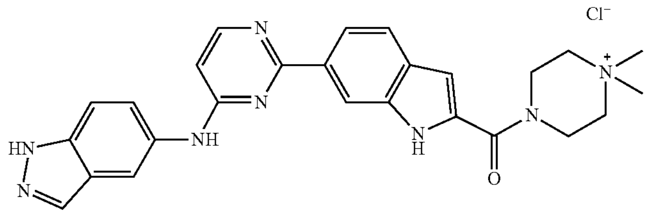 [SMILES: [Cl-] ; C[N+]1(C)CCN(C(=O)c2cc3ccc(-c4nccc(Nc5ccc6[nH]ncc6c5)n4)cc3[nH]2)CC1] |
| 545. | 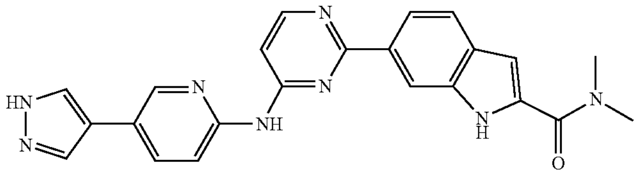 [SMILES: CN(C)C(=O)c1cc2ccc(-c3nccc(Nc4ccc(-c5cn[nH]c5)cn4)n3)cc2[nH]1] |
| 546. | 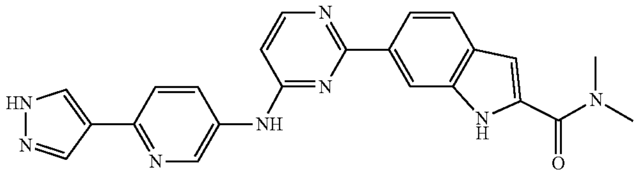 [SMILES: CN(C)C(=O)c1cc2ccc(-c3nccc(Nc4ccc(-c5cn[nH]c5)nc4)n3)cc2[nH]1] |
| 547. | 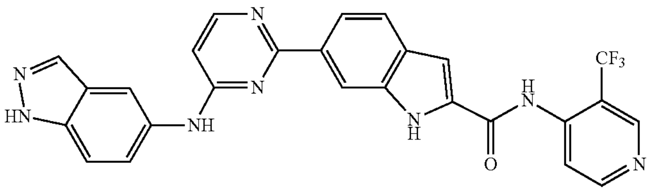 |
| 548. | 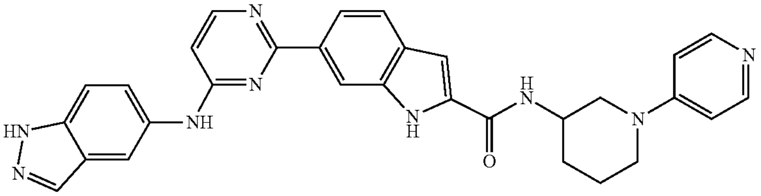 [SMILES: O=C(NC1CCCN(c2ccncc2)C1)c1cc2ccc(-c3nccc(Nc4ccc5[nH]ncc5c4)n3)cc2[nH]1] |
| 549. | 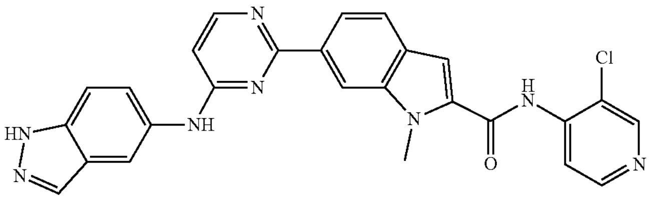 [SMILES: Cn1c(C(=O)Nc2ccncc2Cl)cc2ccc(-c3nccc(Nc4ccc5[nH]ncc5c4)n3)cc21] |
| 550. | 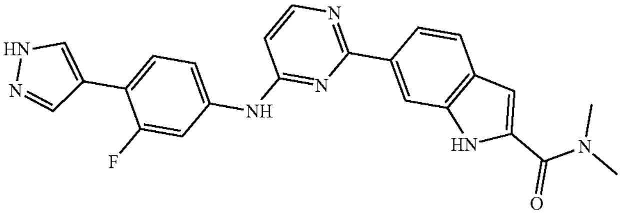 [SMILES: CN(C)C(=O)c1cc2ccc(-c3nccc(Nc4ccc(-c5cn[nH]c5)c(F)c4)n3)cc2[nH]1] |

-continued
| No. | Structure |
|---|---|
| 551. | 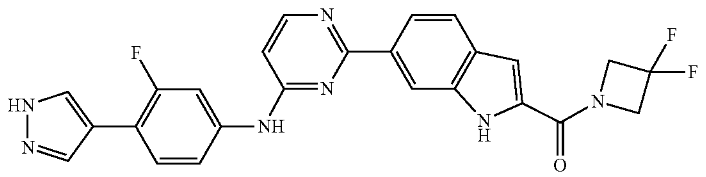 [SMILES: O=C(c1cc2ccc(-c3nccc(Nc4ccc(-c5cn[nH]c5)c(F)c4)n3)cc2[nH]1)N1CC(F)(F)C1] |
| 552. | 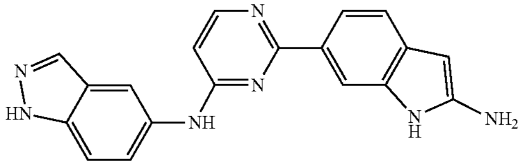 [SMILES: Nc1cc2ccc(-c3nccc(Nc4ccc5[nH]ncc5c4)n3)cc2[nH]1] |
| 553. | 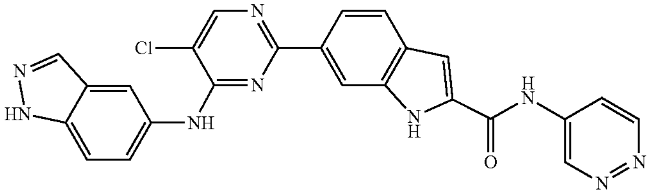 [SMILES: O=C(Nc1ccnnc1)c1cc2ccc(-c3ncc(Cl)c(Nc4ccc5[nH]ncc5c4)n3)cc2[nH]1] |
| 554. | 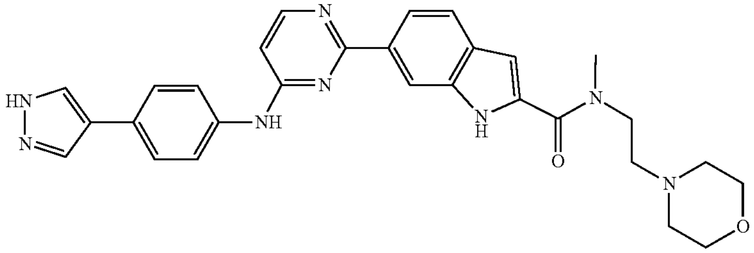 [SMILES: CN(CCN1CCOCC1)C(=O)c1cc2ccc(-c3nccc(Nc4ccc(-c5cn[nH]c5)cc4)n3)cc2[nH]1] |
| 555. | 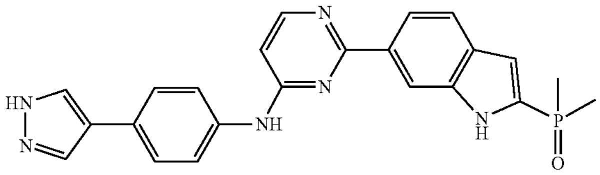 [SMILES: CP(C)(=O)c1cc2ccc(-c3nccc(Nc4ccc(-c5cn[nH]c5)cc4)n3)cc2[nH]1] |
| 556. | 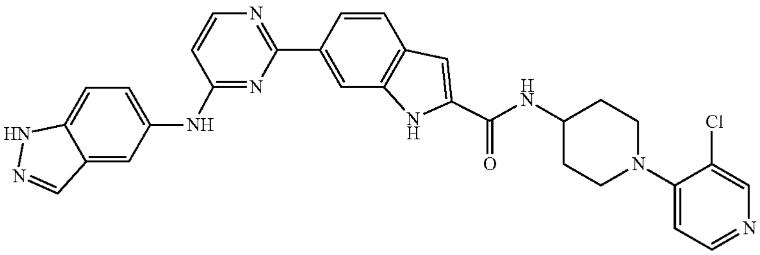 [SMILES: O=C(NC1CCN(c2ccncc2Cl)CC1)c1cc2ccc(-c3nccc(Nc4ccc5[nH]ncc5c4)n3)cc2[nH]1] |
| 557. | 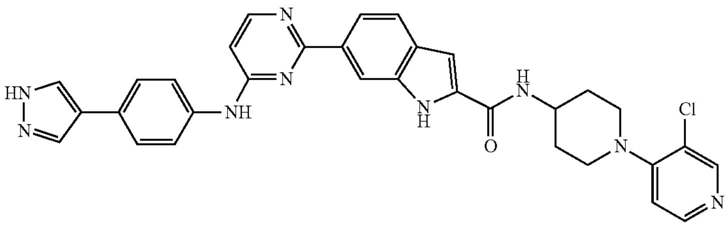 [SMILES: O=C(NC1CCN(c2ccncc2Cl)CC1)c1cc2ccc(-c3nccc(Nc4ccc(-c5cn[nH]c5)cc4)n3)cc2[nH]1] |

-continued
| No. | Structure |
|---|---|
| 558. | 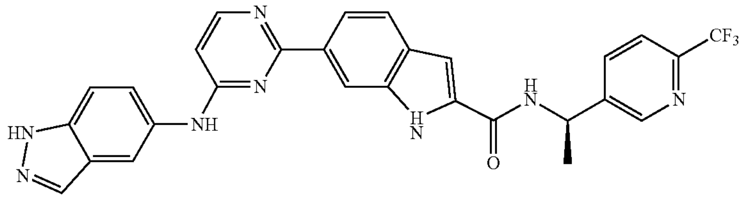 [SMILES: C[C@@H](NC(=O)c1cc2ccc(-c3nccc(Nc4ccc5[nH]ncc5c4)n3)cc2[nH]1)c1ccc(C(F)(F)F)nc1] |
| 559. | 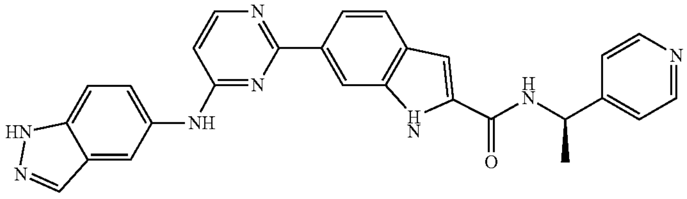 [SMILES: C[C@@H](NC(=O)c1cc2ccc(-c3nccc(Nc4ccc5[nH]ncc5c4)n3)cc2[nH]1)c1ccncc1] |
| 560. | 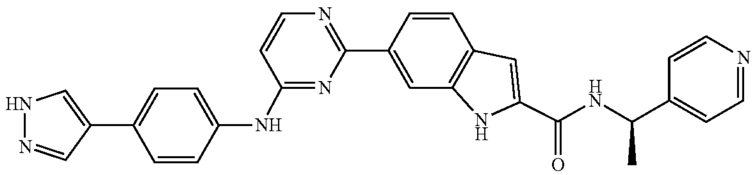 [SMILES: C[C@@H](NC(=O)c1cc2ccc(-c3nccc(Nc4ccc(-c5cn[nH]c5)cc4)n3)cc2[nH]1)c1ccncc1] |
| 561. | 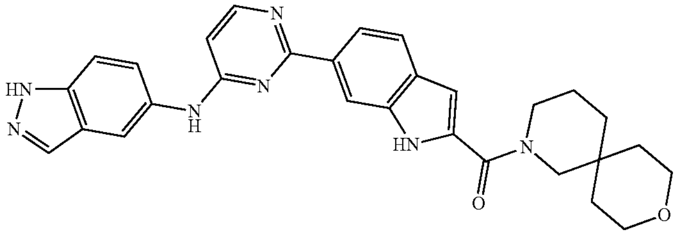 [SMILES: O=C(c1cc2ccc(-c3nccc(Nc4ccc5[nH]ncc5c4)n3)cc2[nH]1)N1CCCC2(CCOCC2)C1] |
| 562. | 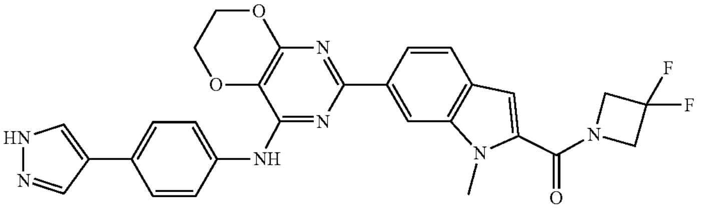 [SMILES: Cn1c(C(=O)N2CC(F)(F)C2)cc2ccc(-c3nc(Nc4ccc(-c5cn[nH]c5)cc4)c4c(n3)OCCO4)cc21] |
| 563. | 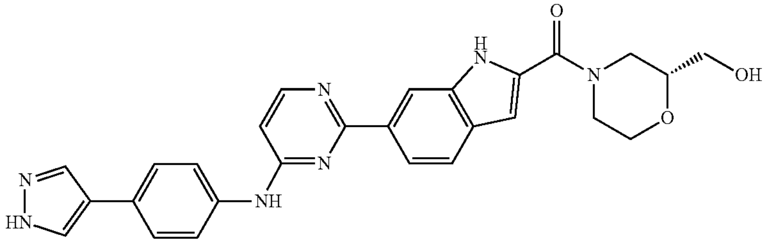 [SMILES: O=C(c1cc2ccc(-c3nccc(Nc4ccc(-c5cn[nH]c5)cc4)n3)cc2[nH]1)N1CCO[C@@H](CO)C1] |
| 564. | 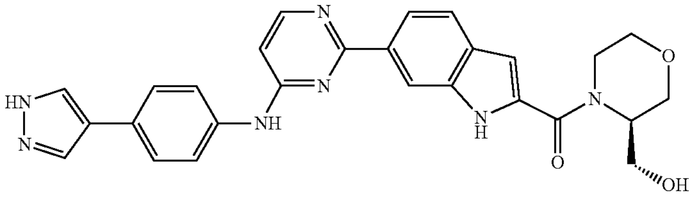 |

-continued
| No. | Structure |
| --- | --- |
| 565. | 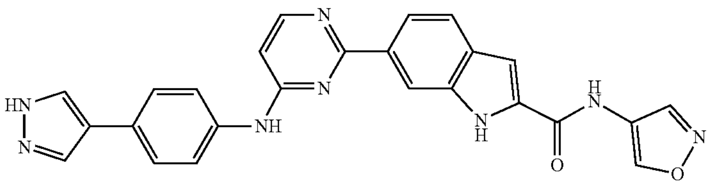 [SMILES: O=C(Nc1cnoc1)c1cc2ccc(-c3nccc(Nc4ccc(-c5cn[nH]c5)cc4)n3)cc2[nH]1] |
| 566. | 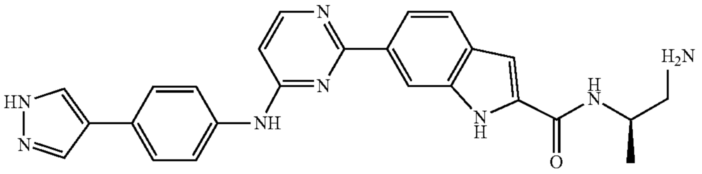 [SMILES: C[C@H](CN)NC(=O)c1cc2ccc(-c3nccc(Nc4ccc(-c5cn[nH]c5)cc4)n3)cc2[nH]1] |
| 567. | 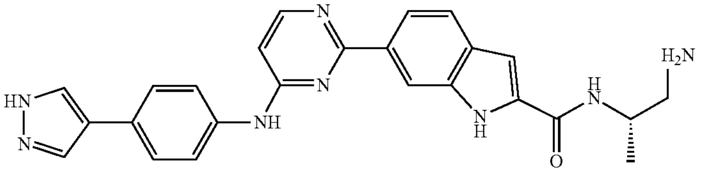 [SMILES: C[C@@H](CN)NC(=O)c1cc2ccc(-c3nccc(Nc4ccc(-c5cn[nH]c5)cc4)n3)cc2[nH]1] |
| 568. | 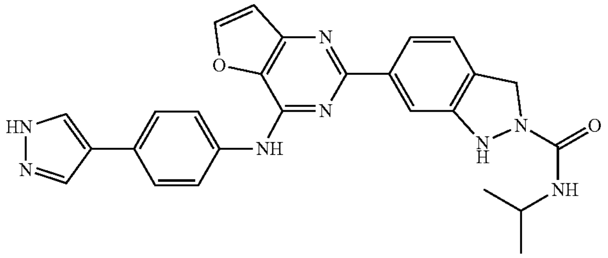 [SMILES: CC(C)NC(=O)N1Cc2ccc(-c3nc(Nc4ccc(-c5cn[nH]c5)cc4)c4occc4n3)cc2N1] |
| 569. | 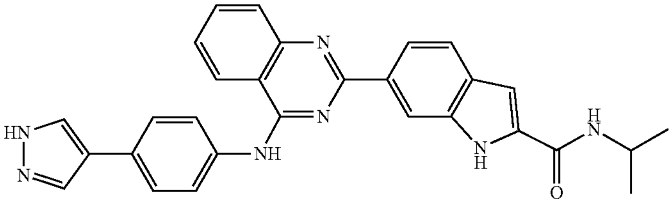 [SMILES: CC(C)NC(=O)c1cc2ccc(-c3nc(Nc4ccc(-c5cn[nH]c5)cc4)c4ccccc4n3)cc2[nH]1] |
| 570. | 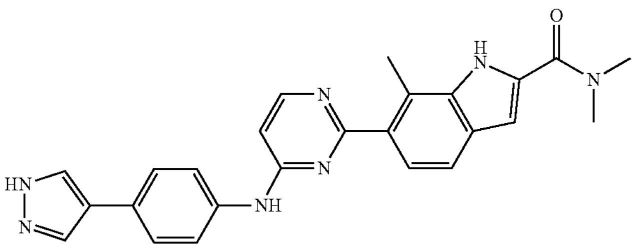 [SMILES: Cc1c(-c2nccc(Nc3ccc(-c4cn[nH]c4)cc3)n2)ccc2cc(C(=O)N(C)C)[nH]c12] |
| 571. | 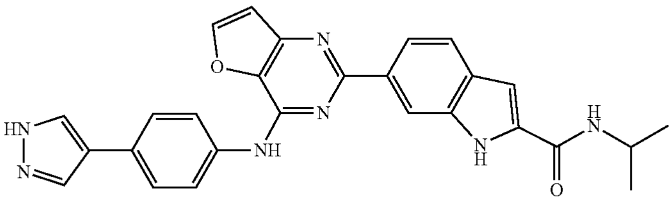 [SMILES: CC(C)NC(=O)c1cc2ccc(-c3nc(Nc4ccc(-c5cn[nH]c5)cc4)c4occc4n3)cc2[nH]1] |

-continued
| No. | Structure |
|---|---|
| 572. | 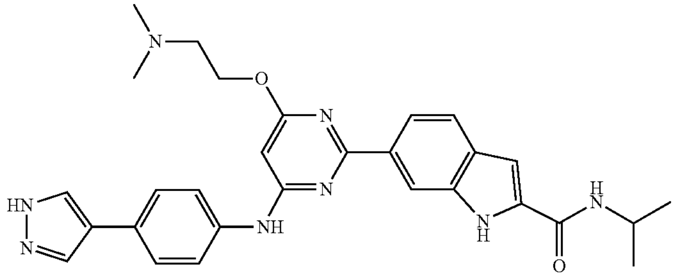 [SMILES: CC(C)NC(=O)c1cc2ccc(-c3nc(Nc4ccc(-c5cn[nH]c5)cc4)cc(OCCN(C)C)n3)cc2[nH]1] |
| 573. | 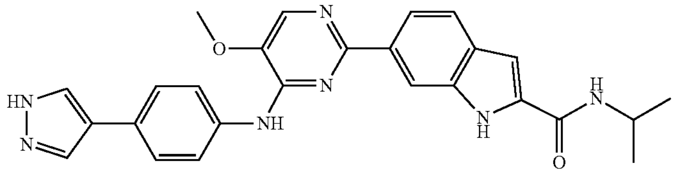 [SMILES: COc1cnc(-c2ccc3cc(C(=O)NC(C)C)[nH]c3c2)nc1Nc1ccc(-c2cn[nH]c2)cc1] |
| 574. | 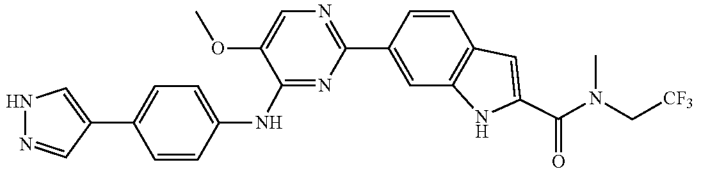 [SMILES: COc1cnc(-c2ccc3cc(C(=O)N(C)CC(F)(F)F)[nH]c3c2)nc1Nc1ccc(-c2cn[nH]c2)cc1] |
| 575. | 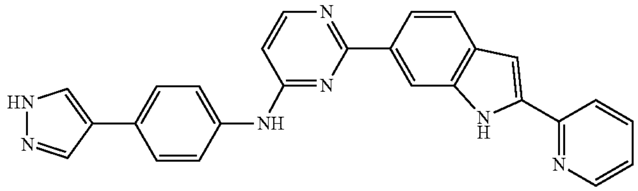 [SMILES: c1ccc(-c2cc3ccc(-c4nccc(Nc5ccc(-c6cn[nH]c6)cc5)n4)cc3[nH]2)nc1] |
| 576. | 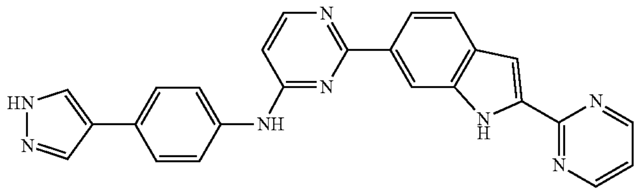 [SMILES: c1cnc(-c2cc3ccc(-c4nccc(Nc5ccc(-c6cn[nH]c6)cc5)n4)cc3[nH]2)nc1] |
| 577. | 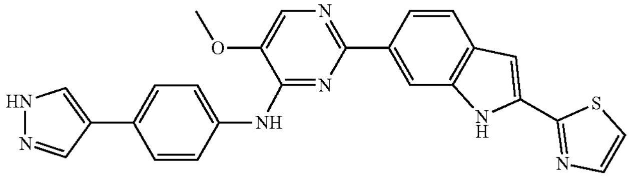 [SMILES: COc1cnc(-c2ccc3cc(-c4nccs4)[nH]c3c2)nc1Nc1ccc(-c2cn[nH]c2)cc1] |
| 578. | 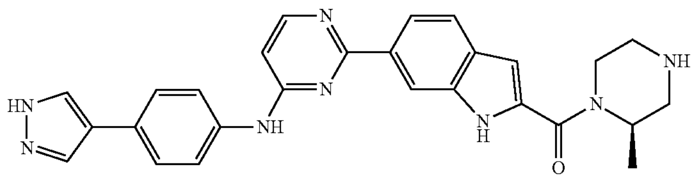 [SMILES: C[C@@H]1CNCCN1C(=O)c1cc2ccc(-c3nccc(Nc4ccc(-c5cn[nH]c5)cc4)n3)cc2[nH]1] |

-continued
| No. | Structure |
| --- | --- |
| 579. | 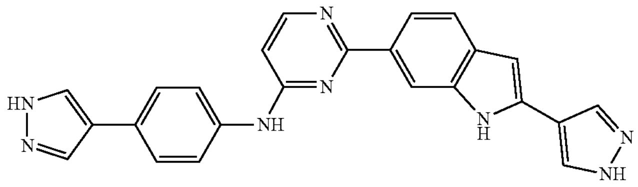 [SMILES: c1cc(Nc2ccc(-c3cn[nH]c3)cc2)nc(-c2ccc3cc(-c4cn[nH]c4)[nH]c3c2)n1] |
| 580. | 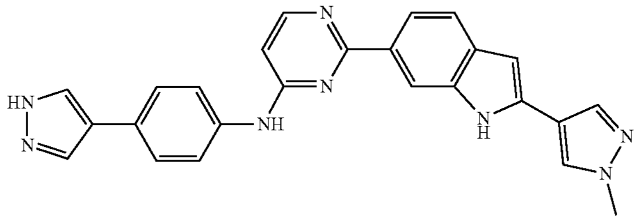 [SMILES: Cn1cc(-c2cc3ccc(-c4nccc(Nc5ccc(-c6cn[nH]c6)cc5)n4)cc3[nH]2)cn1] |
| 581. | 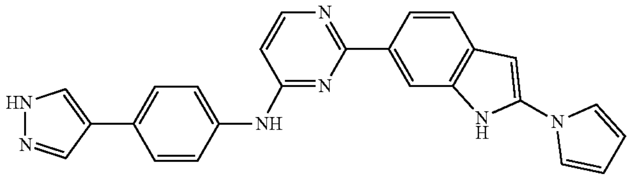 [SMILES: c1ccn(-c2cc3ccc(-c4nccc(Nc5ccc(-c6cn[nH]c6)cc5)n4)cc3[nH]2)c1] |
| 582. | 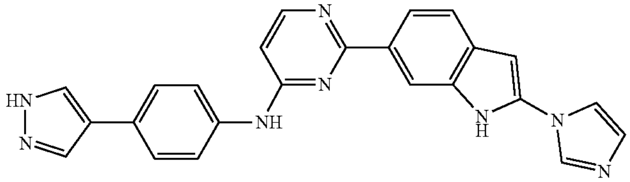 [SMILES: c1cn(-c2cc3ccc(-c4nccc(Nc5ccc(-c6cn[nH]c6)cc5)n4)cc3[nH]2)cn1] |
| 583. | 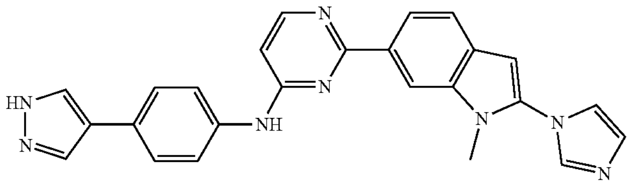 [SMILES: Cn1c(-n2ccnc2)cc2ccc(-c3nccc(Nc4ccc(-c5cn[nH]c5)cc4)n3)cc21] |
| 584. | 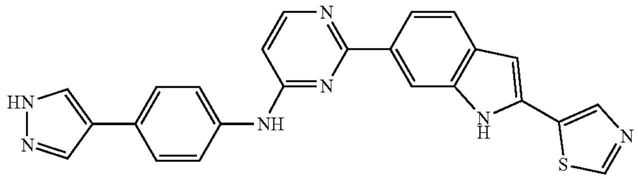 [SMILES: c1cc(Nc2ccc(-c3cn[nH]c3)cc2)nc(-c2ccc3cc(-c4cncs4)[nH]c3c2)n1] |
| 585. | 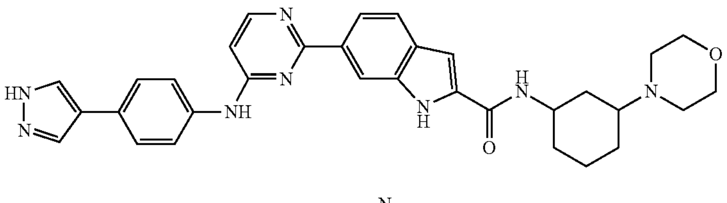 |
| 586. | 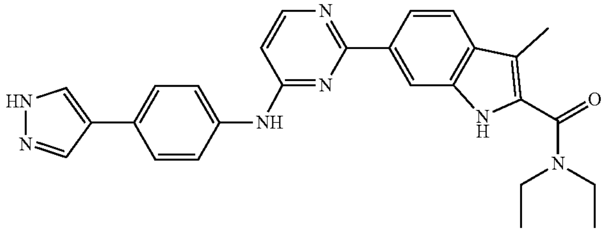 [SMILES: CCN(CC)C(=O)c1[nH]c2cc(-c3nccc(Nc4ccc(-c5cn[nH]c5)cc4)n3)ccc2c1C] |

-continued
| No. | Structure |
|---|---|
| 587. | 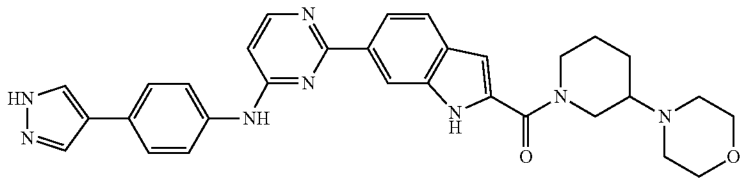 [SMILES: O=C(c1cc2ccc(-c3nccc(Nc4ccc(-c5cn[nH]c5)cc4)n3)cc2[nH]1)N1CCCC(N2CCOCC2)C1] |
| 588. | 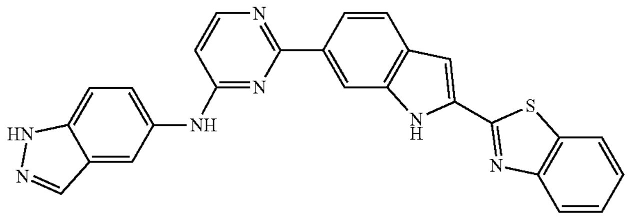 [SMILES: c1ccc2sc(-c3cc4ccc(-c5nccc(Nc6ccc7[nH]ncc7c6)n5)cc4[nH]3)nc2c1] |
| 589. | 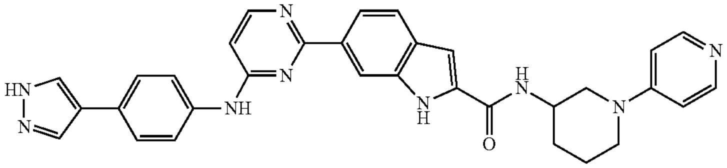 [SMILES: O=C(NC1CCCN(c2ccncc2)C1)c1cc2ccc(-c3nccc(Nc4ccc(-c5cn[nH]c5)cc4)n3)cc2[nH]1] |
| 590. | 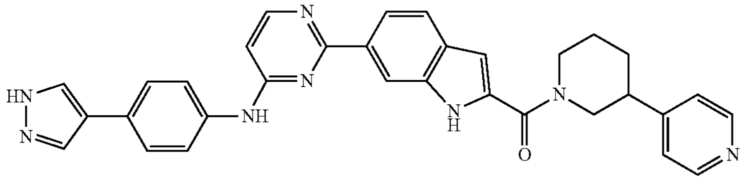 [SMILES: O=C(c1cc2ccc(-c3nccc(Nc4ccc(-c5cn[nH]c5)cc4)n3)cc2[nH]1)N1CCCC(c2ccncc2)C1] |
| 591. | 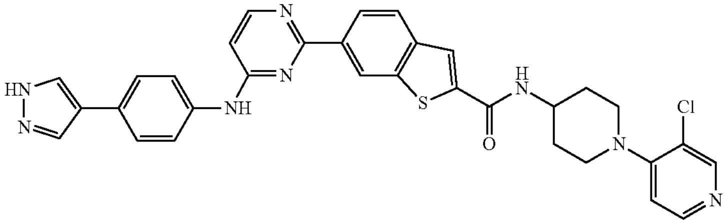 [SMILES: O=C(NC1CCN(c2ccncc2Cl)CC1)c1cc2ccc(-c3nccc(Nc4ccc(-c5cn[nH]c5)cc4)n3)cc2s1] |
| 592. | 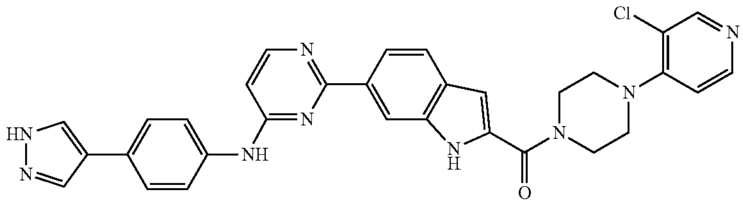 [SMILES: O=C(c1cc2ccc(-c3nccc(Nc4ccc(-c5cn[nH]c5)cc4)n3)cc2[nH]1)N1CCN(c2ccncc2Cl)CC1] |
| 593. | 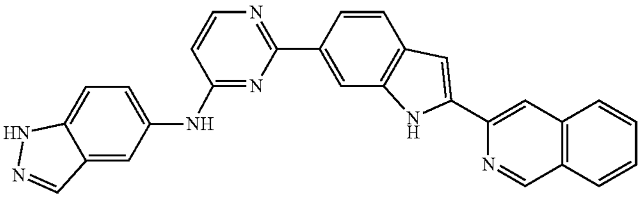 [SMILES: c1ccc2cc(-c3cc4ccc(-c5nccc(Nc6ccc7[nH]ncc7c6)n5)cc4[nH]3)ncc2c1] |

-continued
| No. | Structure |
|---|---|
| 594. | 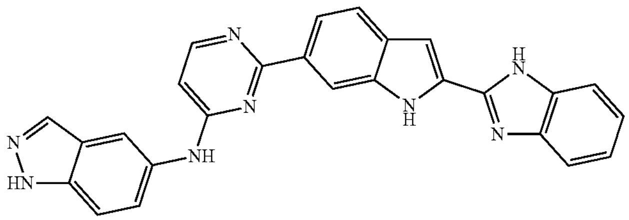 [SMILES: c1ccc2[nH]c(-c3cc4ccc(-c5nccc(Nc6ccc7[nH]ncc7c6)n5)cc4[nH]3)nc2c1] |
| 595. | 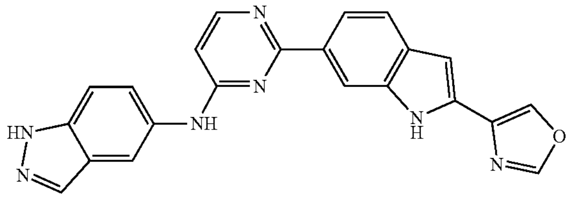 [SMILES: c1cc(Nc2ccc3[nH]ncc3c2)nc(-c2ccc3cc(-c4cocn4)[nH]c3c2)n1] |
| 596. | 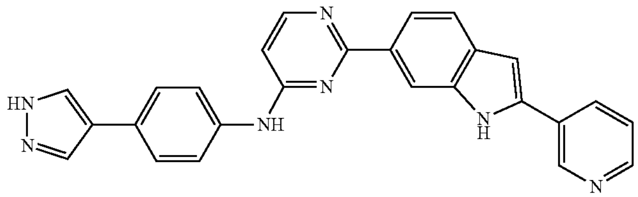 [SMILES: c1cncc(-c2cc3ccc(-c4nccc(Nc5ccc(-c6cn[nH]c6)cc5)n4)cc3[nH]2)c1] |
| 597. | 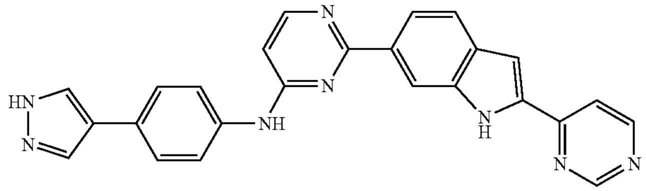 [SMILES: c1cc(-c2cc3ccc(-c4nccc(Nc5ccc(-c6cn[nH]c6)cc5)n4)cc3[nH]2)ncn1] |
| 598. | 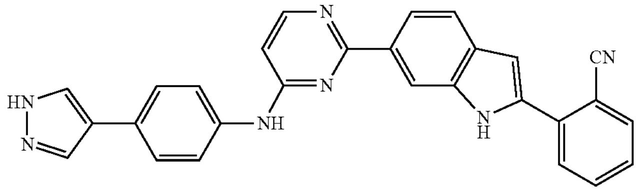 [SMILES: N#Cc1ccccc1-c1cc2ccc(-c3nccc(Nc4ccc(-c5cn[nH]c5)cc4)n3)cc2[nH]1] |
| 599. | 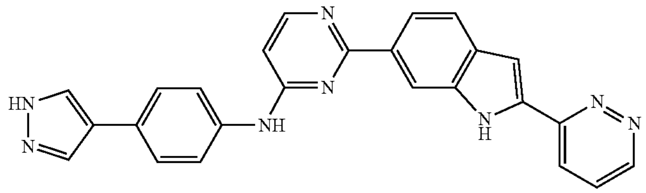 [SMILES: c1cnnc(-c2cc3ccc(-c4nccc(Nc5ccc(-c6cn[nH]c6)cc5)n4)cc3[nH]2)c1] |
| 600. | 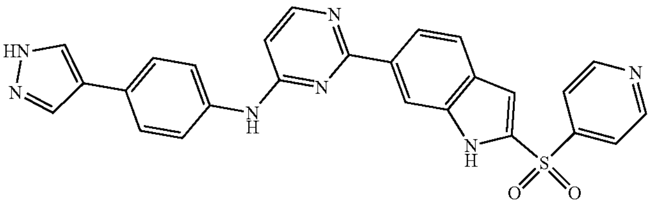 [SMILES: O=S(=O)(c1ccncc1)c1cc2ccc(-c3nccc(Nc4ccc(-c5cn[nH]c5)cc4)n3)cc2[nH]1]

-continued
| No. | Structure |
| --- | --- |
| 601. | 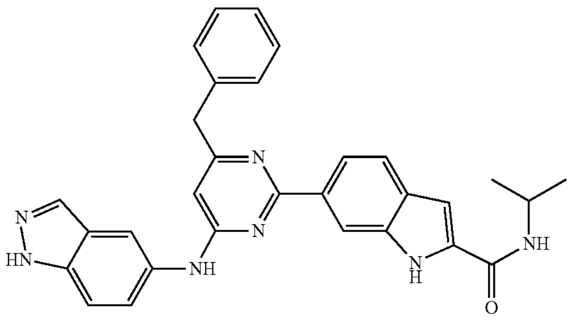 [SMILES: CC(C)NC(=O)c1cc2ccc(-c3nc(Cc4ccccc4)cc(Nc4ccc5[nH]ncc5c4)n3)cc2[nH]1] |
| 602. | 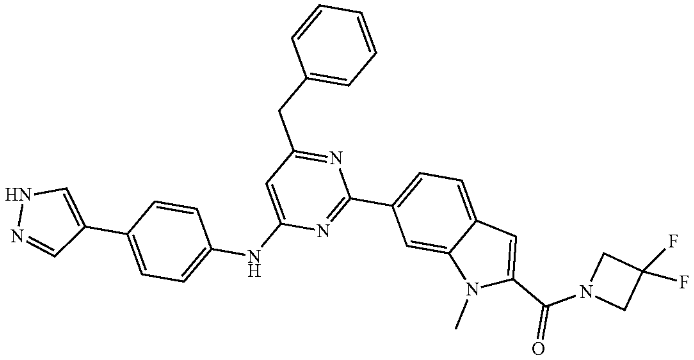 [SMILES: Cn1c(C(=O)N2CC(F)(F)C2)cc2ccc(-c3nc(Cc4ccccc4)cc(Nc4ccc(-c5cn[nH]c5)cc4)n3)cc21] |
| 603. | 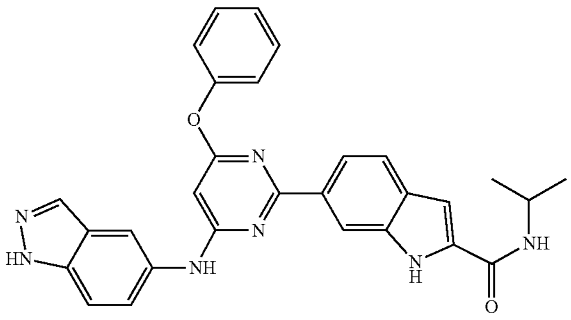 [SMILES: CC(C)NC(=O)c1cc2ccc(-c3nc(Nc4ccc5[nH]ncc5c4)cc(Oc4ccccc4)n3)cc2[nH]1] |
| 604. | 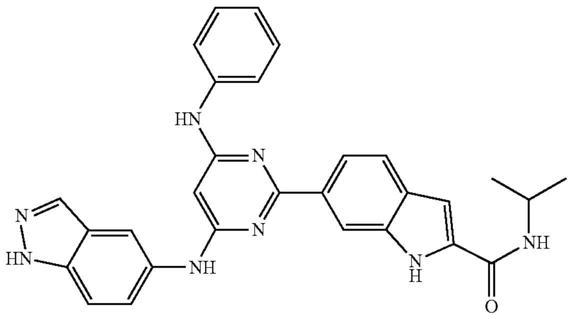 [SMILES: CC(C)NC(=O)c1cc2ccc(-c3nc(Nc4ccccc4)cc(Nc4ccc5[nH]ncc5c4)n3)cc2[nH]1] |
| 605. | 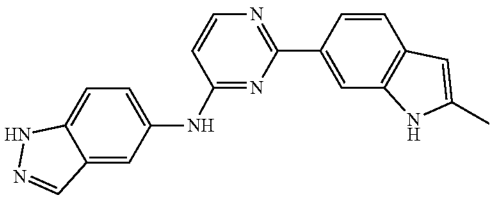 [SMILES: Cc1cc2ccc(-c3nccc(Nc4ccc5[nH]ncc5c4)n3)cc2[nH]1] |

-continued
| No. | Structure |
|---|---|
| 606. | 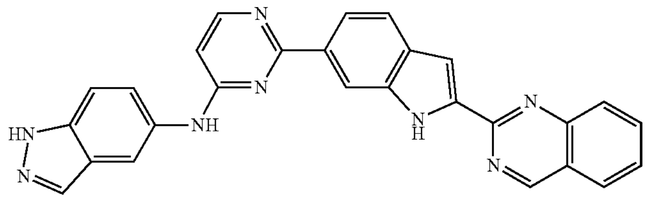 [SMILES: c1ccc2nc(-c3cc4ccc(-c5nccc(Nc6ccc7[nH]ncc7c6)n5)cc4[nH]3)ncc2c1] |
| 607. | 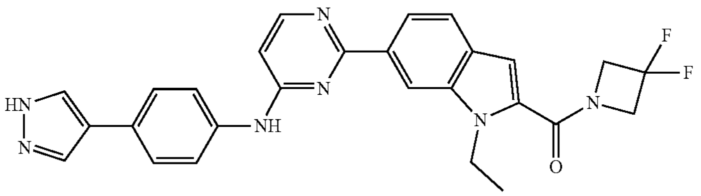 [SMILES: CCn1c(C(=O)N2CC(F)(F)C2)cc2ccc(-c3nccc(Nc4ccc(-c5cn[nH]c5)cc4)n3)cc21] |
| 608. | 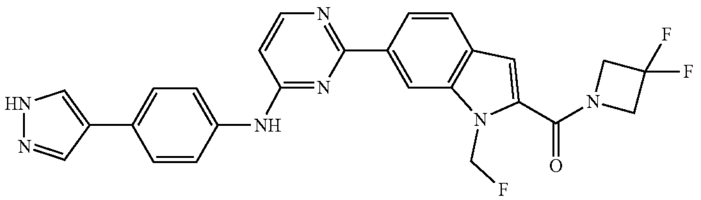 [SMILES: O=C(c1cc2ccc(-c3nccc(Nc4ccc(-c5cn[nH]c5)cc4)n3)cc2n1CF)N1CC(F)(F)C1] |
| 609. | 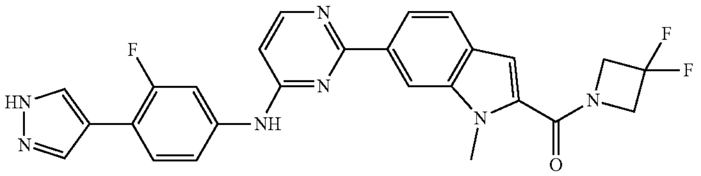 [SMILES: Cn1c(C(=O)N2CC(F)(F)C2)cc2ccc(-c3nccc(Nc4ccc(-c5cn[nH]c5)c(F)c4)n3)cc21] |
| 610. | 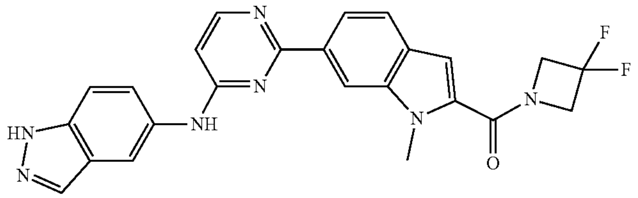 [SMILES: Cn1c(C(=O)N2CC(F)(F)C2)cc2ccc(-c3nccc(Nc4ccc5[nH]ncc5c4)n3)cc21] |
| 611. | 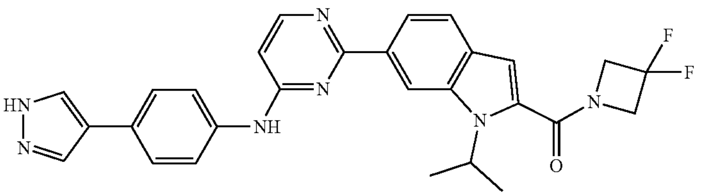 [SMILES: CC(C)n1c(C(=O)N2CC(F)(F)C2)cc2ccc(-c3nccc(Nc4ccc(-c5cn[nH]c5)cc4)n3)cc21] |
| 612. | 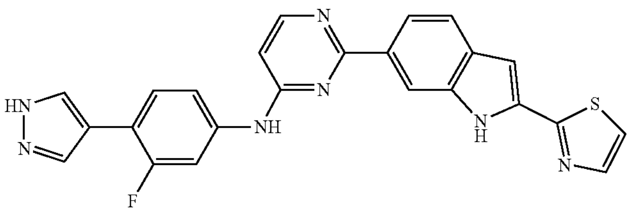 [SMILES: Fc1cc(Nc2ccnc(-c3ccc4cc(-c5nccs5)[nH]c4c3)n2)ccc1-c1cn[nH]c1] |

-continued
| No. | Structure |
|---|---|
| 613. | 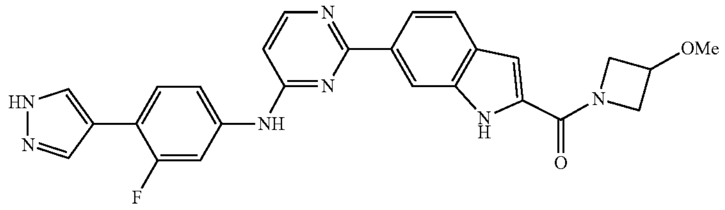 [SMILES: COC1CN(C(=O)c2cc3ccc(-c4nccc(Nc5ccc(-c6cn[nH]c6)c(F)c5)n4)cc3[nH]2)C1] |
| 614. | 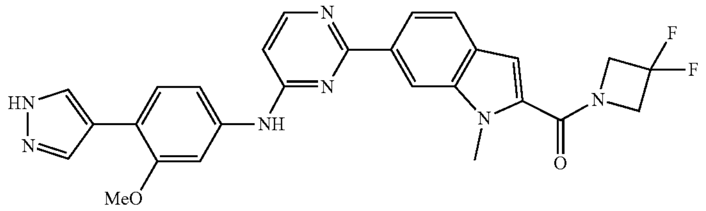 [SMILES: COc1cc(Nc2ccnc(-c3ccc4cc(C(=O)N5CC(F)(F)C5)n(C)c4c3)n2)ccc1-c1cn[nH]c1] |
| 615. | 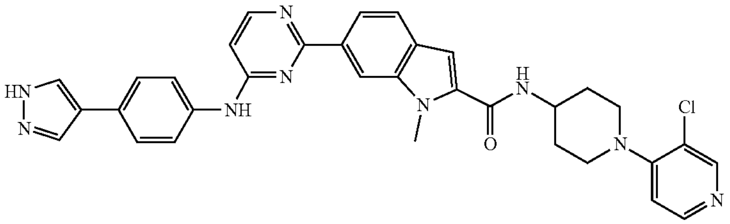 [SMILES: Cn1c(C(=O)NC2CCN(c3ccncc3Cl)CC2)cc2ccc(-c3nccc(Nc4ccc(-c5cn[nH]c5)cc4)n3)cc21] |
| 616. | 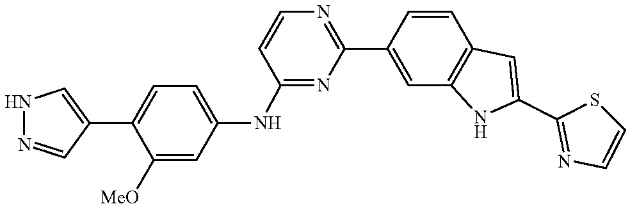 [SMILES: COc1cc(Nc2ccnc(-c3ccc4cc(-c5nccs5)[nH]c4c3)n2)ccc1-c1cn[nH]c1] |
| 617. | 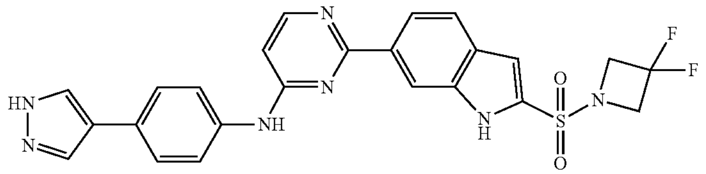 [SMILES: O=S(=O)(c1cc2ccc(-c3nccc(Nc4ccc(-c5cn[nH]c5)cc4)n3)cc2[nH]1)N1CC(F)(F)C1] |
| 618. | 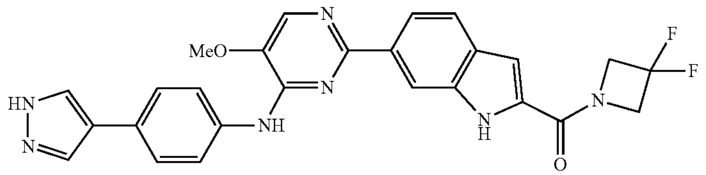 [SMILES: COc1cnc(-c2ccc3cc(C(=O)N4CC(F)(F)C4)[nH]c3c2)nc1Nc1ccc(-c2cn[nH]c2)cc1] |
| 619. | 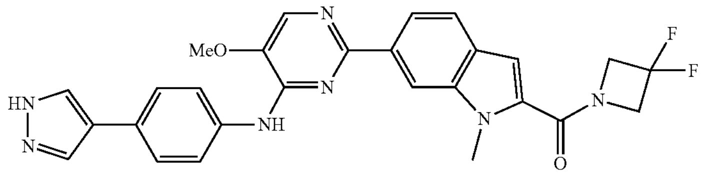 [SMILES: COc1cnc(-c2ccc3cc(C(=O)N4CC(F)(F)C4)n(C)c3c2)nc1Nc1ccc(-c2cn[nH]c2)cc1] |

-continued
| No. | Structure |
| --- | --- |
| 620. | 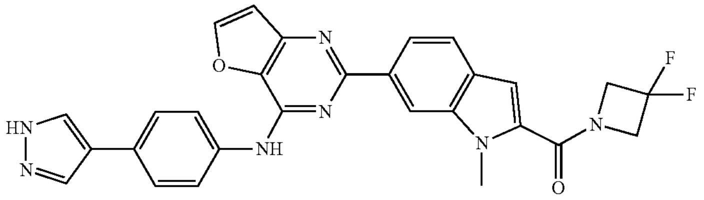 [SMILES: Cn1c(C(=O)N2CC(F)(F)C2)cc2ccc(-c3nc(Nc4ccc(-c5cn[nH]c5)cc4)c4occc4n3)cc21] |
| 621. | 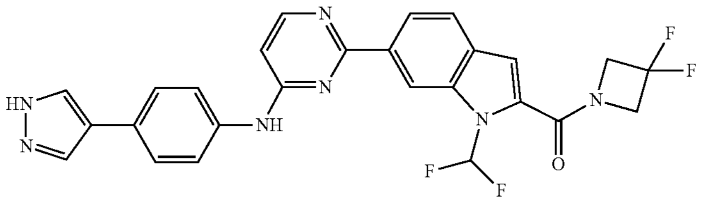 [SMILES: O=C(c1cc2ccc(-c3nccc(Nc4ccc(-c5cn[nH]c5)cc4)n3)cc2n1C(F)F)N1CC(F)(F)C1] |
| 622. | 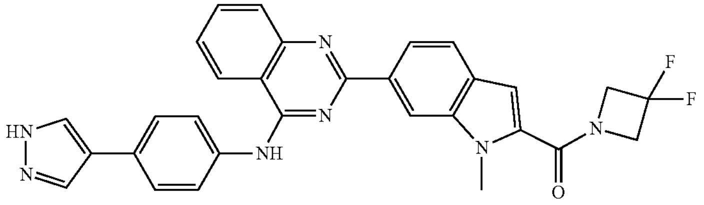 [SMILES: Cn1c(C(=O)N2CC(F)(F)C2)cc2ccc(-c3nc(Nc4ccc(-c5cn[nH]c5)cc4)c4ccccc4n3)cc21] |
| 623. | 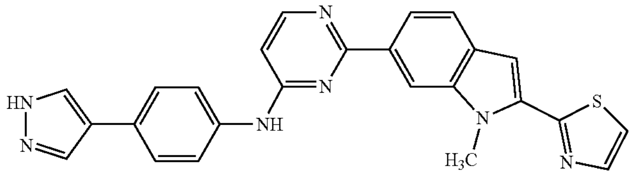 [SMILES: Cn1c(-c2nccs2)cc2ccc(-c3nccc(Nc4ccc(-c5cn[nH]c5)cc4)n3)cc21] |
| 624. | 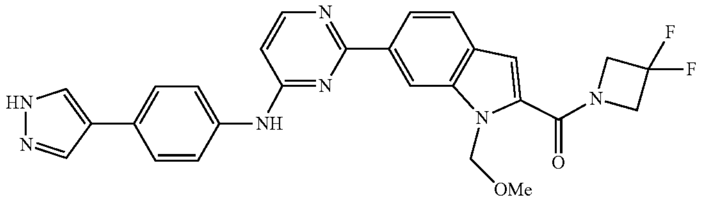 [SMILES: COCn1c(C(=O)N2CC(F)(F)C2)cc2ccc(-c3nccc(Nc4ccc(-c5cn[nH]c5)cc4)n3)cc21] |
| 625. | 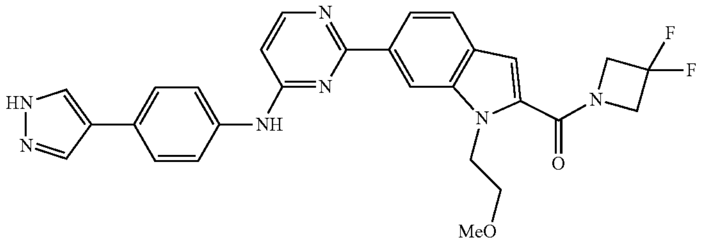 [SMILES: COCCn1c(C(=O)N2CC(F)(F)C2)cc2ccc(-c3nccc(Nc4ccc(-c5cn[nH]c5)cc4)n3)cc21] |
| 626. | 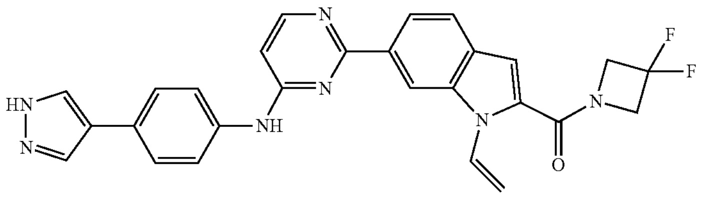 [SMILES: C=Cn1c(C(=O)N2CC(F)(F)C2)cc2ccc(-c3nccc(Nc4ccc(-c5cn[nH]c5)cc4)n3)cc21] |

-continued
| No. | Structure |
|---|---|
| 627. | 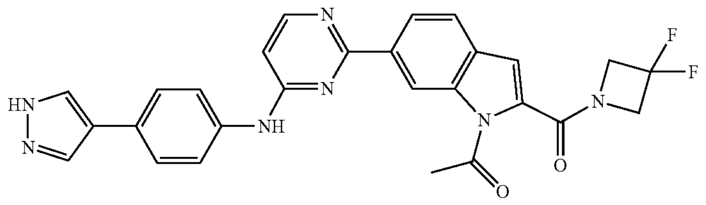 [SMILES: CC(=O)n1c(C(=O)N2CC(F)(F)C2)cc2ccc(-c3nccc(Nc4ccc(-c5cn[nH]c5)cc4)n3)cc21] |
| 628. | 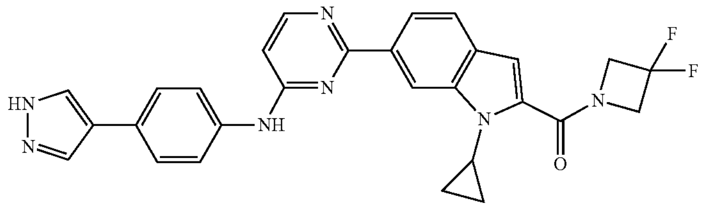 [SMILES: O=C(c1cc2ccc(-c3nccc(Nc4ccc(-c5cn[nH]c5)cc4)n3)cc2n1C1CC1)N1CC(F)(F)C1] |
| 629. | 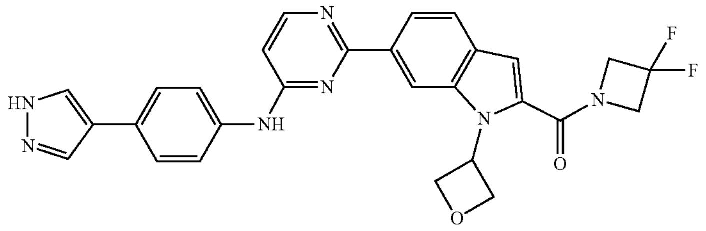 [SMILES: O=C(c1cc2ccc(-c3nccc(Nc4ccc(-c5cn[nH]c5)cc4)n3)cc2n1C1COC1)N1CC(F)(F)C1] |
| 630. | 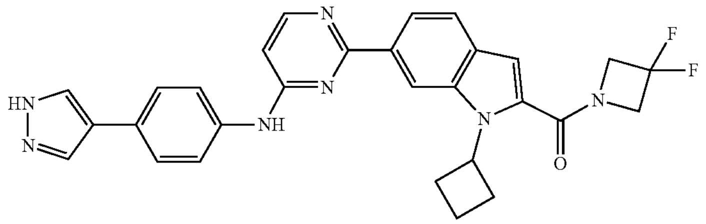 [SMILES: O=C(c1cc2ccc(-c3nccc(Nc4ccc(-c5cn[nH]c5)cc4)n3)cc2n1C1CCC1)N1CC(F)(F)C1] |
| 631. | 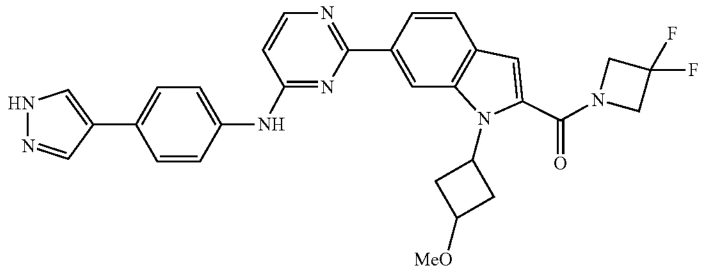 [SMILES: COC1CC(n2c(C(=O)N3CC(F)(F)C3)cc3ccc(-c4nccc(Nc5ccc(-c6cn[nH]c6)cc5)n4)cc32)C1] |
| 632. | 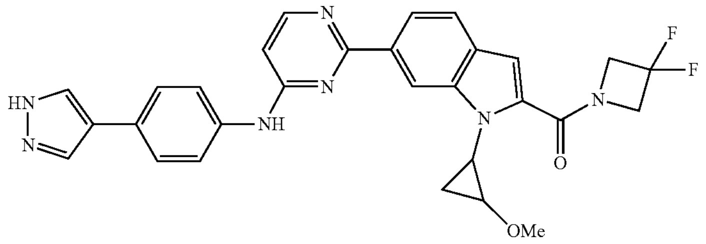 [SMILES: COC1CC1n1c(C(=O)N2CC(F)(F)C2)cc2ccc(-c3nccc(Nc4ccc(-c5cn[nH]c5)cc4)n3)cc21] |

-continued
| No. | Structure |
| --- | --- |
| 633. | 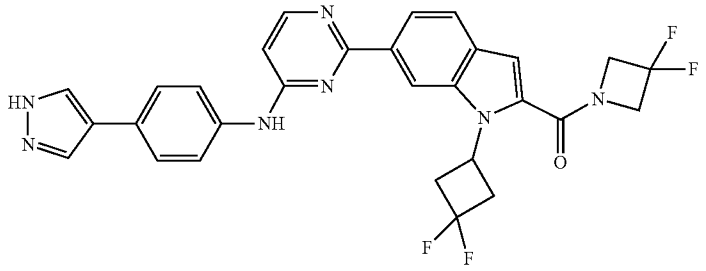 [SMILES: O=C(c1cc2ccc(-c3nccc(Nc4ccc(-c5cn[nH]c5)cc4)n3)cc2n1C1CC(F)(F)C1)N1CC(F)(F)C1] |
| 634. | 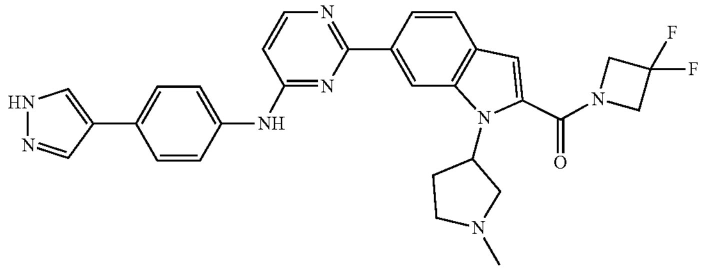 [SMILES: CN1CCC(n2c(C(=O)N3CC(F)(F)C3)cc3ccc(-c4nccc(Nc5ccc(-c6cn[nH]c6)cc5)n4)cc32)C1] |
| 635. | 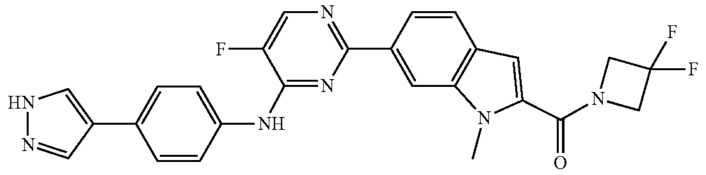 [SMILES: Cn1c(C(=O)N2CC(F)(F)C2)cc2ccc(-c3ncc(F)c(Nc4ccc(-c5cn[nH]c5)cc4)n3)cc21] |
| 636. | 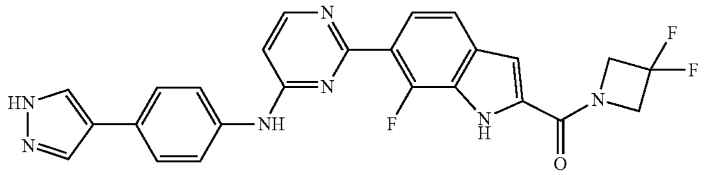 [SMILES: O=C(c1cc2ccc(-c3nccc(Nc4ccc(-c5cn[nH]c5)cc4)n3)c(F)c2[nH]1)N1CC(F)(F)C1] |
| 637. | 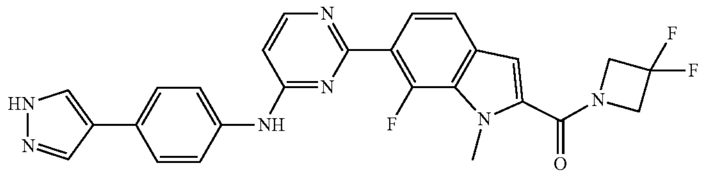 [SMILES: Cn1c(C(=O)N2CC(F)(F)C2)cc2ccc(-c3nccc(Nc4ccc(-c5cn[nH]c5)cc4)n3)c(F)c21] |
| 638. | 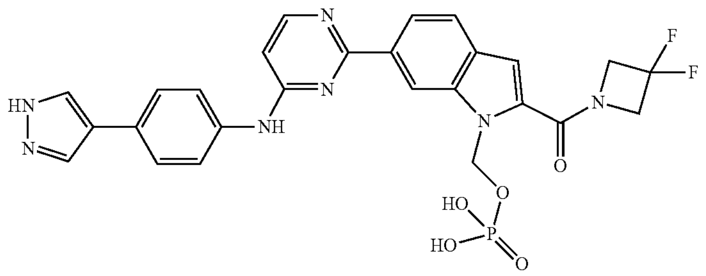 [SMILES: O=C(c1cc2ccc(-c3nccc(Nc4ccc(-c5cn[nH]c5)cc4)n3)cc2n1COP(=O)(O)O)N1CC(F)(F)C1] |
| 639. | 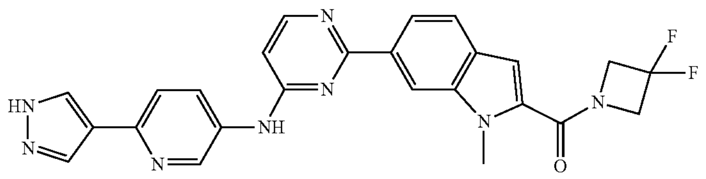 [SMILES: Cn1c(C(=O)N2CC(F)(F)C2)cc2ccc(-c3nccc(Nc4ccc(-c5cn[nH]c5)nc4)n3)cc21] |

-continued
| No. | Structure |
| --- | --- |
| 640. | 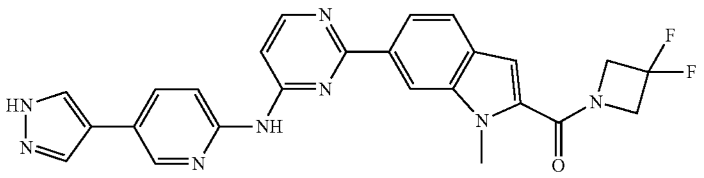 [SMILES: Cn1c(C(=O)N2CC(F)(F)C2)cc2ccc(-c3nccc(Nc4ccc(-c5cn[nH]c5)cn4)n3)cc21] |
| 641. | 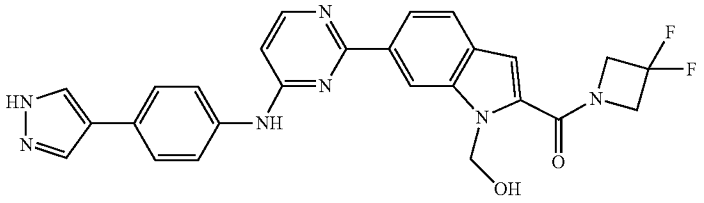 |
| 642. | 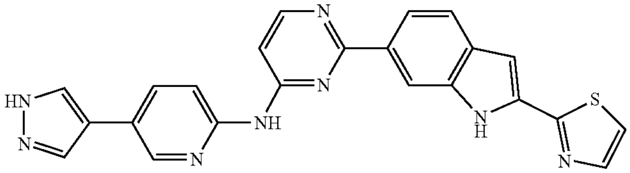 [SMILES: c1cc(Nc2ccc(-c3cn[nH]c3)cn2)nc(-c2ccc3cc(-c4nccs4)[nH]c3c2)n1] |
| 643. | 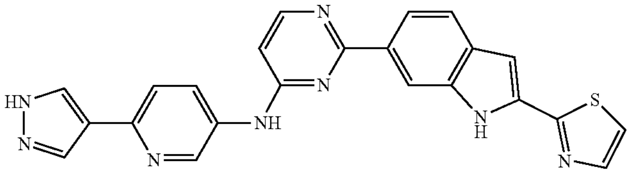 [SMILES: c1cc(Nc2ccc(-c3cn[nH]c3)nc2)nc(-c2ccc3cc(-c4nccs4)[nH]c3c2)n1] |
| 644. | 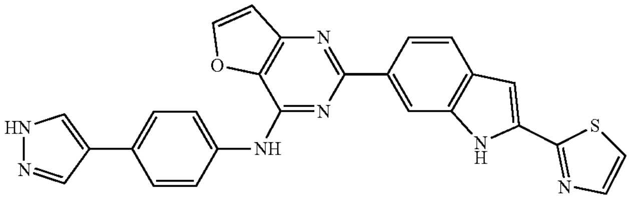 [SMILES: c1csc(-c2cc3ccc(-c4nc(Nc5ccc(-c6cn[nH]c6)cc5)c5occc5n4)cc3[nH]2)n1] |
| 645. | 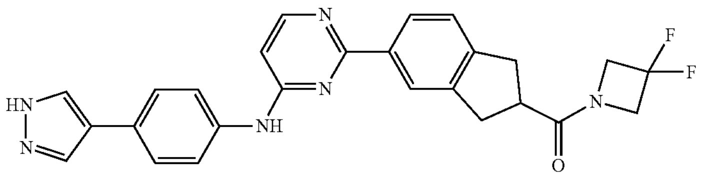 [SMILES: O=C(C1Cc2ccc(-c3nccc(Nc4ccc(-c5cn[nH]c5)cc4)n3)cc2C1)N1CC(F)(F)C1] |
| 646. | 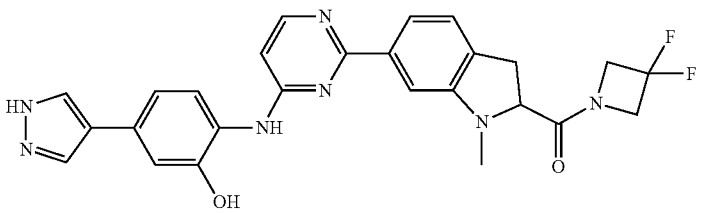 |

-continued
| No. | Structure |
| --- | --- |
| 647. | 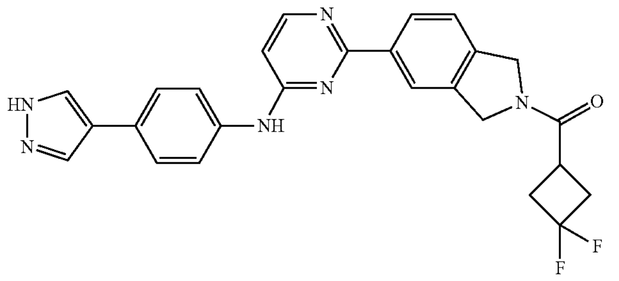 [SMILES: O=C(C1CC(F)(F)C1)N1Cc2ccc(-c3nccc(Nc4ccc(-c5cn[nH]c5)cc4)n3)cc2C1] |
| 648. | 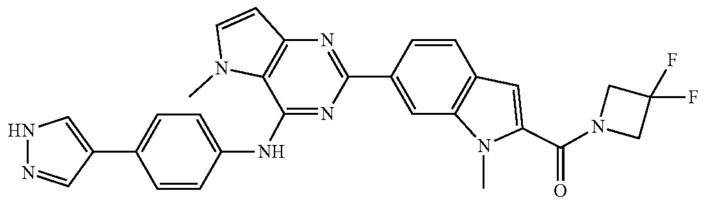 [SMILES: Cn1ccc2nc(-c3ccc4cc(C(=O)N5CC(F)(F)C5)n(C)c4c3)nc(Nc3ccc(-c4cn[nH]c4)cc3)c21] |
| 649. | 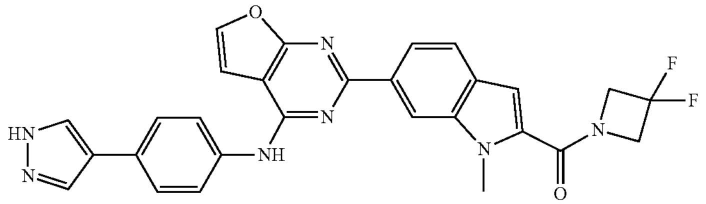 [SMILES: Cn1c(C(=O)N2CC(F)(F)C2)cc2ccc(-c3nc(Nc4ccc(-c5cn[nH]c5)cc4)c4ccoc4n3)cc21] |
| 650. | 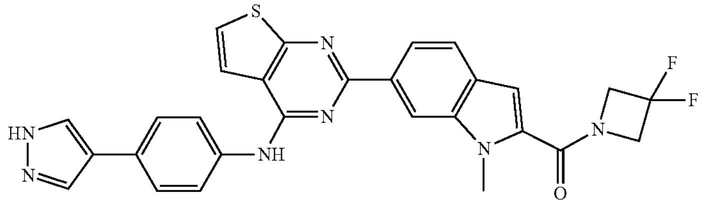 [SMILES: Cn1c(C(=O)N2CC(F)(F)C2)cc2ccc(-c3nc(Nc4ccc(-c5cn[nH]c5)cc4)c4ccsc4n3)cc21] |
| 651. | 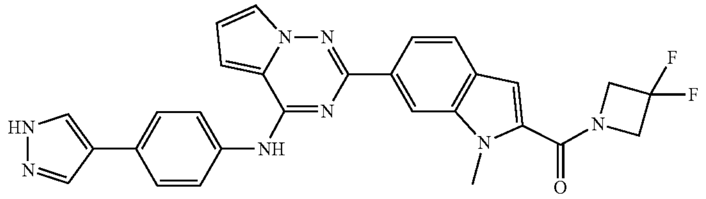 [SMILES: Cn1c(C(=O)N2CC(F)(F)C2)cc2ccc(-c3nc(Nc4ccc(-c5cn[nH]c5)cc4)c4cccn4n3)cc21] |
| 652. | 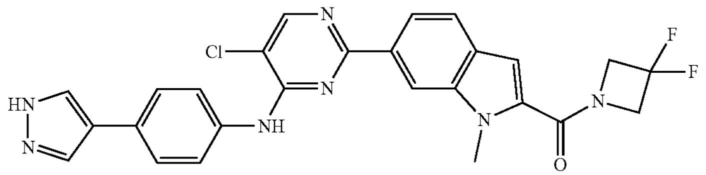 [SMILES: Cn1c(C(=O)N2CC(F)(F)C2)cc2ccc(-c3ncc(Cl)c(Nc4ccc(-c5cn[nH]c5)cc4)n3)cc21] |
| 653. | 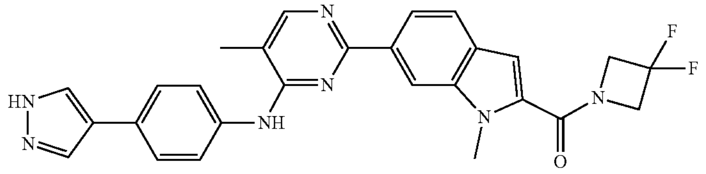 |

-continued
| No. | Structure |
| --- | --- |
| 654. | 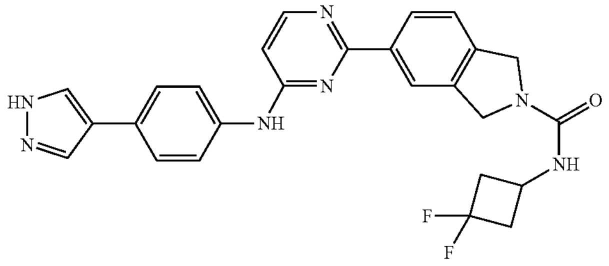 [SMILES: O=C(NC1CC(F)(F)C1)N1Cc2ccc(-c3nccc(Nc4ccc(-c5cn[nH]c5)cc4)n3)cc2C1] |
| 655. | 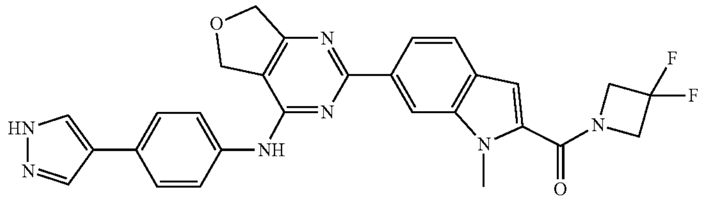 |
| 656. | 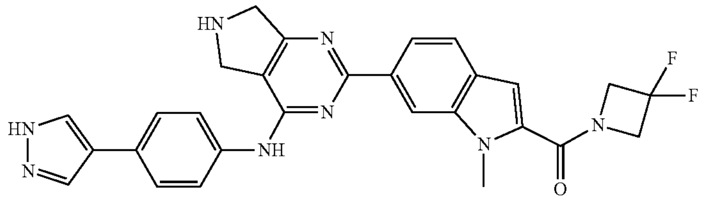 [SMILES: Cn1c(C(=O)N2CC(F)(F)C2)cc2ccc(-c3nc4c(c(Nc5ccc(-c6cn[nH]c6)cc5)n3)CNC4)cc21] |
| 657. | 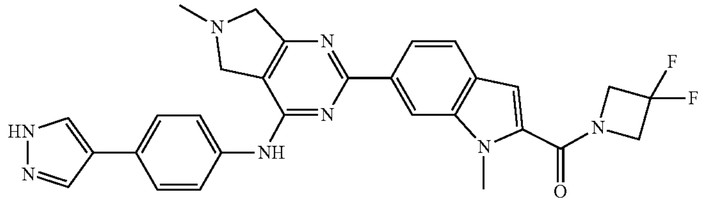 [SMILES: CN1Cc2nc(-c3ccc4cc(C(=O)N5CC(F)(F)C5)n(C)c4c3)nc(Nc3ccc(-c4cn[nH]c4)cc3)c2C1] |
| 658. | 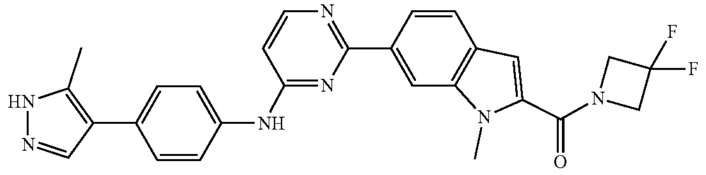 [SMILES: Cc1[nH]ncc1-c1ccc(Nc2ccnc(-c3ccc4cc(C(=O)N5CC(F)(F)C5)n(C)c4c3)n2)cc1] |
| 659. | 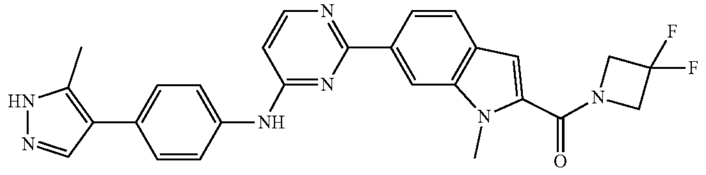 [SMILES: Cc1[nH]ncc1-c1ccc(Nc2ccnc(-c3ccc4cc(C(=O)N5CC(F)(F)C5)n(C)c4c3)n2)cc1] |
| 660. | 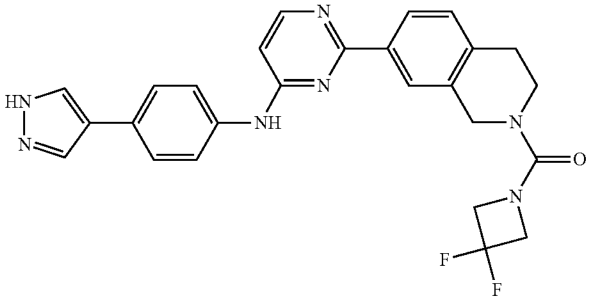 [SMILES: O=C(N1CCc2ccc(-c3nccc(Nc4ccc(-c5cn[nH]c5)cc4)n3)cc2C1)N1CC(F)(F)C1] |

-continued
| No. | Structure |
|---|---|
| 661. | 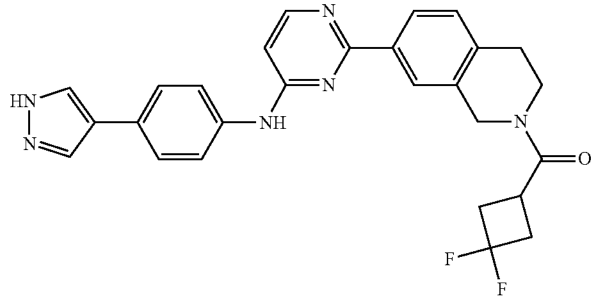 [SMILES: O=C(C1CC(F)(F)C1)N1CCc2ccc(-c3nccc(Nc4ccc(-c5cn[nH]c5)cc4)n3)cc2C1] |
| 662. | 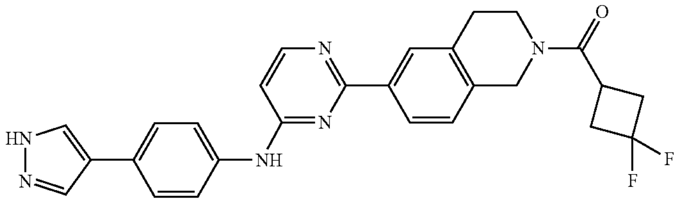 [SMILES: O=C(C1CC(F)(F)C1)N1CCc2cc(-c3nccc(Nc4ccc(-c5cn[nH]c5)cc4)n3)ccc2C1] |
| 663. | 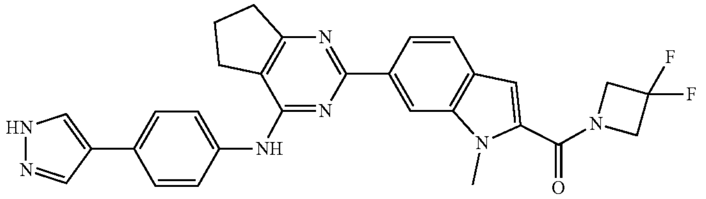 [SMILES: Cn1c(C(=O)N2CC(F)(F)C2)cc2ccc(-c3nc4c(c(Nc5ccc(-c6cn[nH]c6)cc5)n3)CCC4)cc21] |
| 664. | 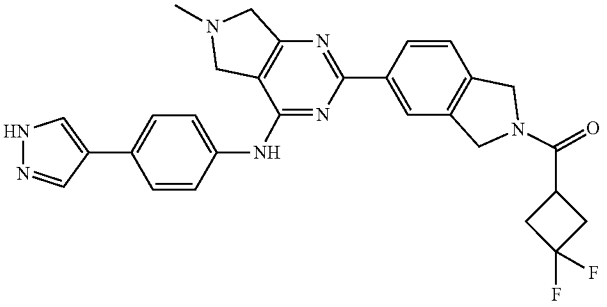 [SMILES: CN1Cc2nc(-c3ccc4c(c3)CN(C(=O)C3CC(F)(F)C3)C4)nc(Nc3ccc(-c4cn[nH]c4)cc3)c2C1] |
| 665. | 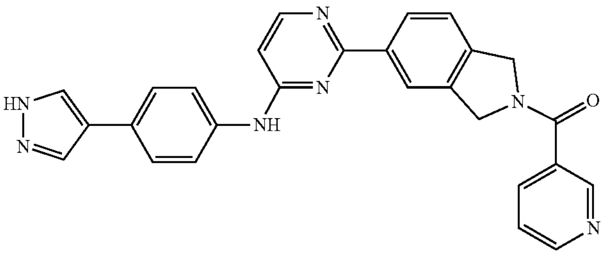 [SMILES: O=C(c1cccnc1)N1Cc2ccc(-c3nccc(Nc4ccc(-c5cn[nH]c5)cc4)n3)cc2C1] |
| 666. | 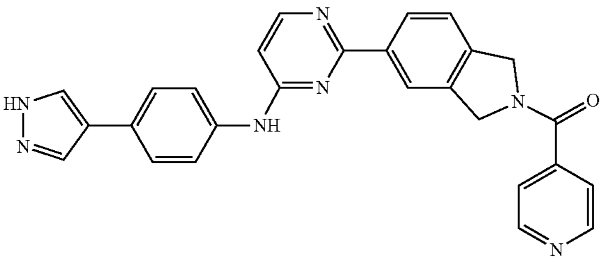 [SMILES: O=C(c1ccncc1)N1Cc2ccc(-c3nccc(Nc4ccc(-c5cn[nH]c5)cc4)n3)cc2C1] |

-continued
| No. | Structure |
| --- | --- |
| 667. | 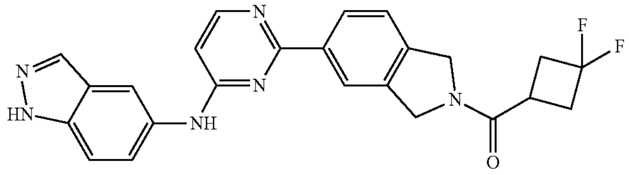 [SMILES: O=C(C1CC(F)(F)C1)N1Cc2ccc(-c3nccc(Nc4ccc5[nH]ncc5c4)n3)cc2C1] |
| 668. | 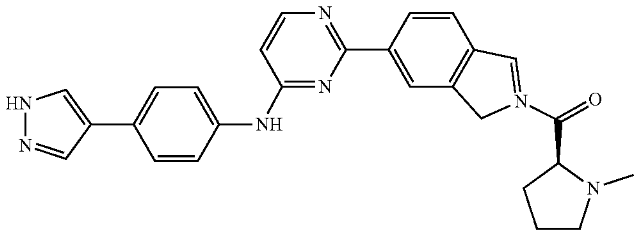 |
| 669. | 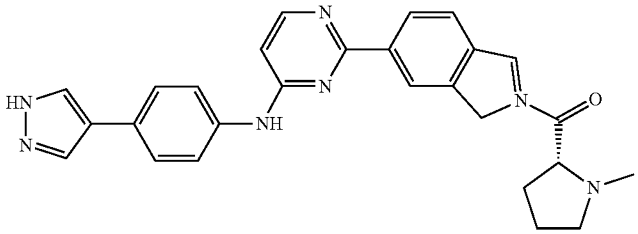 |
| 670. | 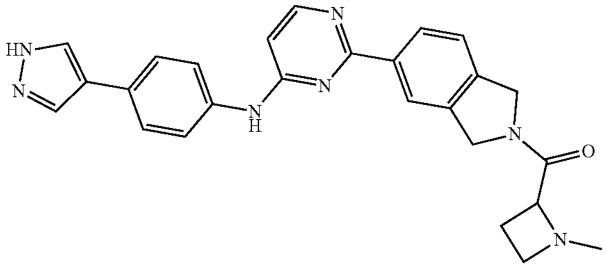 [SMILES: CN1CCC1C(=O)N1Cc2ccc(-c3nccc(Nc4ccc(-c5cn[nH]c5)cc4)n3)cc2C1] |
| 671. | 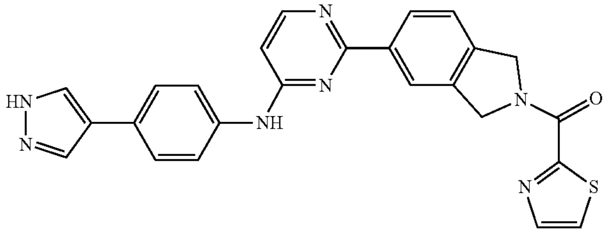 [SMILES: O=C(c1nccs1)N1Cc2ccc(-c3nccc(Nc4ccc(-c5cn[nH]c5)cc4)n3)cc2C1] |
| 672. | 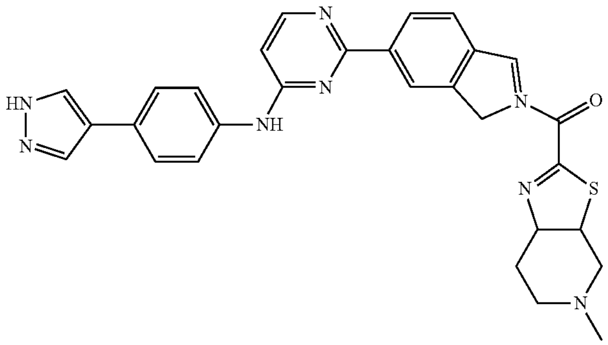

-continued
| No. | Structure |
|---|---|
| 673. | 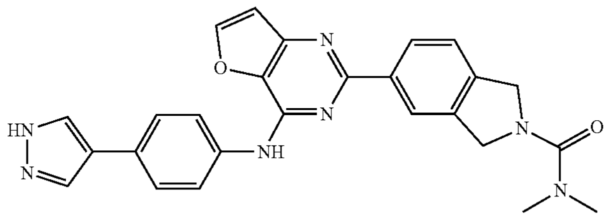 [SMILES: CN(C)C(=O)N1Cc2ccc(-c3nc(Nc4ccc(-c5cn[nH]c5)cc4)c4occc4n3)cc2C1] |
| 674. | 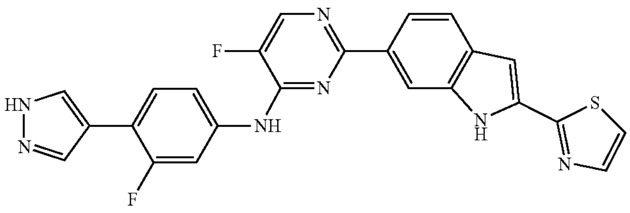 [SMILES: Fc1cc(Nc2nc(-c3ccc4cc(-c5nccs5)[nH]c4c3)ncc2F)ccc1-c1cn[nH]c1] |
| 675. | 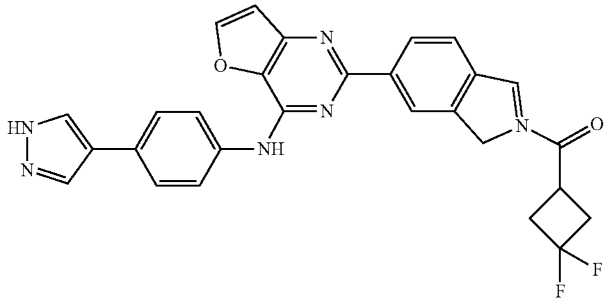 |
| 676. | 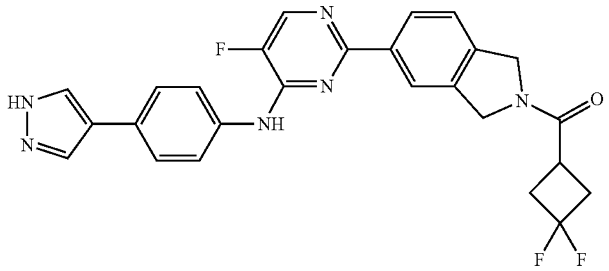 [SMILES: O=C(C1CC(F)(F)C1)N1Cc2ccc(-c3ncc(F)c(Nc4ccc(-c5cn[nH]c5)cc4)n3)cc2C1] |
| 677. | 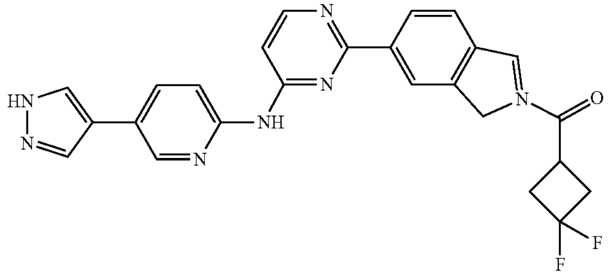 |
| 678. | 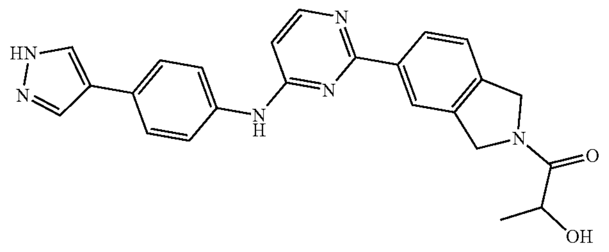 [SMILES: CC(O)C(=O)N1Cc2ccc(-c3nccc(Nc4ccc(-c5cn[nH]c5)cc4)n3)cc2C1] |

-continued

| No. | Structure |
|---|---|
| 679. | 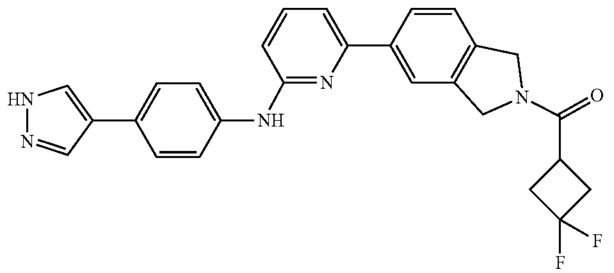 [SMILES: O=C(C1CC(F)(F)C1)N1Cc2ccc(-c3cccc(Nc4ccc(-c5cn[nH]c5)cc4)n3)cc2C1] |
| 680. | 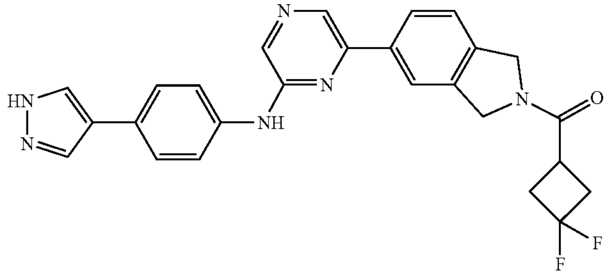 [SMILES: O=C(C1CC(F)(F)C1)N1Cc2ccc(-c3cncc(Nc4ccc(-c5cn[nH]c5)cc4)n3)cc2C1] |
| 681. | 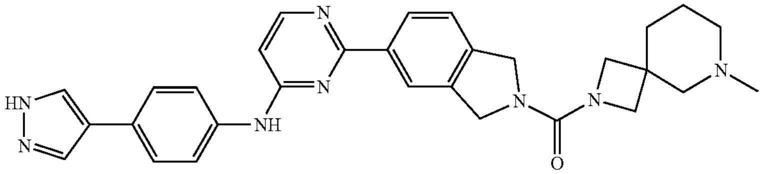 [SMILES: CN1CCCC2(C1)CN(C(=O)N1Cc3ccc(-c4nccc(Nc5ccc(-c6cn[nH]c6)cc5)n4)cc3C1)C2] |
| 682. | 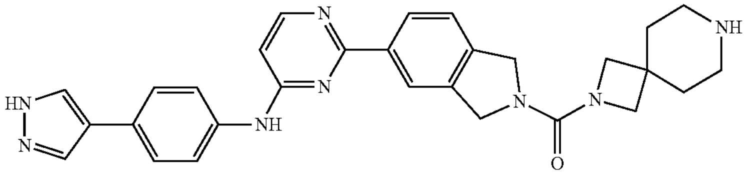 [SMILES: O=C(N1Cc2ccc(-c3nccc(Nc4ccc(-c5cn[nH]c5)cc4)n3)cc2C1)N1CC2(CCNCC2)C1] |
| 683. | 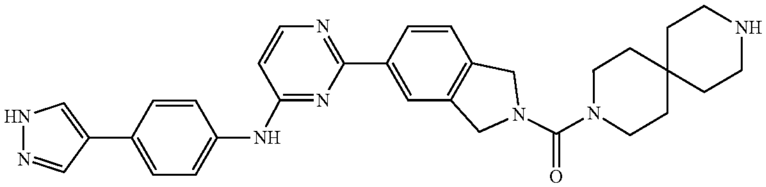 [SMILES: O=C(N1CCC2(CCNCC2)CC1)N1Cc2ccc(-c3nccc(Nc4ccc(-c5cn[nH]c5)cc4)n3)cc2C1] |
| 684. | 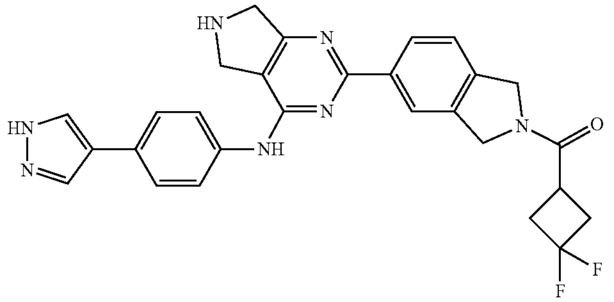 [SMILES: O=C(C1CC(F)(F)C1)N1Cc2ccc(-c3nc4c(c(Nc5ccc(-c6cn[nH]c6)cc5)n3)CNC4)cc2C1] |

In some embodiments, the compounds are prepared according to the methods disclosed in WO 2019/001572 A1 (incorporated herein by reference).

In some embodiments, the compound of Formula (I) or a pharmaceutically acceptable salt, ester, stereoisomer, polymorph, solvate, N-oxide, isotopically labeled compound, metabolite or prodrug thereof is administered in an amount of about 0.005 mg/day to about 5000 mg/day, e.g., in an amount of about 0.005, 0.05, 0.5, 5, 10, 20, 30, 40, 50, 100, 150, 200, 250, 300, 350, 400, 450, 500, 550, 600, 650, 700, 750, 800, 850, 900, 950, 1000, 1500, 2000, 2500, 3000, 3500, 4000, 4500 or 5000 mg/day.

In some embodiments, the compound of Formula (I) or a pharmaceutically acceptable salt, ester, stereoisomer, polymorph, solvate, N-oxide, isotopically labeled compound, metabolite or prodrug thereof is administered in an amount of about 1 ng/kg to about 200 mg/kg, about 1 μg/kg to about 100 mg/kg or about 1 mg/kg to about 50 mg/kg body weight per day, e.g., is administered in an amount of about 1 μg/kg, about g/kg, about 25 μg/kg, about 50 μg/kg, about 75 μg/kg, about 100 μg/kg, about 125 μg/kg, about 150 g/kg, about 175 μg/kg, about 200 μg/kg, about 225 μg/kg, about 250 μg/kg, about 275 μg/kg, about 300 g/kg, about 325 μg/kg, about 350 μg/kg, about 375 μg/kg, about 400 μg/kg, about 425 μg/kg, about 450 μg/kg, about 475 μg/kg, about 500 μg/kg, about 525 μg/kg, about 550 μg/kg, about 575 μg/kg, about 600 μg/kg, about 625 μg/kg, about 650 μg/kg, about 675 μg/kg, about 700 μg/kg, about 725 μg/kg, about 750 μg/kg, about 775 μg/kg, about 800 μg/kg, about 825 μg/kg, about 850 μg/kg, about 875 μg/kg, about 900 μg/kg, about 925 μg/kg, about 950 μg/kg, about 975 μg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg or about 300 mg/kg body weight per unit dose.

In some embodiments, the daily dose of the compound of Formula (I) or a pharmaceutically acceptable salt, ester, stereoisomer, polymorph, solvate, N-oxide, isotopically labeled compound, metabolite or prodrug thereof is administered at one time or is administered in two, three or four doses.

In some embodiments, the compound of Formula (I) or a pharmaceutically acceptable salt, ester, stereoisomer, polymorph, solvate, N-oxide, isotopically labeled compound, metabolite or prodrug thereof is administered continuously for at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 30 days, at least 35 days, at least 40 days, at least 45 days or at least 50 days.

In some embodiments, the compound of Formula (I) or a pharmaceutically acceptable salt, ester, stereoisomer, polymorph, solvate, N-oxide, isotopically labeled compound, metabolite or prodrug thereof is administered for one or more (e.g., 1, 2, 3, 4, 5, 6, 7, 8, 9 or 10) courses of treatment, wherein each course of treatment lasts for at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 30 days, at least 35 days, at least 40 days, at least 45 days or at least 50 days; and the interval between every two courses of treatment is 0, 1, 2, 3, 4, 5, 6, 7, 8, 9, 10 days, two weeks, three weeks, or four weeks.

In some embodiments, the compound of Formula (I) or a pharmaceutically acceptable salt, ester, stereoisomer, polymorph, solvate, N-oxide, isotopically labeled compound, metabolite or prodrug thereof is administered through injection (e.g., intravenous, intraarterial, subcutaneous, intraperitoneal, intramuscular injection, including dripping), or transdermal administration, or is administered via oral, buccal, nasal, transmucosal, topical, as an ophthalmic formulation, or via inhalation.

In some embodiments, the compound of Formula (I) or a pharmaceutically acceptable salt, ester, stereoisomer, polymorph, solvate, N-oxide, isotopically labeled compound, metabolite or prodrug thereof is administered in a dosage form selected from the group consisting of tablet, capsule, lozenge, hard candy, powder, spray, cream, salve, suppository, gel, paste, lotion, ointment, aqueous suspensions, injectable solution, elixir, and syrup.

In some embodiments, the prevention or treatment comprises reduction in fatty degeneration, reduction in collagen accumulation and/or reduction in ballooning degeneration.

In some embodiments, the method further comprises administering one or more additional therapeutic agents.

EXAMPLE

In order to make the objects and technical solutions of the invention clearer, the invention will be further described below with reference to specific examples. It should be understood that the following examples are only intended for illustrating the invention and are not to be understood as limiting the scope of the invention. Further, specific experimental methods not mentioned in the following examples are carried out in accordance with conventional experimental methods.

Compound C employed in the examples is compound 331, and it was prepared according to the method disclosed in WO 2019/001572 A1.

Example 1

Figure 1B:
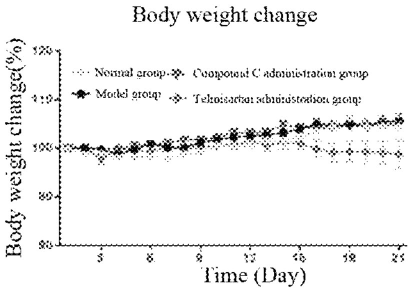
Figure 2A:
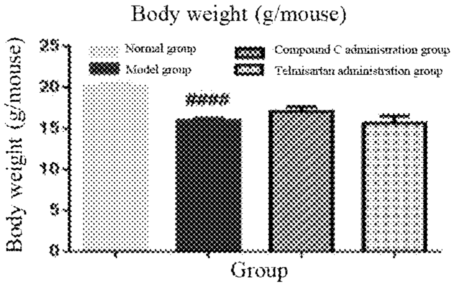
FIG. 2 shows the average body weight of each group of animals (FIG. 2A) and liver weight/body weight percentage (FIG. 2B) at the end of the administration.
Figure 2B:
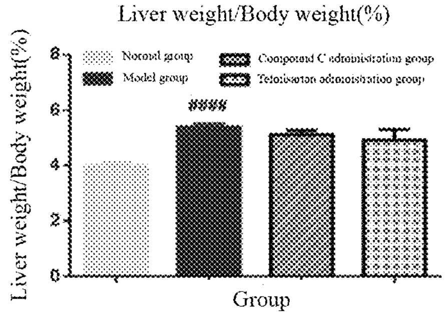
Figure 3A:
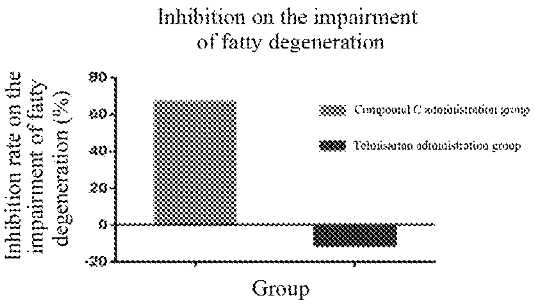
FIG. 3 shows the inhibition rate on fatty degeneration (FIG. 3A), inhibition rate on collagen accumulation (FIG. 3B), and inhibition rate on ballooning degeneration (FIG. 3C) in the liver tissue after the administration.
Figure 3B:
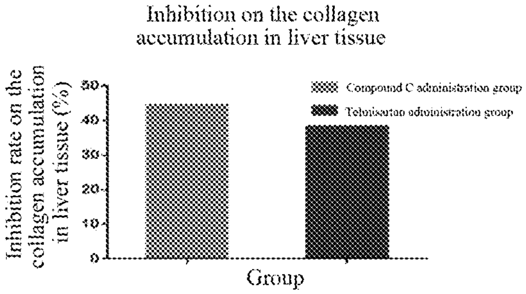
Figure 3C:
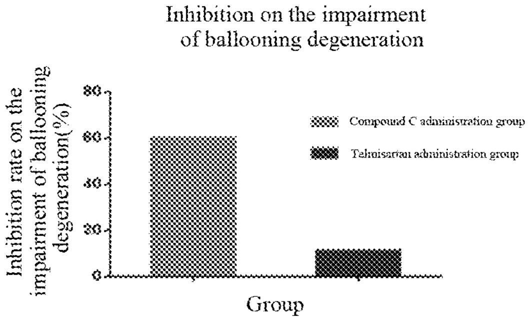

Therapeutic Effect of Compound C in a High Fat+Streptozotocin Induced Mouse Model Pregnant mice were purchased from Shanghai Lingchang Laboratory Animal Co., Ltd. Thirty 2-day-old newborn male mice were chosen for the test. Each mouse was injected with 200 μg of streptozotocin (STZ, purchased from Sigma) and fed a high-fat diet for 2 weeks from 4-week-old to induce a steatohepatitis model. Meanwhile, another ten mice were selected as a normal group where they were fed a normal diet without injection of STZ. After 2 weeks of high-fat diet feeding, the mice were divided into 3 groups according to their body weights and fasting blood glucose levels: a model group, a compound C administration group, and a telmisartan (purchased from TOKYO CHEMICAL) administration group. Each group underwent once-a-day oral administration of the corresponding substance for 21 consecutive days. The grouping of animals is listed in Table 1. The body weights of mice were recorded each day (see FIG. 1A and FIG. 1B), and after the final administration, the body weights of mice after fasting were recorded (see Table 2 and FIG. 2A and FIG. 2B). The animals were euthanized, and their liver tissues were harvested. The liver tissues were weighed and subjected to histologic scoring (blind assessment) in respect of ballooning degeneration, fatty degeneration, and collagen accumulation, etc. Histologic changes were assessed by hematoxylin and eosin (H&E) staining, oil red O staining and Picrosirius red staining of the liver tissues, where the H&E staining was used for assessing the ballooning degeneration of liver cells, the oil red O staining was used for reflecting the fatty degeneration of liver and the Picrosirius red staining was used for assessing collagen accumulation. Relevant scores are shown in FIG. 3A, FIG. 3B and FIG. 3C, and inhibition rates of various histologic changes are shown in Table 3.

Scoring criteria: fatty degeneration is scored on a scale from 0 to 3, where lesion area <5% is scored as 0, lesion area of 5-33% is scored as 1, lesion area of 33-66% is scored as 2 and lesion area >66% is scored as 3. Ballooning degeneration of liver cells is scored on a scale from 0 to 2, where no ballooning degeneration is scored as 0, little ballooning degeneration is a scored as 1, and ballooning degeneration of most cells or significant ballooning degeneration is scored as 2. Collagen accumulation is scored on a scale from 0 to 4 with reference to the scoring criteria reported in Brunt E M, et al., Hepatology (2011).

The inhibition rates (%) on fatty degeneration, ballooning degeneration of liver cells and collagen accumulation in liver tissue shown in Table 3 were calculated according to the following formulae, respectively (the normal group was scored as 0):

Inhibition rate (%) on fatty degeneration=100%×(the average score of the model group−the average score of the administration group)/(the average score of the model group−the average score of the normal group)

Inhibition rate (%) on ballooning degeneration of liver cells=100%×(the average score of the model group−the average score of the administration group)/(the average score of the model group−the average score of the normal group)

Inhibition rate (%) on collagen accumulation in liver tissue=100%×(the average score of the model group−the average score of the administration group)/(the average score of the model group−the average score of the normal group)

TABLE 1

Grouping of Test Animals

| Group | Number of Animals | Dosage of Administration (mg/kg body weight) | Volume of Administration (ml/kg body weight) | Route of Administration | Frequency of Administration |
|---|---|---|---|---|---|
| Normal group | 10 | None* | 5 | Oral administration | Once a day, for 21 consecutive days |
| Model group | 10 | None* | 5 | Oral administration | Once a day, for 21 consecutive days |
| Compound C administration group | 10 | 100 | 5 | Oral administration | Once a day, for 21 consecutive days |
| Telmisartan administration group | 10 | 50 | 5 | Oral administration | Once a day, for 21 consecutive days |

*The animals in the normal group and the model group were administrated with a vehicle (composed of PEG400, Tween-80 and water).

TABLE 2

Body Weight Changes and Liver Weight Changes of Animals at the End of the Test

| Group | Body Weight (g) | Liver Weight (mg) | Liver Weight/Body Weight (%) |
|---|---|---|---|
| Normal group | 20.3 ± 0.33 | 805.8 ± 25.27 | 4.0 ± 0.11 |
| Model group | 16.0 ± 0.27 | 862.4 ± 13.46 | 5.4 ± 0.13 |
| Compound C administration group | 17.1 ± 0.59 | 872.3 ± 17.91 | 5.1 ± 0.15 |
| Telmisartan administration group | 15.7 ± 0.84 | 760.1 ± 48.78 | 4.9 ± 0.39 |

TABLE 3

Inhibition Rates of Compound C on Fatty Degeneration, Ballooning Degeneration of Liver Cells and Collagen Accumulation

| Group | Inhibition Rate (%) on Fatty Degeneration | Inhibition Rate (%) on Ballooning Degeneration of Liver Cells | Inhibition Rate (%) on Collagen Accumulation in Liver Tissue |
|---|---|---|---|
| Compound C administration group | 66.67 | 60.00 | 44.44 |
| Telmisartan administration group | −11.17 | 11.12 | 38.27 |

According to the test results, the compound C exhibited good tolerance and significant therapeutic effects in the STZ and high fat induced mouse model. Compound C mainly exerted the therapeutic effects mainly by improving fatty degeneration, ballooning degeneration and collagen accumulation of the liver tissue.

Example 2

Therapeutic Effect of Compound C in a High Fat+High Cholesterol+High Sugar+Carbon Tetrachloride Induced Mouse Model Mice which were 8-10 weeks old (purchased from Jiangsu GemPharmatech Co., Ltd.) were fed a western diet (a high fat+high cholesterol feed, purchased from Beijing Hfk Bioscience Co., Ltd.) and a high-sugar solution (23.1 g/L D-fructose and 18.9 g/L D-glucose) and injected intraperitoneally with carbon tetrachloride to induce a steatohepatitis model. Starting from day 7 (D7) of western diet+high-sugar solution feeding, the mice were injected intraperitoneally with 0.05 ml of 20% carbon tetrachloride once a week, for 12 weeks. Animals were divided into groups (8 animals in each group) on day 28: a model group (administrated with a vehicle composed of PEG400, Tween-80 and deionized water), a compound C (100 mg/kg) administration group, and a telmisartan (10 mg/kg) administration group. Starting from day 28, the vehicle, compound C and telmisartan were each administered orally once a day, for three 21-day treatment courses at one-week intervals. Meanwhile, a normal control group was set wherein the mice were fed a normal diet combined with normal drinking water. Peripheral blood was taken from animals 2 h after the final administration, and serum was isolated. The animals were euthanized, and their liver tissues were harvested. The serum was mainly used to measure the levels of cholesterol and low density lipoprotein. The liver tissues were stained with Picrosirius red to assess collagen accumulation, and the ratio of endothelial cells to macrophages was measured by flow cytometry to reflect liver damage.

Figure 4A:
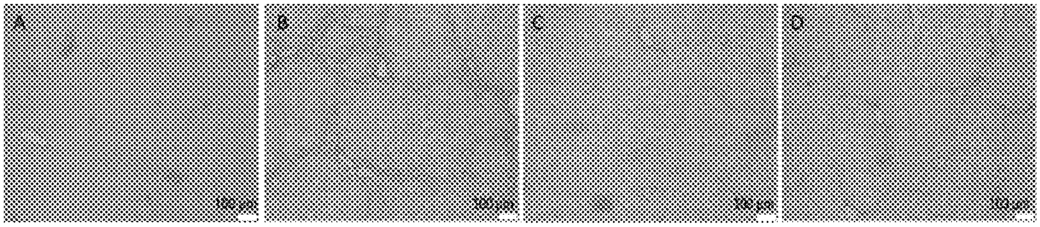
FIG. 4A shows the image stained with Picrosirius red (100×) of the liver tissue in Example 2, wherein A is the normal group, B is the model group, C is the compound C (100 mg/kg) administration group, and D is the telmisartan administration group.
Figure 4B:
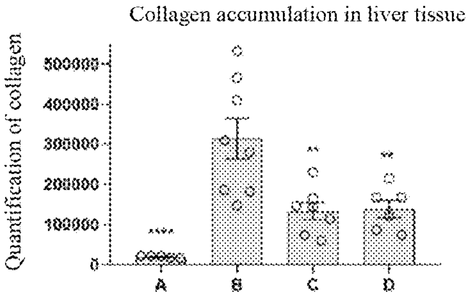
FIG. 4B shows the collagen accumulation of liver tissue in Example 2.

As shown in FIG. 4A and FIG. 4B, the mice in the model group had significantly increased collagen accumulation compared with the normal control group. Compared with the model group, collagen accumulation in liver tissue was significantly reduced in the compound C administration group ($p<0.01$) and the telmisartan administration group ($p<0.01$).

Figure 5A:
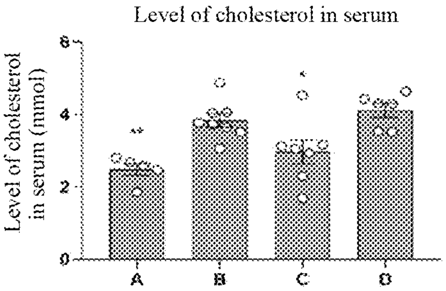
FIG. 5A shows the serum cholesterol level in the mouse model of Example 2.

As shown in FIG. 5A and FIG. 5B, the mice in the model group had significantly increased levels of cholesterol ($p<0.01$) and low density lipoprotein ($p<0.001$) in serum compared with the normal control group. Compared with the model group, the levels of cholesterol ($p<0.05$) and low density lipoprotein ($p<0.05$) in serum were significantly reduced in the compound C administration group. Telmisartan had no effect on both.

As shown in FIG. 6A and FIG. 6B, the mice in the model group had a reduction in endothelial cells in liver tissue and an increase in the level of macrophages compared with the normal control group. Compared with the model group, the proportion of endothelial cells ($p<0.01$) in mouse liver tissue was increased in the compound C administration group, and the proportion of macrophages was reduced at a certain extent. Compared with the telmisartan administration group, compound C had a stronger effect on endothelial cells than telmisartan, and had a comparable effect on macrophage reduction to telmisartan.

Example 3

Therapeutic Effect of Compound C in High Fat+High Cholesterol+Carbon Tetrachloride Induced Mouse Model Mice which were 8-10 weeks old (purchased from Jiangsu GemPharmatech Co., Ltd.) were fed a western diet (a high fat+high cholesterol feed, purchased from Beijing Hfk Bioscience Co., Ltd.) and injected intraperitoneally with carbon tetrachloride to induce a steatohepatitis model. Experimental animals were randomly divided into 3 groups (8 animals in each group) according to their body weights: a model group (administrated with a vehicle composed of PEG400, Tween-80 and deionized water), a compound C (100 mg/kg) administration group, and a telmisartan (10 mg/kg) administration group. Starting from day 5 (D5) of western diet feeding, each group underwent an intraperitoneal injection of 0.05 ml of 20% $CCl_4$ once a week, for 12 weeks. Starting from day 21, the vehicle, compound C and telmisartan were each administered orally once a day, for three 21-day treatment courses at one-week intervals. Meanwhile, a normal control group was set wherein the mice were fed a normal diet combined with normal drinking water. Peripheral blood was taken from animals 2 h after the final administration, and serum was isolated. The animals were euthanized and their liver tissues were harvested. The serum was mainly used to measure the levels of cholesterol and low density lipoprotein. The liver tissues were stained with Picrosirius red to assess collagen accumulation.

Figure 7A:
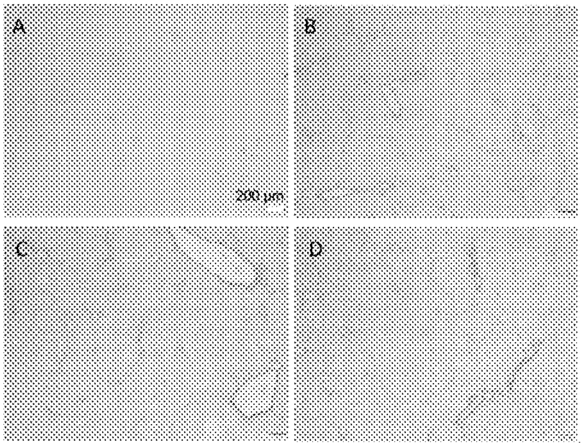
FIG. 7A shows the Picrosirius red staining (200×) image of the liver tissue in Example 3, wherein A is the normal group, B is the model group, C is the compound C (100 mg/kg) administration group, and D is the telmisartan administration group.
Figure 7B:
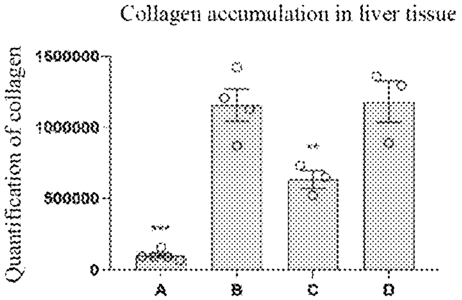
FIG. 7B shows the collagen accumulation of liver tissue in Example 3.

As shown in FIG. 7A and FIG. 7B, the western diet+carbon tetrachloride induced steatohepatitis mice models in the model group had significantly increased collagen accumulation compared with the normal control group. Compared with the model group, collagen accumulation in liver tissue was significantly reduced in the compound C administration group ($p<0.01$). Collagen accumulation was not inhibited in the telmisartan administration group and there was no significant difference from the model group ($p>0.05$).

Figure 8A:
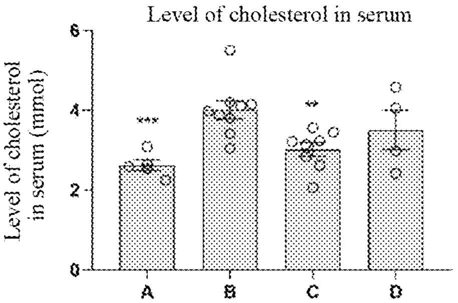
FIG. 8A shows the serum cholesterol level in the mouse model of Example 3.
Figure 8B:
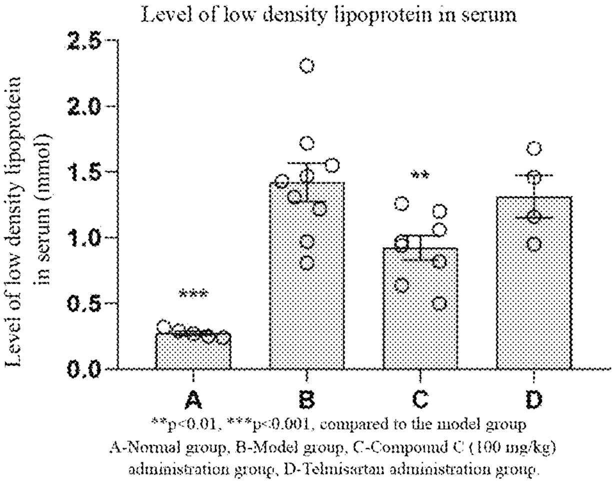
FIG. 8B shows the serum low density lipoprotein level in the mouse model of Example 3.

As shown in FIG. 8A and FIG. 8B, the mice in the model group had significantly increased levels of cholesterol ($p<0.001$) and low density lipoprotein ($p<0.001$) in serum compared with the normal control group. Compared with the model group, the levels of cholesterol ($p<0.01$) and low density lipoprotein ($p<0.01$) in serum were significantly reduced in the compound C administration group. Telmisartan had no effect on both.

Example 4

Therapeutic Effect of Compound C in Carbon Tetrachloride Induced Mouse Model

Mice which were 8-10 weeks old (purchased from Jiangsu GemPharmatech Co., Ltd.) were randomly divided into 4 groups (8 animals in each group) according to their body weights: a model group (administrated with a vehicle, 0.5% CMC-Na), a compound C (300 mg/kg) administration group, a compound C (100 mg/kg) administration group, and a telmisartan (10 mg/kg) administration group. Each mouse was injected intraperitoneally with 0.05 ml of 40% $CCl_4$ twice a week, for 6 consecutive weeks. Starting from day 15, each group underwent an intragastric administration of the corresponding substance once a day, for 28 consecutive days. Meanwhile, a normal control group was set wherein the mice in this group were fed a normal diet combined with normal drinking water. Animals were euthanized 2 h after the final administration, and their liver tissues were harvested and stained with Picrosirius red to assess collagen accumulation.

Figure 9A:
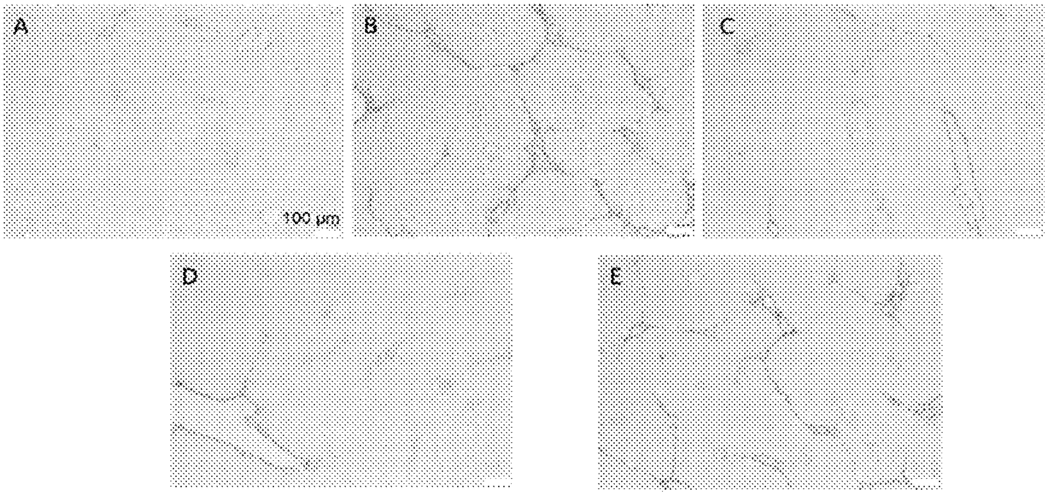
FIG. 9A shows the image stained with Picrosirius red (100×) of the liver tissue in Example 4, wherein A is the normal group, B is the model group, C is the compound C (300 mg/kg) administration group, and D is the compound C (100 mg/kg) administration group, and E is telmisartan administration group.
Figure 9B:
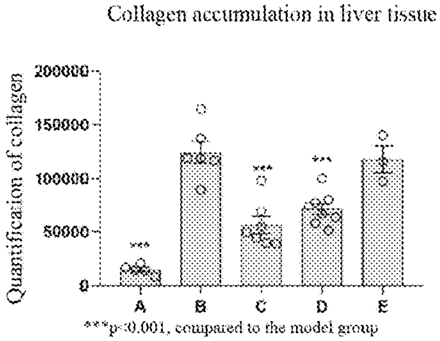
FIG. 9B shows the collagen accumulation of liver tissue in Example 4.

As shown in FIG. 9A and FIG. 9B, in the carbon tetrachloride induced mice models, the mice had significantly increased collagen accumulation compared with the normal control group. Compared with the model group, collagen accumulation in liver tissue was significantly reduced in both the compound C (300 mg/kg) administration group ($p<0.001$) and the compound C (100 mg/kg) administration group ($p<0.001$), and the high dosage group had a better effect than the low dosage group. Collagen accumulation was not inhibited in the telmisartan administration group and there was no significant difference from the model group ($p>0.05$).

Example 5

Therapeutic Effect of Compound C in High Fat+High Cholesterol Diet and N-Diethylnitrosamine Induced Rat Model Pregnant SD rats were purchased from Shanghai Jihui Laboratory Animal Care Co., Ltd, and neonatal rats obtained therefrom were used in this study. Forty male neonatal rats were chosen to receive a single injection of N-diethylnitrosamine (DEN, purchased from Sigma) at 2 weeks of age. After the neonatal rats were fed rat milk for 2 weeks, they were randomly divided into 4 groups (10 animals in each group) according to their body weights: a model group (0.5% CMC-Na), a compound C (50 mg/kg) administration group, a compound C (100 mg/kg) administration group, and an obeticholic acid (OCA, purchased from WuXi AppTec (Wuhan), 30 mg/kg) administration group. Each neonatal rat was fed a western diet (a high fat+high cholesterol feed, purchased from Trophic Animal Feed High-Tech Co., Ltd, China, Su Si certificate (2014) No. 06092) for 8 weeks. Meanwhile, another 8 male neonatal rats were selected as a normal group, which were fed rat milk for 4 weeks and then fed a normal diet instead of the high fat+high cholesterol diet. Starting from day 8 of high fat+high cholesterol diet feeding, the vehicle (0.5% CMC-Na), compound C and OCA were each administrated intragastrically once a day, for 49 consecutive days. The dosage regimen is shown in Table 4.

Figure 10A:
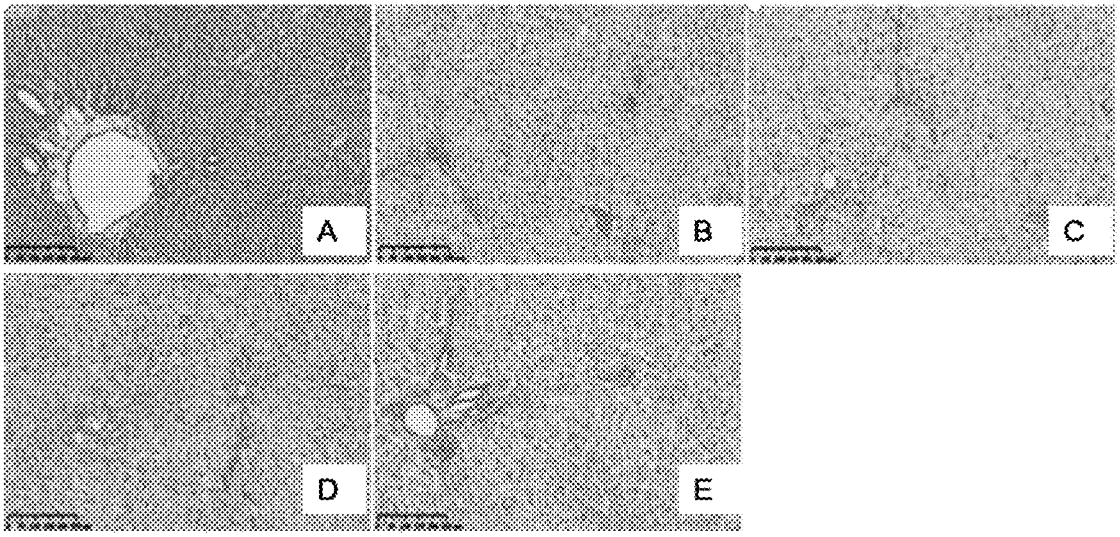
FIG. 10A shows the image stained with H&E of liver tissue in Example 5, wherein A is the normal control group, in which the liver tissue structure is complete, and the cells are arranged regularly; B is the model group, in which the liver tissue has obvious fatty degeneration of liver cells (appearing to be transparent vacuoles), ballooning degeneration and inflammatory cell infiltration lesions; C is an OCA (30 mg/kg) administration group; D is a compound C (50 mg/kg) administration group; and E is a compound C (100 mg/kg) administration group.

Animals were euthanized 2 h after the final administration, and their liver tissues were harvested. After being fixed and embedded, the liver tissues were stained with H&E (see FIG. 10A for the staining image) for NAS scoring. The relevant scoring criteria are shown in Table 5.

TABLE 4

Dosage Regimen

| Group | Number of Animals | Whether or Not Feeding with a High Fat + High Cholesterol Diet | Administration | Route of Administration | Course of Administration |
|---|---|---|---|---|---|
| Group 1 | 8 | No | Vehicle (0.5% CMC-Na) | Oral administration | Once a day, for 49 consecutive days |
| Group 2 | 10 | Yes | Vehicle (0.5% CMC-Na) | Oral administration | Once a day, for 49 consecutive days |
| Group 3 | 10 | Yes | OCA-30 mg/kg | Oral administration | Once a day, for 49 consecutive days |
| Group 4 | 10 | Yes | Compound C-50 mg/kg | Oral administration | Once a day, for 49 consecutive days |
| Group 5 | 10 | Yes | Compound C-100 mg/kg | Oral administration | Once a day, for 49 consecutive days |

TABLE 5

NAS Scoring Criteria

| Pathological Manifestation | Scoring Criterion | Score |
|---|---|---|
| Ballooning degeneration of liver cells | None | 0 |
| | Ballooning degeneration of a few cells | 1 |
| | Ballooning degeneration of a large number of cells | 2 |
| Lobular inflammation: inflammatory cell infiltration lesions | None | 0 |
| | <2 inflammatory cell infiltration lesions present in the field of view at 200 × magnification | 1 |
| | 2-4 inflammatory cell infiltration lesions present in the field of view at 200 × magnification | 2 |
| | >4 inflammatory cell infiltration lesions present in the field of view at 200 × magnification | 3 |
| Fatty degeneration of liver cells: proportion of the whole slice area | <5% | 0 |
| | 5%-33% | 1 |
| | >33%-66% | 2 |
| | >66% | 3 |

Figure 10B:
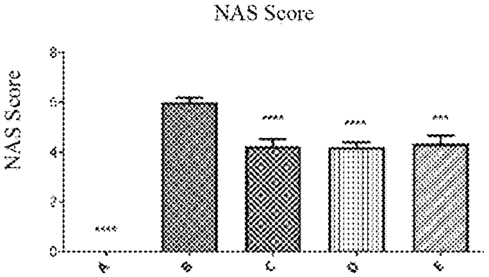
FIG. 10B shows the NAS score of liver tissue in Example 5.

An NAS score is the sum of a score on fatty degeneration of liver, a score on inflammatory cell infiltration and a score on ballooning degeneration of liver cells. The NAS score was significantly increased in the model group (which was 6) compared with the normal control group. The NAS score on the animal liver tissue was significantly reduced to about 4.2 in the compound C administration groups (see FIG. 10B).

Various modifications to the invention in addition to those described herein will become apparent to those skilled in the art from the foregoing description. Such modifications are intended to fall within the scope of the appended claims. Each reference, including all patents, applications, journal articles, books and any other disclosure, referred to herein is hereby incorporated by reference in its entirety.

What is claimed is:

1. A method for preventing, alleviating and/or treating a fatty liver disease and/or steatohepatitis, comprising administering to a subject in need thereof an effective amount of a compound or a pharmaceutically acceptable salt, ester, stereoisomer, polymorph, solvate, N-oxide, isotopically labeled compound, metabolite or prodrug thereof, wherein the compound has the following structure:

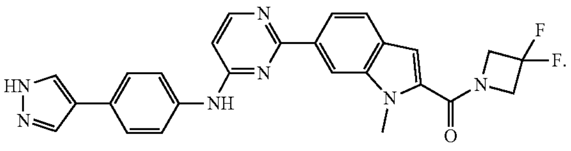 [SMILES: Cn1c(C(=O)N2CC(F)(F)C2)cc2ccc(-c3nccc(Nc4ccc(-c5cn[nH]c5)cc4)n3)cc21]

2. The method according to claim 1, wherein the compound or a pharmaceutically acceptable salt, ester, stereoisomer, polymorph, solvate, N-oxide, isotopically labeled compound, metabolite or prodrug thereof is administered in an amount of 0.005 mg/day to 5000 mg/day.

3. The method according to claim 1, wherein the compound or a pharmaceutically acceptable salt, ester, stereoisomer, polymorph, solvate, N-oxide, isotopically labeled compound, metabolite or prodrug thereof is administered in an amount of 1 ng/kg to 200 mg/kg, 1 μg/kg to 100 mg/kg or 1 mg/kg to 50 mg/kg body weight per day.

4. The method according to claim 1, wherein the daily dose of the compound or a pharmaceutically acceptable salt, ester, stereoisomer, polymorph, solvate, N-oxide, isotopically labeled compound, metabolite or prodrug thereof is administered at one time or is administered in two, three or four doses.

5. The method according to claim 1, wherein the compound or a pharmaceutically acceptable salt, ester, stereoisomer, polymorph, solvate, N-oxide, isotopically labeled compound, metabolite or prodrug thereof is administered continuously for at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 30 days, at least 35 days, at least 40 days, at least 45 days or at least 50 days.

6. The method according to claim 1, wherein the compound or a pharmaceutically acceptable salt, ester, stereoisomer, polymorph, solvate, N-oxide, isotopically labeled compound, metabolite or prodrug thereof is administered for one or more courses of treatment, wherein each course of treatment lasts for at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 30 days, at least 35 days, at least 40 days, at least 45 days or at least 50 days; and the interval between every two courses of treatment is 0, 1, 2, 3, 4, 5, 6, 7, 8, 9, 10 days, two weeks, three weeks, or four weeks.

7. The method according to claim 1, wherein the compound or a pharmaceutically acceptable salt, ester, stereoisomer, polymorph, solvate, N-oxide, isotopically labeled compound, metabolite or prodrug thereof is administered through injection, or transdermal administration, or is administered via oral, buccal, nasal, transmucosal, topical, as an ophthalmic formulation, or via inhalation.

8. The method according to claim 1, wherein the compound or a pharmaceutically acceptable salt, ester, stereoisomer, polymorph, solvate, N-oxide, isotopically labeled compound, metabolite or prodrug thereof is administered in a dosage form selected from the group consisting of tablet, capsule, lozenge, hard candy, powder, spray, cream, salve, suppository, gel, paste, lotion, ointment, aqueous suspensions, injectable solution, elixir, and syrup.

9. The method according to claim 1, wherein the prevention or treatment comprises reduction in fatty degeneration, reduction in collagen accumulation and/or reduction in ballooning degeneration.

10. The method according to claim 1, further comprising administering one or more additional therapeutic agents which are suitable for preventing, alleviating and/or treating a fatty liver disease and/or steatohepatitis.

11. The method according to claim 1, wherein the fatty liver disease is an alcoholic fatty liver disease (AFLD) or a non-alcoholic fatty liver disease (NAFLD).

12. The method according to claim 1, wherein the steatohepatitis is an alcoholic steatohepatitis (ASH) or a non-alcoholic steatohepatitis (NASH).

13. The method according to claim 2, wherein the compound or a pharmaceutically acceptable salt, ester, stereoisomer, polymorph, solvate, N-oxide, isotopically labeled compound, metabolite or prodrug thereof is administered in an amount of 0.005, 0.05, 0.5, 5, 10, 20, 30, 40, 50, 100, 150, 200, 250, 300, 350, 400, 450, 500, 550, 600, 650, 700, 750, 800, 850, 900, 950, 1000, 1500, 2000, 2500, 3000, 3500, 4000, 4500 or 5000 mg/day.

14. The method according to claim 3, wherein the compound or a pharmaceutically acceptable salt, ester, stereoisomer, polymorph, solvate, N-oxide, isotopically labeled compound, metabolite or prodrug thereof is administered in an amount of 1 μg/kg, 10 μg/kg, 25 μg/kg, 50 μg/kg, 75 μg/kg, 100 μg/kg, 125 μg/kg, 150 μg/kg, 175 μg/kg, 200 μg/kg, 225 μg/kg, 250 μg/kg, 275 μg/kg, 300 μg/kg, 325 μg/kg, 350 μg/kg, 375 μg/kg, 400 μg/kg, 425 μg/kg, 450 μg/kg, 475 μg/kg, 500 μg/kg, 525 μg/kg, 550 μg/kg, 575 μg/kg, 600 μg/kg, 625 μg/kg, 650 μg/kg, 675 μg/kg, 700 μg/kg, 725 μg/kg, 750 μg/kg, 775 μg/kg, 800 μg/kg, 825 μg/kg, 850 μg/kg, 875 μg/kg, 900 μg/kg, 925 μg/kg, 950 μg/kg, 975 μg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg or 300 mg/kg body weight per unit dose.

15. The method according to claim 6, wherein the compound or a pharmaceutically acceptable salt, ester, stereoisomer, polymorph, solvate, N-oxide, isotopically labeled compound, metabolite or prodrug thereof is administered for 1, 2, 3, 4, 5, 6, 7, 8, 9 or 10 courses of treatment.

16. The method according to claim 7, wherein the compound or a pharmaceutically acceptable salt, ester, stereoisomer, polymorph, solvate, N-oxide, isotopically labeled compound, metabolite or prodrug thereof is administered through intravenous, intraarterial, subcutaneous, intraperitoneal, intramuscular injection.

17. The method according to claim 16, wherein the compound or a pharmaceutically acceptable salt, ester, stereoisomer, polymorph, solvate, N-oxide, isotopically labeled compound, metabolite or prodrug thereof is administered through dripping injection.

* * * * *